(12) United States Patent
Baldino et al.

(10) Patent No.: US 8,901,145 B2
(45) Date of Patent: *Dec. 2, 2014

(54) AMINOPYRIMIDINE KINASE INHIBITORS

(75) Inventors: Carmen M. Baldino, Woburn, MA (US); Justin L. Caserta, Billerica, MA (US); Stephane A. Dumas, Cambridge, MA (US); Chee-Seng Lee, Somerville, MA (US); Yvonne L. Flanders, Medford, MA (US)

(73) Assignee: Jasco Pharmaceuticals, LLC, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/452,250

(22) Filed: Apr. 20, 2012

(65) Prior Publication Data

US 2012/0270892 A1 Oct. 25, 2012

Related U.S. Application Data

(60) Provisional application No. 61/478,302, filed on Apr. 22, 2011, provisional application No. 61/555,617, filed on Nov. 4, 2011.

(51) Int. Cl.
*A01N 43/54* (2006.01)
*A61K 31/505* (2006.01)
*C07D 417/14* (2006.01)

(52) U.S. Cl.
CPC .................................. *C07D 417/14* (2013.01)
USPC .......................................... 514/275; 544/331

(58) Field of Classification Search
USPC .......................................... 544/180, 331, 332
See application file for complete search history.

(56) References Cited

U.S. PATENT DOCUMENTS

| 5,955,481 | A | 9/1999 | Ohara et al. | |
| 2011/0152235 | A1* | 6/2011 | Baldino et al. | 514/210.2 |
| 2013/0310342 | A1* | 11/2013 | Baldino et al. | 514/86 |

FOREIGN PATENT DOCUMENTS

| EP | 0787725 A1 | 8/1997 |
| WO | WO-9526347 A1 | 10/1995 |
| WO | WO-2006024666 A1 | 3/2006 |
| WO | WO-2006/040318 A2 | 4/2006 |
| WO | WO-2009064486 A2 | 5/2009 |

OTHER PUBLICATIONS

M. Traynor et al., Drugs of Today, 40(8), 697-710, 698 (2004).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
International Search Report and Written Opinion from corresponding PCT application PCT/US2012/034436 dated Oct. 12, 2012.
International Search Report and Written Opinion from PCT/US2012/061597 dated Dec. 11, 2012.
International Search Report from PCT/US2010/062024 dated Mar. 2, 2011.
Written Opinion of the International Search Authority from PCT/US2010/062024 dated Mar. 2, 2011.

* cited by examiner

*Primary Examiner* — James O. Wilson
*Assistant Examiner* — Alexander R Pagano
(74) *Attorney, Agent, or Firm* — Dana M. Gordon; Foley Hoag LLP

(57) ABSTRACT

Disclosed are compounds, pharmaceutical compositions containing those compounds, and uses of the compounds and compositions as modulators of casein kinase 1 (e.g., CK1γ), casein kinase 2 (CK2), Pim-1, Pim-2, Pim-3, the TGFβ pathway, the Wnt pathway, the JAK/STAT pathway, and/or the mTOR pathway. Uses are also disclosed for the treatment or prevention of a range of therapeutic indications due at least in part to aberrant physiological activity of casein kinase 1 (e.g., CK1γ), casein kinase 2 (CK2), Pim-1, Pim-2, Pim-3, the TGFβ pathway, the Wnt pathway, the JAK/STAT pathway, and/or the mTOR pathway.

11 Claims, No Drawings

AMINOPYRIMIDINE KINASE INHIBITORS

RELATED APPLICATIONS

This application claims benefit of priority under 35 U.S.C. 119(e) to U.S. Provisional Patent Application No. 61/478,302, filed Apr. 22, 2011; and U.S. Provisional Patent Application No. 61/555,617, filed Nov. 4, 2011.

BACKGROUND OF THE INVENTION

Casein kinase 1 (CK1) is a family of evolutionarily conserved serine/threonine kinases including seven known members in vertebrates (CK1α, -β, -γ1, -γ2, -γ3, -δ and -ε). The CK1s contain a typical kinase domain followed by a C-terminal tail region, which has been implicated in the regulation of CK1 localization, substrate selectivity and kinase activity. Myriad proteins have been found to be phosphorylated by CK1s, which are involved in a wide range of cellular functions including vesicular trafficking, DNA damage repair, cell cycle progression, cytokinesis and circadian rhythms (reviewed by Gross and Anderson (1998); Vielhaber and Virshup (2001); Knippschild et al. (2005)). Moreover, CK1 family members (-α, -δ/ε and -γ) modulate the activities of major signaling pathways (for example, Wnt and Shh) through several mechanisms (Peters et al., 1999; Liu et al., 2002; Price and Kalderon, 2002; Davidson et al., 2005; Zeng et al., 2005 and reviewed by Price (2006)).

In mammals seven CK1 isoforms, namely CK1α, β, γ$_{1-3}$, δ and ε, and several splice variants have been described. They all contain a highly conserved kinase domain, a short N-terminal domain of 6 to 76 amino acids and a highly variable C-terminal domain of 24 to more than 200 amino acids. The constitutive phosphotransferase activity of CK1 isoforms is tightly controlled by several mechanisms. For example, the closely related isoforms CK1δ and ε, which share a 98% identity at the amino acid level in their catalytic domain, are regulated by autophosphorylation, dephosphorylation and proteolytic cleavage. Members of the CK1 family are found in the nucleus, the cytoplasm and in the plasma membrane. By phosphorylating many different substrates bearing either a canonical or non-canonical consensus sequence, they modulate the activity of key regulator proteins involved in many cellular processes such as cell differentiation, cell proliferation, apoptosis, circadian rhythm, chromosome segregation, and vesicle transport.

The Pim kinase family contains three isoforms, Pim-1, Pim-2 and Pim-3, and has recently emerged as targets of interest in oncology and immune regulation. Ongoing studies have identified a role for these proteins in cell survival and proliferation, both functionally and mechanistically, and overexpression has been observed in a number of human cancers and inflammatory states.

Pim kinases suppress apoptosis and regulate cell-cycle progression. Elevated levels of Pim kinases have been reported in solid tumors such as prostate cancer and pancreatic cancer. Pim-1 was initially discovered in murine leukemia and several independent studies have shown this kinase to be upregulated in human prostate cancer. Pim-1, 2 and 3 make up a distinct and highly homologous family of serine/threonine kinases belonging to the calmodulin-dependent protein kinase-related (CAMK) family. In addition to the three gene-encoded proteins, translational variants have also been reported for Pim-1 and 2 resulting from utilization of alternative start codons. The name Pim refers to the original identification of the pim-1 gene as a frequent proviral insertion site in Moloney murine leukemia virus-induced T-cell lymphomas, and the gene encoding Pim-2 was subsequently found to have similar susceptibility. Pim-3, originally designated kinase induced by depolarization (KID)-1, was later renamed due to high sequence similarity to Pim-1 (71% identity at the amino acid level). Considering all three isoforms, Pim proteins are widely expressed with high levels in hematopoietic tissue and are aberrantly expressed in a variety of human malignancies. Pim kinases positively regulate cell survival and proliferation, affording therapeutic opportunities in oncology. The Pim protein kinases are frequently overexpressed in prostate cancer and certain forms of leukemia and lymphoma.

A role for Pim kinases in immune regulation has also been observed. Pim-2 has been reported to have enhanced levels of expression in a variety of inflammatory states and may function as a positive regulator of interleukin-6 (IL-6), whereby overexpression of the kinase augments stimulus-induced IL-6 levels. Pim-1 and 2 have also been implicated in cytokine-induced T-cell growth and survival. Comparing the sensitivity of stimulated T cells from Pim-1$^{-/-}$Pim-2$^{-/-}$ mice to wild-type mice following treatment with the immunosuppressant rapamycin, it was found that T-cell activation was significantly impaired by Pim-1/Pim-2 deficiency, suggesting that Pim kinases promote lymphocyte growth and survival through a PI3K/AKT (PKB, protein kinase B)/mammalian target of rapamycin (mTOR)-independent pathway. Other parallel but independent functions and overlapping substrate specificity for proteins in these pathways have been reported as well, including the positive regulation of transcription of nuclear factor kappa-B (NF-κB)-responsive genes, which have implications in both inflammation and oncology. Therefore, Pim kinases are attractive targets for both therapeutic areas.

Further, Pim kinases have been reported to play a role in the protection of the ATP-binding cassette (ABC) transporter P-glycoprotein (Pgp; ABCB1) from proteolytic and proteasomal degradation. Pgp is known to mediate drug efflux, and, as such, inhibitors of Pim kinases may provide a novel approach to abrogating drug resistance.

SUMMARY OF THE INVENTION

An aspect of the present invention relates to compounds that inhibit casein kinase 1 and/or casein kinase 2 and/or a PIM kinase. For example, an embodiment relates to a compound of formula 1 or a pharmaceutically acceptable salt thereof:

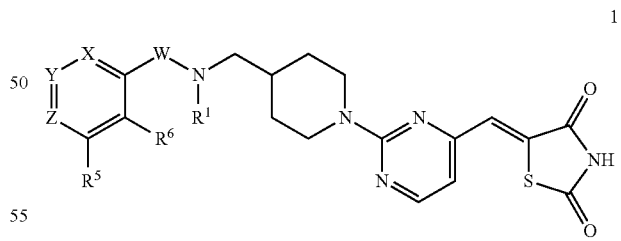

1 wherein independently for each occurrence:
W is C(R$^1$)$_2$, C(R$^1$)$_2$C(R$^1$)$_2$, C(R$^1$)$_2$C(R$^1$)$_2$C(R$^1$)$_2$, or S(O)$_2$;
X is nitrogen or CR$^2$;
Y is nitrogen or CR$^3$;
Z is nitrogen or CR$^4$;
R$^1$ is hydrogen or alkyl;
R$^2$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^3$ and $R^4$ are each independently selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl; or $R^3$ and $R^4$ are joined together to form an optionally substituted heterocyclic ring;

$R^5$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^6$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

wherein any one of the aforementioned alkyl, alkenyl, alkynyl, aryl, heteroaryl, heterocyclyl, aralkyl, heteroaralkyl, and heterocyclylalkyl may be optionally substituted;

wherein the compound is not

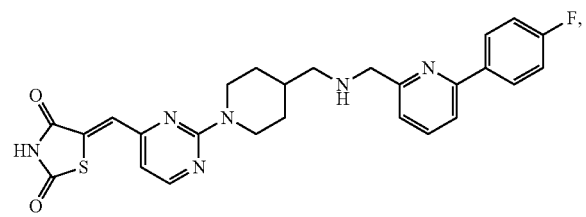

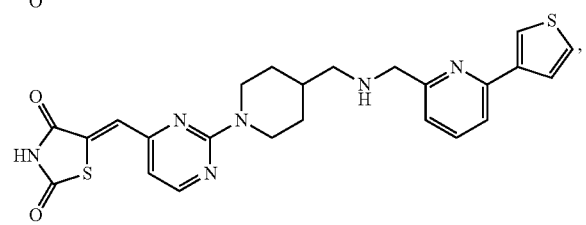

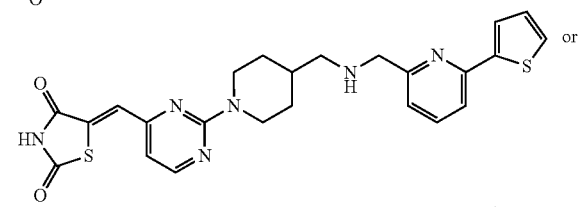

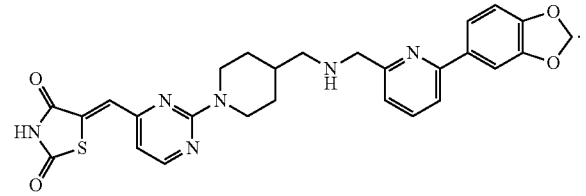

An embodiment relates to a compound of formula 2 or a pharmaceutically acceptable salt thereof:

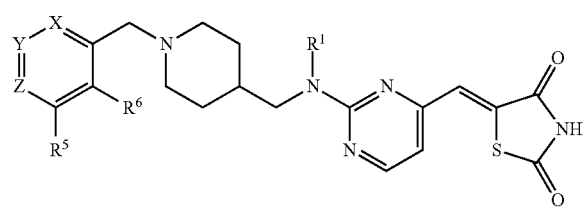

2 wherein independently for each occurrence:

X is nitrogen or $CR^2$;

Y is nitrogen or $CR^3$;

Z is nitrogen or $CR^4$;

$R^1$ is hydrogen or alkyl;

$R^2$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^3$ and $R^4$ are each independently selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl; or $R^3$ and $R^4$ are joined together to form an optionally substituted heterocyclic ring;

$R^5$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^6$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

wherein any one of the aforementioned alkyl, alkenyl, alkynyl, aryl, heteroaryl, heterocyclyl, aralkyl, heteroaralkyl, and heterocyclylalkyl may be optionally substituted.

An aspect of the invention relates to a compound, or a pharmaceutically acceptable salt thereof, selected from the group consisting of:

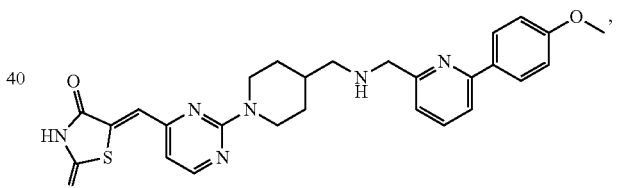

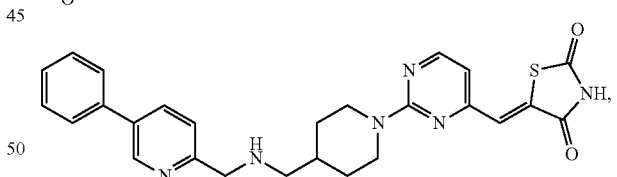

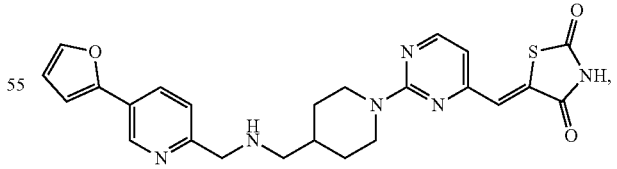

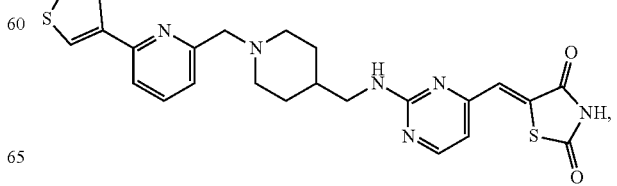

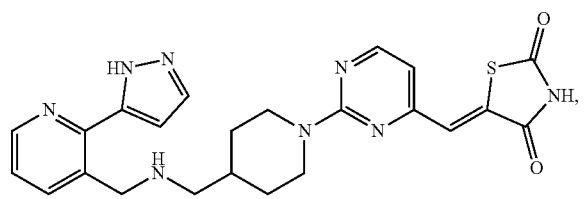
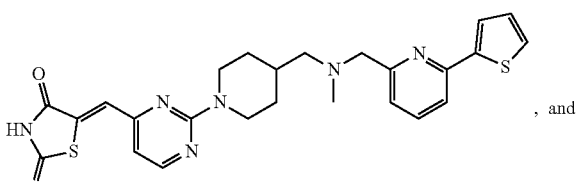, and
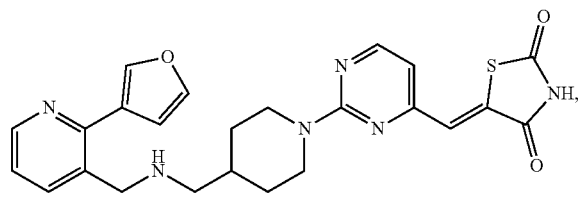
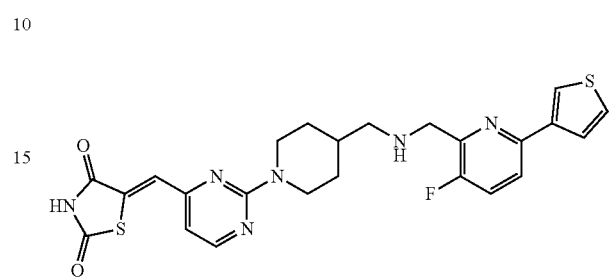
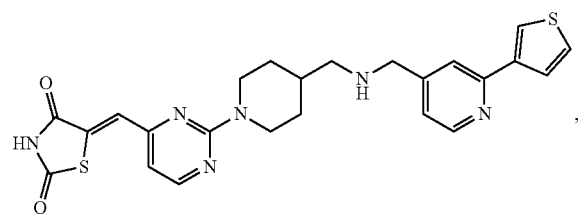 [SMILES: O=C1NC(=O)/C(=C/c2ccnc(N3CCC(CNCc4nc(-c5ccsc5)ccc4F)CC3)n2)S1]
An aspect of the invention relates to a compound, or a pharmaceutically acceptable salt thereof, selected from the group consisting of:
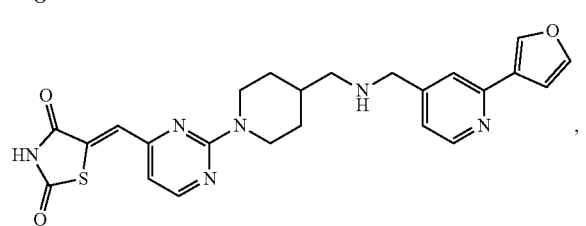
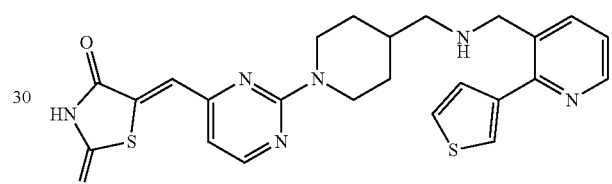
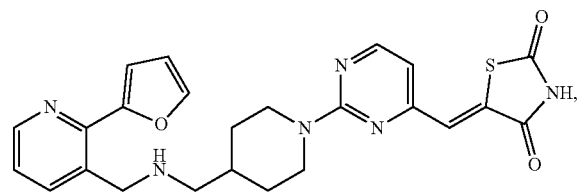
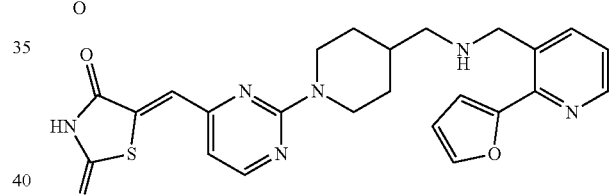
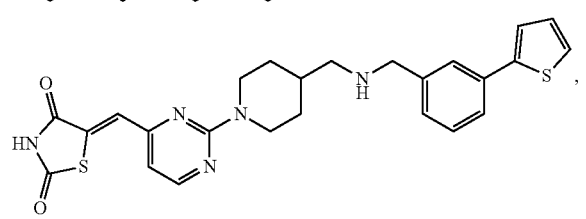
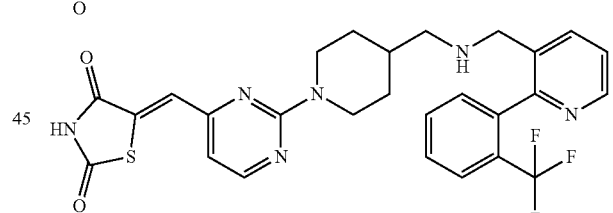
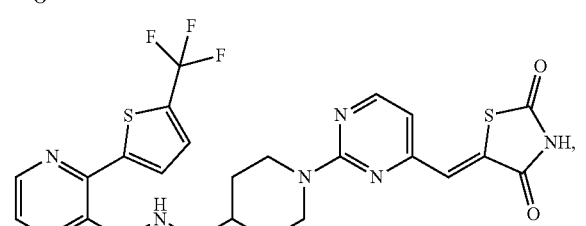
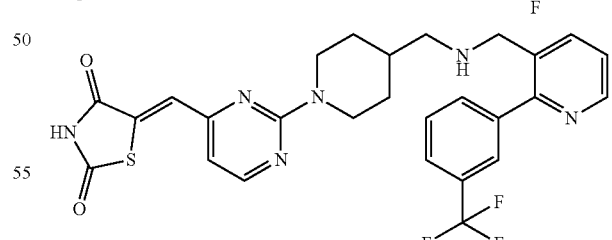
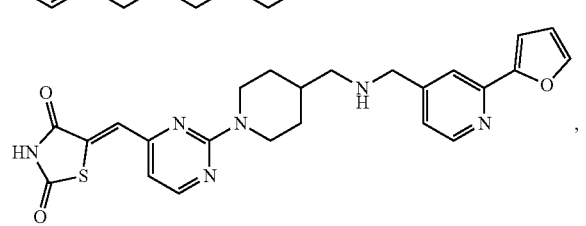
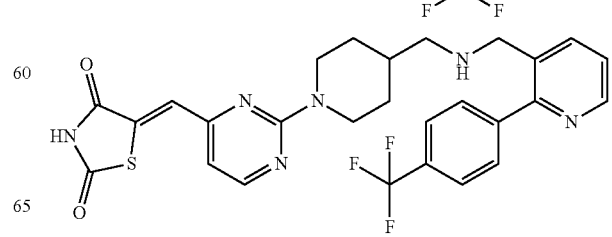

-continued
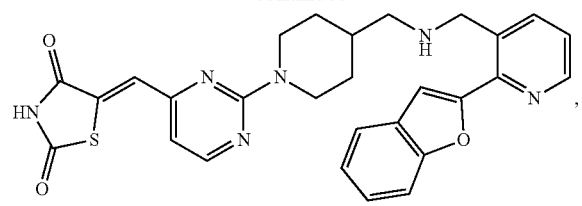,
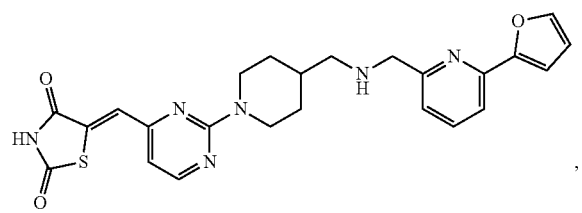,
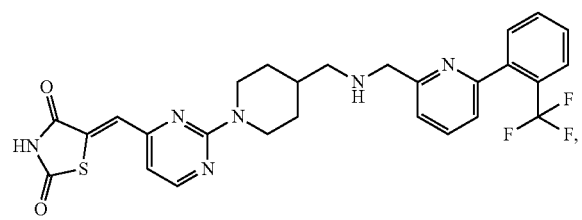,
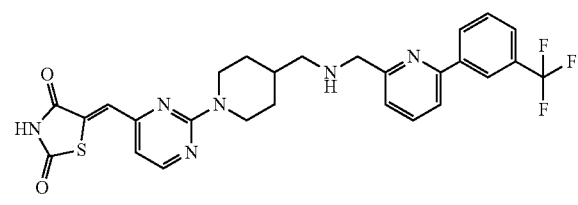,
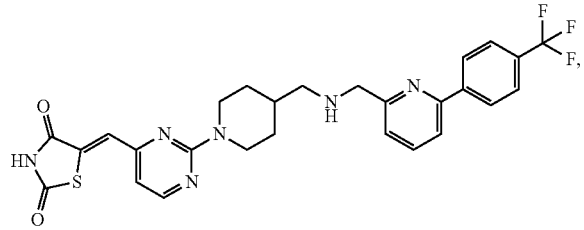,
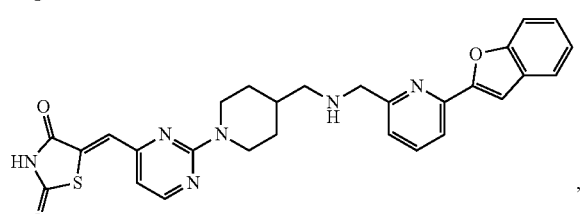,
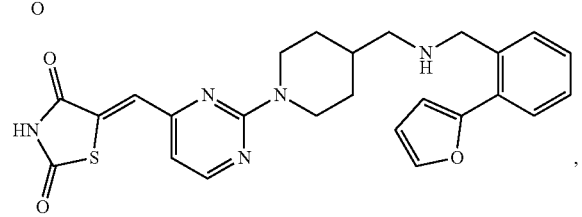,
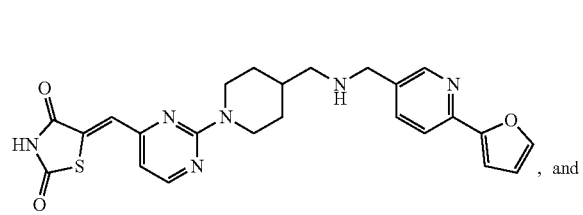, and
-continued
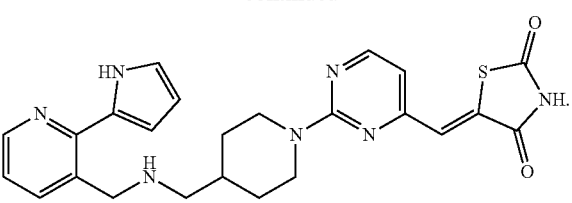 [SMILES: O=C1NC(=O)/C(=C/c2ccnc(N3CCC(CNCc4cccnc4-c4ccc[nH]4)CC3)n2)S1]
An aspect of the invention relates to a compound, or a pharmaceutically acceptable salt thereof, selected from the group consisting of:
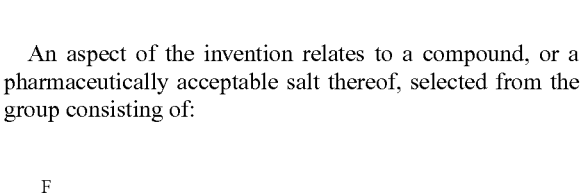,
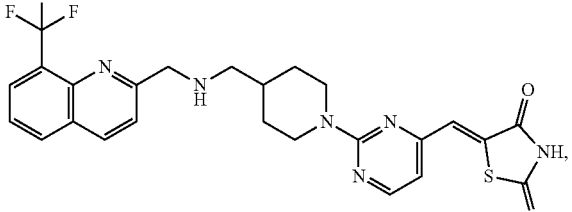,
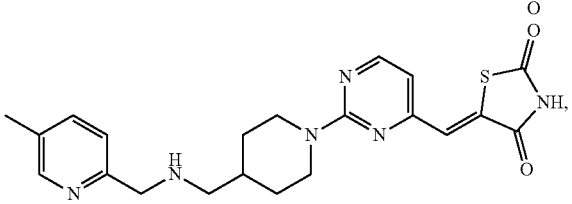,
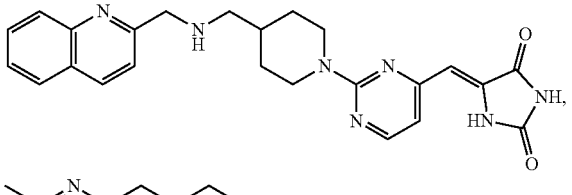,
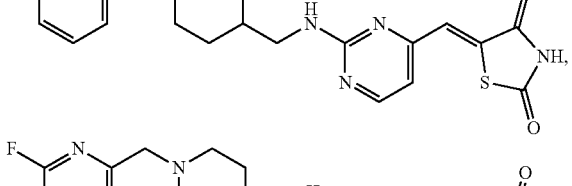,
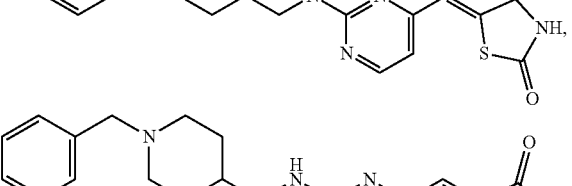,
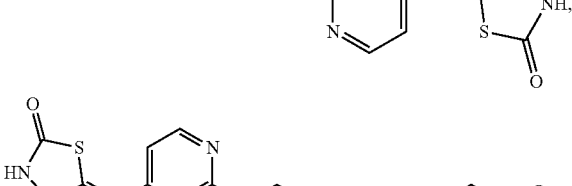,

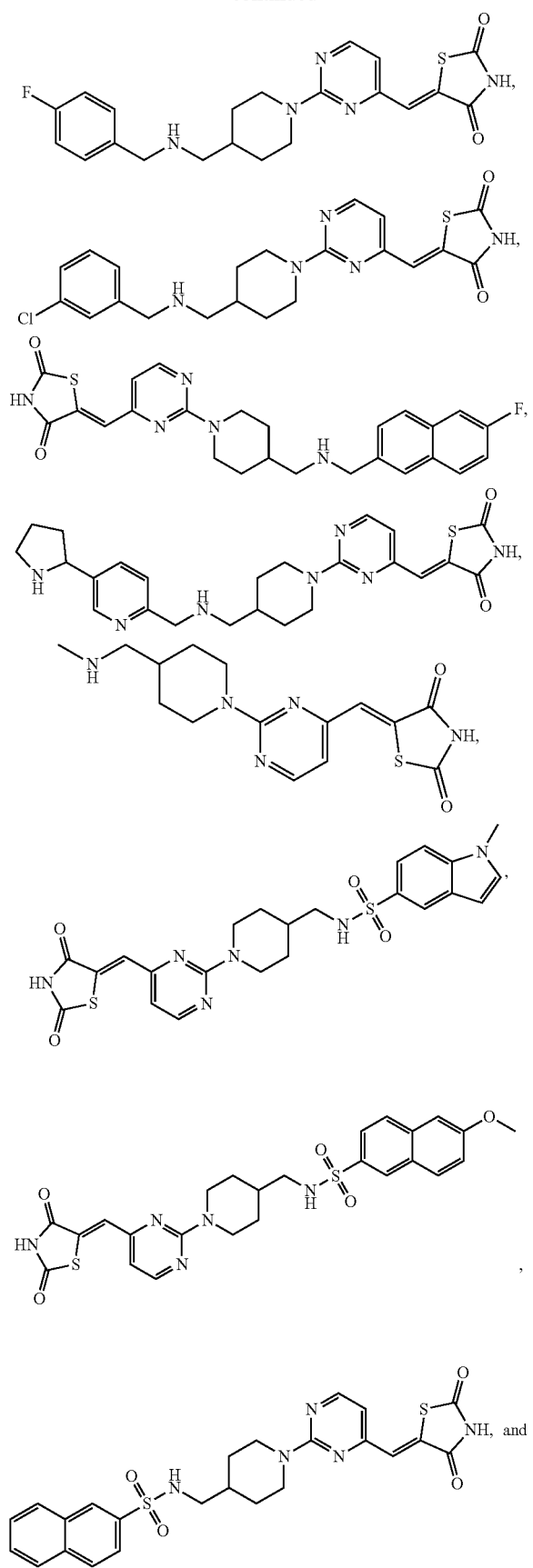
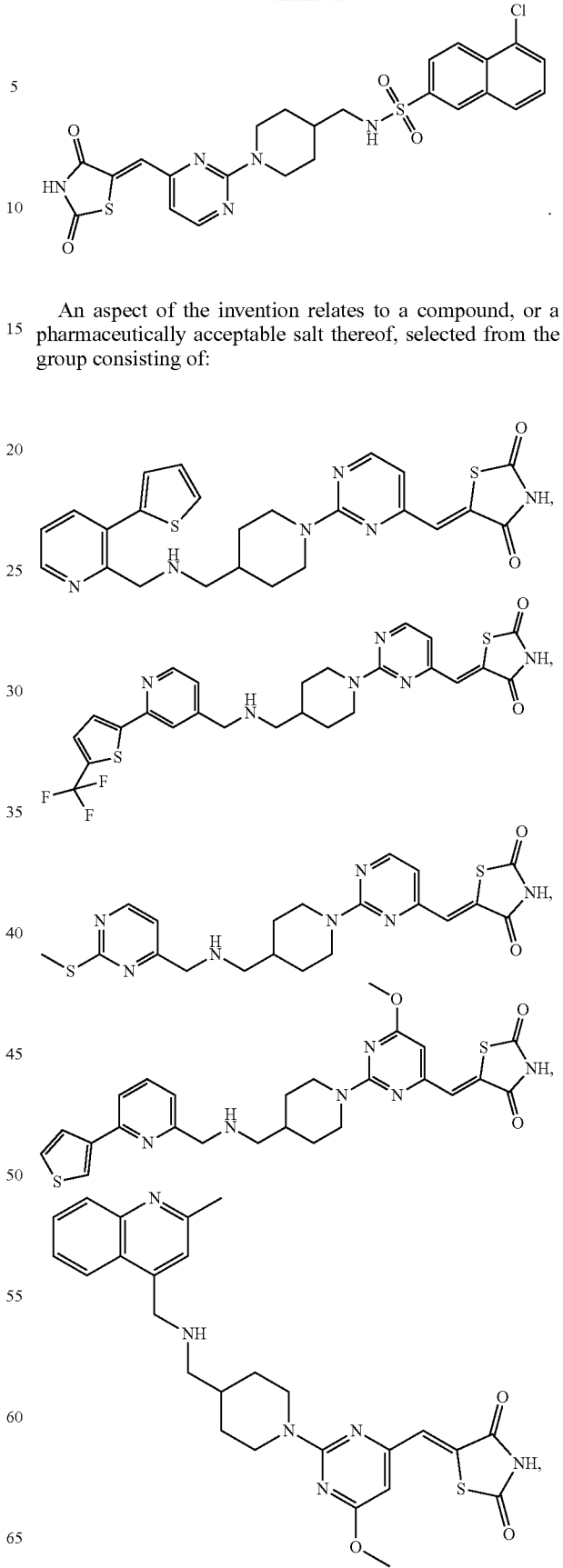
An aspect of the invention relates to a compound, or a pharmaceutically acceptable salt thereof, selected from the group consisting of:

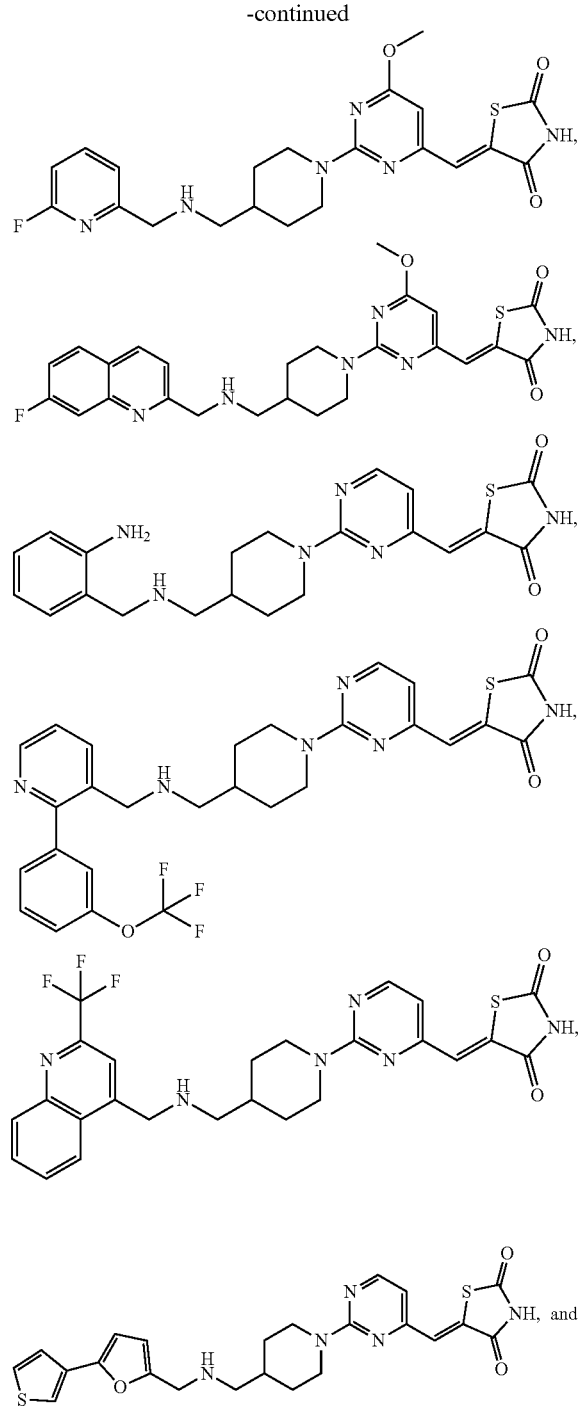
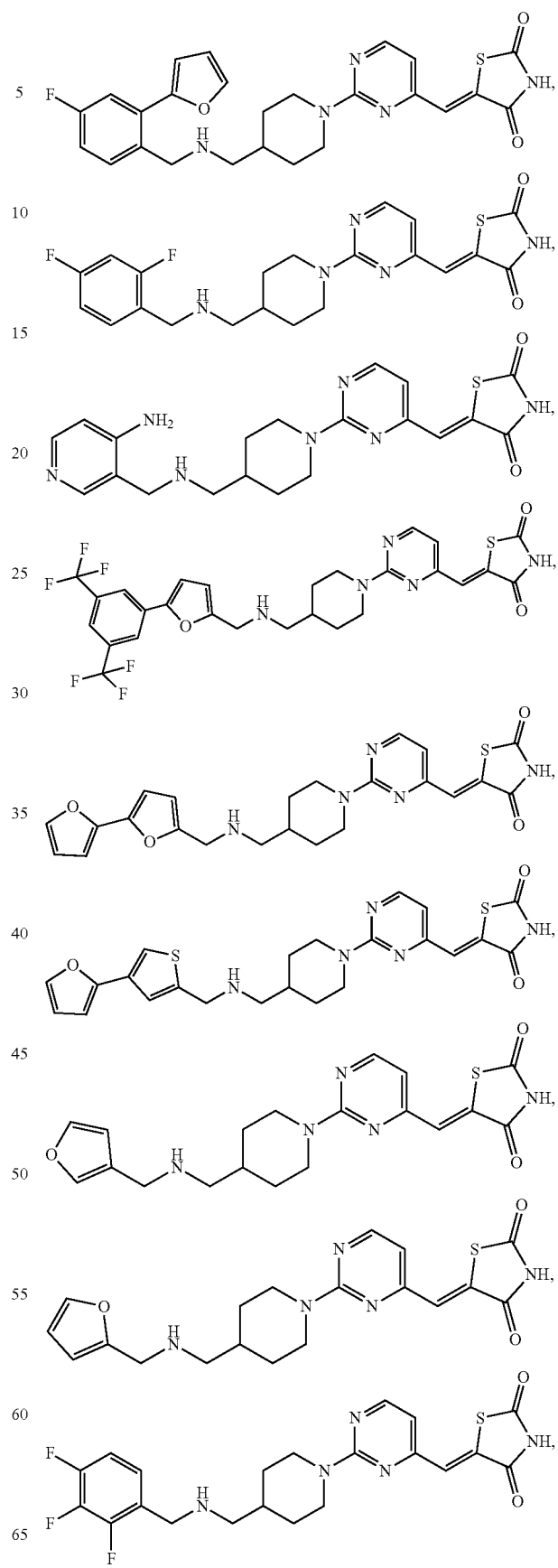
An aspect of the invention relates to a compound, or a pharmaceutically acceptable salt thereof, selected from the group consisting of:

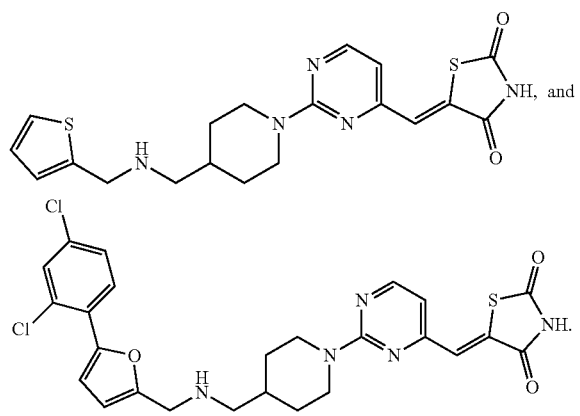
An aspect of the invention relates to a compound, or a pharmaceutically acceptable salt thereof, selected from the group consisting of:
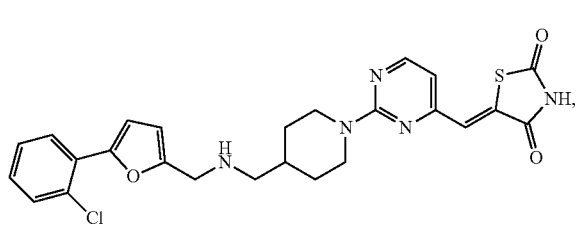
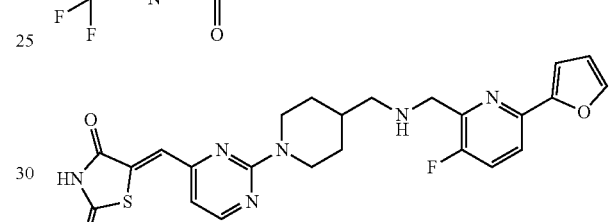
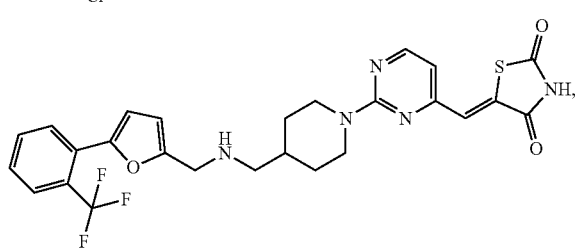
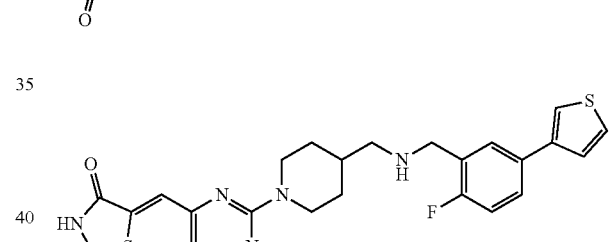
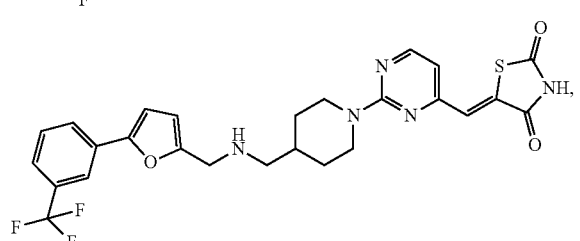
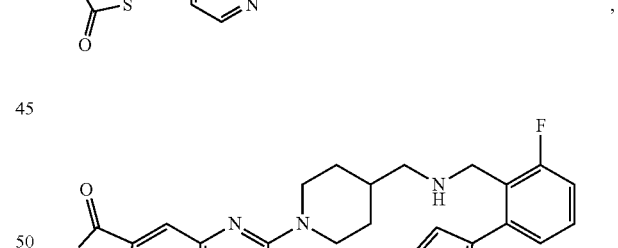
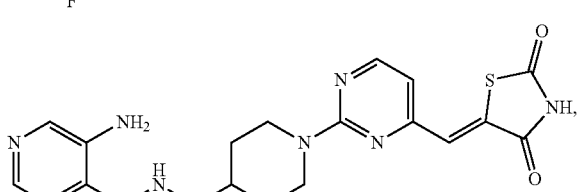
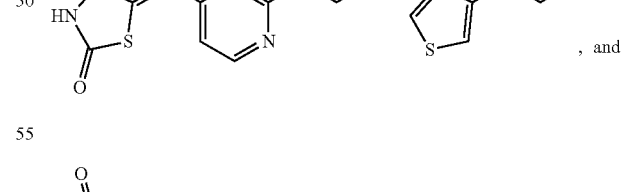
, and
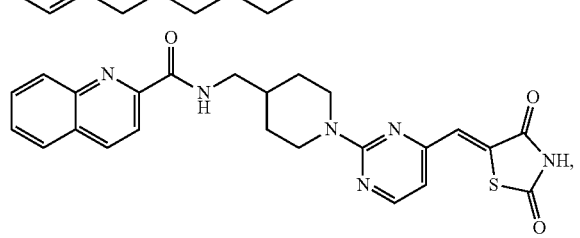
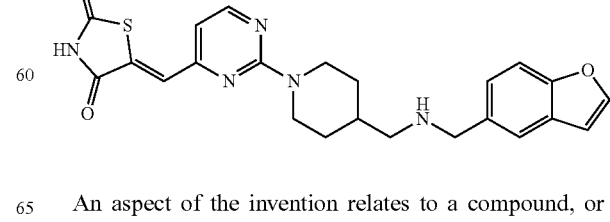
.
An aspect of the invention relates to a compound, or a pharmaceutically acceptable salt thereof, selected from the group consisting of:

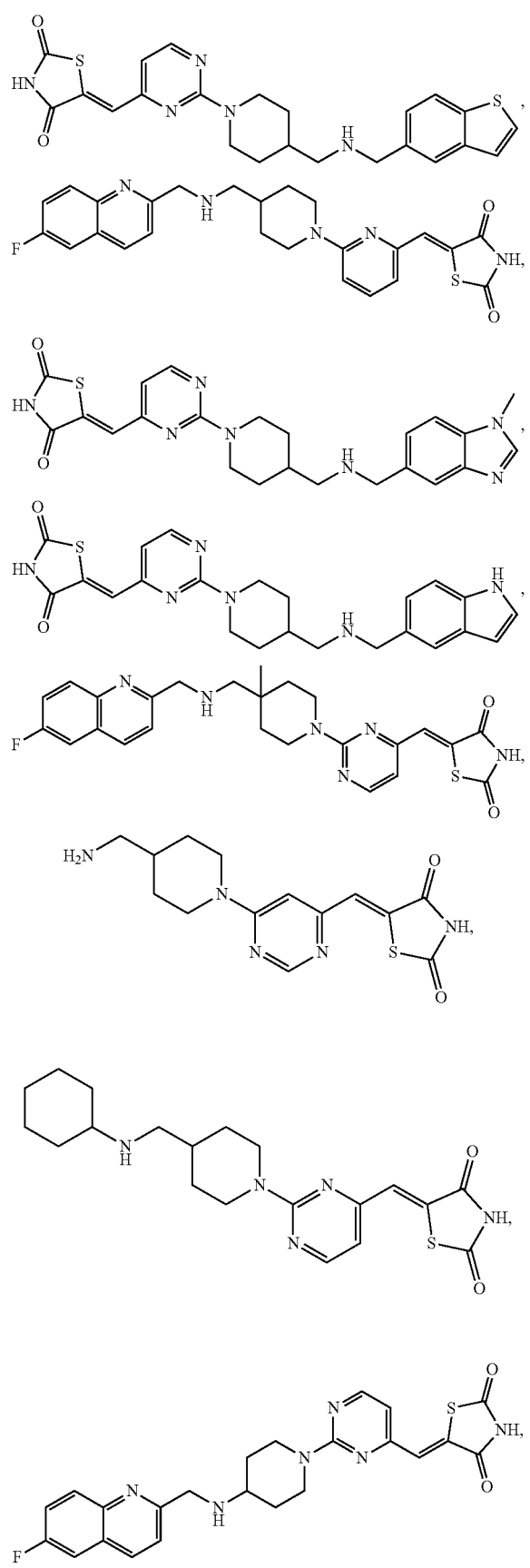
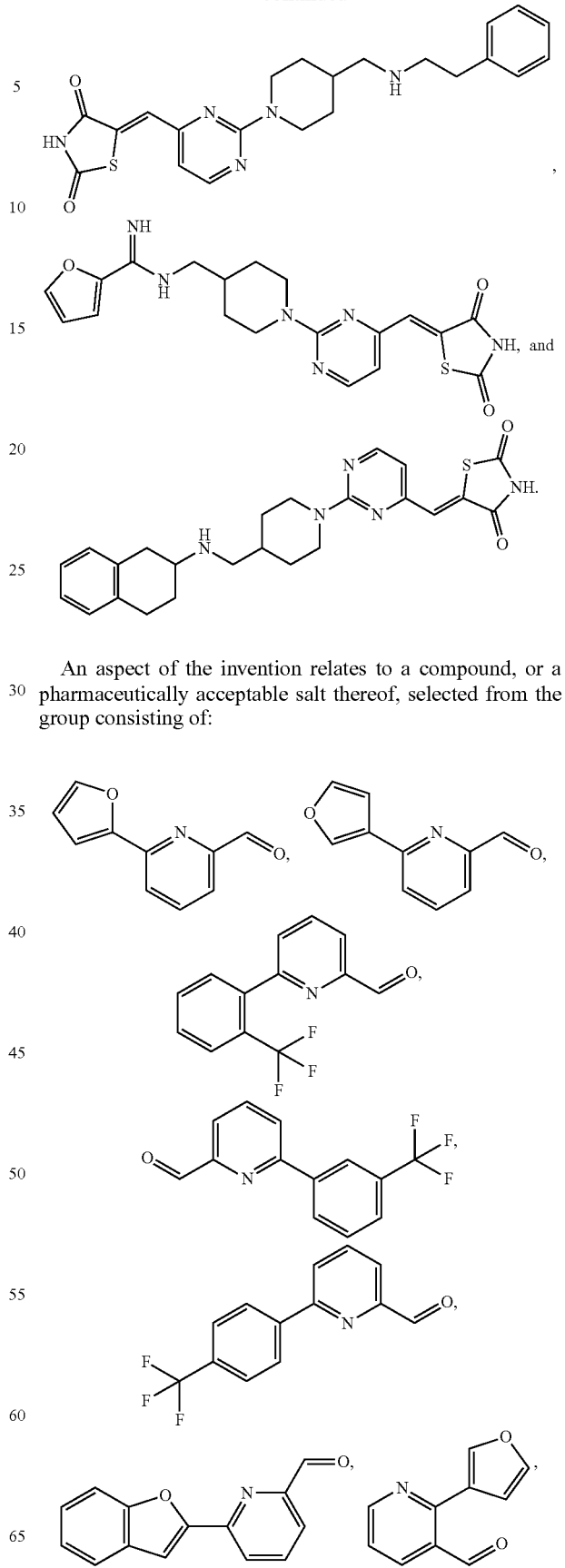
An aspect of the invention relates to a compound, or a pharmaceutically acceptable salt thereof, selected from the group consisting of:

An aspect of the invention relates to a compound, or a pharmaceutically acceptable salt thereof, selected from the group consisting of:

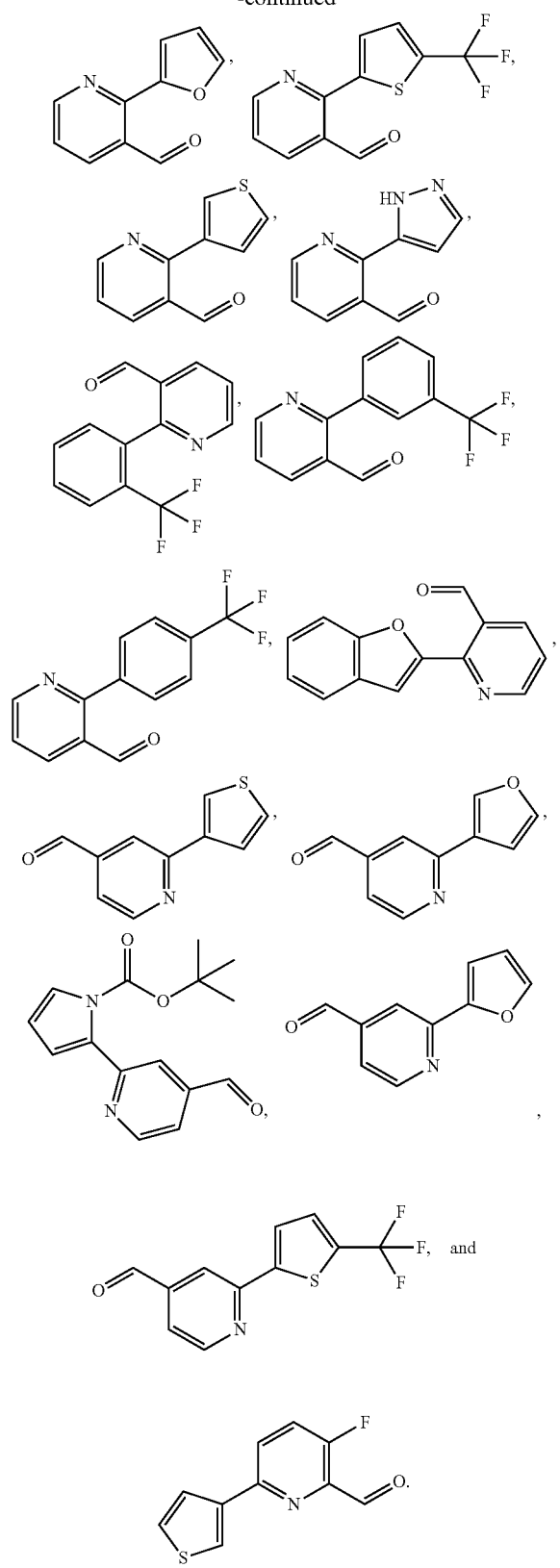

An embodiment relates to any one of the aforementioned compounds, wherein the compound is an inhibitor of CK1, CK1γ1, CK1γ2, or CK1γ3. In one embodiment the compound has an $IC_{50}$ of less than 5000 nM for CK1, CK1γ1, CK1γ2, or CK1γ3. In one embodiment the compound has an $IC_{50}$ of less than 1000 nM for CK1, CK1γ1, CK1γ2, or CK1γ3. In one embodiment the compound has an $IC_{50}$ of less than 500 nM for CK1, CK1γ1, CK1γ2, or CK1γ3.

An embodiment relates to any one of the aforementioned compounds, wherein the compound is an inhibitor of CK2. In one embodiment the compound has an $IC_{50}$ of less than 5000 nM for CK2. In one embodiment the compound has an $IC_{50}$ of less than 1000 nM for CK2. In one embodiment the compound has an $IC_{50}$ of less than 500 nM for CK2.

An embodiment relates to any one of the aforementioned compounds, wherein the compound is an inhibitor of Pim-1, Pim-2, or Pim-3. In one embodiment the compound has an $IC_{50}$ of less than 5000 nM for Pim-1, Pim-2, or Pim-3. In one embodiment the compound has an $IC_{50}$ of less than 1000 nM for Pim-1, Pim-2, or Pim-3. In one embodiment the compound has an $IC_{50}$ of less than 500 nM for Pim-1, Pim-2, or Pim-3.

An embodiment relates to any one of the aforementioned compounds, wherein the compound is an inhibitor of the Wnt pathway.

An embodiment relates to any one of the aforementioned compounds, wherein the compound is an inhibitor of the TGFβ pathway.

An embodiment relates to any one of the aforementioned compounds, wherein the compound is an inhibitor of the JAK/STAT pathway.

An embodiment relates to any one of the aforementioned compounds, wherein the compound is an inhibitor of the mTOR pathway.

An embodiment relates to any one of the aforementioned compounds, wherein the compound is a modulator of Pgp degradation, drug efflux, or drug resistance.

An embodiment relates to a pharmaceutical composition comprising any one or combination of the aforementioned compounds, and a pharmaceutically acceptable carrier.

Another embodiment relates to a method of inhibiting CK1 activity, comprising contacting CK1, CK1γ1, CK1γ2, or CK1γ3 with any one of the aforementioned compounds or pharmaceutical compositions.

Another embodiment relates to a method of inhibiting CK2 activity, comprising contacting CK2 with any one of the aforementioned compounds or pharmaceutical compositions.

Another embodiment relates to a method of treating or preventing a condition associated with aberrant CK1, CK1γ1, CK1γ2, or CK1γ3 activity, comprising administering to a mammal in need thereof a therapeutically effective amount of any one of the aforementioned compounds or pharmaceutical compositions.

Another embodiment relates to a method of treating or preventing a condition associated with aberrant CK2 activity, comprising administering to a mammal in need thereof a therapeutically effective amount of any one of the aforementioned compounds or pharmaceutical compositions.

Another embodiment relates to a method of treating cancer, comprising administering to a mammal in need thereof a therapeutically effective amount of any one of the aforementioned compounds or pharmaceutical compositions. In one embodiment the cancer is a cancer of a system selected from the group consisting of the hematopoietic system, immune system, endocrine system, pulmonary system, gastrointestinal system, musculoskeletal system, reproductive system, central nervous system, and urologic system. In one embodiment the cancer is located in the mammal's myeloid tissues, lymphoid tissues, pancreatic tissues, thyroid tissues, lung tissues, colon tissues, rectal tissues, anal tissues, liver tissues, skin, bone, ovarian tissues, uterine tissues, cervical tissues, breast, prostate, testicular tissues, brain, brainstem, meningeal tissues, kidney or bladder. In one embodiment the cancer is selected from the group consisting of breast cancer, colon cancer, multiple myeloma, prostate cancer, Hodgkin's lymphoma, non-Hodgkin's lymphoma, leukemia, hematologic malignancy, renal cell carcinoma, renal cancer, malignant melanoma, pancreatic cancer, lung cancer, colorectal carcinoma, brain cancer, head and neck cancer, bladder cancer, thyroid cancer, ovarian cancer, cervical cancer, and myelodysplastic syndrome.

Another embodiment relates to a method of treating leukemia, multiple myeloma, or other hematologic malignancies, comprising administering to a mammal in need thereof a therapeutically effective amount of any one of the aforementioned compounds or pharmaceutical compositions.

Another embodiment relates to a method of treating Alzheimer's disease, comprising administering to a mammal in need thereof a therapeutically effective amount of any one of the aforementioned compounds or pharmaceutical compositions.

Another embodiment relates to a method of treating a Wnt-dependent disease, comprising administering to a mammal in need thereof a therapeutically effective amount of any one of the aforementioned compounds or pharmaceutical compositions.

Another embodiment relates to a method of treating a TGFβ-dependent disease, comprising administering to a mammal in need thereof a therapeutically effective amount of any one of the aforementioned compounds or pharmaceutical compositions.

Another embodiment relates to a method of treating a JAK/STAT-dependent disease, comprising administering to a mammal in need thereof a therapeutically effective amount of any one of the aforementioned compounds or pharmaceutical compositions.

Another embodiment relates to a method of treating an mTOR-dependent disease, comprising administering to a mammal in need thereof a therapeutically effective amount of any one of the aforementioned compounds or pharmaceutical compositions.

Another embodiment relates to a method of treating or preventing inflammation, inflammatory diseases (e.g., osteoarthritis and rheumatoid arthritis), neurological conditions (e.g., Alzheimer's disease) and neurodegeneration, comprising administering to a mammal in need thereof a therapeutically effective amount of any one of the aforementioned compounds or pharmaceutical compositions.

Another embodiment relates to a method of treating or preventing bone-related diseases and conditions, including osteoporosis and bone formation, or facilitating bone restoration, comprising administering to a mammal in need thereof a therapeutically effective amount of any one of the aforementioned compounds or pharmaceutical compositions.

Another embodiment relates to a method of treating or preventing hypoglycemia, metabolic syndrome and diabetes, comprising administering to a mammal in need thereof a therapeutically effective amount of any one of the aforementioned compounds or pharmaceutical compositions.

Another embodiment relates to a method of influencing apoptosis (e.g., increasing the rate of apoptosis in cancerous cells), comprising administering to a mammal in need thereof a therapeutically effective amount of any one of the aforementioned compounds or pharmaceutical compositions.

Another embodiment relates to a method of treating or preventing aberrant embryonic development, comprising administering to a mammal in need thereof a therapeutically effective amount of any one of the aforementioned compounds or pharmaceutical compositions.

Another embodiment relates to a method of inhibiting PIM activity, comprising contacting Pim-1, Pim-2 or Pim-3 with any one of the aforementioned compounds or pharmaceutical compositions.

Another embodiment relates to a method for treating or preventing a condition associated with aberrant PIM activity, comprising administering to a mammal in need thereof a therapeutically effective amount of any one of the aforementioned compounds or pharmaceutical compositions.

Another embodiment relates to a method of modulating Pgp degradation and/or drug efflux activity, comprising contacting a cell with any one of the aforementioned compounds or pharmaceutical compositions.

Another embodiment relates to a method for treating a malignancy based upon modulation of Pgp, comprising administering to a mammal in need thereof a therapeutically effective amount of any one of the aforementioned compounds or pharmaceutical compositions.

Another embodiment relates to a method for treating a malignancy based upon modulation of Pgp, comprising administering to a mammal in need thereof a therapeutically effective amount of any one of the aforementioned compounds or pharmaceutical compositions, in conjunction with another drug, compound, or material, to abrogate resistance to the drug, compound, or material.

DETAILED DESCRIPTION OF THE INVENTION

Definitions

The definitions of terms used herein are meant to incorporate the present state-of-the-art definitions recognized for each term in the chemical and pharmaceutical fields. Where appropriate, illustration is provided. The definitions apply to the terms as they are used throughout this specification, unless otherwise limited in specific instances, either individually or as part of a larger group.

Where stereochemistry is not specifically indicated, all stereoisomers of the inventive compounds are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

As used herein, the term "isolated" in connection with a compound of the present invention means the compound is not in a cell or organism and the compound is separated from some or all of the components that typically accompany it in nature.

As used herein, the term "pure" in connection with an isolated sample of a compound of the present invention means the isolated sample contains at least 60% by weight of the compound. In certain embodiments, the isolated sample contains at least 70% by weight of the compound. In certain embodiments, the isolated sample contains at least 80% by weight of the compound. In certain embodiments, the isolated sample contains at least 90% by weight of the compound. In certain embodiments, the isolated sample contains at least 95% by weight of the compound. The purity of an isolated sample of a compound of the present invention may be assessed by a number of methods or a combination of them; e.g., thin-layer, preparative or flash chromatography, mass spectrometry, HPLC, NMR analysis, and the like.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, piperonyl, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a substituent as described herein, including but not limited to halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of *Advanced Inorganic Chemistry* by Cotton and Wilkinson.

The terms "amine" and "amino" are art-recognized and refer to both unsubstituted and substituted amines, e.g., a moiety that may be represented by the general formulas:

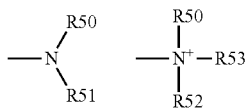

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

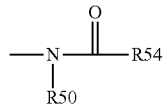

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

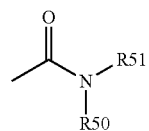

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

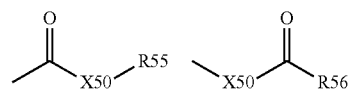

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

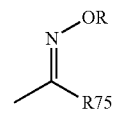

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

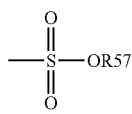

in which R57 is an electron pair, hydrogen, alkyl, cycloalkyl, or aryl.

The term "sulfate" is art recognized and includes a moiety that may be represented by the general formula:

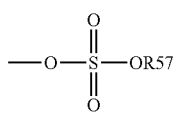

in which R57 is as defined above.

The term "sulfonamido" is art recognized and includes a moiety that may be represented by the general formula:

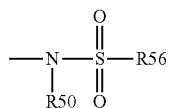

in which R50 and R56 are as defined above.

The term "sulfamoyl" is art-recognized and refers to a moiety that may be represented by the general formula:

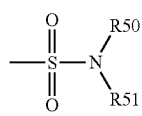

in which R50 and R51 are as defined above.

The term "sulfonyl" is art-recognized and refers to a moiety that may be represented by the general formula:

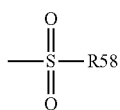

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

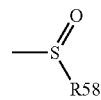

in which R58 is defined above.

The term "phosphoryl" is art-recognized and may in general be represented by the formula:

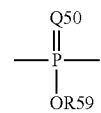

wherein Q50 represents S or O, and R59 represents hydrogen, a lower alkyl or an aryl. When used to substitute, e.g., an alkyl, the phosphoryl group of the phosphorylalkyl may be represented by the general formulas:

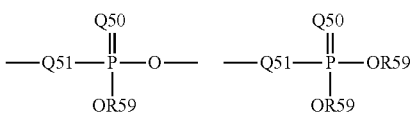

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

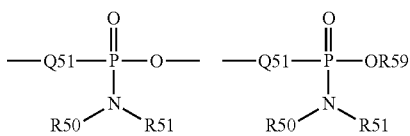

wherein Q51, R50, R51 and R59 are as defined above.

The term "phosphonamidite" is art-recognized and may be represented in the general formulas:

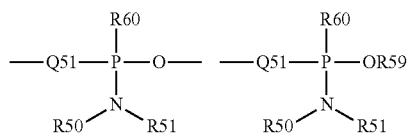

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled "Standard List of Abbreviations."

Certain compounds contained in compositions of the present invention may exist in particular geometric or stereoisomeric forms. In addition, polymers of the present invention may also be optically active. The present invention contemplates all such compounds, including cis- and trans-isomers, E- and Z-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Additionally, the enantiomers may be separated using a chiral chromatographic method including HPLC or SFC approaches.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. Examples of nitrogen protecting groups include an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

The term "pharmaceutically acceptable salt" or "salt" refers to a salt of one or more compounds. Suitable pharmaceutically acceptable salts of compounds include acid addition salts, such as those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Where the compounds carry one or more acidic moieties, pharmaceutically acceptable salts may be formed by treatment of a solution of the compound with a solution of a pharmaceutically acceptable base. Suitable bases for forming pharmaceutically acceptable salts with acidic functional groups include, but are not limited to, hydroxides and carbonates of alkali metals such as sodium, potassium, and lithium; alkaline earth metal such as calcium and magnesium; and other metals, such as aluminum and zinc. Suitable bases also include ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl) amine, or tri-(2-hydroxyethyl)amine; N-methyl-D-glucamine; and amino acids such as arginine, lysine, and the like.

Certain compounds of the invention and their salts may exist in more than one crystalline form (i.e., polymorph); the present invention includes each of the crystal forms and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support; suitable include chiral supports (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the various diastereoisomers of compounds of the invention, and mixtures thereof. Compounds of the invention may exist in different tautomeric forms or as different geometric isomers, and the present invention includes each tautomer and/or geometric isomer of compounds of the invention, and mixtures thereof. For example, any olefins present in the compounds may exist as either the E- or Z-geometric isomers or a mixture thereof unless stated otherwise. Compounds of the invention may exist in zwitterionic form. The present invention includes each zwitterionic form of compounds of the invention, and mixtures thereof.

As used herein the term "pro-drug" refers to an agent, which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs release an amine of a compound of the invention wherein the free hydrogen of an amine or alcohol is replaced by $(C_1\text{-}C_6)$alkanoyloxymethyl, 1-(($(C_1\text{-}C_6)$alkanoyloxy)ethyl, 1-methyl-1-(($(C_1\text{-}C_6)$alkanoyloxy)ethyl, $(C_1\text{-}C_6)$alkoxycarbonyloxymethyl, N—$(C_1\text{-}C_6)$alkoxycarbonylamino-methyl, succinoyl, $(C_1\text{-}C_6)$alkanoyl, α-amino $(C_1\text{-}C_4)$alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O$(C_1\text{-}C_6)$alkyl)$_2$ or glycosyl (the radical resulting from detachment of the hydroxyl of the hemiacetal of a carbohydrate).

Other exemplary pro-drugs upon cleavage release a corresponding free acid, and such hydrolyzable ester-forming residues of the compounds of this invention include but are not limited to carboxylic acid substituents (e.g., —(CH$_2$)C(O) OH or a moiety that contains a carboxylic acid) wherein the free hydrogen is replaced by $(C_1\text{-}C_4)$alkyl, $(C_2\text{-}C_{12})$alkanoyloxymethyl, $(C_4\text{-}C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1\text{-}C_2)$alkylamino$(C_2\text{-}C_3)$alkyl (such as β-dimethylaminoethyl), carbamoyl-$(C_1\text{-}C_2)$alkyl, N,N-di$(C_1\text{-}C_2)$-alkylcarbamoyl-$(C_1\text{-}C_2)$alkyl and piperidino-, pyrrolidino- or morpholino$(C_2\text{-}C_3)$alkyl.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

Compounds

An aspect of the present invention relates to compounds that inhibit casein kinase 1 and/or casein kinase 2 and/or a PIM kinase. For example, an embodiment relates to a compound of formula 1 or a pharmaceutically acceptable salt thereof,

1 wherein independently for each occurrence:

W is $C(R^1)_2$, $C(R^1)_2C(R^1)_2$, $C(R^1)_2C(R^1)_2C(R^1)_2$, or $S(O)_2$;

X is nitrogen or $CR^2$;

Y is nitrogen or $CR^3$;

Z is nitrogen or $CR^4$;

$R^1$ is hydrogen or alkyl;

$R^2$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^3$ and $R^4$ are each independently selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl; or $R^3$ and $R^4$ are joined together to form an optionally substituted heterocyclic ring;

$R^5$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^6$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

wherein any one of the aforementioned alkyl, alkenyl, alkynyl, aryl, heteroaryl, heterocyclyl, aralkyl, heteroaralkyl, and heterocyclylalkyl may be optionally substituted;

wherein the compound is not

In one embodiment, $R^1$ is hydrogen.
In one embodiment, $R^1$ is methyl.
In one embodiment, W is $S(O)_2$.
In one embodiment, W is $CH_2$.
In one embodiment, $R^2$ is selected from the group consisting of hydrogen, alkyl, aryl, heterocyclylalkyl, aralkyl, heteroaryl, heteroaralkyl, and halo.
In one embodiment, $R^2$ is hydrogen.
In one embodiment, $R^2$ is methyl.
In one embodiment, $R^2$ is fluorine.
In one embodiment, $R^2$ is an optionally substituted heteroaryl.
In one embodiment, $R^2$ is an optionally substituted aryl.
In one embodiment, $R^3$ is selected from the group consisting of hydrogen, alkyl, aryl, heterocyclylalkyl, aralkyl, heteroaryl, heteroaralkyl, and halo.
In one embodiment, $R^3$ is hydrogen.
In one embodiment, $R^3$ is methyl.
In one embodiment, $R^3$ is fluorine.
In one embodiment, $R^3$ is an optionally substituted heteroaryl.
In one embodiment, $R^3$ is an optionally substituted aryl.
In one embodiment, $R^3$ is an optionally substituted heterocyclylalkyl.
In one embodiment, $R^3$ and $R^4$ are joined together to form an optionally substituted aryl.
In one embodiment, $R^3$ and $R^4$ are joined together to form an optionally substituted heterocyclyl.
In one embodiment, $R^3$ and $R^4$ are joined together to form an optionally substituted heteroaryl.
In one embodiment, $R^4$ is selected from the group consisting of hydrogen, alkyl, aryl, heterocyclylalkyl, aralkyl, heteroaryl, heteroaralkyl, and halo.
In one embodiment, $R^4$ is hydrogen.
In one embodiment, $R^4$ is methyl.
In one embodiment, $R^4$ is fluorine.
In one embodiment, $R^4$ is an optionally substituted heteroaryl.
In one embodiment, $R^4$ is an optionally substituted aryl.
In one embodiment, $R^4$ is an optionally substituted heterocyclylalkyl.

In one embodiment, $R^5$ is selected from the group consisting of hydrogen, alkyl, aryl, heterocyclylalkyl, aralkyl, heteroaryl, heteroaralkyl, and halo.

In one embodiment, $R^5$ is hydrogen.

In one embodiment, $R^5$ is methyl.

In one embodiment, $R^5$ is fluorine.

In one embodiment, $R^5$ is an optionally substituted heteroaryl.

In one embodiment, $R^5$ is an optionally substituted aryl.

In one embodiment, $R^5$ is an optionally substituted heterocyclylalkyl.

In one embodiment, $R^6$ is selected from the group consisting of hydrogen, alkyl, aryl, heterocyclylalkyl, aralkyl, heteroaryl, heteroaralkyl, and halo.

In one embodiment, $R^6$ is hydrogen.

In one embodiment, $R^6$ is methyl.

In one embodiment, $R^6$ is fluorine.

In one embodiment, $R^6$ is an optionally substituted heteroaryl.

In one embodiment, $R^6$ is an optionally substituted aryl.

In one embodiment, $R^6$ is an optionally substituted heterocyclylalkyl.

An aspect of the present invention relates to compounds that inhibit casein kinase 1 and/or casein kinase 2 and/or a PIM kinase. For example, an embodiment relates to a compound of formula 2 or a pharmaceutically acceptable salt thereof,

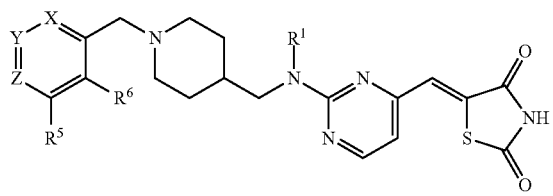

2 wherein independently for each occurrence:

X is nitrogen or $CR^2$;

Y is nitrogen or $CR^3$;

Z is nitrogen or $CR^4$;

$R^1$ is hydrogen or alkyl;

$R^2$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^3$ and $R^4$ are each independently selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl; or $R^3$ and $R^4$ are joined together to form an optionally substituted heterocyclic ring;

$R^5$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

$R^6$ is selected from the group consisting of hydrogen, alkyl, alkenyl, alkynyl, aryl, trifluoromethyl, perfluoroalkyl, heterocyclylalkyl, aralkyl, heteroaryl, heteroaralkyl, halo, hydroxy, alkoxy, trifluoromethoxy, hydroxyalkyl, and alkoxyalkyl;

wherein any one of the aforementioned alkyl, alkenyl, alkynyl, aryl, heteroaryl, heterocyclyl, aralkyl, heteroaralkyl, and heterocyclylalkyl may be optionally substituted.

In one embodiment, $R^1$ is hydrogen.

In one embodiment, $R^1$ is methyl.

In one embodiment, $R^2$ is selected from the group consisting of hydrogen, alkyl, aryl, heterocyclylalkyl, aralkyl, heteroaryl, heteroaralkyl, and halo.

In one embodiment, $R^2$ is hydrogen.

In one embodiment, $R^2$ is methyl.

In one embodiment, $R^2$ is fluorine.

In one embodiment, $R^2$ is an optionally substituted heteroaryl.

In one embodiment, $R^2$ is an optionally substituted aryl.

In one embodiment, $R^3$ is selected from the group consisting of hydrogen, alkyl, aryl, heterocyclylalkyl, aralkyl, heteroaryl, heteroaralkyl, and halo.

In one embodiment, $R^3$ is hydrogen.

In one embodiment, $R^3$ is methyl.

In one embodiment, $R^3$ is fluorine.

In one embodiment, $R^3$ is an optionally substituted heteroaryl.

In one embodiment, $R^3$ is an optionally substituted aryl.

In one embodiment, $R^3$ is an optionally substituted heterocyclylalkyl.

In one embodiment, $R^3$ and $R^4$ are joined together to form an optionally substituted aryl.

In one embodiment, $R^3$ and $R^4$ are joined together to form an optionally substituted heterocyclyl.

In one embodiment, $R^3$ and $R^4$ are joined together to form an optionally substituted heteroaryl.

In one embodiment, $R^4$ is selected from the group consisting of hydrogen, alkyl, aryl, heterocyclylalkyl, aralkyl, heteroaryl, heteroaralkyl, and halo.

In one embodiment, $R^4$ is hydrogen.

In one embodiment, $R^4$ is methyl.

In one embodiment, $R^4$ is fluorine.

In one embodiment, $R^4$ is an optionally substituted heteroaryl.

In one embodiment, $R^4$ is an optionally substituted aryl.

In one embodiment, $R^4$ is an optionally substituted heterocyclylalkyl.

In one embodiment, $R^5$ is selected from the group consisting of hydrogen, alkyl, aryl, heterocyclylalkyl, aralkyl, heteroaryl, heteroaralkyl, and halo.

In one embodiment, $R^5$ is hydrogen.

In one embodiment, $R^5$ is methyl.

In one embodiment, $R^5$ is fluorine.

In one embodiment, $R^5$ is an optionally substituted heteroaryl.

In one embodiment, $R^5$ is an optionally substituted aryl.

In one embodiment, $R^5$ is an optionally substituted heterocyclylalkyl.

In one embodiment, $R^6$ is selected from the group consisting of hydrogen, alkyl, aryl, heterocyclylalkyl, aralkyl, heteroaryl, heteroaralkyl, and halo.

In one embodiment, $R^6$ is hydrogen.

In one embodiment, $R^6$ is methyl.

In one embodiment, $R^6$ is fluorine.

In one embodiment, $R^6$ is an optionally substituted heteroaryl.

In one embodiment, $R^6$ is an optionally substituted aryl.

In one embodiment, $R^6$ is an optionally substituted heterocyclylalkyl.

In one embodiment, a compound, or a pharmaceutically acceptable salt thereof, is selected from the group consisting of:

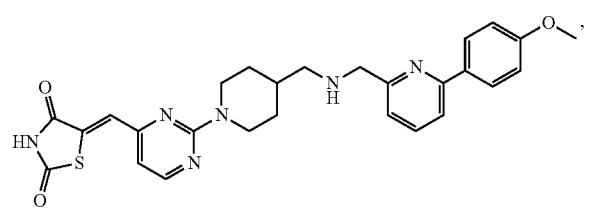
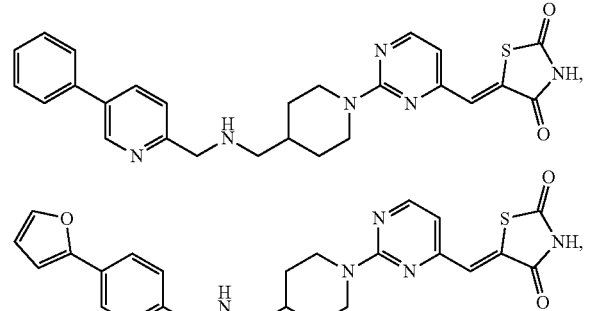
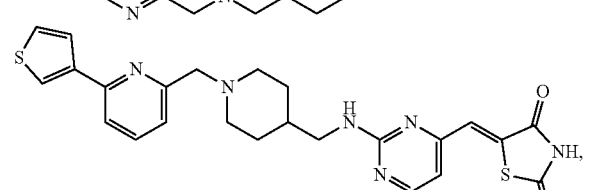
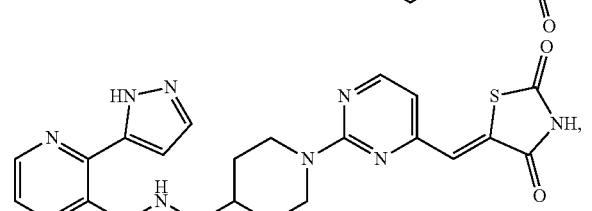
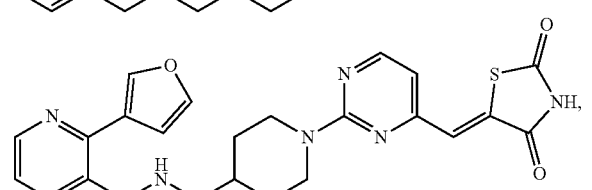
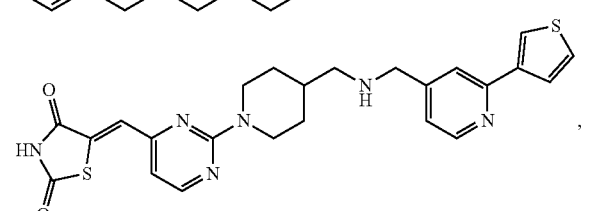
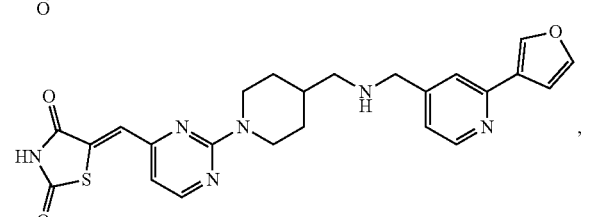
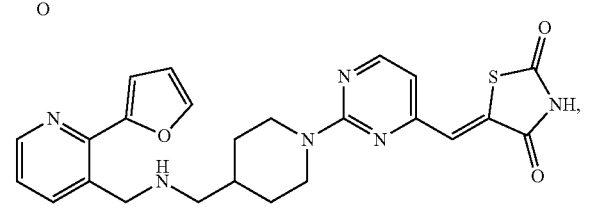
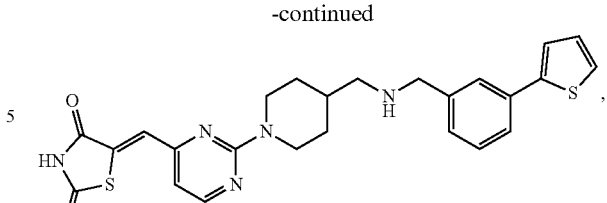
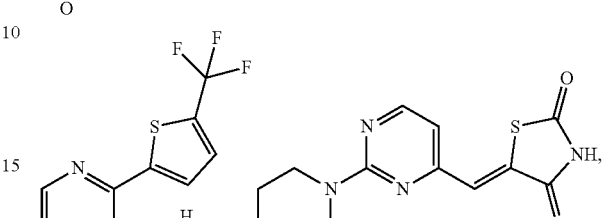
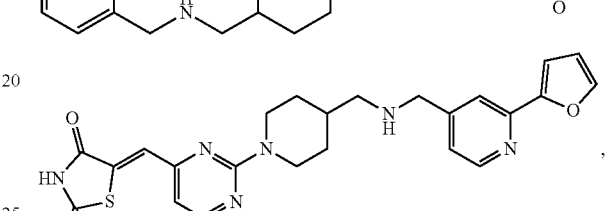
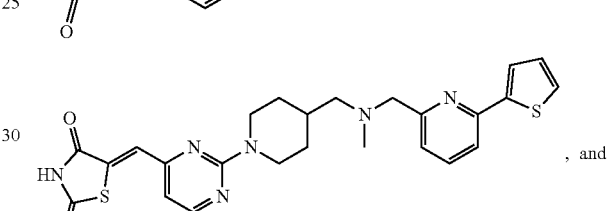
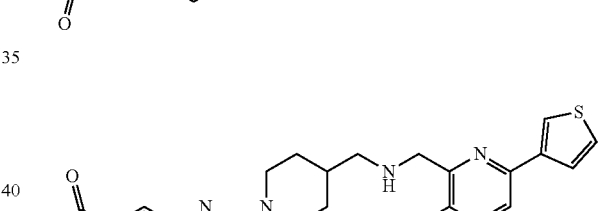
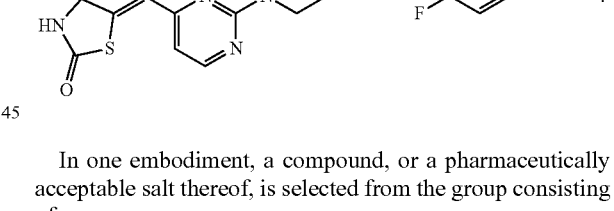
, and
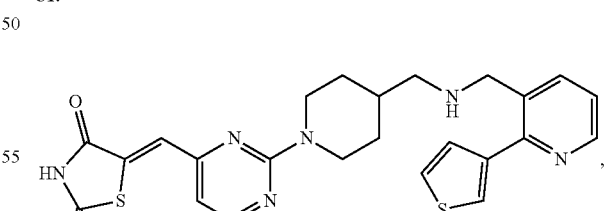
.
In one embodiment, a compound, or a pharmaceutically acceptable salt thereof, is selected from the group consisting of:
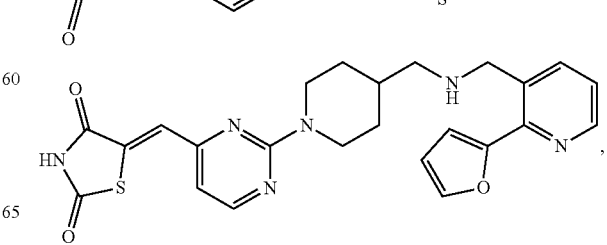

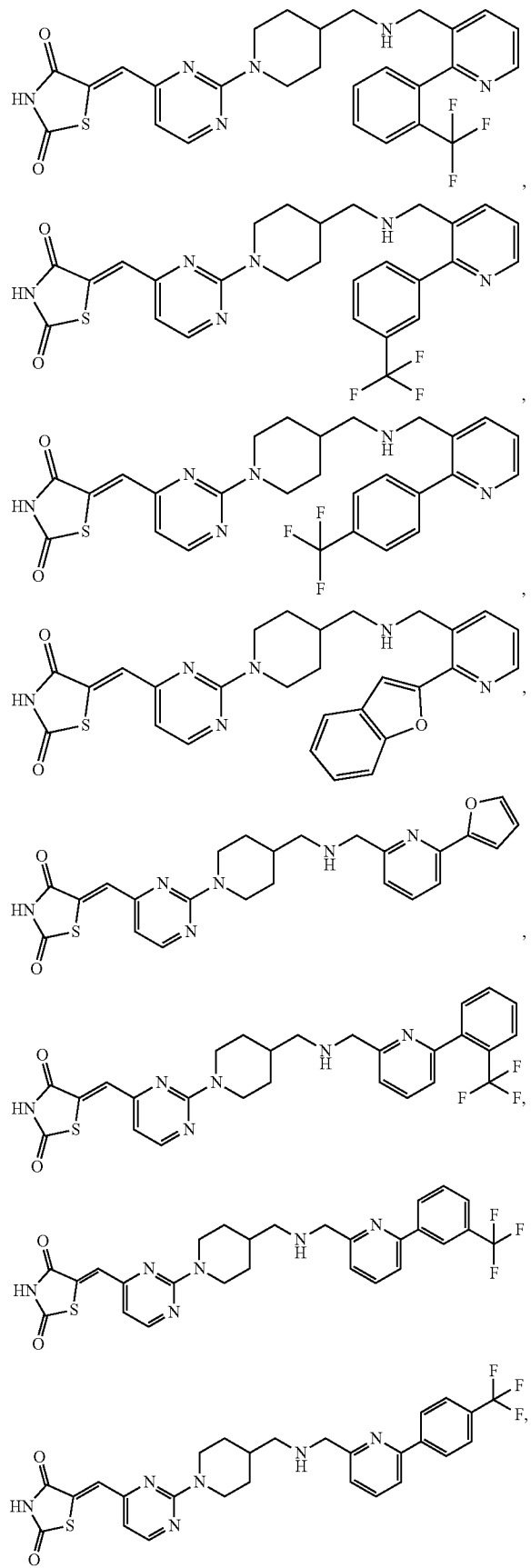
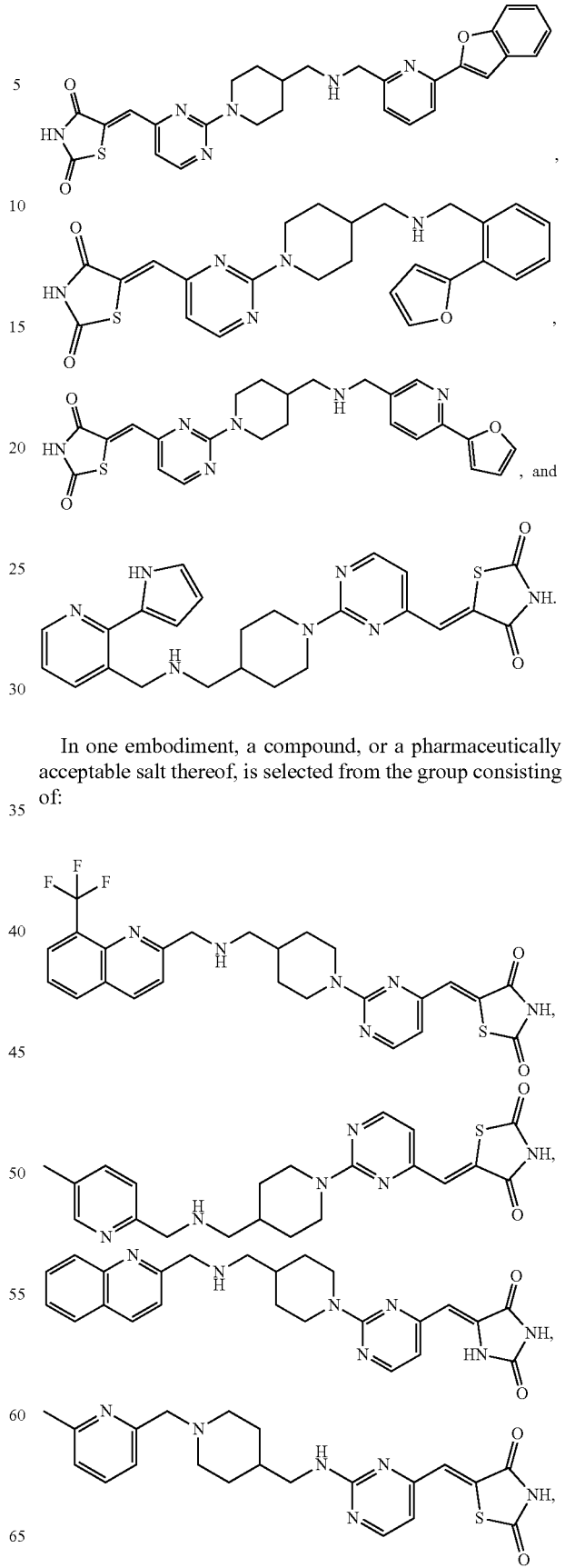
In one embodiment, a compound, or a pharmaceutically acceptable salt thereof, is selected from the group consisting of:

-continued

In one embodiment, a compound, or a pharmaceutically acceptable salt thereof, is selected from the group consisting of:

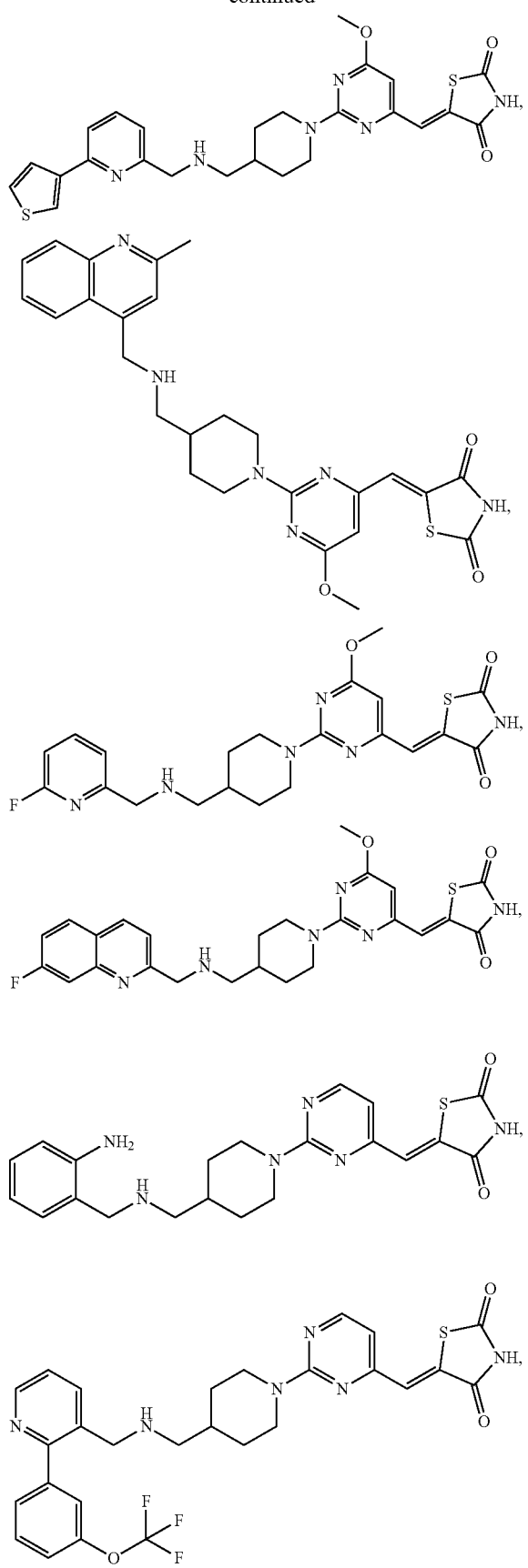
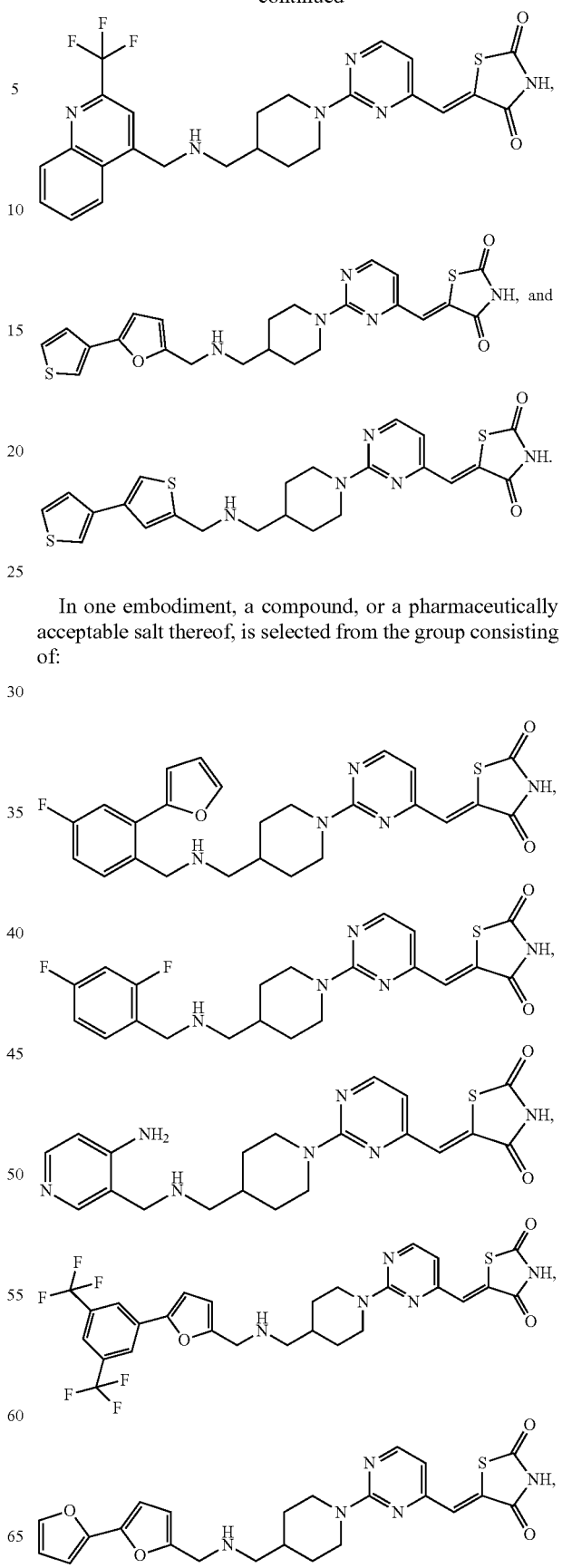
In one embodiment, a compound, or a pharmaceutically acceptable salt thereof, is selected from the group consisting of:

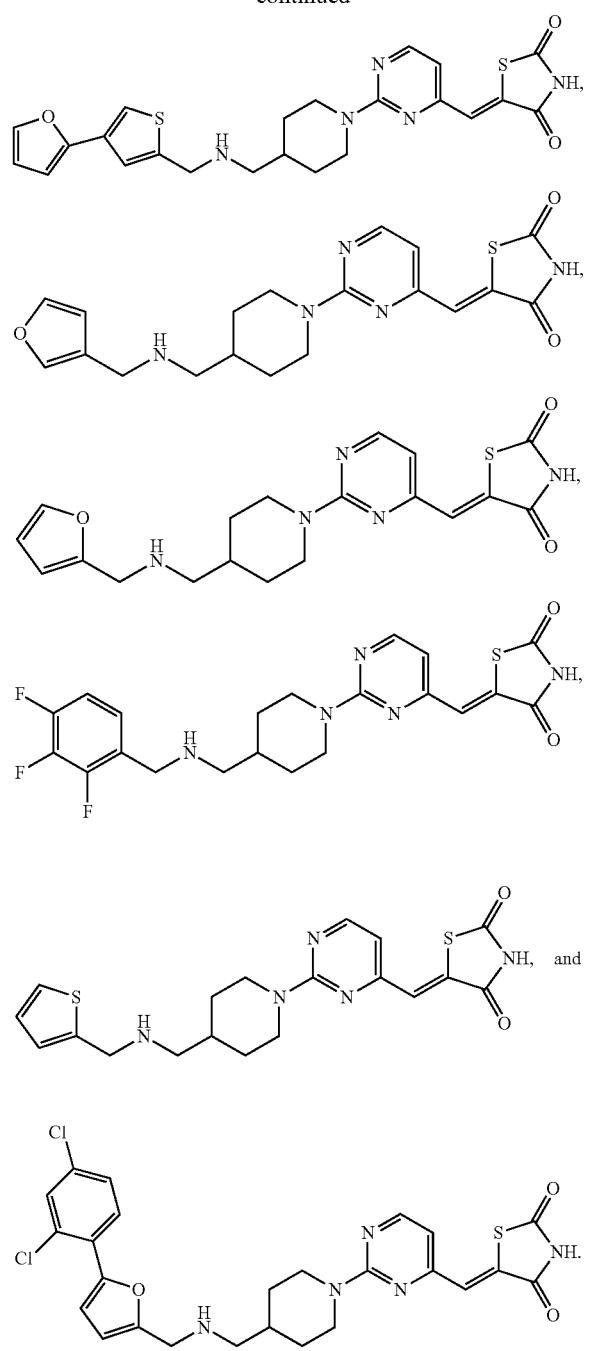
In one embodiment, a compound, or a pharmaceutically acceptable salt thereof, is selected from the group consisting of:
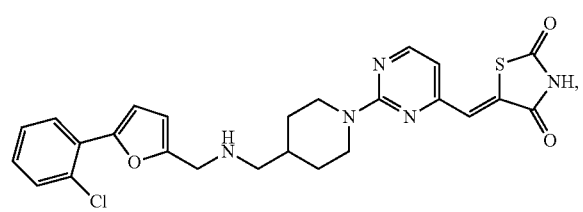
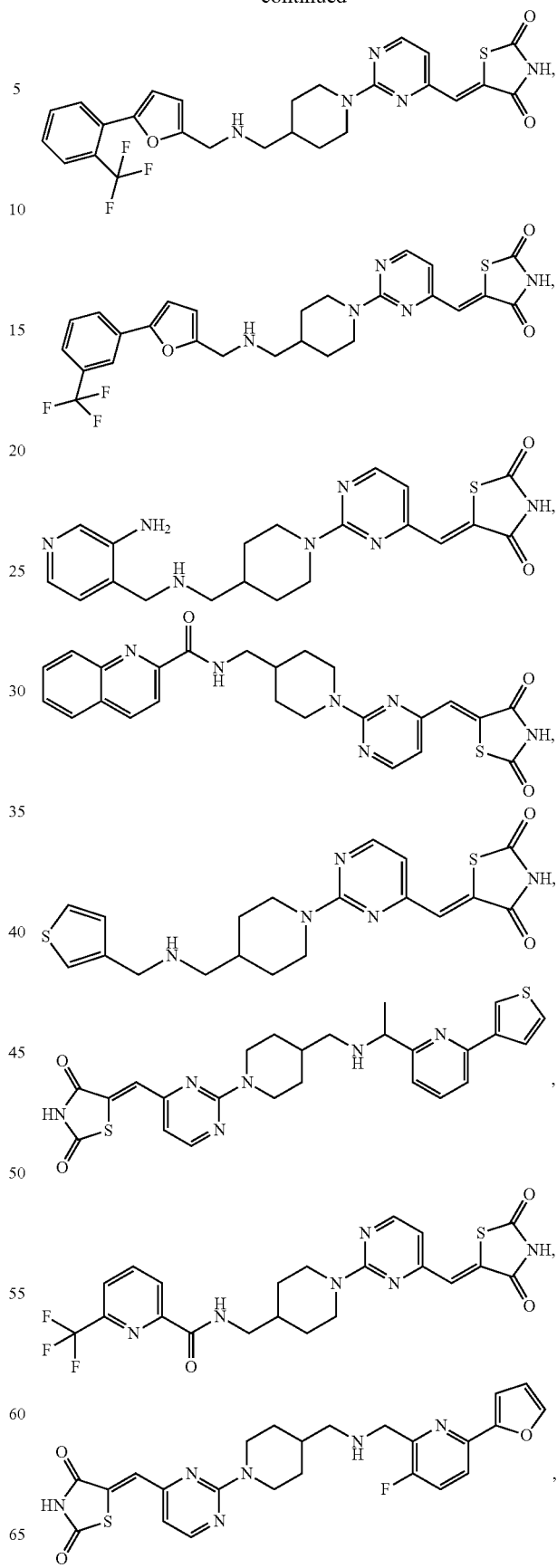

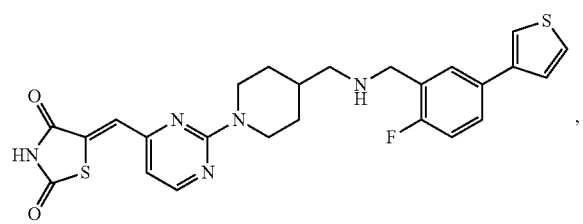
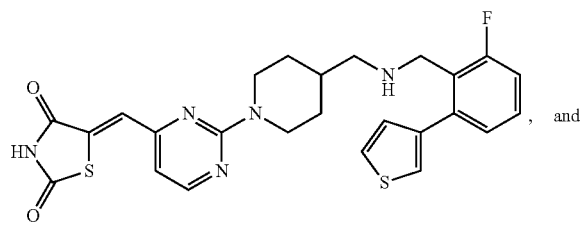
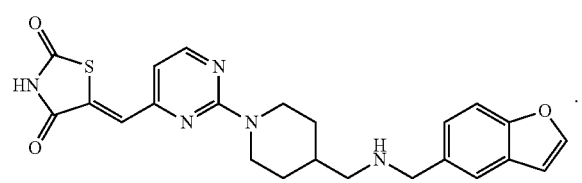
In one embodiment, a compound, or a pharmaceutically acceptable salt thereof, is selected from the group consisting of:
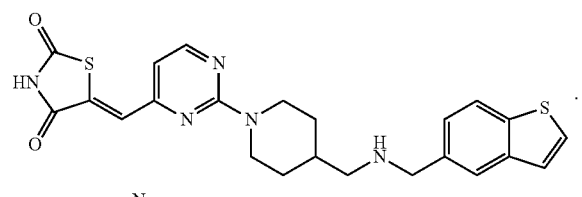
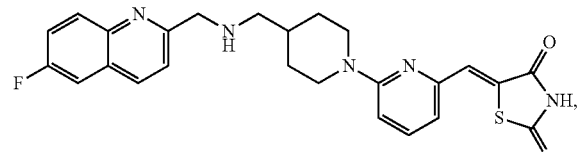
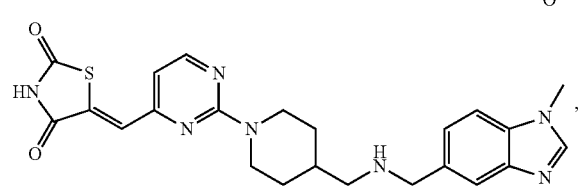
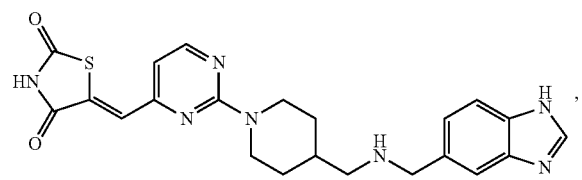
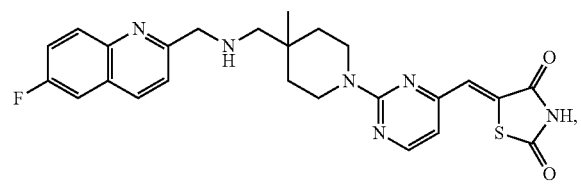
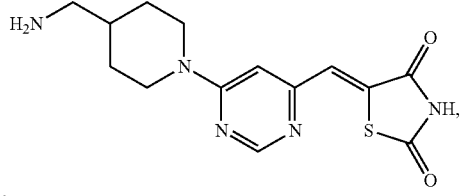
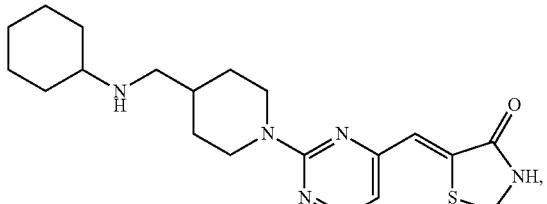
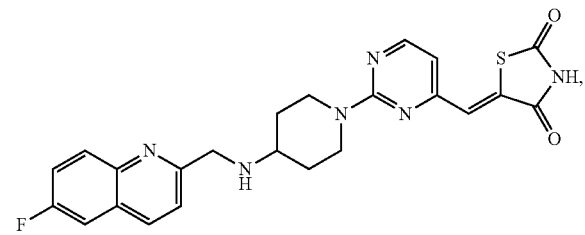
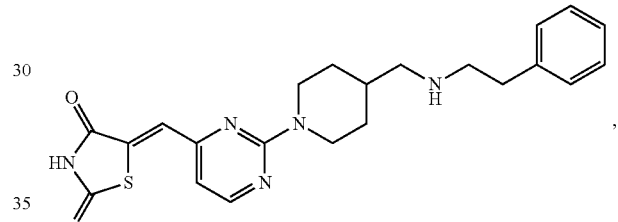
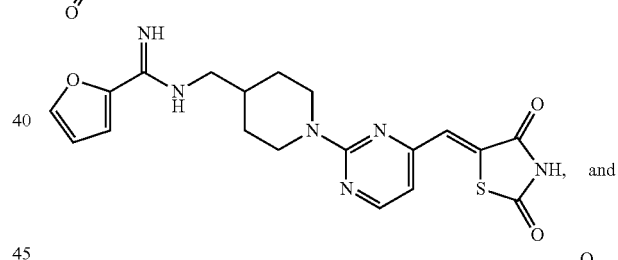
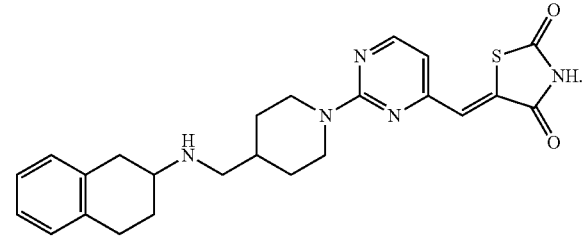
In one embodiment, a compound, or a pharmaceutically acceptable salt thereof, is selected from the group consisting of:
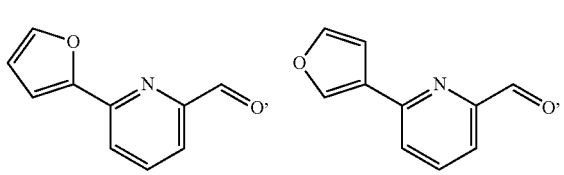

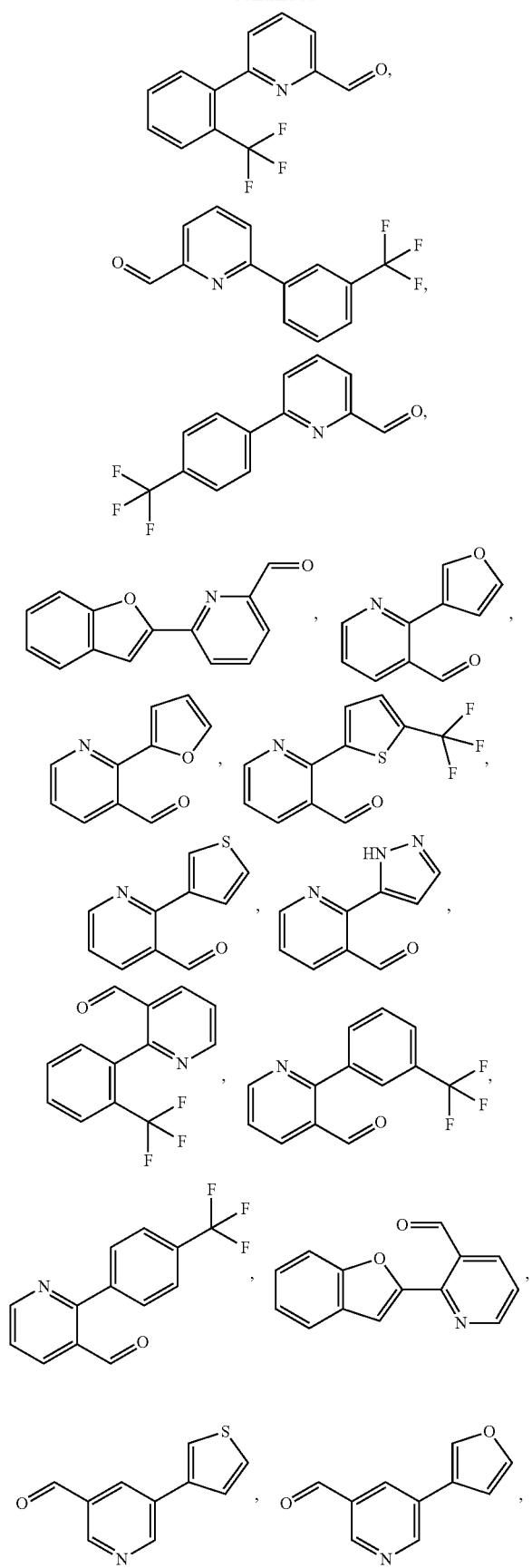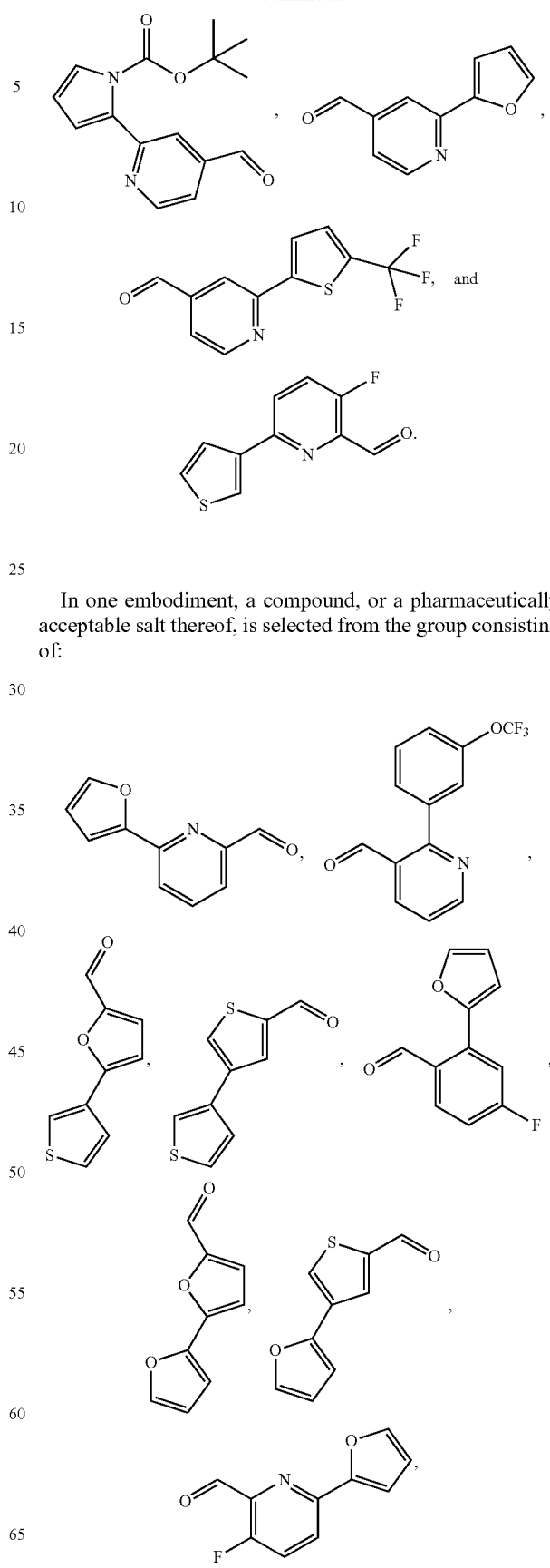
In one embodiment, a compound, or a pharmaceutically acceptable salt thereof, is selected from the group consisting of:

-continued

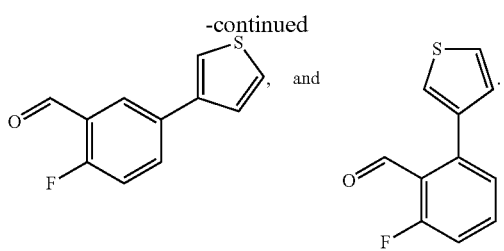
and

Any one of the aforementioned compounds may exist as the E-geometric isomer, the Z-geometric isomer, or mixtures thereof. For example, in one embodiment,

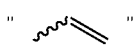

in the aforementioned structures represents the E-isomer of the particular compound. In another embodiment,

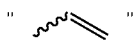

represents the Z-isomer of the particular compound. In yet another embodiment,

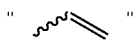

represents a mixture of E and Z isomers of the particular compound.

In one embodiment, any one of the aforementioned compounds is an inhibitor of CK1γ1, CK1γ2, or CK1γ3.

In one embodiment, any one of the aforementioned compounds is an inhibitor of CK2.

In one embodiment, any one of the aforementioned compounds is an inhibitor of the Wnt pathway.

In one embodiment, any one of the aforementioned compounds is an inhibitor of the JAK/STAT pathway.

In one embodiment, any one of the aforementioned compounds is an inhibitor of the mTOR pathway.

In one embodiment, any one of the aforementioned compounds is a mediator of Pgp degradation and/or drug efflux.

In one embodiment, any one of the aforementioned compounds is an inhibitor of the TGFβ pathway.

In some embodiments, the compound has an $IC_{50}$ of less than 5000 nM for CK1γ1, CK1γ2, or CK1γ3.

In some embodiments, the compound has an $IC_{50}$ of less than 1000 nM for CK1γ1, CK1γ2, or CK1γ3.

In some embodiments, the compound has an $IC_{50}$ of less than 500 nM for CK1γ1, CK1γ2, or CK1γ3.

In one embodiment, any one of the aforementioned compounds is an inhibitor of CK2.

In one embodiment, the compound has an $IC_{50}$ of less than 5000 nM for CK2.

In one embodiment, the compound has an $IC_{50}$ of less than 1000 nM for CK2.

In one embodiment, the compound has an $IC_{50}$ of less than 500 nM for CK2.

In one embodiment, any on of the aforementioned compounds is an inhibitor of Pim-1, Pim-2, or Pim-3.

In one embodiment, the compound has an $IC_{50}$ of less than 5000 nM for Pim-1, Pim-2 or Pim-3.

In one embodiment, the compound has an $IC_{50}$ of less than 1000 nM for Pim-1, Pim-2 or Pim-3.

In one embodiment, the compound has an $IC_{50}$ of less than 500 nM for Pim-1, Pim-2 or Pim-3.

Prophetic Embodiments

Certain compounds of the invention could be made in accordance with the above schemes by reacting an amine (Reactant A) with the hydantoin core (Reactant B). Non-limiting prophetic examples of Reactant A and Reactant B are shown in Table 1 and Table 2, respectively.

TABLE 1

Reactant A Prophetic Examples.

| Structure | ID | MW | Name |
| --- | --- | --- | --- |
| ![A1] $C_6H_3BrFNO$ | A1 | 203.997 | 6-bromo-4-fluoropicolinaldehyde |
| ![A2] $C_6H_4BrNO$ | A2 | 186.006 | 6-bromopicolinaldehyde |
| ![A3] $C_7H_6BrNO$ | A3 | 200.033 | 6-bromo-4-methylpicolinaldehyde |
| ![A4] $C_7H_6BrNO_2$ | A4 | 216.032 | 6-bromo-3-methoxypicolinaldehyde |
| ![A5] $C_7H_3BrF_3NO$ | A5 | 254.004 | 6-bromo-4-(trifluoromethyl)picolinaldehyde |
| ![A6] $C_{10}H_6BrNO$ | A6 | 236.065 | 3-bromoisoquinoline-1-carbaldehyde |
| ![A7] $C_6H_4BrNO$ | A7 | 186.006 | 2-bromonicotinaldehyde |

TABLE 1-continued

Reactant A Prophetic Examples.

| Structure | ID | MW | Name |
|---|---|---|---|
| 2-bromoquinoline-3-carbaldehyde structure; $C_{10}H_6BrNO$ | A8 | 236.065 | 2-bromoquinoline-3-carbaldehyde |
| 6-bromonicotinaldehyde structure; $C_6H_4BrNO$ | A9 | 186.006 | 6-bromonicotinaldehyde |
| 2-bromo-5-formylnicotinonitrile structure; $C_7H_3BrN_2O$ | A10 | 211.016 | 2-bromo-5-formylnicotinonitrile |
| ethyl 2-bromo-5-formylnicotinate structure; $C_9H_8BrNO_3$ | A11 | 258.069 | ethyl 2-bromo-5-formylnicotinate |
| 2-bromoisonicotinaldehyde structure; $C_6H_4BrNO$ | A12 | 186.006 | 2-bromoisonicotinaldehyde |
| 2-bromo-6-(trifluoromethyl)isonicotinaldehyde structure; $C_7H_3BrF_3NO$ | A13 | 254.004 | 2-bromo-6-(trifluoromethyl)isonicotinaldehyde |
| 2-bromo-5-fluoroisonicotinaldehyde structure; $C_6H_3BrFNO$ | A14 | 203.997 | 2-bromo-5-fluoroisonicotinaldehyde |
| 6-amino-2-bromonicotinaldehyde structure; $C_6H_5BrN_2O$ | A15 | 201.021 | 6-amino-2-bromonicotinaldehyde |

TABLE 1-continued

Reactant A Prophetic Examples.

| Structure | ID | MW | Name |
|---|---|---|---|
| 2-bromobenzaldehyde structure; $C_7H_5BrO$ | A16 | 185.018 | 2-bromobenzaldehyde |
| 3-bromobenzaldehyde structure; $C_7H_5BrO$ | A17 | 185.018 | 3-bromobenzaldehyde |

TABLE 2

Reactant B Prophetic Examples.

| Structure | ID | MW | Name |
|---|---|---|---|
| (2,4-bis(trifluoromethyl)phenyl)boronic acid structure; $C_8H_5BF_6O_2$ | B1 | 257.926 | (2,4-bis(trifluoromethyl)phenyl)boronic acid |
| (2,4-dimethoxyphenyl)boronic acid structure; $C_8H_{11}BO_4$ | B2 | 181.982 | (2,4-dimethoxyphenyl)boronic acid |
| (2-(trifluoromethoxy)phenyl)boronic acid structure; $C_7H_6BF_3O_3$ | B3 | 205.927 | (2-(trifluoromethoxy)phenyl)boronic acid |
| 2-borono-4-methylbenzoic acid structure; $C_8H_9BO_4$ | B4 | 179.966 | 2-borono-4-methylbenzoic acid |
| benzo[d][1,3]dioxol-5-ylboronic acid structure; $C_7H_7BO_4$ | B5 | 165.939 | benzo[d][1,3]dioxol-5-ylboronic acid |

TABLE 2-continued

Reactant B Prophetic Examples.

| Structure | ID | MW | Name |
|---|---|---|---|
| Bn-N(H)-C(=O)-[phenyl]-B(OH)₂  C₁₄H₁₄BNO₃ | B6 | 255.077 | (3-(benzylcarbamoyl)phenyl)boronic acid |
| (CH₃)₂N-[phenyl]-B(OH)₂  C₈H₁₂BNO₂ | B7 | 164.997 | (3-(dimethylamino)phenyl)boronic acid |
| CH₃C(=O)NH-[phenyl]-B(OH)₂  C₈H₁₀BNO₃ | B8 | 178.981 | (3-acetamidophenyl)boronic acid |
| Ph-O-[phenyl]-B(OH)₂  C₁₂H₁₁BO₃ | B9 | 214.025 | (4-phenoxyphenyl)boronic acid |
| 1H-indol-5-yl-B(OH)₂  C₈H₈BNO₂ | B10 | 160.966 | (1H-indol-5-yl)boronic acid |
| isoquinolin-5-yl-B(OH)₂  C₉H₈BNO₂ | B11 | 172.976 | isoquinolin-5-ylboronic acid |
| thiophen-3-yl-B(OH)₂  C₄H₅BO₂S | B12 | 127.957 | thiophen-3-ylboronic acid |
| benzo[b]thiophen-3-yl-B(OH)₂  C₈H₇BO₂S | B13 | 178.016 | benzo[b]thiophen-3-ylboronic acid |
| 5-acetylthiophen-2-yl-B(OH)₂  C₆H₇BO₃S | B14 | 169.994 | (5-acetylthiophen-2-yl)boronic acid |
| furan-2-yl-B(OH)₂  C₄H₅BO₃ | B15 | 111.892 | furan-2-ylboronic acid |
| benzofuran-2-yl-B(OH)₂  C₈H₇BO₃ | B16 | 161.95 | benzofuran-2-ylboronic acid |
| furan-3-yl-B(OH)₂  C₄H₅BO₃ | B17 | 111.892 | furan-3-ylboronic acid |
| 1H-pyrrol-2-yl-B(OH)₂  C₄H₆BNO₂ | B18 | 110.907 | (1H-pyrrol-2-yl)boronic acid |
| isoquinolin-4-yl-B(OH)₂  C₉H₈BNO₂ | B19 | 172.976 | isoquinolin-4-ylboronic acid |
| quinolin-4-yl-B(OH)₂  C₉H₈BNO₂ | B20 | 172.976 | quinolin-4-ylboronic acid |
| 3-fluoropyridin-4-yl-B(OH)₂  C₅H₅BFNO₂ | B21 | 140.908 | (3-fluoropyridin-4-yl)boronic acid |
| 2,6-difluoropyridin-4-yl-B(OH)₂  C₅H₄BF₂NO₂ | B22 | 158.899 | (2,6-difluoropyridin-4-yl)boronic acid |

TABLE 2-continued

Reactant B Prophetic Examples.

| Structure | ID | MW | Name |
|---|---|---|---|
| B(OH)₂ attached to pyridine with N(CH₃)₂; C₇H₁₁BN₂O₂ | B23 | 165.985 | (6-(dimethylamino)pyridin-3-yl)boronic acid |
| B(OH)₂ attached to pyrimidine with N(CH₃)₂; C₆H₁₀BN₃O₂ | B24 | 166.973 | (2-(dimethylamino)pyrimidin-5-yl)boronic acid |
| B(OH)₂ attached to 3,5-dimethylisoxazole; C₅H₈BNO₃ | B25 | 140.933 | (3,5-dimethylisoxazol-4-yl)boronic acid |
| B(OH)₂ attached to 1H-pyrazole at 4-position; C₃H₅BN₂O₂ | B26 | 111.895 | (1H-pyrazol-4-yl)boronic acid |
| B(OH)₂ attached to 1H-pyrazole at 5-position; C₃H₅BN₂O₂ | B27 | 111.895 | (1H-pyrazol-5-yl)boronic acid |

Additional prophetic embodiments of the invention that may be made in accordance with the above reaction schemes using Reactants A and B are listed in Table 3. The geometric isomers listed in Table 3 are believed to reflect the actual geometry of the prophetic compounds if they were to be made; however, final structural assignments may only be made if the compounds are synthesized and subjected to appropriate 2D NMR experiments. Further, although the compounds are listed as the "Z" geometric isomer, both the E and Z geometric isomers and mixtures thereof are contemplated.

TABLE 3

Additional prophetic embodiments of the invention.

| No. | Chemical Name | Formula | Mol. Weight | Reactant A | Reactant B |
|---|---|---|---|---|---|
| 1 | (Z)-5-((2-(4-((((6-(2,4-bis(trifluoromethyl)phenyl)-4-fluoropyridin-2-yl)methyl)amino)methyl)piperidin-1-yl)pyrimidin-4-yl)methylene)thiazolidine-2,4-dione | $C_{28}H_{23}F_7N_6O_2S$ | 640.575 | A1 | B1 |
| 2 | (Z)-5-((2-(4-((((6-(2,4-bis(trifluoromethyl)phenyl)pyridin-2-yl)methyl)amino)methyl)piperidin-1-yl)pyrimidin-4-yl)methylene)thiazolidine-2,4-dione | $C_{28}H_{24}F_6N_6O_2S$ | 622.585 | A2 | B1 |
| 3 | (Z)-5-((2-(4-((((6-(2,4-bis(trifluoromethyl)phenyl)-4-methylpyridin-2-yl)methyl)amino)methyl)piperidin-1-yl)pyrimidin-4-yl)methylene)thiazolidine-2,4-dione | $C_{29}H_{26}F_6N_6O_2S$ | 636.611 | A3 | B1 |
| 4 | (Z)-5-((2-(4-((((6-(2,4-bis(trifluoromethyl)phenyl)-3-methoxypyridin-2-yl)methyl)amino)methyl)piperidin-1-yl)pyrimidin-4-yl)methylene)thiazolidine-2,4-dione | $C_{29}H_{26}F_6N_6O_3S$ | 652.611 | A4 | B1 |
| 5 | (Z)-5-((2-(4-((((6-(2,4-bis(trifluoromethyl)phenyl)-4-(trifluoromethyl)pyridin-2-yl)methyl)amino)methyl)piperidin-1-yl)pyrimidin-4-yl)methylene)thiazolidine-2,4-dione | $C_{29}H_{23}F_9N_6O_2S$ | 690.583 | A5 | B1 |
| 6 | (Z)-5-((2-(4-((((3-(2,4-bis(trifluoromethyl)phenyl)isoquinolin-1-yl)methyl)amino)methyl)piperidin-1-yl)pyrimidin-4-yl)methylene)thiazolidine-2,4-dione | $C_{32}H_{26}F_6N_6O_2S$ | 672.643 | A6 | B1 |
| 7 | (Z)-5-((2-(4-((((2-(2,4-bis(trifluoromethyl)phenyl)pyridin-3-yl)methyl)amino)methyl)piperidin-1-yl)pyrimidin-4-yl)methylene)thiazolidine-2,4-dione | $C_{28}H_{24}F_6N_6O_2S$ | 622.585 | A7 | B1 |
| 8 | (Z)-5-((2-(4-((((2-(2,4-bis(trifluoromethyl)phenyl)quinolin-3-yl)methyl)amino)methyl)piperidin-1-yl)pyrimidin-4-yl)methylene)thiazolidine-2,4-dione | $C_{32}H_{26}F_6N_6O_2S$ | 672.643 | A8 | B1 |

TABLE 3-continued

Additional prophetic embodiments of the invention.

| No. | Chemical Name | Formula | Mol. Weight | Reactant A | Reactant B |
|---|---|---|---|---|---|
| 9 | (Z)-5-((2-(4-((((6-(2,4-bis(trifluoromethyl)phenyl)pyridin-3-yl)methyl)amino)methyl)piperidin-1-yl)pyrimidin-4-yl)methylene)thiazolidine-2,4-dione | $C_{28}H_{24}F_6N_6O_2S$ | 622.585 | A9 | B1 |
| 10 | (Z)-2-(2,4-bis(trifluoromethyl)phenyl)-5-((((1-(4-((2,4-dioxothiazolidin-5-ylidene)methyl)pyrimidin-2-yl)piperidin-4-yl)methyl)amino)methyl)nicotinonitrile | $C_{29}H_{23}F_6N_7O_2S$ | 647.594 | A10 | B1 |
| 11 | (Z)-ethyl 2-(2,4-bis(trifluoromethyl)phenyl)-5-((((1-(4-((2,4-dioxothiazolidin-5-ylidene)methyl)pyrimidin-2-yl)piperidin-4-yl)methyl)amino)methyl)nicotinate | $C_{31}H_{28}F_6N_6O_4S$ | 694.647 | A11 | B1 |
| 12 | (Z)-5-((2-(4-((((2-(2,4-bis(trifluoromethyl)phenyl)pyridin-4-yl)methyl)amino)methyl)piperidin-1-yl)pyrimidin-4-yl)methylene)thiazolidine-2,4-dione | $C_{28}H_{24}F_6N_6O_2S$ | 622.585 | A12 | B1 |
| 13 | (Z)-5-((2-(4-((((2-(2,4-bis(trifluoromethyl)phenyl)-6-(trifluoromethyl)pyridin-4-yl)methyl)amino)methyl)piperidin-1-yl)pyrimidin-4-yl)methylene)thiazolidine-2,4-dione | $C_{29}H_{23}F_9N_6O_2S$ | 690.583 | A13 | B1 |
| 14 | (Z)-5-((2-(4-((((2-(2,4-bis(trifluoromethyl)phenyl)-5-fluoropyridin-4-yl)methyl)amino)methyl)piperidin-1-yl)pyrimidin-4-yl)methylene)thiazolidine-2,4-dione | $C_{28}H_{23}F_7N_6O_2S$ | 640.575 | A14 | B1 |
| 15 | (Z)-5-((2-(4-((((6-amino-2-(2,4-bis(trifluoromethyl)phenyl)pyridin-3-yl)methyl)amino)methyl)piperidin-1-yl)pyrimidin-4-yl)methylene)thiazolidine-2,4-dione | $C_{28}H_{25}F_6N_7O_2S$ | 637.599 | A15 | B1 |
| 16 | (Z)-5-((2-(4-((((6-(2,4-dimethoxyphenyl)-4-fluoropyridin-2-yl)methyl)amino)methyl)piperidin-1-yl)pyrimidin-4-yl)methylene)thiazolidine-2,4-dione | $C_{28}H_{29}FN_6O_4S$ | 564.631 | A1 | B2 |
| 17 | (Z)-5-((2-(4-((((6-(2,4-dimethoxyphenyl)pyridin-2-yl)methyl)amino)methyl)piperidin-1-yl)pyrimidin-4-yl)methylene)thiazolidine-2,4-dione | $C_{28}H_{30}N_6O_4S$ | 546.641 | A2 | B2 |
| 18 | (Z)-5-((2-(4-((((6-(2,4-dimethoxyphenyl)-4-methylpyridin-2-yl)methyl)amino)methyl)piperidin-1-yl)pyrimidin-4-yl)methylene)thiazolidine-2,4-dione | $C_{29}H_{32}N_6O_4S$ | 560.667 | A3 | B2 |
| 19 | (Z)-5-((2-(4-((((6-(2,4-dimethoxyphenyl)-3-methoxypyridin-2-yl)methyl)amino)methyl)piperidin-1-yl)pyrimidin-4-yl)methylene)thiazolidine-2,4-dione | $C_{29}H_{32}N_6O_5S$ | 576.667 | A4 | B2 |
| 20 | (Z)-5-((2-(4-((((6-(2,4-dimethoxyphenyl)-4-(trifluoromethyl)pyridin-2-yl)methyl)amino)methyl)piperidin-1-yl)pyrimidin-4-yl)methylene)thiazolidine-2,4-dione | $C_{29}H_{29}F_3N_6O_4S$ | 614.639 | A5 | B2 |
| 21 | (Z)-5-((2-(4-((((3-(2,4-dimethoxyphenyl)isoquinolin-1-yl)methyl)amino)methyl)piperidin-1-yl)pyrimidin-4-yl)methylene)thiazolidine-2,4-dione | $C_{32}H_{32}N_6O_4S$ | 596.699 | A6 | B2 |
| 22 | (Z)-5-((2-(4-((((2-(2,4-dimethoxyphenyl)pyridin-3-yl)methyl)amino)methyl)piperidin-1-yl)pyrimidin-4-yl)methylene)thiazolidine-2,4-dione | $C_{28}H_{30}N_6O_4S$ | 546.641 | A7 | B2 |
| 23 | (Z)-5-((2-(4-((((2-(2,4-dimethoxyphenyl)quinolin-3-yl)methyl)amino)methyl)piperidin-1-yl)pyrimidin-4-yl)methylene)thiazolidine-2,4-dione | $C_{32}H_{32}N_6O_4S$ | 596.699 | A8 | B2 |
| 24 | (Z)-5-((2-(4-((((6-(2,4-dimethoxyphenyl)pyridin-3-yl)methyl)amino)methyl)piperidin-1-yl)pyrimidin-4-yl)methylene)thiazolidine-2,4-dione | $C_{28}H_{30}N_6O_4S$ | 546.641 | A9 | B2 |
| 25 | (Z)-2-(2,4-dimethoxyphenyl)-5-((((1-(4-((2,4-dioxothiazolidin-5-ylidene)methyl)pyrimidin-2-yl)piperidin-4-yl)methyl)amino)methyl)nicotinonitrile | $C_{29}H_{29}N_7O_4S$ | 571.65 | A10 | B2 |
| 26 | (Z)-ethyl 2-(2,4-dimethoxyphenyl)-5-((((1-(4-((2,4-dioxothiazolidin-5-ylidene)methyl)pyrimidin-2-yl)piperidin-4-yl)methyl)amino)methyl)nicotinate | $C_{31}H_{34}N_6O_6S$ | 618.703 | A11 | B2 |
| 27 | (Z)-5-((2-(4-((((2-(2,4-dimethoxyphenyl)pyridin-4-yl)methyl)amino)methyl)piperidin-1-yl)pyrimidin-4-yl)methylene)thiazolidine-2,4-dione | $C_{28}H_{30}N_6O_4S$ | 546.641 | A12 | B2 |
| 28 | (Z)-5-((2-(4-((((2-(2,4-dimethoxyphenyl)-6-(trifluoromethyl)pyridin-4-yl)methyl)amino)methyl)piperidin-1-yl)pyrimidin-4-yl)methylene)thiazolidine-2,4-dione | $C_{29}H_{29}F_3N_6O_4S$ | 614.639 | A13 | B2 |

TABLE 3-continued

Additional prophetic embodiments of the invention.

| No. | Chemical Name | Formula | Mol. Weight | Reactant A | Reactant B |
|---|---|---|---|---|---|
| 29 | (Z)-5-((2-(4-(((((2-(2,4-dimethoxyphenyl)-5-fluoropyridin-4-yl)methyl)amino)methyl)piperidin-1-yl)pyrimidin-4-yl)methylene)thiazolidine-2,4-dione | $C_{28}H_{29}FN_6O_4S$ | 564.631 | A14 | B2 |
| 30 | (Z)-5-((2-(4-(((((6-amino-2-(2,4-dimethoxyphenyl)pyridin-3-yl)methyl)amino)methyl)piperidin-1-yl)pyrimidin-4-yl)methylene)thiazolidine-2,4-dione | $C_{28}H_{31}N_7O_4S$ | 561.655 | A15 | B2 |
| 31 | (Z)-5-((2-(4-(((((4-fluoro-6-(2-(trifluoromethoxy)phenyl)pyridin-2-yl)methyl)amino)methyl)piperidin-1-yl)pyrimidin-4-yl)methylene)thiazolidine-2,4-dione | $C_{27}H_{24}F_4N_6O_3S$ | 588.576 | A1 | B3 |
| 32 | (Z)-5-((2-(4-(((((6-(2-(trifluoromethoxy)phenyl)pyridin-2-yl)methyl)amino)methyl)piperidin-1-yl)pyrimidin-4-yl)methylene)thiazolidine-2,4-dione | $C_{27}H_{25}F_3N_6O_3S$ | 570.586 | A2 | B3 |
| 33 | (Z)-5-((2-(4-(((((4-methyl-6-(2-(trifluoromethoxy)phenyl)pyridin-2-yl)methyl)amino)methyl)piperidin-1-yl)pyrimidin-4-yl)methylene)thiazolidine-2,4-dione | $C_{28}H_{27}F_3N_6O_3S$ | 584.613 | A3 | B3 |
| 34 | (Z)-5-((2-(4-(((((3-methoxy-6-(2-(trifluoromethoxy)phenyl)pyridin-2-yl)methyl)amino)methyl)piperidin-1-yl)pyrimidin-4-yl)methylene)thiazolidine-2,4-dione | $C_{28}H_{27}F_3N_6O_4S$ | 600.612 | A4 | B3 |
| 35 | (Z)-5-((2-(4-((((6-(2-(trifluoromethoxy)phenyl)-4-(trifluoromethyl)pyridin-2-yl)methyl)amino)methyl)piperidin-1-yl)pyrimidin-4-yl)methylene)thiazolidine-2,4-dione | $C_{28}H_{24}F_6N_6O_3S$ | 638.584 | A5 | B3 |
| 36 | (Z)-5-((2-(4-((((3-(2-(trifluoromethoxy)phenyl)isoquinolin-1-yl)methyl)amino)methyl)piperidin-1-yl)pyrimidin-4-yl)methylene)thiazolidine-2,4-dione | $C_{31}H_{27}F_3N_6O_3S$ | 620.645 | A6 | B3 |
| 37 | (Z)-5-((2-(4-(((((2-(2-(trifluoromethoxy)phenyl)pyridin-3-yl)methyl)amino)methyl)piperidin-1-yl)pyrimidin-4-yl)methylene)thiazolidine-2,4-dione | $C_{27}H_{25}F_3N_6O_3S$ | 570.586 | A7 | B3 |
| 38 | (Z)-5-((2-(4-(((((2-(2-(trifluoromethoxy)phenyl)quinolin-3-yl)methyl)amino)methyl)piperidin-1-yl)pyrimidin-4-yl)methylene)thiazolidine-2,4-dione | $C_{31}H_{27}F_3N_6O_3S$ | 620.645 | A8 | B3 |
| 39 | (Z)-5-((2-(4-(((((6-(2-(trifluoromethoxy)phenyl)pyridin-3-yl)methyl)amino)methyl)piperidin-1-yl)pyrimidin-4-yl)methylene)thiazolidine-2,4-dione | $C_{27}H_{25}F_3N_6O_3S$ | 570.586 | A9 | B3 |
| 40 | (Z)-5-(((((1-(4-((2,4-dioxothiazolidin-5-ylidene)methyl)pyrimidin-2-yl)piperidin-4-yl)methyl)amino)methyl)-2-(2-(trifluoromethoxy)phenyl)nicotinonitrile | $C_{28}H_{24}F_3N_7O_3S$ | 595.595 | A10 | B3 |
| 41 | (Z)-ethyl 5-(((((1-(4-((2,4-dioxothiazolidin-5-ylidene)methyl)pyrimidin-2-yl)piperidin-4-yl)methyl)amino)methyl)-2-(2-(trifluoromethoxy)phenyl)nicotinate | $C_{30}H_{29}F_3N_6O_5S$ | 642.649 | A11 | B3 |
| 42 | (Z)-5-((2-(4-(((((2-(2-(trifluoromethoxy)phenyl)pyridin-4-yl)methyl)amino)methyl)piperidin-1-yl)pyrimidin-4-yl)methylene)thiazolidine-2,4-dione | $C_{27}H_{25}F_3N_6O_3S$ | 570.586 | A12 | B3 |
| 43 | (Z)-5-((2-(4-(((((2-(2-(trifluoromethoxy)phenyl)-6-(trifluoromethyl)pyridin-4-yl)methyl)amino)methyl)piperidin-1-yl)pyrimidin-4-yl)methylene)thiazolidine-2,4-dione | $C_{28}H_{24}F_6N_6O_3S$ | 638.584 | A13 | B3 |
| 44 | (Z)-5-((2-(4-(((((5-fluoro-2-(2-(trifluoromethoxy)phenyl)pyridin-4-yl)methyl)amino)methyl)piperidin-1-yl)pyrimidin-4-yl)methylene)thiazolidine-2,4-dione | $C_{27}H_{24}F_4N_6O_3S$ | 588.576 | A14 | B3 |
| 45 | (Z)-5-((2-(4-(((((6-amino-2-(2-(trifluoromethoxy)phenyl)pyridin-3-yl)methyl)amino)methyl)piperidin-1-yl)pyrimidin-4-yl)methylene)thiazolidine-2,4-dione | $C_{27}H_{26}F_3N_7O_3S$ | 585.601 | A15 | B3 |
| 46 | (Z)-2-(6-(((((1-(4-((2,4-dioxothiazolidin-5-ylidene)methyl)pyrimidin-2-yl)piperidin-4-yl)methyl)amino)methyl)-4-fluoropyridin-2-yl)-4-methylbenzoic acid | $C_{28}H_{27}FN_6O_4S$ | 562.615 | A1 | B4 |

TABLE 3-continued

Additional prophetic embodiments of the invention.

| No. | Chemical Name | Formula | Mol. Weight | Reactant A | B |
|---|---|---|---|---|---|
| 47 | (Z)-2-(6-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{28}H_{28}N_6O_4S$ | 544.625 | A2 | B4 |
| 48 | (Z)-2-(6-((((1-(4-((2,4-dioxothiazolidin-5-ylidene)methyl)pyrimidin-2-yl)piperidin-4-yl)methyl)amino)methyl)-4-methylpyridin-2-yl)-4-methylbenzoic acid | $C_{29}H_{30}N_6O_4S$ | 558.651 | A3 | B4 |
| 49 | (Z)-2-(6-((((1-(4-((2,4-dioxothiazolidin-5-ylidene)methyl)pyrimidin-2-yl)piperidin-4-yl)methyl)amino)methyl)-5-methoxypyridin-2-yl)-4-methylbenzoic acid | $C_{29}H_{30}N_6O_5S$ | 574.651 | A4 | B4 |
| 50 | (Z)-2-(6-((((1-(4-((2,4-dioxothiazolidin-5-ylidene)methyl)pyrimidin-2-yl)piperidin-4-yl)methyl)amino)methyl)-4-(trifluoromethyl)pyridin-2-yl)-4-methylbenzoic acid | $C_{29}H_{27}F_3N_6O_4S$ | 612.623 | A5 | B4 |
| 51 | (Z)-2-(1-((((1-(4-((2,4-dioxothiazolidin-5-ylidene)methyl)pyrimidin-2-yl)piperidin-4-yl)methyl)amino)methyl)isoquinolin-3-yl)-4-methylbenzoic acid | $C_{32}H_{30}N_6O_4S$ | 594.683 | A6 | B4 |
| 52 | (Z)-2-(3-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{28}H_{28}N_6O_4S$ | 544.625 | A7 | B4 |
| 53 | (Z)-2-(3-((((1-(4-((2,4-dioxothiazolidin-5-ylidene)methyl)pyrimidin-2-yl)piperidin-4-yl)methyl)amino)methyl)quinolin-2-yl)-4-methylbenzoic acid | $C_{32}H_{30}N_6O_4S$ | 594.683 | A8 | B4 |
| 54 | (Z)-2-(5-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{28}H_{28}N_6O_4S$ | 544.625 | A9 | B4 |
| 55 | (Z)-2-(3-cyano-5-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{29}H_{27}N_7O_4S$ | 569.634 | A10 | B4 |
| 56 | (Z)-2-(5-((((1-(4-((2,4-dioxothiazolidin-5-ylidene)methyl)pyrimidin-2-yl)piperidin-4-yl)methyl)amino)methyl)-3-(ethoxycarbonyl)pyridin-2-yl)-4-methylbenzoic acid | $C_{31}H_{32}N_6O_6S$ | 616.687 | A11 | B4 |
| 57 | (Z)-2-(4-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{28}H_{28}N_6O_4S$ | 544.625 | A12 | B4 |
| 58 | (Z)-2-(4-((((1-(4-((2,4-dioxothiazolidin-5-ylidene)methyl)pyrimidin-2-yl)piperidin-4-yl)methyl)amino)methyl)-6-(trifluoromethyl)pyridin-2-yl)-4-methylbenzoic acid | $C_{29}H_{27}F_3N_6O_4S$ | 612.623 | A13 | B4 |
| 59 | (Z)-2-(4-((((1-(4-((2,4-dioxothiazolidin-5-ylidene)methyl)pyrimidin-2-yl)piperidin-4-yl)methyl)amino)methyl)-5-fluoropyridin-2-yl)-4-methylbenzoic acid | $C_{28}H_{27}FN_6O_4S$ | 562.615 | A14 | B4 |
| 60 | (Z)-2-(6-amino-3-((((1-(4-((2,4-dioxothiazolidin-5-ylidene)methyl)pyrimidin-2-yl)piperidin-4-yl)methyl)amino)methyl)pyridin-2-yl)-4-methylbenzoic acid | $C_{28}H_{29}N_7O_4S$ | 559.639 | A15 | B4 |
| 61 | (Z)-5-((2-(4-(((((6-(benzo[d][1,3]dioxol-5-yl)-4-fluoropyridin-2-yl)methyl)amino)methyl)piperidin-1-yl)pyrimidin-4-yl)methylene)thiazolidine-2,4-dione | $C_{27}H_{25}FN_6O_4S$ | 548.589 | A1 | B5 |
| 62 | (Z)-5-((2-(4-(((((6-(benzo[d][1,3]dioxol-5-yl)pyridin-2-yl)methyl)amino)methyl)piperidin-1-yl)pyrimidin-4-yl)methylene)thiazolidine-2,4-dione | $C_{27}H_{26}N_6O_4S$ | 530.598 | A2 | B5 |
| 63 | (Z)-5-((2-(4-(((((6-(benzo[d][1,3]dioxol-5-yl)-4-methylpyridin-2-yl)methyl)amino)methyl)piperidin-1-yl)pyrimidin-4-yl)methylene)thiazolidine-2,4-dione | $C_{28}H_{28}N_6O_4S$ | 544.625 | A3 | B5 |
| 64 | (Z)-5-((2-(4-(((((6-(benzo[d][1,3]dioxol-5-yl)-3-methoxypyridin-2-yl)methyl)amino)methyl)piperidin-1-yl)pyrimidin-4-yl)methylene)thiazolidine-2,4-dione | $C_{28}H_{28}N_6O_5S$ | 560.624 | A4 | B5 |
| 65 | (Z)-5-((2-(4-(((((6-(benzo[d][1,3]dioxol-5-yl)-4-(trifluoromethyl)pyridin-2-yl)methyl)amino)methyl)piperidin-1-yl)pyrimidin-4-yl)methylene)thiazolidine-2,4-dione | $C_{28}H_{25}F_3N_6O_4S$ | 598.596 | A5 | B5 |

TABLE 3-continued

Additional prophetic embodiments of the invention.

| No. | Chemical Name | Formula | Mol. Weight | Reactant A | Reactant B |
|---|---|---|---|---|---|
| 66 | (Z)-5-((2-(4-((((3-(benzo[d][1,3]dioxol-5-yl)isoquinolin-1-yl)methyl)amino)methyl)piperidin-1-yl)pyrimidin-4-yl)methylene)thiazolidine-2,4-dione | $C_{31}H_{28}N_6O_4S$ | 580.657 | A6 | B5 |
| 67 | (Z)-5-((2-(4-((((2-(benzo[d][1,3]dioxol-5-yl)pyridin-3-yl)methyl)amino)methyl)piperidin-1-yl)pyrimidin-4-yl)methylene)thiazolidine-2,4-dione | $C_{27}H_{26}N_6O_4S$ | 530.598 | A7 | B5 |
| 68 | (Z)-5-((2-(4-((((2-(benzo[d][1,3]dioxol-5-yl)quinolin-3-yl)methyl)amino)methyl)piperidin-1-yl)pyrimidin-4-yl)methylene)thiazolidine-2,4-dione | $C_{31}H_{28}N_6O_4S$ | 580.657 | A8 | B5 |
| 69 | (Z)-5-((2-(4-((((6-(benzo[d][1,3]dioxol-5-yl)pyridin-3-yl)methyl)amino)methyl)piperidin-1-yl)pyrimidin-4-yl)methylene)thiazolidine-2,4-dione | $C_{27}H_{26}N_6O_4S$ | 530.598 | A9 | B5 |
| 70 | (Z)-2-(benzo[d][1,3]dioxol-5-yl)-5-((((1-(4-((2,4-dioxothiazolidin-5-ylidene)methyl)pyrimidin-2-yl)piperidin-4-yl)methyl)amino)methyl)nicotinonitrile | $C_{28}H_{25}N_7O_4S$ | 555.608 | A10 | B5 |
| 71 | (Z)-ethyl 2-(benzo[d][1,3]dioxol-5-yl)-5-((((1-(4-((2,4-dioxothiazolidin-5-ylidene)methyl)pyrimidin-2-yl)piperidin-4-yl)methyl)amino)methyl)nicotinate | $C_{30}H_{30}N_6O_6S$ | 602.661 | A11 | B5 |
| 72 | (Z)-5-((2-(4-((((2-(benzo[d][1,3]dioxol-5-yl)pyridin-4-yl)methyl)amino)methyl)piperidin-1-yl)pyrimidin-4-yl)methylene)thiazolidine-2,4-dione | $C_{27}H_{26}N_6O_4S$ | 530.598 | A12 | B5 |
| 73 | (Z)-5-((2-(4-((((2-(benzo[d][1,3]dioxol-5-yl)-6-(trifluoromethyl)pyridin-4-yl)methyl)amino)methyl)piperidin-1-yl)pyrimidin-4-yl)methylene)thiazolidine-2,4-dione | $C_{28}H_{25}F_3N_6O_4S$ | 598.596 | A13 | B5 |
| 74 | (Z)-5-((2-(4-((((2-(benzo[d][1,3]dioxol-5-yl)-5-fluoropyridin-4-yl)methyl)amino)methyl)piperidin-1-yl)pyrimidin-4-yl)methylene)thiazolidine-2,4-dione | $C_{27}H_{25}FN_6O_4S$ | 548.589 | A14 | B5 |
| 75 | (Z)-5-((2-(4-(((((6-amino-2-(benzo[d][1,3]dioxol-5-yl)pyridin-3-yl)methyl)amino)methyl)piperidin-1-yl)pyrimidin-4-yl)methylene)thiazolidine-2,4-dione | $C_{27}H_{27}N_7O_4S$ | 545.613 | A15 | B5 |
| 76 | (Z)-N-benzyl-3-(6-((((1-(4-((2,4-dioxothiazolidin-5-ylidene)methyl)pyrimidin-2-yl)piperidin-4-yl)methyl)amino)methyl)-4-fluoropyridin-2-yl)benzamide | $C_{34}H_{32}FN_7O_3S$ | 637.726 | A1 | B6 |
| 77 | (Z)-N-benzyl-3-(6-((((1-(4-((2,4-dioxothiazolidin-5-ylidene)methyl)pyrimidin-2-yl)piperidin-4-yl)methyl)amino)methyl)pyridin-2-yl)benzamide | $C_{34}H_{33}N_7O_3S$ | 619.736 | A2 | B6 |
| 78 | (Z)-N-benzyl-3-(6-((((1-(4-((2,4-dioxothiazolidin-5-ylidene)methyl)pyrimidin-2-yl)piperidin-4-yl)methyl)amino)methyl)-4-methylpyridin-2-yl)benzamide | $C_{35}H_{35}N_7O_3S$ | 633.763 | A3 | B6 |
| 79 | (Z)-N-benzyl-3-(6-((((1-(4-((2,4-dioxothiazolidin-5-ylidene)methyl)pyrimidin-2-yl)piperidin-4-yl)methyl)amino)methyl)-5-methoxypyridin-2-yl)benzamide | $C_{35}H_{35}N_7O_4S$ | 649.762 | A4 | B6 |
| 80 | (Z)-N-benzyl-3-(6-((((1-(4-((2,4-dioxothiazolidin-5-ylidene)methyl)pyrimidin-2-yl)piperidin-4-yl)methyl)amino)methyl)-4-(trifluoromethyl)pyridin-2-yl)benzamide | $C_{35}H_{32}F_3N_7O_3S$ | 687.734 | A5 | B6 |
| 81 | (Z)-N-benzyl-3-(1-((((1-(4-((2,4-dioxothiazolidin-5-ylidene)methyl)pyrimidin-2-yl)piperidin-4-yl)methyl)amino)methyl)isoquinolin-3-yl)benzamide | $C_{38}H_{35}N_7O_3S$ | 669.795 | A6 | B6 |
| 82 | (Z)-N-benzyl-3-(3-((((1-(4-((2,4-dioxothiazolidin-5-ylidene)methyl)pyrimidin-2-yl)piperidin-4-yl)methyl)amino)methyl)pyridin-2-yl)benzamide | $C_{34}H_{33}N_7O_3S$ | 619.736 | A7 | B6 |
| 83 | (Z)-N-benzyl-3-(3-((((1-(4-((2,4-dioxothiazolidin-5-ylidene)methyl)pyrimidin-2-yl)piperidin-4-yl)methyl)amino)methyl)quinolin-2-yl)benzamide | $C_{38}H_{35}N_7O_3S$ | 669.795 | A8 | B6 |
| 84 | (Z)-N-benzyl-3-(5-((((1-(4-((2,4-dioxothiazolidin-5-ylidene)methyl)pyrimidin-2-yl)piperidin-4-yl)methyl)amino)methyl)pyridin-2-yl)benzamide | $C_{34}H_{33}N_7O_3S$ | 619.736 | A9 | B6 |
| 85 | (Z)-N-benzyl-3-(3-cyano-5-((((1-(4-((2,4-dioxothiazolidin-5-ylidene)methyl)pyrimidin-2-yl)piperidin-4-yl)methyl)amino)methyl)pyridin-2-yl)benzamide | $C_{35}H_{32}N_8O_3S$ | 644.745 | A10 | B6 |
| 86 | (Z)-ethyl 2-(3-(benzylcarbamoyl)phenyl)-5-((((1-(4-((2,4-dioxothiazolidin-5-ylidene)methyl)pyrimidin-2-yl)piperidin-4-yl)methyl)amino)methyl)nicotinate | $C_{37}H_{37}N_7O_5S$ | 691.799 | A11 | B6 |
| 87 | (Z)-N-benzyl-3-(4-((((1-(4-((2,4-dioxothiazolidin-5-ylidene)methyl)pyrimidin-2-yl)piperidin-4-yl)methyl)amino)methyl)pyridin-2-yl)benzamide | $C_{34}H_{33}N_7O_3S$ | 619.736 | A12 | B6 |

TABLE 3-continued

Additional prophetic embodiments of the invention.

| No. | Chemical Name | Formula | Mol. Weight | Reactant A | Reactant B |
|---|---|---|---|---|---|
| 88 | (Z)-N-benzyl-3-(4-(((((1-(4-((2,4-dioxothiazolidin-5-ylidene)methyl)pyrimidin-2-yl)piperidin-4-yl)methyl)amino)methyl)-6-(trifluoromethyl)pyridin-2-yl)benzamide | $C_{35}H_{32}F_3N_7O_3S$ | 687.734 | A13 | B6 |
| 89 | (Z)-N-benzyl-3-(4-(((((1-(4-((2,4-dioxothiazolidin-5-ylidene)methyl)pyrimidin-2-yl)piperidin-4-yl)methyl)amino)methyl)-5-fluoropyridin-2-yl)benzamide | $C_{34}H_{32}FN_7O_3S$ | 637.726 | A14 | B6 |
| 90 | (Z)-3-(6-amino-3-(((((1-(4-((2,4-dioxothiazolidin-5-ylidene)methyl)pyrimidin-2-yl)piperidin-4-yl)methyl)amino)methyl)pyridin-2-yl)-N-benzylbenzamide | $C_{34}H_{34}N_8O_3S$ | 634.751 | A15 | B6 |
| 91 | (Z)-5-((2-(4-(((((6-(3-(dimethylamino)phenyl)-4-fluoropyridin-2-yl)methyl)amino)methyl)piperidin-1-yl)pyrimidin-4-yl)methylene)thiazolidine-2,4-dione | $C_{28}H_{30}FN_7O_2S$ | 547.647 | A1 | B7 |
| 92 | (Z)-5-((2-(4-(((((6-(3-(dimethylamino)phenyl)pyridin-2-yl)methyl)amino)methyl)piperidin-1-yl)pyrimidin-4-yl)methylene)thiazolidine-2,4-dione | $C_{28}H_{31}N_7O_2S$ | 529.656 | A2 | B7 |
| 93 | (Z)-5-((2-(4-(((((6-(3-(dimethylamino)phenyl)-4-methylpyridin-2-yl)methyl)amino)methyl)piperidin-1-yl)pyrimidin-4-yl)methylene)thiazolidine-2,4-dione | $C_{29}H_{33}N_7O_2S$ | 543.683 | A3 | B7 |
| 94 | (Z)-5-((2-(4-(((((6-(3-(dimethylamino)phenyl)-3-methoxypyridin-2-yl)methyl)amino)methyl)piperidin-1-yl)pyrimidin-4-yl)methylene)thiazolidine-2,4-dione | $C_{29}H_{33}N_7O_3S$ | 559.682 | A4 | B7 |
| 95 | (Z)-5-((2-(4-(((((6-(3-(dimethylamino)phenyl)-4-(trifluoromethyl)pyridin-2-yl)methyl)amino)methyl)piperidin-1-yl)pyrimidin-4-yl)methylene)thiazolidine-2,4-dione | $C_{29}H_{30}F_3N_7O_2S$ | 597.654 | A5 | B7 |
| 96 | (Z)-5-((2-(4-(((((3-(3-(dimethylamino)phenyl)isoquinolin-1-yl)methyl)amino)methyl)piperidin-1-yl)pyrimidin-4-yl)methylene)thiazolidine-2,4-dione | $C_{32}H_{33}N_7O_2S$ | 579.715 | A6 | B7 |
| 97 | (Z)-5-((2-(4-(((((2-(3-(dimethylamino)phenyl)pyridin-3-yl)methyl)amino)methyl)piperidin-1-yl)pyrimidin-4-yl)methylene)thiazolidine-2,4-dione | $C_{28}H_{31}N_7O_2S$ | 529.656 | A7 | B7 |
| 98 | (Z)-5-((2-(4-(((((2-(3-(dimethylamino)phenyl)quinolin-3-yl)methyl)amino)methyl)piperidin-1-yl)pyrimidin-4-yl)methylene)thiazolidine-2,4-dione | $C_{32}H_{33}N_7O_2S$ | 579.715 | A8 | B7 |
| 99 | (Z)-5-((2-(4-(((((6-(3-(dimethylamino)phenyl)pyridin-3-yl)methyl)amino)methyl)piperidin-1-yl)pyrimidin-4-yl)methylene)thiazolidine-2,4-dione | $C_{28}H_{31}N_7O_2S$ | 529.656 | A9 | B7 |
| 100 | (Z)-2-(3-(dimethylamino)phenyl)-5-(((((1-(4-((2,4-dioxothiazolidin-5-ylidene)methyl)pyrimidin-2-yl)piperidin-4-yl)methyl)amino)methyl)nicotinonitrile | $C_{29}H_{30}N_8O_2S$ | 554.666 | A10 | B7 |
| 101 | (Z)-ethyl 2-(3-(dimethylamino)phenyl)-5-(((((1-(4-((2,4-dioxothiazolidin-5-ylidene)methyl)pyrimidin-2-yl)piperidin-4-yl)methyl)amino)methyl)nicotinate | $C_{31}H_{35}N_7O_4S$ | 601.719 | A11 | B7 |
| 102 | (Z)-5-((2-(4-(((((2-(3-(dimethylamino)phenyl)pyridin-4-yl)methyl)amino)methyl)piperidin-1-yl)pyrimidin-4-yl)methylene)thiazolidine-2,4-dione | $C_{28}H_{31}N_7O_2S$ | 529.656 | A12 | B7 |
| 103 | (Z)-5-((2-(4-(((((2-(3-(dimethylamino)phenyl)-6-(trifluoromethyl)pyridin-4-yl)methyl)amino)methyl)piperidin-1-yl)pyrimidin-4-yl)methylene)thiazolidine-2,4-dione | $C_{29}H_{30}F_3N_7O_2S$ | 597.654 | A13 | B7 |
| 104 | (Z)-5-((2-(4-(((((2-(3-(dimethylamino)phenyl)-5-fluoropyridin-4-yl)methyl)amino)methyl)piperidin-1-yl)pyrimidin-4-yl)methylene)thiazolidine-2,4-dione | $C_{28}H_{30}FN_7O_2S$ | 547.647 | A14 | B7 |
| 105 | (Z)-5-((2-(4-(((((6-amino-2-(3-(dimethylamino)phenyl)pyridin-3-yl)methyl)amino)methyl)piperidin-1-yl)pyrimidin-4-yl)methylene)thiazolidine-2,4-dione | $C_{28}H_{32}N_8O_2S$ | 544.671 | A15 | B7 |
| 106 | (Z)-N-(3-(6-(((((1-(4-((2,4-dioxothiazolidin-5-ylidene)methyl)pyrimidin-2-yl)piperidin-4-yl)methyl)amino)methyl)-4-fluoropyridin-2-yl)phenyl)acetamide | $C_{28}H_{28}FN_7O_3S$ | 561.63 | A1 | B8 |
| 107 | (Z)-N-(3-(6-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{28}H_{29}N_7O_3S$ | 543.64 | A2 | B8 |

TABLE 3-continued

Additional prophetic embodiments of the invention.

| No. | Chemical Name | Formula | Mol. Weight | Reactant A | Reactant B |
|---|---|---|---|---|---|
| 108 | (Z)-N-(3-(6-(((((1-(4-((2,4-dioxothiazolidin-5-ylidene)methyl)pyrimidin-2-yl)piperidin-4-yl)methyl)amino)methyl)-4-methylpyridin-2-yl)phenyl)acetamide | $C_{29}H_{31}N_7O_3S$ | 557.667 | A3 | B8 |
| 109 | (Z)-N-(3-(6-(((((1-(4-((2,4-dioxothiazolidin-5-ylidene)methyl)pyrimidin-2-yl)piperidin-4-yl)methyl)amino)methyl)-5-methoxypyridin-2-yl)phenyl)acetamide | $C_{29}H_{31}N_7O_4S$ | 573.666 | A4 | B8 |
| 110 | (Z)-N-(3-(6-(((((1-(4-((2,4-dioxothiazolidin-5-ylidene)methyl)pyrimidin-2-yl)piperidin-4-yl)methyl)amino)methyl)-4-(trifluoromethyl)pyridin-2-yl)phenyl)acetamide | $C_{29}H_{28}F_3N_7O_3S$ | 611.638 | A5 | B8 |
| 111 | (Z)-N-(3-(1-(((((1-(4-((2,4-dioxothiazolidin-5-ylidene)methyl)pyrimidin-2-yl)piperidin-4-yl)methyl)amino)methyl)isoquinolin-3-yl)phenyl)acetamide | $C_{32}H_{31}N_7O_3S$ | 593.699 | A6 | B8 |
| 112 | (Z)-N-(3-(3-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{28}H_{29}N_7O_3S$ | 543.64 | A7 | B8 |
| 113 | (Z)-N-(3-(3-(((((1-(4-((2,4-dioxothiazolidin-5-ylidene)methyl)pyrimidin-2-yl)piperidin-4-yl)methyl)amino)methyl)quinolin-2-yl)phenyl)acetamide | $C_{32}H_{31}N_7O_3S$ | 593.699 | A8 | B8 |
| 114 | (Z)-N-(3-(5-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{28}H_{29}N_7O_3S$ | 543.64 | A9 | B8 |
| 115 | (Z)-N-(3-(3-cyano-5-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{29}H_{28}N_8O_3S$ | 568.649 | A10 | B8 |
| 116 | (Z)-ethyl 2-(3-acetamidophenyl)-5-(((((1-(4-((2,4-dioxothiazolidin-5-ylidene)methyl)pyrimidin-2-yl)piperidin-4-yl)methyl)amino)methyl)nicotinate | $C_{31}H_{33}N_7O_5S$ | 615.703 | A11 | B8 |
| 117 | (Z)-N-(3-(4-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{28}H_{29}N_7O_3S$ | 543.64 | A12 | B8 |
| 118 | (Z)-N-(3-(4-(((((1-(4-((2,4-dioxothiazolidin-5-ylidene)methyl)pyrimidin-2-yl)piperidin-4-yl)methyl)amino)methyl)-6-(trifluoromethyl)pyridin-2-yl)phenyl)acetamide | $C_{29}H_{28}F_3N_7O_3S$ | 611.638 | A13 | B8 |
| 119 | (Z)-N-(3-(4-(((((1-(4-((2,4-dioxothiazolidin-5-ylidene)methyl)pyrimidin-2-yl)piperidin-4-yl)methyl)amino)methyl)-5-fluoropyridin-2-yl)phenyl)acetamide | $C_{28}H_{28}FN_7O_3S$ | 561.63 | A14 | B8 |
| 120 | (Z)-N-(3-(6-amino-3-(((((1-(4-((2,4-dioxothiazolidin-5-ylidene)methyl)pyrimidin-2-yl)piperidin-4-yl)methyl)amino)methyl)pyridin-2-yl)phenyl)acetamide | $C_{28}H_{30}N_8O_3S$ | 558.655 | A15 | B8 |
| 121 | (Z)-5-((2-(4-(((((4-fluoro-6-(4-phenoxyphenyl)pyridin-2-yl)methyl)amino)methyl)piperidin-1-yl)pyrimidin-4-yl)methylene)thiazolidine-2,4-dione | $C_{32}H_{29}FN_6O_3S$ | 596.674 | A1 | B9 |
| 122 | (Z)-5-((2-(4-(((((6-(4-phenoxyphenyl)pyridin-2-yl)methyl)amino)methyl)piperidin-1-yl)pyrimidin-4-yl)methylene)thiazolidine-2,4-dione | $C_{32}H_{30}N_6O_3S$ | 578.684 | A2 | B9 |
| 123 | (Z)-5-((2-(4-(((((4-methyl-6-(4-phenoxyphenyl)pyridin-2-yl)methyl)amino)methyl)piperidin-1-yl)pyrimidin-4-yl)methylene)thiazolidine-2,4-dione | $C_{33}H_{32}N_6O_3S$ | 592.711 | A3 | B9 |
| 124 | (Z)-5-((2-(4-(((((3-methoxy-6-(4-phenoxyphenyl)pyridin-2-yl)methyl)amino)methyl)piperidin-1-yl)pyrimidin-4-yl)methylene)thiazolidine-2,4-dione | $C_{33}H_{32}N_6O_4S$ | 608.71 | A4 | B9 |
| 125 | (Z)-5-((2-(4-(((((6-(4-phenoxyphenyl)-4-(trifluoromethyl)pyridin-2-yl)methyl)amino)methyl)piperidin-1-yl)pyrimidin-4-yl)methylene)thiazolidine-2,4-dione | $C_{33}H_{29}F_3N_6O_3S$ | 646.682 | A5 | B9 |
| 126 | (Z)-5-((2-(4-(((((3-(4-phenoxyphenyl)isoquinolin-1-yl)methyl)amino)methyl)piperidin-1-yl)pyrimidin-4-yl)methylene)thiazolidine-2,4-dione | $C_{36}H_{32}N_6O_3S$ | 628.743 | A6 | B9 |

TABLE 3-continued

Additional prophetic embodiments of the invention.

| No. | Chemical Name | Formula | Mol. Weight | Reactant A | B |
|---|---|---|---|---|---|
| 127 | (Z)-5-((2-(4-((((2-(4-phenoxyphenyl)pyridin-3-yl)methyl)amino)methyl)piperidin-1-yl)pyrimidin-4-yl)methylene)thiazolidine-2,4-dione | $C_{32}H_{30}N_6O_3S$ | 578.684 | A7 | B9 |
| 128 | (Z)-5-((2-(4-((((2-(4-phenoxyphenyl)quinolin-3-yl)methyl)amino)methyl)piperidin-1-yl)pyrimidin-4-yl)methylene)thiazolidine-2,4-dione | $C_{36}H_{32}N_6O_3S$ | 628.743 | A8 | B9 |
| 129 | (Z)-5-((2-(4-((((6-(4-phenoxyphenyl)pyridin-3-yl)methyl)amino)methyl)piperidin-1-yl)pyrimidin-4-yl)methylene)thiazolidine-2,4-dione | $C_{32}H_{30}N_6O_3S$ | 578.684 | A9 | B9 |
| 130 | (Z)-5-((((1-(4-((2,4-dioxothiazolidin-5-ylidene)methyl)pyrimidin-2-yl)piperidin-4-yl)methyl)amino)methyl)-2-(4-phenoxyphenyl)nicotinonitrile | $C_{33}H_{29}N_7O_3S$ | 603.693 | A10 | B9 |
| 131 | (Z)-ethyl 5-((((1-(4-((2,4-dioxothiazolidin-5-ylidene)methyl)pyrimidin-2-yl)piperidin-4-yl)methyl)amino)methyl)-2-(4-phenoxyphenyl)nicotinate | $C_{35}H_{34}N_6O_5S$ | 650.747 | A11 | B9 |
| 132 | (Z)-5-((2-(4-((((2-(4-phenoxyphenyl)pyridin-4-yl)methyl)amino)methyl)piperidin-1-yl)pyrimidin-4-yl)methylene)thiazolidine-2,4-dione | $C_{32}H_{30}N_6O_3S$ | 578.684 | A12 | B9 |
| 133 | (Z)-5-((2-(4-((((2-(4-phenoxyphenyl)-6-(trifluoromethyl)pyridin-4-yl)methyl)amino)methyl)piperidin-1-yl)pyrimidin-4-yl)methylene)thiazolidine-2,4-dione | $C_{33}H_{29}F_3N_6O_3S$ | 646.682 | A13 | B9 |
| 134 | (Z)-5-((2-(4-((((5-fluoro-2-(4-phenoxyphenyl)pyridin-4-yl)methyl)amino)methyl)piperidin-1-yl)pyrimidin-4-yl)methylene)thiazolidine-2,4-dione | $C_{32}H_{29}FN_6O_3S$ | 596.674 | A14 | B9 |
| 135 | (Z)-5-((2-(4-((((6-amino-2-(4-phenoxyphenyl)pyridin-3-yl)methyl)amino)methyl)piperidin-1-yl)pyrimidin-4-yl)methylene)thiazolidine-2,4-dione | $C_{32}H_{31}N_7O_3S$ | 593.699 | A15 | B9 |
| 136 | (Z)-5-((2-(4-((((4-fluoro-6-(1H-indol-5-yl)pyridin-2-yl)methyl)amino)methyl)piperidin-1-yl)pyrimidin-4-yl)methylene)thiazolidine-2,4-dione | $C_{28}H_{26}FN_7O_2S$ | 543.615 | A1 | B10 |
| 137 | (Z)-5-((2-(4-((((6-(1H-indol-5-yl)pyridin-2-yl)methyl)amino)methyl)piperidin-1-yl)pyrimidin-4-yl)methylene)thiazolidine-2,4-dione | $C_{28}H_{27}N_7O_2S$ | 525.625 | A2 | B10 |
| 138 | (Z)-5-((2-(4-((((6-(1H-indol-5-yl)-4-methylpyridin-2-yl)methyl)amino)methyl)piperidin-1-yl)pyrimidin-4-yl)methylene)thiazolidine-2,4-dione | $C_{29}H_{29}N_7O_2S$ | 539.651 | A3 | B10 |
| 139 | (Z)-5-((2-(4-((((6-(1H-indol-5-yl)-3-methoxypyridin-2-yl)methyl)amino)methyl)piperidin-1-yl)pyrimidin-4-yl)methylene)thiazolidine-2,4-dione | $C_{29}H_{29}N_7O_3S$ | 555.651 | A4 | B10 |
| 140 | (Z)-5-((2-(4-((((6-(1H-indol-5-yl)-4-(trifluoromethyl)pyridin-2-yl)methyl)amino)methyl)piperidin-1-yl)pyrimidin-4-yl)methylene)thiazolidine-2,4-dione | $C_{29}H_{26}F_3N_7O_2S$ | 593.623 | A5 | B10 |
| 141 | (Z)-5-((2-(4-((((3-(1H-indol-5-yl)isoquinolin-1-yl)methyl)amino)methyl)piperidin-1-yl)pyrimidin-4-yl)methylene)thiazolidine-2,4-dione | $C_{32}H_{29}N_7O_2S$ | 575.683 | A6 | B10 |
| 142 | (Z)-5-((2-(4-((((2-(1H-indol-5-yl)pyridin-3-yl)methyl)amino)methyl)piperidin-1-yl)pyrimidin-4-yl)methylene)thiazolidine-2,4-dione | $C_{28}H_{27}N_7O_2S$ | 525.625 | A7 | B10 |
| 143 | (Z)-5-((2-(4-((((2-(1H-indol-5-yl)quinolin-3-yl)methyl)amino)methyl)piperidin-1-yl)pyrimidin-4-yl)methylene)thiazolidine-2,4-dione | $C_{32}H_{29}N_7O_2S$ | 575.683 | A8 | B10 |
| 144 | (Z)-5-((2-(4-((((6-(1H-indol-5-yl)pyridin-3-yl)methyl)amino)methyl)piperidin-1-yl)pyrimidin-4-yl)methylene)thiazolidine-2,4-dione | $C_{28}H_{27}N_7O_2S$ | 525.625 | A9 | B10 |
| 145 | (Z)-5-((((1-(4-((2,4-dioxothiazolidin-5-ylidene)methyl)pyrimidin-2-yl)piperidin-4-yl)methyl)amino)methyl)-2-(1H-indol-5-yl)nicotinonitrile | $C_{29}H_{26}N_8O_2S$ | 550.634 | A10 | B10 |
| 146 | (Z)-ethyl 5-((((1-(4-((2,4-dioxothiazolidin-5-ylidene)methyl)pyrimidin-2-yl)piperidin-4-yl)methyl)amino)methyl)-2-(1H-indol-5-yl)nicotinate | $C_{31}H_{31}N_7O_4S$ | 597.687 | A11 | B10 |
| 147 | (Z)-5-((2-(4-((((2-(1H-indol-5-yl)pyridin-4-yl)methyl)amino)methyl)piperidin-1-yl)pyrimidin-4-yl)methylene)thiazolidine-2,4-dione | $C_{28}H_{27}N_7O_2S$ | 525.625 | A12 | B10 |
| 148 | (Z)-5-((2-(4-((((2-(1H-indol-5-yl)-6-(trifluoromethyl)pyridin-4-yl)methyl)amino)methyl)piperidin-1-yl)pyrimidin-4-yl)methylene)thiazolidine-2,4-dione | $C_{29}H_{26}F_3N_7O_2S$ | 593.623 | A13 | B10 |

TABLE 3-continued

Additional prophetic embodiments of the invention.

| No. | Chemical Name | Formula | Mol. Weight | Reactant A | Reactant B |
|---|---|---|---|---|---|
| 149 | (Z)-5-((2-(4-(((((5-fluoro-2-(1H-indol-5-yl)pyridin-4-yl)methyl)amino)methyl)piperidin-1-yl)pyrimidin-4-yl)methylene)thiazolidine-2,4-dione | $C_{28}H_{26}FN_7O_2S$ | 543.615 | A14 | B10 |
| 150 | (Z)-5-((2-(4-(((((6-amino-2-(1H-indol-5-yl)pyridin-3-yl)methyl)amino)methyl)piperidin-1-yl)pyrimidin-4-yl)methylene)thiazolidine-2,4-dione | $C_{28}H_{28}N_8O_2S$ | 540.639 | A15 | B10 |
| 151 | (Z)-5-((2-(4-(((((4-fluoro-6-(isoquinolin-5-yl)pyridin-2-yl)methyl)amino)methyl)piperidin-1-yl)pyrimidin-4-yl)methylene)thiazolidine-2,4-dione | $C_{29}H_{26}FN_7O_2S$ | 555.626 | A1 | B11 |
| 152 | (Z)-5-((2-(4-(((((6-(isoquinolin-5-yl)pyridin-2-yl)methyl)amino)methyl)piperidin-1-yl)pyrimidin-4-yl)methylene)thiazolidine-2,4-dione | $C_{29}H_{27}N_7O_2S$ | 537.635 | A2 | B11 |
| 153 | (Z)-5-((2-(4-(((((6-(isoquinolin-5-yl)-4-methylpyridin-2-yl)methyl)amino)methyl)piperidin-1-yl)pyrimidin-4-yl)methylene)thiazolidine-2,4-dione | $C_{30}H_{29}N_7O_2S$ | 551.662 | A3 | B11 |
| 154 | (Z)-5-((2-(4-(((((6-(isoquinolin-5-yl)-3-methoxypyridin-2-yl)methyl)amino)methyl)piperidin-1-yl)pyrimidin-4-yl)methylene)thiazolidine-2,4-dione | $C_{30}H_{29}N_7O_3S$ | 567.661 | A4 | B11 |
| 155 | (Z)-5-((2-(4-(((((6-(isoquinolin-5-yl)-4-(trifluoromethyl)pyridin-2-yl)methyl)amino)methyl)piperidin-1-yl)pyrimidin-4-yl)methylene)thiazolidine-2,4-dione | $C_{30}H_{26}F_3N_7O_2S$ | 605.633 | A5 | B11 |
| 156 | (Z)-5-((2-(4-(((([3,5'-biisoquinolin]-1-ylmethyl)amino)methyl)piperidin-1-yl)pyrimidin-4-yl)methylene)thiazolidine-2,4-dione | $C_{33}H_{29}N_7O_2S$ | 587.694 | A6 | B11 |
| 157 | (Z)-5-((2-(4-(((((2-(isoquinolin-5-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A7 | B11 |
| 158 | (Z)-5-((2-(4-(((((2-(isoquinolin-5-yl)quinolin-3-yl)methyl)amino)methyl)piperidin-1-yl)pyrimidin-4-yl)methylene)thiazolidine-2,4-dione | $C_{33}H_{29}N_7O_2S$ | 587.694 | A8 | B11 |
| 159 | (Z)-5-((2-(4-(((((6-(isoquinolin-5-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A9 | B11 |
| 160 | (Z)-5-(((((1-(4-((2,4-dioxothiazolidin-5-ylidene)methyl)pyrimidin-2-yl)piperidin-4-yl)methyl)amino)methyl)-2-(isoquinolin-5-yl)nicotinonitrile | $C_{30}H_{26}N_8O_2S$ | 562.645 | A10 | B11 |
| 161 | (Z)-ethyl 5-(((((1-(4-((2,4-dioxothiazolidin-5-ylidene)methyl)pyrimidin-2-yl)piperidin-4-yl)methyl)amino)methyl)-2-(isoquinolin-5-yl)nicotinate | $C_{32}H_{31}N_7O_4S$ | 609.698 | A11 | B11 |
| 162 | (Z)-5-((2-(4-(((((2-(isoquinolin-5-yl)pyridin-4-yl)methyl)amino)methyl)piperidin-1-yl)pyrimidin-4-yl)methylene)thiazolidine-2,4-dione | $C_{29}H_{27}N_7O_2S$ | 537.635 | A12 | B11 |
| 163 | (Z)-5-((2-(4-(((((2-(isoquinolin-5-yl)-6-(trifluoromethyl)pyridin-4-yl)methyl)amino)methyl)piperidin-1-yl)pyrimidin-4-yl)methylene)thiazolidine-2,4-dione | $C_{30}H_{26}F_3N_7O_2S$ | 605.633 | A13 | B11 |
| 164 | (Z)-5-((2-(4-(((((5-fluoro-2-(isoquinolin-5-yl)pyridin-4-yl)methyl)amino)methyl)piperidin-1-yl)pyrimidin-4-yl)methylene)thiazolidine-2,4-dione | $C_{29}H_{26}FN_7O_2S$ | 555.626 | A14 | B11 |
| 165 | (Z)-5-((2-(4-(((((6-amino-2-(isoquinolin-5-yl)pyridin-3-yl)methyl)amino)methyl)piperidin-1-yl)pyrimidin-4-yl)methylene)thiazolidine-2,4-dione | $C_{29}H_{28}N_8O_2S$ | 552.65 | A15 | B11 |
| 166 | (Z)-5-((2-(4-(((((4-fluoro-6-(thiophen-3-yl)pyridin-2-yl)methyl)amino)methyl)piperidin-1-yl)pyrimidin-4-yl)methylene)thiazolidine-2,4-dione | $C_{24}H_{23}FN_6O_2S_2$ | 510.607 | A1 | B12 |
| 167 | (Z)-5-((2-(4-(((((6-(thiophen-3-yl)pyridin-2-yl)methyl)amino)methyl)piperidin-1-yl)pyrimidin-4-yl)methylene)thiazolidine-2,4-dione | $C_{24}H_{24}N_6O_2S_2$ | 492.616 | A2 | B12 |
| 168 | (Z)-5-((2-(4-(((((4-methyl-6-(thiophen-3-yl)pyridin-2-yl)methyl)amino)methyl)piperidin-1-yl)pyrimidin-4-yl)methylene)thiazolidine-2,4-dione | $C_{25}H_{26}N_6O_2S_2$ | 506.643 | A3 | B12 |
| 169 | (Z)-5-((2-(4-(((((3-methoxy-6-(thiophen-3-yl)pyridin-2-yl)methyl)amino)methyl)piperidin-1-yl)pyrimidin-4-yl)methylene)thiazolidine-2,4-dione | $C_{25}H_{26}N_6O_3S_2$ | 522.642 | A4 | B12 |
| 170 | (Z)-5-((2-(4-(((((6-(thiophen-3-yl)-4-(trifluoromethyl)pyridin-2-yl)methyl)amino)methyl)piperidin-1-yl)pyrimidin-4-yl)methylene)thiazolidine-2,4-dione | $C_{25}H_{23}F_3N_6O_2S_2$ | 560.614 | A5 | B12 |

TABLE 3-continued

Additional prophetic embodiments of the invention.

| No. | Chemical Name | Formula | Mol. Weight | Reactant A | Reactant B |
|---|---|---|---|---|---|
| 171 | (Z)-5-((2-(4-((((3-(thiophen-3-yl)isoquinolin-1-yl)methyl)amino)methyl)piperidin-1-yl)pyrimidin-4-yl)methylene)thiazolidine-2,4-dione | $C_{28}H_{26}N_6O_2S_2$ | 542.675 | A6 | B12 |
| 172 | (Z)-5-((2-(4-((((2-(thiophen-3-yl)pyridin-3-yl)methyl)amino)methyl)piperidin-1-yl)pyrimidin-4-yl)methylene)thiazolidine-2,4-dione | $C_{24}H_{24}N_6O_2S_2$ | 492.616 | A7 | B12 |
| 173 | (Z)-5-((2-(4-((((2-(thiophen-3-yl)quinolin-3-yl)methyl)amino)methyl)piperidin-1-yl)pyrimidin-4-yl)methylene)thiazolidine-2,4-dione | $C_{28}H_{26}N_6O_2S_2$ | 542.675 | A8 | B12 |
| 174 | (Z)-5-((2-(4-((((6-(thiophen-3-yl)pyridin-3-yl)methyl)amino)methyl)piperidin-1-yl)pyrimidin-4-yl)methylene)thiazolidine-2,4-dione | $C_{24}H_{24}N_6O_2S_2$ | 492.616 | A9 | B12 |
| 175 | (Z)-5-((((1-(4-((2,4-dioxothiazolidin-5-ylidene)methyl)pyrimidin-2-yl)piperidin-4-yl)methyl)amino)methyl)-2-(thiophen-3-yl)nicotinonitrile | $C_{25}H_{23}N_7O_2S_2$ | 517.626 | A10 | B12 |
| 176 | (Z)-ethyl 5-((((1-(4-((2,4-dioxothiazolidin-5-ylidene)methyl)pyrimidin-2-yl)piperidin-4-yl)methyl)amino)methyl)-2-(thiophen-3-yl)nicotinate | $C_{27}H_{28}N_6O_4S_2$ | 564.679 | A11 | B12 |
| 177 | (Z)-5-((2-(4-((((2-(thiophen-3-yl)pyridin-4-yl)methyl)amino)methyl)piperidin-1-yl)pyrimidin-4-yl)methylene)thiazolidine-2,4-dione | $C_{24}H_{24}N_6O_2S_2$ | 492.616 | A12 | B12 |
| 178 | (Z)-5-((2-(4-((((2-(thiophen-3-yl)-6-(trifluoromethyl)pyridin-4-yl)methyl)amino)methyl)piperidin-1-yl)pyrimidin-4-yl)methylene)thiazolidine-2,4-dione | $C_{25}H_{23}F_3N_6O_2S_2$ | 560.614 | A13 | B12 |
| 179 | (Z)-5-((2-(4-((((5-fluoro-2-(thiophen-3-yl)pyridin-4-yl)methyl)amino)methyl)piperidin-1-yl)pyrimidin-4-yl)methylene)thiazolidine-2,4-dione | $C_{24}H_{23}FN_6O_2S_2$ | 510.607 | A14 | B12 |
| 180 | (Z)-5-((2-(4-((((6-amino-2-(thiophen-3-yl)pyridin-3-yl)methyl)amino)methyl)piperidin-1-yl)pyrimidin-4-yl)methylene)thiazolidine-2,4-dione | $C_{24}H_{25}N_7O_2S_2$ | 507.631 | A15 | B12 |
| 181 | (Z)-5-((2-(4-((((6-(benzo[b]thiophen-3-yl)-4-fluoropyridin-2-yl)methyl)amino)methyl)piperidin-1-yl)pyrimidin-4-yl)methylene)thiazolidine-2,4-dione | $C_{28}H_{25}FN_6O_2S_2$ | 560.666 | A1 | B13 |
| 182 | (Z)-5-((2-(4-((((6-(benzo[b]thiophen-3-yl)pyridin-2-yl)methyl)amino)methyl)piperidin-1-yl)pyrimidin-4-yl)methylene)thiazolidine-2,4-dione | $C_{28}H_{26}N_6O_2S_2$ | 542.675 | A2 | B13 |
| 183 | (Z)-5-((2-(4-((((6-(benzo[b]thiophen-3-yl)-4-methylpyridin-2-yl)methyl)amino)methyl)piperidin-1-yl)pyrimidin-4-yl)methylene)thiazolidine-2,4-dione | $C_{29}H_{28}N_6O_2S_2$ | 556.702 | A3 | B13 |
| 184 | (Z)-5-((2-(4-((((6-(benzo[b]thiophen-3-yl)-3-methoxypyridin-2-yl)methyl)amino)methyl)piperidin-1-yl)pyrimidin-4-yl)methylene)thiazolidine-2,4-dione | $C_{29}H_{28}N_6O_3S_2$ | 572.701 | A4 | B13 |
| 185 | (Z)-5-((2-(4-((((6-(benzo[b]thiophen-3-yl)-4-(trifluoromethyl)pyridin-2-yl)methyl)amino)methyl)piperidin-1-yl)pyrimidin-4-yl)methylene)thiazolidine-2,4-dione | $C_{29}H_{25}F_3N_6O_2S_2$ | 610.673 | A5 | B13 |
| 186 | (Z)-5-((2-(4-((((3-(benzo[b]thiophen-3-yl)isoquinolin-1-yl)methyl)amino)methyl)piperidin-1-yl)pyrimidin-4-yl)methylene)thiazolidine-2,4-dione | $C_{32}H_{28}N_6O_2S_2$ | 592.734 | A6 | B13 |
| 187 | (Z)-5-((2-(4-((((2-(benzo[b]thiophen-3-yl)pyridin-3-yl)methyl)amino)methyl)piperidin-1-yl)pyrimidin-4-yl)methylene)thiazolidine-2,4-dione | $C_{28}H_{26}N_6O_2S_2$ | 542.675 | A7 | B13 |
| 188 | (Z)-5-((2-(4-((((2-(benzo[b]thiophen-3-yl)quinolin-3-yl)methyl)amino)methyl)piperidin-1-yl)pyrimidin-4-yl)methylene)thiazolidine-2,4-dione | $C_{32}H_{28}N_6O_2S_2$ | 592.734 | A8 | B13 |
| 189 | (Z)-5-((2-(4-((((6-(benzo[b]thiophen-3-yl)pyridin-3-yl)methyl)amino)methyl)piperidin-1-yl)pyrimidin-4-yl)methylene)thiazolidine-2,4-dione | $C_{28}H_{26}N_6O_2S_2$ | 542.675 | A9 | B13 |
| 190 | (Z)-2-(benzo[b]thiophen-3-yl)-5-((((1-(4-((2,4-dioxothiazolidin-5-ylidene)methyl)pyrimidin-2-yl)piperidin-4-yl)methyl)amino)methyl)nicotinonitrile | $C_{29}H_{25}N_7O_2S_2$ | 567.685 | A10 | B13 |
| 191 | (Z)-ethyl 2-(benzo[b]thiophen-3-yl)-5-((((1-(4-((2,4-dioxothiazolidin-5-ylidene)methyl)pyrimidin-2-yl)piperidin-4-yl)methyl)amino)methyl)nicotinate | $C_{31}H_{30}N_6O_4S_2$ | 614.738 | A11 | B13 |
| 192 | (Z)-5-((2-(4-((((2-(benzo[b]thiophen-3-yl)pyridin-4-yl)methyl)amino)methyl)piperidin-1-yl)pyrimidin-4-yl)methylene)thiazolidine-2,4-dione | $C_{28}H_{26}N_6O_2S_2$ | 542.675 | A12 | B13 |

TABLE 3-continued

Additional prophetic embodiments of the invention.

| No. | Chemical Name | Formula | Mol. Weight | Reactant A | Reactant B |
|---|---|---|---|---|---|
| 193 | (Z)-5-((2-(4-((((2-(benzo[b]thiophen-3-yl)-6-(trifluoromethyl)pyridin-4-yl)methyl)amino)methyl)piperidin-1-yl)pyrimidin-4-yl)methylene)thiazolidine-2,4-dione | $C_{29}H_{25}F_3N_6O_2S_2$ | 610.673 | A13 | B13 |
| 194 | (Z)-5-((2-(4-((((2-(benzo[b]thiophen-3-yl)-5-fluoropyridin-4-yl)methyl)amino)methyl)piperidin-1-yl)pyrimidin-4-yl)methylene)thiazolidine-2,4-dione | $C_{28}H_{25}FN_6O_2S_2$ | 560.666 | A14 | B13 |
| 195 | (Z)-5-((2-(4-((((6-amino-2-(benzo[b]thiophen-3-yl)pyridin-3-yl)methyl)amino)methyl)piperidin-1-yl)pyrimidin-4-yl)methylene)thiazolidine-2,4-dione | $C_{28}H_{27}N_7O_2S_2$ | 557.69 | A15 | B13 |
| 196 | (Z)-5-((2-(4-((((6-(5-acetylthiophen-2-yl)-4-fluoropyridin-2-yl)methyl)amino)methyl)piperidin-1-yl)pyrimidin-4-yl)methylene)thiazolidine-2,4-dione | $C_{26}H_{25}FN_6O_3S_2$ | 552.644 | A1 | B14 |
| 197 | (Z)-5-((2-(4-((((6-(5-acetylthiophen-2-yl)pyridin-2-yl)methyl)amino)methyl)piperidin-1-yl)pyrimidin-4-yl)methylene)thiazolidine-2,4-dione | $C_{26}H_{26}N_6O_3S_2$ | 534.653 | A2 | B14 |
| 198 | (Z)-5-((2-(4-((((6-(5-acetylthiophen-2-yl)-4-methylpyridin-2-yl)methyl)amino)methyl)piperidin-1-yl)pyrimidin-4-yl)methylene)thiazolidine-2,4-dione | $C_{27}H_{28}N_6O_3S_2$ | 548.68 | A3 | B14 |
| 199 | (Z)-5-((2-(4-((((6-(5-acetylthiophen-2-yl)-3-methoxypyridin-2-yl)methyl)amino)methyl)piperidin-1-yl)pyrimidin-4-yl)methylene)thiazolidine-2,4-dione | $C_{27}H_{28}N_6O_4S_2$ | 564.679 | A4 | B14 |
| 200 | (Z)-5-((2-(4-((((6-(5-acetylthiophen-2-yl)-4-(trifluoromethyl)pyridin-2-yl)methyl)amino)methyl)piperidin-1-yl)pyrimidin-4-yl)methylene)thiazolidine-2,4-dione | $C_{27}H_{25}F_3N_6O_3S_2$ | 602.651 | A5 | B14 |
| 201 | (Z)-5-((2-(4-((((3-(5-acetylthiophen-2-yl)isoquinolin-1-yl)methyl)amino)methyl)piperidin-1-yl)pyrimidin-4-yl)methylene)thiazolidine-2,4-dione | $C_{30}H_{28}N_6O_3S_2$ | 584.712 | A6 | B14 |
| 202 | (Z)-5-((2-(4-((((2-(5-acetylthiophen-2-yl)pyridin-3-yl)methyl)amino)methyl)piperidin-1-yl)pyrimidin-4-yl)methylene)thiazolidine-2,4-dione | $C_{26}H_{26}N_6O_3S_2$ | 534.653 | A7 | B14 |
| 203 | (Z)-5-((2-(4-((((2-(5-acetylthiophen-2-yl)quinolin-3-yl)methyl)amino)methyl)piperidin-1-yl)pyrimidin-4-yl)methylene)thiazolidine-2,4-dione | $C_{30}H_{28}N_6O_3S_2$ | 584.712 | A8 | B14 |
| 204 | (Z)-5-((2-(4-((((6-(5-acetylthiophen-2-yl)pyridin-3-yl)methyl)amino)methyl)piperidin-1-yl)pyrimidin-4-yl)methylene)thiazolidine-2,4-dione | $C_{26}H_{26}N_6O_3S_2$ | 534.653 | A9 | B14 |
| 205 | (Z)-2-(5-acetylthiophen-2-yl)-5-((((1-(4-((2,4-dioxothiazolidin-5-ylidene)methyl)pyrimidin-2-yl)piperidin-4-yl)methyl)amino)methyl)nicotinonitrile | $C_{27}H_{25}N_7O_3S_2$ | 559.663 | A10 | B14 |
| 206 | (Z)-ethyl 2-(5-acetylthiophen-2-yl)-5-((((1-(4-((2,4-dioxothiazolidin-5-ylidene)methyl)pyrimidin-2-yl)piperidin-4-yl)methyl)amino)methyl)nicotinate | $C_{29}H_{30}N_6O_5S_2$ | 606.716 | A11 | B14 |
| 207 | (Z)-5-((2-(4-((((2-(5-acetylthiophen-2-yl)pyridin-4-yl)methyl)amino)methyl)piperidin-1-yl)pyrimidin-4-yl)methylene)thiazolidine-2,4-dione | $C_{26}H_{26}N_6O_3S_2$ | 534.653 | A12 | B14 |
| 208 | (Z)-5-((2-(4-((((2-(5-acetylthiophen-2-yl)-6-(trifluoromethyl)pyridin-4-yl)methyl)amino)methyl)piperidin-1-yl)pyrimidin-4-yl)methylene)thiazolidine-2,4-dione | $C_{27}H_{25}F_3N_6O_3S_2$ | 602.651 | A13 | B14 |
| 209 | (Z)-5-((2-(4-((((2-(5-acetylthiophen-2-yl)-5-fluoropyridin-4-yl)methyl)amino)methyl)piperidin-1-yl)pyrimidin-4-yl)methylene)thiazolidine-2,4-dione | $C_{26}H_{25}FN_6O_3S_2$ | 552.644 | A14 | B14 |
| 210 | (Z)-5-((2-(4-((((2-(5-acetylthiophen-2-yl)-6-aminopyridin-3-yl)methyl)amino)methyl)piperidin-1-yl)pyrimidin-4-yl)methylene)thiazolidine-2,4-dione | $C_{26}H_{27}N_7O_3S_2$ | 549.668 | A15 | B14 |
| 211 | (Z)-5-((2-(4-((((4-fluoro-6-(furan-2-yl)pyridin-2-yl)methyl)amino)methyl)piperidin-1-yl)pyrimidin-4-yl)methylene)thiazolidine-2,4-dione | $C_{24}H_{23}FN_6O_3S$ | 494.541 | A1 | B15 |
| 212 | (Z)-5-((2-(4-((((6-(furan-2-yl)pyridin-2-yl)methyl)amino)methyl)piperidin-1-yl)pyrimidin-4-yl)methylene)thiazolidine-2,4-dione | $C_{24}H_{24}N_6O_3S$ | 476.551 | A2 | B15 |
| 213 | (Z)-5-((2-(4-((((6-(furan-2-yl)-4-methylpyridin-2-yl)methyl)amino)methyl)piperidin-1-yl)pyrimidin-4-yl)methylene)thiazolidine-2,4-dione | $C_{25}H_{26}N_6O_3S$ | 490.577 | A3 | B15 |
| 214 | (Z)-5-((2-(4-((((6-(furan-2-yl)-3-methoxypyridin-2-yl)methyl)amino)methyl)piperidin-1-yl)pyrimidin-4-yl)methylene)thiazolidine-2,4-dione | $C_{25}H_{26}N_6O_4S$ | 506.577 | A4 | B15 |

TABLE 3-continued

Additional prophetic embodiments of the invention.

| No. | Chemical Name | Formula | Mol. Weight | Reactant A | Reactant B |
|---|---|---|---|---|---|
| 215 | (Z)-5-((2-(4-(((6-(furan-2-yl)-4-(trifluoromethyl)pyridin-2-yl)methyl)amino)methyl)piperidin-1-yl)pyrimidin-4-yl)methylene)thiazolidine-2,4-dione | $C_{25}H_{23}F_3N_6O_3S$ | 544.549 | A5 | B15 |
| 216 | (Z)-5-((2-(4-((((3-(furan-2-yl)isoquinolin-1-yl)methyl)amino)methyl)piperidin-1-yl)pyrimidin-4-yl)methylene)thiazolidine-2,4-dione | $C_{28}H_{26}N_6O_3S$ | 526.609 | A6 | B15 |
| 217 | (Z)-5-((2-(4-((((2-(furan-2-yl)pyridin-3-yl)methyl)amino)methyl)piperidin-1-yl)pyrimidin-4-yl)methylene)thiazolidine-2,4-dione | $C_{24}H_{24}N_6O_3S$ | 476.551 | A7 | B15 |
| 218 | (Z)-5-((2-(4-((((2-(furan-2-yl)quinolin-3-yl)methyl)amino)methyl)piperidin-1-yl)pyrimidin-4-yl)methylene)thiazolidine-2,4-dione | $C_{28}H_{26}N_6O_3S$ | 526.609 | A8 | B15 |
| 219 | (Z)-5-((2-(4-((((6-(furan-2-yl)pyridin-3-yl)methyl)amino)methyl)piperidin-1-yl)pyrimidin-4-yl)methylene)thiazolidine-2,4-dione | $C_{24}H_{24}N_6O_3S$ | 476.551 | A9 | B15 |
| 220 | (Z)-5-((((1-(4-((2,4-dioxothiazolidin-5-ylidene)methyl)pyrimidin-2-yl)piperidin-4-yl)methyl)amino)methyl)-2-(furan-2-yl)nicotinonitrile | $C_{25}H_{23}N_7O_3S$ | 501.56 | A10 | B15 |
| 221 | (Z)-ethyl 5-((((1-(4-((2,4-dioxothiazolidin-5-ylidene)methyl)pyrimidin-2-yl)piperidin-4-yl)methyl)amino)methyl)-2-(furan-2-yl)nicotinate | $C_{27}H_{28}N_6O_5S$ | 548.613 | A11 | B15 |
| 222 | (Z)-5-((2-(4-((((2-(furan-2-yl)pyridin-4-yl)methyl)amino)methyl)piperidin-1-yl)pyrimidin-4-yl)methylene)thiazolidine-2,4-dione | $C_{24}H_{24}N_6O_3S$ | 476.551 | A12 | B15 |
| 223 | (Z)-5-((2-(4-((((2-(furan-2-yl)-6-(trifluoromethyl)pyridin-4-yl)methyl)amino)methyl)piperidin-1-yl)pyrimidin-4-yl)methylene)thiazolidine-2,4-dione | $C_{25}H_{23}F_3N_6O_3S$ | 544.549 | A13 | B15 |
| 224 | (Z)-5-((2-(4-((((5-fluoro-2-(furan-2-yl)pyridin-4-yl)methyl)amino)methyl)piperidin-1-yl)pyrimidin-4-yl)methylene)thiazolidine-2,4-dione | $C_{24}H_{23}FN_6O_3S$ | 494.541 | A14 | B15 |
| 225 | (Z)-5-((2-(4-((((6-amino-2-(furan-2-yl)pyridin-3-yl)methyl)amino)methyl)piperidin-1-yl)pyrimidin-4-yl)methylene)thiazolidine-2,4-dione | $C_{24}H_{25}N_7O_3S$ | 491.565 | A15 | B15 |
| 226 | (Z)-5-((2-(4-((((6-(benzofuran-2-yl)-4-fluoropyridin-2-yl)methyl)amino)methyl)piperidin-1-yl)pyrimidin-4-yl)methylene)thiazolidine-2,4-dione | $C_{28}H_{25}FN_6O_3S$ | 544.6 | A1 | B16 |
| 227 | (Z)-5-((2-(4-((((6-(benzofuran-2-yl)pyridin-2-yl)methyl)amino)methyl)piperidin-1-yl)pyrimidin-4-yl)methylene)thiazolidine-2,4-dione | $C_{28}H_{26}N_6O_3S$ | 526.609 | A2 | B16 |
| 228 | (Z)-5-((2-(4-((((6-(benzofuran-2-yl)-4-methylpyridin-2-yl)methyl)amino)methyl)piperidin-1-yl)pyrimidin-4-yl)methylene)thiazolidine-2,4-dione | $C_{29}H_{28}N_6O_3S$ | 540.636 | A3 | B16 |
| 229 | (Z)-5-((2-(4-((((6-(benzofuran-2-yl)-3-methoxypyridin-2-yl)methyl)amino)methyl)piperidin-1-yl)pyrimidin-4-yl)methylene)thiazolidine-2,4-dione | $C_{29}H_{28}N_6O_4S$ | 556.635 | A4 | B16 |
| 230 | (Z)-5-((2-(4-((((6-(benzofuran-2-yl)-4-(trifluoromethyl)pyridin-2-yl)methyl)amino)methyl)piperidin-1-yl)pyrimidin-4-yl)methylene)thiazolidine-2,4-dione | $C_{29}H_{25}F_3N_6O_3S$ | 594.607 | A5 | B16 |
| 231 | (Z)-5-((2-(4-((((3-(benzofuran-2-yl)isoquinolin-1-yl)methyl)amino)methyl)piperidin-1-yl)pyrimidin-4-yl)methylene)thiazolidine-2,4-dione | $C_{32}H_{28}N_6O_3S$ | 576.668 | A6 | B16 |
| 232 | (Z)-5-((2-(4-((((2-(benzofuran-2-yl)pyridin-3-yl)methyl)amino)methyl)piperidin-1-yl)pyrimidin-4-yl)methylene)thiazolidine-2,4-dione | $C_{28}H_{26}N_6O_3S$ | 526.609 | A7 | B16 |
| 233 | (Z)-5-((2-(4-((((2-(benzofuran-2-yl)quinolin-3-yl)methyl)amino)methyl)piperidin-1-yl)pyrimidin-4-yl)methylene)thiazolidine-2,4-dione | $C_{32}H_{28}N_6O_3S$ | 576.668 | A8 | B16 |
| 234 | (Z)-5-((2-(4-((((6-(benzofuran-2-yl)pyridin-3-yl)methyl)amino)methyl)piperidin-1-yl)pyrimidin-4-yl)methylene)thiazolidine-2,4-dione | $C_{28}H_{26}N_6O_3S$ | 526.609 | A9 | B16 |
| 235 | (Z)-2-(benzofuran-2-yl)-5-((((1-(4-((2,4-dioxothiazolidin-5-ylidene)methyl)pyrimidin-2-yl)piperidin-4-yl)methyl)amino)methyl)nicotinonitrile | $C_{29}H_{25}N_7O_3S$ | 551.619 | A10 | B16 |
| 236 | (Z)-ethyl 2-(benzofuran-2-yl)-5-((((1-(4-((2,4-dioxothiazolidin-5-ylidene)methyl)pyrimidin-2-yl)piperidin-4-yl)methyl)amino)methyl)nicotinate | $C_{31}H_{30}N_6O_5S$ | 598.672 | A11 | B16 |

TABLE 3-continued

Additional prophetic embodiments of the invention.

| No. | Chemical Name | Formula | Mol. Weight | Reactant A | Reactant B |
|---|---|---|---|---|---|
| 237 | (Z)-5-((2-(4-((((2-(benzofuran-2-yl)pyridin-4-yl)methyl)amino)methyl)piperidin-1-yl)pyrimidin-4-yl)methylene)thiazolidine-2,4-dione | $C_{28}H_{26}N_6O_3S$ | 526.609 | A12 | B16 |
| 238 | (Z)-5-((2-(4-((((2-(benzofuran-2-yl)-6-(trifluoromethyl)pyridin-4-yl)methyl)amino)methyl)piperidin-1-yl)pyrimidin-4-yl)methylene)thiazolidine-2,4-dione | $C_{29}H_{25}F_3N_6O_3S$ | 594.607 | A13 | B16 |
| 239 | (Z)-5-((2-(4-((((2-(benzofuran-2-yl)-5-fluoropyridin-4-yl)methyl)amino)methyl)piperidin-1-yl)pyrimidin-4-yl)methylene)thiazolidine-2,4-dione | $C_{28}H_{25}FN_6O_3S$ | 544.6 | A14 | B16 |
| 240 | (Z)-5-((2-(4-(((((6-amino-2-(benzofuran-2-yl)pyridin-3-yl)methyl)amino)methyl)piperidin-1-yl)pyrimidin-4-yl)methylene)thiazolidine-2,4-dione | $C_{28}H_{27}N_7O_3S$ | 541.624 | A15 | B16 |
| 241 | (Z)-5-((2-(4-((((4-fluoro-6-(furan-3-yl)pyridin-2-yl)methyl)amino)methyl)piperidin-1-yl)pyrimidin-4-yl)methylene)thiazolidine-2,4-dione | $C_{24}H_{23}FN_6O_3S$ | 494.541 | A1 | B17 |
| 242 | (Z)-5-((2-(4-((((6-(furan-3-yl)pyridin-2-yl)methyl)amino)methyl)piperidin-1-yl)pyrimidin-4-yl)methylene)thiazolidine-2,4-dione | $C_{24}H_{24}N_6O_3S$ | 476.551 | A2 | B17 |
| 243 | (Z)-5-((2-(4-((((6-(furan-3-yl)-4-methylpyridin-2-yl)methyl)amino)methyl)piperidin-1-yl)pyrimidin-4-yl)methylene)thiazolidine-2,4-dione | $C_{25}H_{26}N_6O_3S$ | 490.577 | A3 | B17 |
| 244 | (Z)-5-((2-(4-((((6-(furan-3-yl)-3-methoxypyridin-2-yl)methyl)amino)methyl)piperidin-1-yl)pyrimidin-4-yl)methylene)thiazolidine-2,4-dione | $C_{25}H_{26}N_6O_4S$ | 506.577 | A4 | B17 |
| 245 | (Z)-5-((2-(4-((((6-(furan-3-yl)-4-(trifluoromethyl)pyridin-2-yl)methyl)amino)methyl)piperidin-1-yl)pyrimidin-4-yl)methylene)thiazolidine-2,4-dione | $C_{25}H_{23}F_3N_6O_3S$ | 544.549 | A5 | B17 |
| 246 | (Z)-5-((2-(4-((((3-(furan-3-yl)isoquinolin-1-yl)methyl)amino)methyl)piperidin-1-yl)pyrimidin-4-yl)methylene)thiazolidine-2,4-dione | $C_{28}H_{26}N_6O_3S$ | 526.609 | A6 | B17 |
| 247 | (Z)-5-((2-(4-((((2-(furan-3-yl)pyridin-3-yl)methyl)amino)methyl)piperidin-1-yl)pyrimidin-4-yl)methylene)thiazolidine-2,4-dione | $C_{24}H_{24}N_6O_3S$ | 476.551 | A7 | B17 |
| 248 | (Z)-5-((2-(4-((((2-(furan-3-yl)quinolin-3-yl)methyl)amino)methyl)piperidin-1-yl)pyrimidin-4-yl)methylene)thiazolidine-2,4-dione | $C_{28}H_{26}N_6O_3S$ | 526.609 | A8 | B17 |
| 249 | (Z)-5-((2-(4-((((6-(furan-3-yl)pyridin-3-yl)methyl)amino)methyl)piperidin-1-yl)pyrimidin-4-yl)methylene)thiazolidine-2,4-dione | $C_{24}H_{24}N_6O_3S$ | 476.551 | A9 | B17 |
| 250 | (Z)-5-((((1-(4-((2,4-dioxothiazolidin-5-ylidene)methyl)pyrimidin-2-yl)piperidin-4-yl)methyl)amino)methyl)-2-(furan-3-yl)nicotinonitrile | $C_{25}H_{23}N_7O_3S$ | 501.56 | A10 | B17 |
| 251 | (Z)-ethyl 5-((((1-(4-((2,4-dioxothiazolidin-5-ylidene)methyl)pyrimidin-2-yl)piperidin-4-yl)methyl)amino)methyl)-2-(furan-3-yl)nicotinate | $C_{27}H_{28}N_6O_5S$ | 548.613 | A11 | B17 |
| 252 | (Z)-5-((2-(4-((((2-(furan-3-yl)pyridin-4-yl)methyl)amino)methyl)piperidin-1-yl)pyrimidin-4-yl)methylene)thiazolidine-2,4-dione | $C_{24}H_{24}N_6O_3S$ | 476.551 | A12 | B17 |
| 253 | (Z)-5-((2-(4-((((2-(furan-3-yl)-6-(trifluoromethyl)pyridin-4-yl)methyl)amino)methyl)piperidin-1-yl)pyrimidin-4-yl)methylene)thiazolidine-2,4-dione | $C_{25}H_{23}F_3N_6O_3S$ | 544.549 | A13 | B17 |
| 254 | (Z)-5-((2-(4-((((5-fluoro-2-(furan-3-yl)pyridin-4-yl)methyl)amino)methyl)piperidin-1-yl)pyrimidin-4-yl)methylene)thiazolidine-2,4-dione | $C_{24}H_{23}FN_6O_3S$ | 494.541 | A14 | B17 |
| 255 | (Z)-5-((2-(4-(((((6-amino-2-(furan-3-yl)pyridin-3-yl)methyl)amino)methyl)piperidin-1-yl)pyrimidin-4-yl)methylene)thiazolidine-2,4-dione | $C_{24}H_{25}N_7O_3S$ | 491.565 | A15 | B17 |
| 256 | (Z)-5-((2-(4-((((4-fluoro-6-(1H-pyrrol-2-yl)pyridin-2-yl)methyl)amino)methyl)piperidin-1-yl)pyrimidin-4-yl)methylene)thiazolidine-2,4-dione | $C_{24}H_{24}FN_7O_2S$ | 493.556 | A1 | B18 |
| 257 | (Z)-5-((2-(4-((((6-(1H-pyrrol-2-yl)pyridin-2-yl)methyl)amino)methyl)piperidin-1-yl)pyrimidin-4-yl)methylene)thiazolidine-2,4-dione | $C_{24}H_{25}N_7O_2S$ | 475.566 | A2 | B18 |
| 258 | (Z)-5-((2-(4-((((4-methyl-6-(1H-pyrrol-2-yl)pyridin-2-yl)methyl)amino)methyl)piperidin-1-yl)pyrimidin-4-yl)methylene)thiazolidine-2,4-dione | $C_{25}H_{27}N_7O_2S$ | 489.593 | A3 | B18 |
| 259 | (Z)-5-((2-(4-((((3-methoxy-6-(1H-pyrrol-2-yl)pyridin-2-yl)methyl)amino)methyl)piperidin-1-yl)pyrimidin-4-yl)methylene)thiazolidine-2,4-dione | $C_{25}H_{27}N_7O_3S$ | 505.592 | A4 | B18 |

TABLE 3-continued

Additional prophetic embodiments of the invention.

| No. | Chemical Name | Formula | Mol. Weight | Reactant A | Reactant B |
|---|---|---|---|---|---|
| 260 | (Z)-5-((2-(4-(((6-(1H-pyrrol-2-yl)-4-(trifluoromethyl)pyridin-2-yl)methyl)amino)methyl)piperidin-1-yl)pyrimidin-4-yl)methylene)thiazolidine-2,4-dione | $C_{25}H_{24}F_3N_7O_2S$ | 543.564 | A5 | B18 |
| 261 | (Z)-5-((2-(4-((((3-(1H-pyrrol-2-yl)isoquinolin-1-yl)methyl)amino)methyl)piperidin-1-yl)pyrimidin-4-yl)methylene)thiazolidine-2,4-dione | $C_{28}H_{27}N_7O_2S$ | 525.625 | A6 | B18 |
| 262 | (Z)-5-((2-(4-((((2-(1H-pyrrol-2-yl)pyridin-3-yl)methyl)amino)methyl)piperidin-1-yl)pyrimidin-4-yl)methylene)thiazolidine-2,4-dione | $C_{24}H_{25}N_7O_2S$ | 475.566 | A7 | B18 |
| 263 | (Z)-5-((2-(4-((((2-(1H-pyrrol-2-yl)quinolin-3-yl)methyl)amino)methyl)piperidin-1-yl)pyrimidin-4-yl)methylene)thiazolidine-2,4-dione | $C_{28}H_{27}N_7O_2S$ | 525.625 | A8 | B18 |
| 264 | (Z)-5-((2-(4-((((6-(1H-pyrrol-2-yl)pyridin-3-yl)methyl)amino)methyl)piperidin-1-yl)pyrimidin-4-yl)methylene)thiazolidine-2,4-dione | $C_{24}H_{25}N_7O_2S$ | 475.566 | A9 | B18 |
| 265 | (Z)-5-((((1-(4-((2,4-dioxothiazolidin-5-ylidene)methyl)pyrimidin-2-yl)piperidin-4-yl)methyl)amino)methyl)-2-(1H-pyrrol-2-yl)nicotinonitrile | $C_{25}H_{24}N_8O_2S$ | 500.575 | A10 | B18 |
| 266 | (Z)-ethyl 5-((((1-(4-((2,4-dioxothiazolidin-5-ylidene)methyl)pyrimidin-2-yl)piperidin-4-yl)methyl)amino)methyl)-2-(1H-pyrrol-2-yl)nicotinate | $C_{27}H_{29}N_7O_4S$ | 547.629 | A11 | B18 |
| 267 | (Z)-5-((2-(4-((((2-(1H-pyrrol-2-yl)pyridin-4-yl)methyl)amino)methyl)piperidin-1-yl)pyrimidin-4-yl)methylene)thiazolidine-2,4-dione | $C_{24}H_{25}N_7O_2S$ | 475.566 | A12 | B18 |
| 268 | (Z)-5-((2-(4-((((2-(1H-pyrrol-2-yl)-6-(trifluoromethyl)pyridin-4-yl)methyl)amino)methyl)piperidin-1-yl)pyrimidin-4-yl)methylene)thiazolidine-2,4-dione | $C_{25}H_{24}F_3N_7O_2S$ | 543.564 | A13 | B18 |
| 269 | (Z)-5-((2-(4-(((((5-fluoro-2-(1H-pyrrol-2-yl)pyridin-4-yl)methyl)amino)methyl)piperidin-1-yl)pyrimidin-4-yl)methylene)thiazolidine-2,4-dione | $C_{24}H_{24}FN_7O_2S$ | 493.556 | A14 | B18 |
| 270 | (Z)-5-((2-(4-(((((6-amino-2-(1H-pyrrol-2-yl)pyridin-3-yl)methyl)amino)methyl)piperidin-1-yl)pyrimidin-4-yl)methylene)thiazolidine-2,4-dione | $C_{24}H_{26}N_8O_2S$ | 490.581 | A15 | B18 |
| 271 | (Z)-5-((2-(4-((((4-fluoro-6-(isoquinolin-4-yl)pyridin-2-yl)methyl)amino)methyl)piperidin-1-yl)pyrimidin-4-yl)methylene)thiazolidine-2,4-dione | $C_{29}H_{26}FN_7O_2S$ | 555.626 | A1 | B19 |
| 272 | (Z)-5-((2-(4-((((6-(isoquinolin-4-yl)pyridin-2-yl)methyl)amino)methyl)piperidin-1-yl)pyrimidin-4-yl)methylene)thiazolidine-2,4-dione | $C_{29}H_{27}N_7O_2S$ | 537.635 | A2 | B19 |
| 273 | (Z)-5-((2-(4-(((((6-(isoquinolin-4-yl)-4-methylpyridin-2-yl)methyl)amino)methyl)piperidin-1-yl)pyrimidin-4-yl)methylene)thiazolidine-2,4-dione | $C_{30}H_{29}N_7O_2S$ | 551.662 | A3 | B19 |
| 274 | (Z)-5-((2-(4-(((((6-(isoquinolin-4-yl)-3-methoxypyridin-2-yl)methyl)amino)methyl)piperidin-1-yl)pyrimidin-4-yl)methylene)thiazolidine-2,4-dione | $C_{30}H_{29}N_7O_3S$ | 567.661 | A4 | B19 |
| 275 | (Z)-5-((2-(4-(((((6-(isoquinolin-4-yl)-4-(trifluoromethyl)pyridin-2-yl)methyl)amino)methyl)piperidin-1-yl)pyrimidin-4-yl)methylene)thiazolidine-2,4-dione | $C_{30}H_{26}F_3N_7O_2S$ | 605.633 | A5 | B19 |
| 276 | (Z)-5-((2-(4-((([3,4'-biisoquinolin]-1-ylmethyl)amino)methyl)piperidin-1-yl)pyrimidin-4-yl)methylene)thiazolidine-2,4-dione | $C_{33}H_{29}N_7O_2S$ | 587.694 | A6 | B19 |
| 277 | (Z)-5-((2-(4-((((2-(isoquinolin-4-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A7 | B19 |
| 278 | (Z)-5-((2-(4-((((2-(isoquinolin-4-yl)quinolin-3-yl)methyl)amino)methyl)piperidin-1-yl)pyrimidin-4-yl)methylene)thiazolidine-2,4-dione | $C_{33}H_{29}N_7O_2S$ | 587.694 | A8 | B19 |
| 279 | (Z)-5-((2-(4-((((6-(isoquinolin-4-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A9 | B19 |
| 280 | (Z)-5-((((1-(4-((2,4-dioxothiazolidin-5-ylidene)methyl)pyrimidin-2-yl)piperidin-4-yl)methyl)amino)methyl)-2-(isoquinolin-4-yl)nicotinonitrile | $C_{30}H_{26}N_8O_2S$ | 562.645 | A10 | B19 |

TABLE 3-continued

Additional prophetic embodiments of the invention.

| No. | Chemical Name | Formula | Mol. Weight | Reactant A | Reactant B |
|---|---|---|---|---|---|
| 281 | (Z)-ethyl 5-((((1-(4-((2,4-dioxothiazolidin-5-ylidene)methyl)pyrimidin-2-yl)piperidin-4-yl)methyl)amino)methyl)-2-(isoquinolin-4-yl)nicotinate | $C_{32}H_{31}N_7O_4S$ | 609.698 | A11 | B19 |
| 282 | (Z)-5-((2-(4-(((((2-(isoquinolin-4-yl)pyridin-4-yl)methyl)amino)methyl)piperidin-1-yl)pyrimidin-4-yl)methylene)thiazolidine-2,4-dione | $C_{29}H_{27}N_7O_2S$ | 537.635 | A12 | B19 |
| 283 | (Z)-5-((2-(4-(((((2-(isoquinolin-4-yl)-6-(trifluoromethyl)pyridin-4-yl)methyl)amino)methyl)piperidin-1-yl)pyrimidin-4-yl)methylene)thiazolidine-2,4-dione | $C_{30}H_{26}F_3N_7O_2S$ | 605.633 | A13 | B19 |
| 284 | (Z)-5-((2-(4-(((((5-fluoro-2-(isoquinolin-4-yl)pyridin-4-yl)methyl)amino)methyl)piperidin-1-yl)pyrimidin-4-yl)methylene)thiazolidine-2,4-dione | $C_{29}H_{26}FN_7O_2S$ | 555.626 | A14 | B19 |
| 285 | (Z)-5-((2-(4-(((((6-amino-2-(isoquinolin-4-yl)pyridin-3-yl)methyl)amino)methyl)piperidin-1-yl)pyrimidin-4-yl)methylene)thiazolidine-2,4-dione | $C_{29}H_{28}N_8O_2S$ | 552.65 | A15 | B19 |
| 286 | (Z)-5-((2-(4-((((4-fluoro-6-(quinolin-4-yl)pyridin-2-yl)methyl)amino)methyl)piperidin-1-yl)pyrimidin-4-yl)methylene)thiazolidine-2,4-dione | $C_{29}H_{26}FN_7O_2S$ | 555.626 | A1 | B20 |
| 287 | (Z)-5-((2-(4-((((6-(quinolin-4-yl)pyridin-2-yl)methyl)amino)methyl)piperidin-1-yl)pyrimidin-4-yl)methylene)thiazolidine-2,4-dione | $C_{29}H_{27}N_7O_2S$ | 537.635 | A2 | B20 |
| 288 | (Z)-5-((2-(4-((((4-methyl-6-(quinolin-4-yl)pyridin-2-yl)methyl)amino)methyl)piperidin-1-yl)pyrimidin-4-yl)methylene)thiazolidine-2,4-dione | $C_{30}H_{29}N_7O_2S$ | 551.662 | A3 | B20 |
| 289 | (Z)-5-((2-(4-((((3-methoxy-6-(quinolin-4-yl)pyridin-2-yl)methyl)amino)methyl)piperidin-1-yl)pyrimidin-4-yl)methylene)thiazolidine-2,4-dione | $C_{30}H_{29}N_7O_3S$ | 567.661 | A4 | B20 |
| 290 | (Z)-5-((2-(4-((((6-(quinolin-4-yl)-4-(trifluoromethyl)pyridin-2-yl)methyl)amino)methyl)piperidin-1-yl)pyrimidin-4-yl)methylene)thiazolidine-2,4-dione | $C_{30}H_{26}F_3N_7O_2S$ | 605.633 | A5 | B20 |
| 291 | (Z)-5-((2-(4-((((3-(quinolin-4-yl)isoquinolin-1-yl)methyl)amino)methyl)piperidin-1-yl)pyrimidin-4-yl)methylene)thiazolidine-2,4-dione | $C_{33}H_{29}N_7O_2S$ | 587.694 | A6 | B20 |
| 292 | (Z)-5-((2-(4-((((2-(quinolin-4-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A7 | B20 |
| 293 | (Z)-5-((2-(4-((([2,4'-biquinolin]-3-ylmethyl)amino)methyl)piperidin-1-yl)pyrimidin-4-yl)methylene)thiazolidine-2,4-dione | $C_{33}H_{29}N_7O_2S$ | 587.694 | A8 | B20 |
| 294 | (Z)-5-((2-(4-((((6-(quinolin-4-yl)pyridin-3-yl)methyl)amino)methyl)piperidin-1-yl)pyrimidin-4-yl)methylene)thiazolidine-2,4-dione | $C_{29}H_{27}N_7O_2S$ | 537.635 | A9 | B20 |
| 295 | (Z)-5-((((1-(4-((2,4-dioxothiazolidin-5-ylidene)methyl)pyrimidin-2-yl)piperidin-4-yl)methyl)amino)methyl)-2-(quinolin-4-yl)nicotinonitrile | $C_{30}H_{26}N_8O_2S$ | 562.645 | A10 | B20 |
| 296 | (Z)-ethyl 5-((((1-(4-((2,4-dioxothiazolidin-5-ylidene)methyl)pyrimidin-2-yl)piperidin-4-yl)methyl)amino)methyl)-2-(quinolin-4-yl)nicotinate | $C_{32}H_{31}N_7O_4S$ | 609.698 | A11 | B20 |
| 297 | (Z)-5-((2-(4-((((2-(quinolin-4-yl)pyridin-4-yl)methyl)amino)methyl)piperidin-1-yl)pyrimidin-4-yl)methylene)thiazolidine-2,4-dione | $C_{29}H_{27}N_7O_2S$ | 537.635 | A12 | B20 |
| 298 | (Z)-5-((2-(4-((((2-(quinolin-4-yl)-6-(trifluoromethyl)pyridin-4-yl)methyl)amino)methyl)piperidin-1-yl)pyrimidin-4-yl)methylene)thiazolidine-2,4-dione | $C_{30}H_{26}F_3N_7O_2S$ | 605.633 | A13 | B20 |
| 299 | (Z)-5-((2-(4-((((5-fluoro-2-(quinolin-4-yl)pyridin-4-yl)methyl)amino)methyl)piperidin-1-yl)pyrimidin-4-yl)methylene)thiazolidine-2,4-dione | $C_{29}H_{26}FN_7O_2S$ | 555.626 | A14 | B20 |
| 300 | (Z)-5-((2-(4-(((((6-amino-2-(quinolin-4-yl)pyridin-3-yl)methyl)amino)methyl)piperidin-1-yl)pyrimidin-4-yl)methylene)thiazolidine-2,4-dione | $C_{29}H_{28}N_8O_2S$ | 552.65 | A15 | B20 |
| 301 | (Z)-5-((2-(4-(((((3',4-difluoro-[2,4'-bipyridin]-6-yl)methyl)amino)methyl)piperidin-1-yl)pyrimidin-4-yl)methylene)thiazolidine-2,4-dione | $C_{25}H_{23}F_2N_7O_2S$ | 523.558 | A1 | B21 |
| 302 | (Z)-5-((2-(4-(((((3'-fluoro-[2,4'-bipyridin]-6-yl)methyl)amino)methyl)piperidin-1-yl)pyrimidin-4-yl)methylene)thiazolidine-2,4-dione | $C_{25}H_{24}FN_7O_2S$ | 505.567 | A2 | B21 |
| 303 | (Z)-5-((2-(4-(((((3'-fluoro-4-methyl-[2,4'-bipyridin]-6-yl)methyl)amino)methyl)piperidin-1-yl)pyrimidin-4-yl)methylene)thiazolidine-2,4-dione | $C_{26}H_{26}FN_7O_2S$ | 519.594 | A3 | B21 |

TABLE 3-continued

Additional prophetic embodiments of the invention.

| No. | Chemical Name | Formula | Mol. Weight | Reactant A | Reactant B |
|---|---|---|---|---|---|
| 304 | (Z)-5-((2-(4-((((3'-fluoro-5-methoxy-[2,4'-bipyridin]-6-yl)methyl)amino)methyl)piperidin-1-yl)pyrimidin-4-yl)methylene)thiazolidine-2,4-dione | $C_{26}H_{26}FN_7O_3S$ | 535.593 | A4 | B21 |
| 305 | (Z)-5-((2-(4-((((3'-fluoro-4-(trifluoromethyl)-[2,4'-bipyridin]-6-yl)methyl)amino)methyl)piperidin-1-yl)pyrimidin-4-yl)methylene)thiazolidine-2,4-dione | $C_{26}H_{23}F_4N_7O_2S$ | 573.565 | A5 | B21 |
| 306 | (Z)-5-((2-(4-((((3-(3-fluoropyridin-4-yl)isoquinolin-1-yl)methyl)amino)methyl)piperidin-1-yl)pyrimidin-4-yl)methylene)thiazolidine-2,4-dione | $C_{29}H_{26}FN_7O_2S$ | 555.626 | A6 | B21 |
| 307 | (Z)-5-((2-(4-((((3'-fluoro-[2,4'-bipyridin]-3-yl)methyl)amino)methyl)piperidin-1-yl)pyrimidin-4-yl)methylene)thiazolidine-2,4-dione | $C_{25}H_{24}FN_7O_2S$ | 505.567 | A7 | B21 |
| 308 | (Z)-5-((2-(4-((((2-(3-fluoropyridin-4-yl)quinolin-3-yl)methyl)amino)methyl)piperidin-1-yl)pyrimidin-4-yl)methylene)thiazolidine-2,4-dione | $C_{29}H_{26}FN_7O_2S$ | 555.626 | A8 | B21 |
| 309 | (Z)-5-((2-(4-((((3'-fluoro-[2,4'-bipyridin]-5-yl)methyl)amino)methyl)piperidin-1-yl)pyrimidin-4-yl)methylene)thiazolidine-2,4-dione | $C_{25}H_{24}FN_7O_2S$ | 505.567 | A9 | B21 |
| 310 | (Z)-5-((((1-(4-((2,4-dioxothiazolidin-5-ylidene)methyl)pyrimidin-2-yl)piperidin-4-yl)methyl)amino)methyl)-3'-fluoro-[2,4'-bipyridine]-3-carbonitrile | $C_{26}H_{23}FN_8O_2S$ | 530.577 | A10 | B21 |
| 311 | (Z)-ethyl 5-((((1-(4-((2,4-dioxothiazolidin-5-ylidene)methyl)pyrimidin-2-yl)piperidin-4-yl)methyl)amino)methyl)-3'-fluoro-[2,4'-bipyridine]-3-carboxylate | $C_{28}H_{28}FN_7O_4S$ | 577.63 | A11 | B21 |
| 312 | (Z)-5-((2-(4-((((3'-fluoro-[2,4'-bipyridin]-4-yl)methyl)amino)methyl)piperidin-1-yl)pyrimidin-4-yl)methylene)thiazolidine-2,4-dione | $C_{25}H_{24}FN_7O_2S$ | 505.567 | A12 | B21 |
| 313 | (Z)-5-((2-(4-((((3'-fluoro-6-(trifluoromethyl)-[2,4'-bipyridin]-4-yl)methyl)amino)methyl)piperidin-1-yl)pyrimidin-4-yl)methylene)thiazolidine-2,4-dione | $C_{26}H_{23}F_4N_7O_2S$ | 573.565 | A13 | B21 |
| 314 | (Z)-5-((2-(4-((((3',5-difluoro-[2,4'-bipyridin]-4-yl)methyl)amino)methyl)piperidin-1-yl)pyrimidin-4-yl)methylene)thiazolidine-2,4-dione | $C_{25}H_{23}F_2N_7O_2S$ | 523.558 | A14 | B21 |
| 315 | (Z)-5-((2-(4-((((6-amino-3'-fluoro-[2,4'-bipyridin]-3-yl)methyl)amino)methyl)piperidin-1-yl)pyrimidin-4-yl)methylene)thiazolidine-2,4-dione | $C_{25}H_{25}FN_8O_2S$ | 520.582 | A15 | B21 |
| 316 | (Z)-5-((2-(4-((((2',4,6'-trifluoro-[2,4'-bipyridin]-6-yl)methyl)amino)methyl)piperidin-1-yl)pyrimidin-4-yl)methylene)thiazolidine-2,4-dione | $C_{25}H_{22}F_3N_7O_2S$ | 541.548 | A1 | B22 |
| 317 | (Z)-5-((2-(4-((((2',6'-difluoro-[2,4'-bipyridin]-6-yl)methyl)amino)methyl)piperidin-1-yl)pyrimidin-4-yl)methylene)thiazolidine-2,4-dione | $C_{25}H_{23}F_2N_7O_2S$ | 523.558 | A2 | B22 |
| 318 | (Z)-5-((2-(4-((((2',6'-difluoro-4-methyl-[2,4'-bipyridin]-6-yl)methyl)amino)methyl)piperidin-1-yl)pyrimidin-4-yl)methylene)thiazolidine-2,4-dione | $C_{26}H_{25}F_2N_7O_2S$ | 537.584 | A3 | B22 |
| 319 | (Z)-5-((2-(4-((((2',6'-difluoro-5-methoxy-[2,4'-bipyridin]-6-yl)methyl)amino)methyl)piperidin-1-yl)pyrimidin-4-yl)methylene)thiazolidine-2,4-dione | $C_{26}H_{25}F_2N_7O_3S$ | 553.584 | A4 | B22 |
| 320 | (Z)-5-((2-(4-((((2',6'-difluoro-4-(trifluoromethyl)-[2,4'-bipyridin]-6-yl)methyl)amino)methyl)piperidin-1-yl)pyrimidin-4-yl)methylene)thiazolidine-2,4-dione | $C_{26}H_{22}F_5N_7O_2S$ | 591.556 | A5 | B22 |
| 321 | (Z)-5-((2-(4-((((3-(2,6-difluoropyridin-4-yl)isoquinolin-1-yl)methyl)amino)methyl)piperidin-1-yl)pyrimidin-4-yl)methylene)thiazolidine-2,4-dione | $C_{29}H_{25}F_2N_7O_2S$ | 573.616 | A6 | B22 |
| 322 | (Z)-5-((2-(4-((((2',6'-difluoro-[2,4'-bipyridin]-3-yl)methyl)amino)methyl)piperidin-1-yl)pyrimidin-4-yl)methylene)thiazolidine-2,4-dione | $C_{25}H_{23}F_2N_7O_2S$ | 523.558 | A7 | B22 |
| 323 | (Z)-5-((2-(4-((((2-(2,6-difluoropyridin-4-yl)quinolin-3-yl)methyl)amino)methyl)piperidin-1-yl)pyrimidin-4-yl)methylene)thiazolidine-2,4-dione | $C_{29}H_{25}F_2N_7O_2S$ | 573.616 | A8 | B22 |
| 324 | (Z)-5-((2-(4-((((2',6'-difluoro-[2,4'-bipyridin]-5-yl)methyl)amino)methyl)piperidin-1-yl)pyrimidin-4-yl)methylene)thiazolidine-2,4-dione | $C_{25}H_{23}F_2N_7O_2S$ | 523.558 | A9 | B22 |
| 325 | (Z)-5-((((1-(4-((2,4-dioxothiazolidin-5-ylidene)methyl)pyrimidin-2-yl)piperidin-4-yl)methyl)amino)methyl)-2',6'-difluoro-[2,4'-bipyridine]-3-carbonitrile | $C_{26}H_{22}F_2N_8O_2S$ | 548.567 | A10 | B22 |

TABLE 3-continued

Additional prophetic embodiments of the invention.

| No. | Chemical Name | Formula | Mol. Weight | Reactant A | Reactant B |
|-----|---------------|---------|-------------|------------|------------|
| 326 | (Z)-ethyl 5-((((1-(4-((2,4-dioxothiazolidin-5-ylidene)methyl)pyrimidin-2-yl)piperidin-4-yl)methyl)amino)methyl)-2',6'-difluoro-[2,4'-bipyridine]-3-carboxylate | $C_{28}H_{27}F_2N_7O_4S$ | 595.62 | A11 | B22 |
| 327 | (Z)-5-((2-(4-((((2',6'-difluoro-[2,4'-bipyridin]-4-yl)methyl)amino)methyl)piperidin-1-yl)pyrimidin-4-yl)methylene)thiazolidine-2,4-dione | $C_{25}H_{23}F_2N_7O_2S$ | 523.558 | A12 | B22 |
| 328 | (Z)-5-((2-(4-((((2',6'-difluoro-6-(trifluoromethyl)-[2,4'-bipyridin]-4-yl)methyl)amino)methyl)piperidin-1-yl)pyrimidin-4-yl)methylene)thiazolidine-2,4-dione | $C_{26}H_{22}F_5N_7O_2S$ | 591.556 | A13 | B22 |
| 329 | (Z)-5-((2-(4-((((2',5',6'-trifluoro-[2,4'-bipyridin]-4-yl)methyl)amino)methyl)piperidin-1-yl)pyrimidin-4-yl)methylene)thiazolidine-2,4-dione | $C_{25}H_{22}F_3N_7O_2S$ | 541.548 | A14 | B22 |
| 330 | (Z)-5-((2-(4-(((((6-amino-2',6'-difluoro-[2,4'-bipyridin]-3-yl)methyl)amino)methyl)piperidin-1-yl)pyrimidin-4-yl)methylene)thiazolidine-2,4-dione | $C_{25}H_{24}F_2N_8O_2S$ | 538.572 | A15 | B22 |
| 331 | (Z)-5-((2-(4-((((6'-(dimethylamino)-4-fluoro-[2,3'-bipyridin]-6-yl)methyl)amino)methyl)piperidin-1-yl)pyrimidin-4-yl)methylene)thiazolidine-2,4-dione | $C_{27}H_{29}FN_8O_2S$ | 548.635 | A1 | B23 |
| 332 | (Z)-5-((2-(4-(((((6'-(dimethylamino)-[2,3'-bipyridin]-6-yl)methyl)amino)methyl)piperidin-1-yl)pyrimidin-4-yl)methylene)thiazolidine-2,4-dione | $C_{27}H_{30}N_8O_2S$ | 530.645 | A2 | B23 |
| 333 | (Z)-5-((2-(4-(((((6'-(dimethylamino)-4-methyl-[2,3'-bipyridin]-6-yl)methyl)amino)methyl)piperidin-1-yl)pyrimidin-4-yl)methylene)thiazolidine-2,4-dione | $C_{28}H_{32}N_8O_2S$ | 544.671 | A3 | B23 |
| 334 | (Z)-5-((2-(4-((((6'-(dimethylamino)-5-methoxy-[2,3'-bipyridin]-6-yl)methyl)amino)methyl)piperidin-1-yl)pyrimidin-4-yl)methylene)thiazolidine-2,4-dione | $C_{28}H_{32}N_8O_3S$ | 560.67 | A4 | B23 |
| 335 | (Z)-5-((2-(4-((((6'-(dimethylamino)-4-(trifluoromethyl)-[2,3'-bipyridin]-6-yl)methyl)amino)methyl)piperidin-1-yl)pyrimidin-4-yl)methylene)thiazolidine-2,4-dione | $C_{28}H_{29}F_3N_8O_2S$ | 598.642 | A5 | B23 |
| 336 | (Z)-5-((2-(4-(((((3-(6-(dimethylamino)pyridin-3-yl)isoquinolin-1-yl)methyl)amino)methyl)piperidin-1-yl)pyrimidin-4-yl)methylene)thiazolidine-2,4-dione | $C_{31}H_{32}N_8O_2S$ | 580.703 | A6 | B23 |
| 337 | (Z)-5-((2-(4-(((((6'-(dimethylamino)-[2,3'-bipyridin]-3-yl)methyl)amino)methyl)piperidin-1-yl)pyrimidin-4-yl)methylene)thiazolidine-2,4-dione | $C_{27}H_{30}N_8O_2S$ | 530.645 | A7 | B23 |
| 338 | (Z)-5-((2-(4-(((((2-(6-(dimethylamino)pyridin-3-yl)quinolin-3-yl)methyl)amino)methyl)piperidin-1-yl)pyrimidin-4-yl)methylene)thiazolidine-2,4-dione | $C_{31}H_{32}N_8O_2S$ | 580.703 | A8 | B23 |
| 339 | (Z)-5-((2-(4-((((6'-(dimethylamino)-[2,3'-bipyridin]-5-yl)methyl)amino)methyl)piperidin-1-yl)pyrimidin-4-yl)methylene)thiazolidine-2,4-dione | $C_{27}H_{30}N_8O_2S$ | 530.645 | A9 | B23 |
| 340 | (Z)-6'-(dimethylamino)-5-((((1-(4-((2,4-dioxothiazolidin-5-ylidene)methyl)pyrimidin-2-yl)piperidin-4-yl)methyl)amino)methyl)-[2,3'-bipyridine]-3-carbonitrile | $C_{28}H_{29}N_9O_2S$ | 555.654 | A10 | B23 |
| 341 | (Z)-ethyl 6'-(dimethylamino)-5-((((1-(4-((2,4-dioxothiazolidin-5-ylidene)methyl)pyrimidin-2-yl)piperidin-4-yl)methyl)amino)methyl)-[2,3'-bipyridine]-3-carboxylate | $C_{30}H_{34}N_8O_4S$ | 602.707 | A11 | B23 |
| 342 | (Z)-5-((2-(4-(((((6'-(dimethylamino)-[2,3'-bipyridin]-4-yl)methyl)amino)methyl)piperidin-1-yl)pyrimidin-4-yl)methylene)thiazolidine-2,4-dione | $C_{27}H_{30}N_8O_2S$ | 530.645 | A12 | B23 |
| 343 | (Z)-5-((2-(4-((((6'-(dimethylamino)-6-(trifluoromethyl)-[2,3'-bipyridin]-4-yl)methyl)amino)methyl)piperidin-1-yl)pyrimidin-4-yl)methylene)thiazolidine-2,4-dione | $C_{28}H_{29}F_3N_8O_2S$ | 598.642 | A13 | B23 |
| 344 | (Z)-5-((2-(4-(((((6'-(dimethylamino)-5-fluoro-[2,3'-bipyridin]-4-yl)methyl)amino)methyl)piperidin-1-yl)pyrimidin-4-yl)methylene)thiazolidine-2,4-dione | $C_{27}H_{29}FN_8O_2S$ | 548.635 | A14 | B23 |
| 345 | (Z)-5-((2-(4-(((((6-amino-6'-(dimethylamino)-[2,3'-bipyridin]-3-yl)methyl)amino)methyl)piperidin-1-yl)pyrimidin-4-yl)methylene)thiazolidine-2,4-dione | $C_{27}H_{31}N_9O_2S$ | 545.659 | A15 | B23 |
| 346 | (Z)-5-((2-(4-(((((6-(2-(dimethylamino)pyrimidin-5-yl)-4-fluoropyridin-2-yl)methyl)amino)methyl)piperidin-1-yl)pyrimidin-4-yl)methylene)thiazolidine-2,4-dione | $C_{26}H_{28}FN_9O_2S$ | 549.623 | A1 | B24 |
| 347 | (Z)-5-((2-(4-(((((6-(2-(dimethylamino)pyrimidin-5-yl)pyridin-2-yl)methyl)amino)methyl)piperidin-1-yl)pyrimidin-4-yl)methylene)thiazolidine-2,4-dione | $C_{26}H_{29}N_9O_2S$ | 531.633 | A2 | B24 |

TABLE 3-continued

Additional prophetic embodiments of the invention.

| No. | Chemical Name | Formula | Mol. Weight | Reactant A | Reactant B |
|---|---|---|---|---|---|
| 348 | (Z)-5-((2-(4-(((((6-(2-(dimethylamino)pyrimidin-5-yl)-4-methylpyridin-2-yl)methyl)amino)methyl)piperidin-1-yl)pyrimidin-4-yl)methylene)thiazolidine-2,4-dione | $C_{27}H_{31}N_9O_2S$ | 545.659 | A3 | B24 |
| 349 | (Z)-5-((2-(4-(((((6-(2-(dimethylamino)pyrimidin-5-yl)-3-methoxypyridin-2-yl)methyl)amino)methyl)piperidin-1-yl)pyrimidin-4-yl)methylene)thiazolidine-2,4-dione | $C_{27}H_{31}N_9O_3S$ | 561.659 | A4 | B24 |
| 350 | (Z)-5-((2-(4-(((((6-(2-(dimethylamino)pyrimidin-5-yl)-4-(trifluoromethyl)pyridin-2-yl)methyl)amino)methyl)piperidin-1-yl)pyrimidin-4-yl)methylene)thiazolidine-2,4-dione | $C_{27}H_{28}F_3N_9O_2S$ | 599.631 | A5 | B24 |
| 351 | (Z)-5-((2-(4-(((((3-(2-(dimethylamino)pyrimidin-5-yl)isoquinolin-1-yl)methyl)amino)methyl)piperidin-1-yl)pyrimidin-4-yl)methylene)thiazolidine-2,4-dione | $C_{30}H_{31}N_9O_2S$ | 581.691 | A6 | B24 |
| 352 | (Z)-5-((2-(4-(((((2-(2-(dimethylamino)pyrimidin-5-yl)pyridin-3-yl)methyl)amino)methyl)piperidin-1-yl)pyrimidin-4-yl)methylene)thiazolidine-2,4-dione | $C_{26}H_{29}N_9O_2S$ | 531.633 | A7 | B24 |
| 353 | (Z)-5-((2-(4-(((((2-(2-(dimethylamino)pyrimidin-5-yl)quinolin-3-yl)methyl)amino)methyl)piperidin-1-yl)pyrimidin-4-yl)methylene)thiazolidine-2,4-dione | $C_{30}H_{31}N_9O_2S$ | 581.691 | A8 | B24 |
| 354 | (Z)-5-((2-(4-(((((6-(2-(dimethylamino)pyrimidin-5-yl)pyridin-3-yl)methyl)amino)methyl)piperidin-1-yl)pyrimidin-4-yl)methylene)thiazolidine-2,4-dione | $C_{26}H_{29}N_9O_2S$ | 531.633 | A9 | B24 |
| 355 | (Z)-2-(2-(dimethylamino)pyrimidin-5-yl)-5-(((((1-(4-((2,4-dioxothiazolidin-5-ylidene)methyl)pyrimidin-2-yl)piperidin-4-yl)methyl)amino)methyl)nicotinonitrile | $C_{27}H_{28}N_{10}O_2S$ | 556.642 | A10 | B24 |
| 356 | (Z)-ethyl 2-(2-(dimethylamino)pyrimidin-5-yl)-5-(((((1-(4-((2,4-dioxothiazolidin-5-ylidene)methyl)pyrimidin-2-yl)piperidin-4-yl)methyl)amino)methyl)nicotinate | $C_{29}H_{33}N_9O_4S$ | 603.695 | A11 | B24 |
| 357 | (Z)-5-((2-(4-(((((2-(2-(dimethylamino)pyrimidin-5-yl)pyridin-4-yl)methyl)amino)methyl)piperidin-1-yl)pyrimidin-4-yl)methylene)thiazolidine-2,4-dione | $C_{26}H_{29}N_9O_2S$ | 531.633 | A12 | B24 |
| 358 | (Z)-5-((2-(4-(((((2-(2-(dimethylamino)pyrimidin-5-yl)-6-(trifluoromethyl)pyridin-4-yl)methyl)amino)methyl)piperidin-1-yl)pyrimidin-4-yl)methylene)thiazolidine-2,4-dione | $C_{27}H_{28}F_3N_9O_2S$ | 599.631 | A13 | B24 |
| 359 | (Z)-5-((2-(4-(((((2-(2-(dimethylamino)pyrimidin-5-yl)-5-fluoropyridin-4-yl)methyl)amino)methyl)piperidin-1-yl)pyrimidin-4-yl)methylene)thiazolidine-2,4-dione | $C_{26}H_{28}FN_9O_2S$ | 549.623 | A14 | B24 |
| 360 | (Z)-5-((2-(4-(((((6-amino-2-(2-(dimethylamino)pyrimidin-5-yl)pyridin-3-yl)methyl)amino)methyl)piperidin-1-yl)pyrimidin-4-yl)methylene)thiazolidine-2,4-dione | $C_{26}H_{30}N_{10}O_2S$ | 546.647 | A15 | B24 |
| 361 | (Z)-5-((2-(4-(((((6-(3,5-dimethylisoxazol-4-yl)-4-fluoropyridin-2-yl)methyl)amino)methyl)piperidin-1-yl)pyrimidin-4-yl)methylene)thiazolidine-2,4-dione | $C_{25}H_{26}FN_7O_3S$ | 523.582 | A1 | B25 |
| 362 | (Z)-5-((2-(4-(((((6-(3,5-dimethylisoxazol-4-yl)pyridin-2-yl)methyl)amino)methyl)piperidin-1-yl)pyrimidin-4-yl)methylene)thiazolidine-2,4-dione | $C_{25}H_{27}N_7O_3S$ | 505.592 | A2 | B25 |
| 363 | (Z)-5-((2-(4-(((((6-(3,5-dimethylisoxazol-4-yl)-4-methylpyridin-2-yl)methyl)amino)methyl)piperidin-1-yl)pyrimidin-4-yl)methylene)thiazolidine-2,4-dione | $C_{26}H_{29}N_7O_3S$ | 519.619 | A3 | B25 |
| 364 | (Z)-5-((2-(4-(((((6-(3,5-dimethylisoxazol-4-yl)-3-methoxypyridin-2-yl)methyl)amino)methyl)piperidin-1-yl)pyrimidin-4-yl)methylene)thiazolidine-2,4-dione | $C_{26}H_{29}N_7O_4S$ | 535.618 | A4 | B25 |
| 365 | (Z)-5-((2-(4-(((((6-(3,5-dimethylisoxazol-4-yl)-4-(trifluoromethyl)pyridin-2-yl)methyl)amino)methyl)piperidin-1-yl)pyrimidin-4-yl)methylene)thiazolidine-2,4-dione | $C_{26}H_{26}F_3N_7O_3S$ | 573.59 | A5 | B25 |
| 366 | (Z)-5-((2-(4-(((((3-(3,5-dimethylisoxazol-4-yl)isoquinolin-1-yl)methyl)amino)methyl)piperidin-1-yl)pyrimidin-4-yl)methylene)thiazolidine-2,4-dione | $C_{29}H_{29}N_7O_3S$ | 555.651 | A6 | B25 |
| 367 | (Z)-5-((2-(4-(((((2-(3,5-dimethylisoxazol-4-yl)pyridin-3-yl)methyl)amino)methyl)piperidin-1-yl)pyrimidin-4-yl)methylene)thiazolidine-2,4-dione | $C_{25}H_{27}N_7O_3S$ | 505.592 | A7 | B25 |

TABLE 3-continued

Additional prophetic embodiments of the invention.

| No. | Chemical Name | Formula | Mol. Weight | Reactant A | Reactant B |
|---|---|---|---|---|---|
| 368 | (Z)-5-((2-(4-((((2-(3,5-dimethylisoxazol-4-yl)quinolin-3-yl)methyl)amino)methyl)piperidin-1-yl)pyrimidin-4-yl)methylene)thiazolidine-2,4-dione | $C_{29}H_{29}N_7O_3S$ | 555.651 | A8 | B25 |
| 369 | (Z)-5-((2-(4-((((6-(3,5-dimethylisoxazol-4-yl)pyridin-3-yl)methyl)amino)methyl)piperidin-1-yl)pyrimidin-4-yl)methylene)thiazolidine-2,4-dione | $C_{25}H_{27}N_7O_3S$ | 505.592 | A9 | B25 |
| 370 | (Z)-2-(3,5-dimethylisoxazol-4-yl)-5-((((1-(4-((2,4-dioxothiazolidin-5-ylidene)methyl)pyrimidin-2-yl)piperidin-4-yl)methyl)amino)methyl)nicotinonitrile | $C_{26}H_{26}N_8O_3S$ | 530.601 | A10 | B25 |
| 371 | (Z)-ethyl 2-(3,5-dimethylisoxazol-4-yl)-5-((((1-(4-((2,4-dioxothiazolidin-5-ylidene)methyl)pyrimidin-2-yl)piperidin-4-yl)methyl)amino)methyl)nicotinate | $C_{28}H_{31}N_7O_5S$ | 577.655 | A11 | B25 |
| 372 | (Z)-5-((2-(4-((((2-(3,5-dimethylisoxazol-4-yl)pyridin-4-yl)methyl)amino)methyl)piperidin-1-yl)pyrimidin-4-yl)methylene)thiazolidine-2,4-dione | $C_{25}H_{27}N_7O_3S$ | 505.592 | A12 | B25 |
| 373 | (Z)-5-((2-(4-((((2-(3,5-dimethylisoxazol-4-yl)-6-(trifluoromethyl)pyridin-4-yl)methyl)amino)methyl)piperidin-1-yl)pyrimidin-4-yl)methylene)thiazolidine-2,4-dione | $C_{26}H_{26}F_3N_7O_3S$ | 573.59 | A13 | B25 |
| 374 | (Z)-5-((2-(4-((((2-(3,5-dimethylisoxazol-4-yl)-5-fluoropyridin-4-yl)methyl)amino)methyl)piperidin-1-yl)pyrimidin-4-yl)methylene)thiazolidine-2,4-dione | $C_{25}H_{26}FN_7O_3S$ | 523.582 | A14 | B25 |
| 375 | (Z)-5-((2-(4-((((6-amino-2-(3,5-dimethylisoxazol-4-yl)pyridin-3-yl)methyl)amino)methyl)piperidin-1-yl)pyrimidin-4-yl)methylene)thiazolidine-2,4-dione | $C_{25}H_{28}N_8O_3S$ | 520.607 | A15 | B25 |
| 376 | (Z)-5-((2-(4-((((4-fluoro-6-(1H-pyrazol-4-yl)pyridin-2-yl)methyl)amino)methyl)piperidin-1-yl)pyrimidin-4-yl)methylene)thiazolidine-2,4-dione | $C_{23}H_{23}FN_8O_2S$ | 494.545 | A1 | B26 |
| 377 | (Z)-5-((2-(4-((((6-(1H-pyrazol-4-yl)pyridin-2-yl)methyl)amino)methyl)piperidin-1-yl)pyrimidin-4-yl)methylene)thiazolidine-2,4-dione | $C_{23}H_{24}N_8O_2S$ | 476.554 | A2 | B26 |
| 378 | (Z)-5-((2-(4-((((4-methyl-6-(1H-pyrazol-4-yl)pyridin-2-yl)methyl)amino)methyl)piperidin-1-yl)pyrimidin-4-yl)methylene)thiazolidine-2,4-dione | $C_{24}H_{26}N_8O_2S$ | 490.581 | A3 | B26 |
| 379 | (Z)-5-((2-(4-((((3-methoxy-6-(1H-pyrazol-4-yl)pyridin-2-yl)methyl)amino)methyl)piperidin-1-yl)pyrimidin-4-yl)methylene)thiazolidine-2,4-dione | $C_{24}H_{26}N_8O_3S$ | 506.58 | A4 | B26 |
| 380 | (Z)-5-((2-(4-((((6-(1H-pyrazol-4-yl)-4-(trifluoromethyl)pyridin-2-yl)methyl)amino)methyl)piperidin-1-yl)pyrimidin-4-yl)methylene)thiazolidine-2,4-dione | $C_{24}H_{23}F_3N_8O_2S$ | 544.552 | A5 | B26 |
| 381 | (Z)-5-((2-(4-((((3-(1H-pyrazol-4-yl)isoquinolin-1-yl)methyl)amino)methyl)piperidin-1-yl)pyrimidin-4-yl)methylene)thiazolidine-2,4-dione | $C_{27}H_{26}N_8O_2S$ | 526.613 | A6 | B26 |
| 382 | (Z)-5-((2-(4-((((2-(1H-pyrazol-4-yl)pyridin-3-yl)methyl)amino)methyl)piperidin-1-yl)pyrimidin-4-yl)methylene)thiazolidine-2,4-dione | $C_{23}H_{24}N_8O_2S$ | 476.554 | A7 | B26 |
| 383 | (Z)-5-((2-(4-((((2-(1H-pyrazol-4-yl)quinolin-3-yl)methyl)amino)methyl)piperidin-1-yl)pyrimidin-4-yl)methylene)thiazolidine-2,4-dione | $C_{27}H_{26}N_8O_2S$ | 526.613 | A8 | B26 |
| 384 | (Z)-5-((2-(4-((((6-(1H-pyrazol-4-yl)pyridin-3-yl)methyl)amino)methyl)piperidin-1-yl)pyrimidin-4-yl)methylene)thiazolidine-2,4-dione | $C_{23}H_{24}N_8O_2S$ | 476.554 | A9 | B26 |
| 385 | (Z)-5-((((1-(4-((2,4-dioxothiazolidin-5-ylidene)methyl)pyrimidin-2-yl)piperidin-4-yl)methyl)amino)methyl)-2-(1H-pyrazol-4-yl)nicotinonitrile | $C_{24}H_{23}N_9O_2S$ | 501.564 | A10 | B26 |
| 386 | (Z)-ethyl 5-((((1-(4-((2,4-dioxothiazolidin-5-ylidene)methyl)pyrimidin-2-yl)piperidin-4-yl)methyl)amino)methyl)-2-(1H-pyrazol-4-yl)nicotinate | $C_{26}H_{28}N_8O_4S$ | 548.617 | A11 | B26 |
| 387 | (Z)-5-((2-(4-((((2-(1H-pyrazol-4-yl)pyridin-4-yl)methyl)amino)methyl)piperidin-1-yl)pyrimidin-4-yl)methylene)thiazolidine-2,4-dione | $C_{23}H_{24}N_8O_2S$ | 476.554 | A12 | B26 |
| 388 | (Z)-5-((2-(4-((((2-(1H-pyrazol-4-yl)-6-(trifluoromethyl)pyridin-4-yl)methyl)amino)methyl)piperidin-1-yl)pyrimidin-4-yl)methylene)thiazolidine-2,4-dione | $C_{24}H_{23}F_3N_8O_2S$ | 544.552 | A13 | B26 |
| 389 | (Z)-5-((2-(4-((((5-fluoro-2-(1H-pyrazol-4-yl)pyridin-4-yl)methyl)amino)methyl)piperidin-1-yl)pyrimidin-4-yl)methylene)thiazolidine-2,4-dione | $C_{23}H_{23}FN_8O_2S$ | 494.545 | A14 | B26 |

TABLE 3-continued

Additional prophetic embodiments of the invention.

| No. | Chemical Name | Formula | Mol. Weight | Reactant A | Reactant B |
|---|---|---|---|---|---|
| 390 | (Z)-5-((2-(4-(((((6-amino-2-(1H-pyrazol-4-yl)pyridin-3-yl)methyl)amino)methyl)piperidin-1-yl)pyrimidin-4-yl)methylene)thiazolidine-2,4-dione | $C_{23}H_{25}N_9O_2S$ | 491.569 | A15 | B26 |
| 391 | (Z)-5-((2-(4-(((((4-fluoro-6-(1H-pyrazol-5-yl)pyridin-2-yl)methyl)amino)methyl)piperidin-1-yl)pyrimidin-4-yl)methylene)thiazolidine-2,4-dione | $C_{23}H_{23}FN_8O_2S$ | 494.545 | A1 | B27 |
| 392 | (Z)-5-((2-(4-(((((6-(1H-pyrazol-5-yl)pyridin-2-yl)methyl)amino)methyl)piperidin-1-yl)pyrimidin-4-yl)methylene)thiazolidine-2,4-dione | $C_{23}H_{24}N_8O_2S$ | 476.554 | A2 | B27 |
| 393 | (Z)-5-((2-(4-(((((4-methyl-6-(1H-pyrazol-5-yl)pyridin-2-yl)methyl)amino)methyl)piperidin-1-yl)pyrimidin-4-yl)methylene)thiazolidine-2,4-dione | $C_{24}H_{26}N_8O_2S$ | 490.581 | A3 | B27 |
| 394 | (Z)-5-((2-(4-(((((3-methoxy-6-(1H-pyrazol-5-yl)pyridin-2-yl)methyl)amino)methyl)piperidin-1-yl)pyrimidin-4-yl)methylene)thiazolidine-2,4-dione | $C_{24}H_{26}N_8O_3S$ | 506.58 | A4 | B27 |
| 395 | (Z)-5-((2-(4-(((((6-(1H-pyrazol-5-yl)-4-(trifluoromethyl)pyridin-2-yl)methyl)amino)methyl)piperidin-1-yl)pyrimidin-4-yl)methylene)thiazolidine-2,4-dione | $C_{24}H_{23}F_3N_8O_2S$ | 544.552 | A5 | B27 |
| 396 | (Z)-5-((2-(4-(((((3-(1H-pyrazol-5-yl)isoquinolin-1-yl)methyl)amino)methyl)piperidin-1-yl)pyrimidin-4-yl)methylene)thiazolidine-2,4-dione | $C_{27}H_{26}N_8O_2S$ | 526.613 | A6 | B27 |
| 397 | (Z)-5-((2-(4-(((((2-(1H-pyrazol-5-yl)pyridin-3-yl)methyl)amino)methyl)piperidin-1-yl)pyrimidin-4-yl)methylene)thiazolidine-2,4-dione | $C_{23}H_{24}N_8O_2S$ | 476.554 | A7 | B27 |
| 398 | (Z)-5-((2-(4-(((((2-(1H-pyrazol-5-yl)quinolin-3-yl)methyl)amino)methyl)piperidin-1-yl)pyrimidin-4-yl)methylene)thiazolidine-2,4-dione | $C_{27}H_{26}N_8O_2S$ | 526.613 | A8 | B27 |
| 399 | (Z)-5-((2-(4-(((((6-(1H-pyrazol-5-yl)pyridin-3-yl)methyl)amino)methyl)piperidin-1-yl)pyrimidin-4-yl)methylene)thiazolidine-2,4-dione | $C_{23}H_{24}N_8O_2S$ | 476.554 | A9 | B27 |
| 400 | (Z)-5-(((((1-(4-((2,4-dioxothiazolidin-5-ylidene)methyl)pyrimidin-2-yl)piperidin-4-yl)methyl)amino)methyl)-2-(1H-pyrazol-5-yl)nicotinonitrile | $C_{24}H_{23}N_9O_2S$ | 501.564 | A10 | B27 |
| 401 | (Z)-ethyl 5-(((((1-(4-((2,4-dioxothiazolidin-5-ylidene)methyl)pyrimidin-2-yl)piperidin-4-yl)methyl)amino)methyl)-2-(1H-pyrazol-5-yl)nicotinate | $C_{26}H_{28}N_8O_4S$ | 548.617 | A11 | B27 |
| 402 | (Z)-5-((2-(4-((((2-(1H-pyrazol-5-yl)pyridin-4-yl)methyl)amino)methyl)piperidin-1-yl)pyrimidin-4-yl)methylene)thiazolidine-2,4-dione | $C_{23}H_{24}N_8O_2S$ | 476.554 | A12 | B27 |
| 403 | (Z)-5-((2-(4-(((((2-(1H-pyrazol-5-yl)-6-(trifluoromethyl)pyridin-4-yl)methyl)amino)methyl)piperidin-1-yl)pyrimidin-4-yl)methylene)thiazolidine-2,4-dione | $C_{24}H_{23}F_3N_8O_2S$ | 544.552 | A13 | B27 |
| 404 | (Z)-5-((2-(4-(((((5-fluoro-2-(1H-pyrazol-5-yl)pyridin-4-yl)methyl)amino)methyl)piperidin-1-yl)pyrimidin-4-yl)methylene)thiazolidine-2,4-dione | $C_{23}H_{23}FN_8O_2S$ | 494.545 | A14 | B27 |
| 405 | (Z)-5-((2-(4-(((((6-amino-2-(1H-pyrazol-5-yl)pyridin-3-yl)methyl)amino)methyl)piperidin-1-yl)pyrimidin-4-yl)methylene)thiazolidine-2,4-dione | $C_{23}H_{25}N_9O_2S$ | 491.569 | A15 | B27 |
| 406 | (Z)-5-((2-(4-((((2',4'-bis(trifluoromethyl)-[1,1'-biphenyl]-2-yl)methyl)amino)methyl)piperidin-1-yl)pyrimidin-4-yl)methylene)thiazolidine-2,4-dione | $C_{29}H_{25}F_6N_5O_2S$ | 621.597 | A16 | B1 |
| 407 | (Z)-5-((2-(4-((((2',4'-bis(trifluoromethyl)-[1,1'-biphenyl]-3-yl)methyl)amino)methyl)piperidin-1-yl)pyrimidin-4-yl)methylene)thiazolidine-2,4-dione | $C_{29}H_{25}F_6N_5O_2S$ | 621.597 | A17 | B1 |
| 408 | (Z)-5-((2-(4-((((2',4'-dimethoxy-[1,1'-biphenyl]-2-yl)methyl)amino)methyl)piperidin-1-yl)pyrimidin-4-yl)methylene)thiazolidine-2,4-dione | $C_{29}H_{31}N_5O_4S$ | 545.653 | A16 | B2 |
| 409 | (Z)-5-((2-(4-((((2',4'-dimethoxy-[1,1'-biphenyl]-3-yl)methyl)amino)methyl)piperidin-1-yl)pyrimidin-4-yl)methylene)thiazolidine-2,4-dione | $C_{29}H_{31}N_5O_4S$ | 545.653 | A17 | B2 |
| 410 | (Z)-5-((2-(4-((((2'-(trifluoromethoxy)-[1,1'-biphenyl]-2-yl)methyl)amino)methyl)piperidin-1-yl)pyrimidin-4-yl)methylene)thiazolidine-2,4-dione | $C_{28}H_{26}F_3N_5O_3S$ | 569.598 | A16 | B3 |
| 411 | (Z)-5-((2-(4-((((2'-(trifluoromethoxy)-[1,1'-biphenyl]-3-yl)methyl)amino)methyl)piperidin-1-yl)pyrimidin-4-yl)methylene)thiazolidine-2,4-dione | $C_{28}H_{26}F_3N_5O_3S$ | 569.598 | A17 | B3 |
| 412 | (Z)-2'-(((((1-(4-((2,4-dioxothiazolidin-5-ylidene)methyl)pyrimidin-2-yl)piperidin-4-yl)methyl)amino)methyl)-5-methyl-[1,1'-biphenyl]-2-carboxylic acid | $C_{29}H_{29}N_5O_4S$ | 543.637 | A16 | B4 |

TABLE 3-continued

Additional prophetic embodiments of the invention.

| No. | Chemical Name | Formula | Mol. Weight | Reactant A | Reactant B |
|---|---|---|---|---|---|
| 413 | (Z)-3'-(((((1-(4-((2,4-dioxothiazolidin-5-ylidene)methyl)pyrimidin-2-yl)piperidin-4-yl)methyl)amino)methyl)-5-methyl-[1,1'-biphenyl]-2-carboxylic acid | $C_{29}H_{29}N_5O_4S$ | 543.637 | A17 | B4 |
| 414 | (Z)-5-((2-(4-(((2-(benzo[d][1,3]dioxol-5-yl)benzyl)amino)methyl)piperidin-1-yl)pyrimidin-4-yl)methylene)thiazolidine-2,4-dione | $C_{28}H_{27}N_5O_4S$ | 529.61 | A16 | B5 |
| 415 | (Z)-5-((2-(4-(((3-(benzo[d][1,3]dioxol-5-yl)benzyl)amino)methyl)piperidin-1-yl)pyrimidin-4-yl)methylene)thiazolidine-2,4-dione | $C_{28}H_{27}N_5O_4S$ | 529.61 | A17 | B5 |
| 416 | (Z)-N-benzyl-2'-(((((1-(4-((2,4-dioxothiazolidin-5-ylidene)methyl)pyrimidin-2-yl)piperidin-4-yl)methyl)amino)methyl)-[1,1'-biphenyl]-3-carboxamide | $C_{35}H_{34}N_6O_3S$ | 618.748 | A16 | B6 |
| 417 | (Z)-N-benzyl-3'-(((((1-(4-((2,4-dioxothiazolidin-5-ylidene)methyl)pyrimidin-2-yl)piperidin-4-yl)methyl)amino)methyl)-[1,1'-biphenyl]-3-carboxamide | $C_{35}H_{34}N_6O_3S$ | 618.748 | A17 | B6 |
| 418 | (Z)-5-((2-(4-((((3'-(dimethylamino)-[1,1'-biphenyl]-2-yl)methyl)amino)methyl)piperidin-1-yl)pyrimidin-4-yl)methylene)thiazolidine-2,4-dione | $C_{29}H_{32}N_6O_2S$ | 528.668 | A16 | B7 |
| 419 | (Z)-5-((2-(4-((((3'-(dimethylamino)-[1,1'-biphenyl]-3-yl)methyl)amino)methyl)piperidin-1-yl)pyrimidin-4-yl)methylene)thiazolidine-2,4-dione | $C_{29}H_{32}N_6O_2S$ | 528.668 | A17 | B7 |
| 420 | (Z)-N-(2'-(((((1-(4-((2,4-dioxothiazolidin-5-ylidene)methyl)pyrimidin-2-yl)piperidin-4-yl)methyl)amino)methyl)-[1,1'-biphenyl]-3-yl)acetamide | $C_{29}H_{30}N_6O_3S$ | 542.652 | A16 | B8 |
| 421 | (Z)-N-(3'-(((((1-(4-((2,4-dioxothiazolidin-5-ylidene)methyl)pyrimidin-2-yl)piperidin-4-yl)methyl)amino)methyl)-[1,1'-biphenyl]-3-yl)acetamide | $C_{29}H_{30}N_6O_3S$ | 542.652 | A17 | B8 |
| 422 | (Z)-5-((2-(4-((((4'-phenoxy-[1,1'-biphenyl]-2-yl)methyl)amino)methyl)piperidin-1-yl)pyrimidin-4-yl)methylene)thiazolidine-2,4-dione | $C_{33}H_{31}N_5O_3S$ | 577.696 | A16 | B9 |
| 423 | (Z)-5-((2-(4-((((4'-phenoxy-[1,1'-biphenyl]-3-yl)methyl)amino)methyl)piperidin-1-yl)pyrimidin-4-yl)methylene)thiazolidine-2,4-dione | $C_{33}H_{31}N_5O_3S$ | 577.696 | A17 | B9 |
| 424 | (Z)-5-((2-(4-(((2-(1H-indol-5-yl)benzyl)amino)methyl)piperidin-1-yl)pyrimidin-4-yl)methylene)thiazolidine-2,4-dione | $C_{29}H_{28}N_6O_2S$ | 524.637 | A16 | B10 |
| 425 | (Z)-5-((2-(4-(((3-(1H-indol-5-yl)benzyl)amino)methyl)piperidin-1-yl)pyrimidin-4-yl)methylene)thiazolidine-2,4-dione | $C_{29}H_{28}N_6O_2S$ | 524.637 | A17 | B10 |
| 426 | (Z)-5-((2-(4-(((2-(isoquinolin-5-yl)benzyl)amino)methyl)piperidin-1-yl)pyrimidin-4-yl)methylene)thiazolidine-2,4-dione | $C_{30}H_{28}N_6O_2S$ | 536.647 | A16 | B11 |
| 427 | (Z)-5-((2-(4-(((3-(isoquinolin-5-yl)benzyl)amino)methyl)piperidin-1-yl)pyrimidin-4-yl)methylene)thiazolidine-2,4-dione | $C_{30}H_{28}N_6O_2S$ | 536.647 | A17 | B11 |
| 428 | (Z)-5-((2-(4-(((2-(thiophen-3-yl)benzyl)amino)methyl)piperidin-1-yl)pyrimidin-4-yl)methylene)thiazolidine-2,4-dione | $C_{25}H_{25}N_5O_2S_2$ | 491.628 | A16 | B12 |
| 429 | (Z)-5-((2-(4-(((3-(thiophen-3-yl)benzyl)amino)methyl)piperidin-1-yl)pyrimidin-4-yl)methylene)thiazolidine-2,4-dione | $C_{25}H_{25}N_5O_2S_2$ | 491.628 | A17 | B12 |
| 430 | (Z)-5-((2-(4-(((2-(benzo[b]thiophen-3-yl)benzyl)amino)methyl)piperidin-1-yl)pyrimidin-4-yl)methylene)thiazolidine-2,4-dione | $C_{29}H_{27}N_5O_2S_2$ | 541.687 | A16 | B13 |
| 431 | (Z)-5-((2-(4-(((3-(benzo[b]thiophen-3-yl)benzyl)amino)methyl)piperidin-1-yl)pyrimidin-4-yl)methylene)thiazolidine-2,4-dione | $C_{29}H_{27}N_5O_2S_2$ | 541.687 | A17 | B13 |
| 432 | (Z)-5-((2-(4-(((2-(5-acetylthiophen-2-yl)benzyl)amino)methyl)piperidin-1-yl)pyrimidin-4-yl)methylene)thiazolidine-2,4-dione | $C_{27}H_{27}N_5O_3S_2$ | 533.665 | A16 | B14 |
| 433 | (Z)-5-((2-(4-(((3-(5-acetylthiophen-2-yl)benzyl)amino)methyl)piperidin-1-yl)pyrimidin-4-yl)methylene)thiazolidine-2,4-dione | $C_{27}H_{27}N_5O_3S_2$ | 533.665 | A17 | B14 |
| 434 | (Z)-5-((2-(4-(((2-(furan-2-yl)benzyl)amino)methyl)piperidin-1-yl)pyrimidin-4-yl)methylene)thiazolidine-2,4-dione | $C_{25}H_{25}N_5O_3S$ | 475.563 | A16 | B15 |
| 435 | (Z)-5-((2-(4-(((3-(furan-2-yl)benzyl)amino)methyl)piperidin-1-yl)pyrimidin-4-yl)methylene)thiazolidine-2,4-dione | $C_{25}H_{25}N_5O_3S$ | 475.563 | A17 | B15 |

TABLE 3-continued

Additional prophetic embodiments of the invention.

| No. | Chemical Name | Formula | Mol. Weight | Reactant A | Reactant B |
|---|---|---|---|---|---|
| 436 | (Z)-5-((2-(4-(((2-(benzofuran-2-yl)benzyl)amino)methyl)piperidin-1-yl)pyrimidin-4-yl)methylene)thiazolidine-2,4-dione | $C_{29}H_{27}N_5O_3S$ | 525.621 | A16 | B16 |
| 437 | (Z)-5-((2-(4-(((3-(benzofuran-2-yl)benzyl)amino)methyl)piperidin-1-yl)pyrimidin-4-yl)methylene)thiazolidine-2,4-dione | $C_{29}H_{27}N_5O_3S$ | 525.621 | A17 | B16 |
| 438 | (Z)-5-((2-(4-(((2-(furan-3-yl)benzyl)amino)methyl)piperidin-1-yl)pyrimidin-4-yl)methylene)thiazolidine-2,4-dione | $C_{25}H_{25}N_5O_3S$ | 475.563 | A16 | B17 |
| 439 | (Z)-5-((2-(4-(((3-(furan-3-yl)benzyl)amino)methyl)piperidin-1-yl)pyrimidin-4-yl)methylene)thiazolidine-2,4-dione | $C_{25}H_{25}N_5O_3S$ | 475.563 | A17 | B17 |
| 440 | (Z)-5-((2-(4-(((2-(1H-pyrrol-2-yl)benzyl)amino)methyl)piperidin-1-yl)pyrimidin-4-yl)methylene)thiazolidine-2,4-dione | $C_{25}H_{26}N_6O_2S$ | 474.578 | A16 | B18 |
| 441 | (Z)-5-((2-(4-(((3-(1H-pyrrol-2-yl)benzyl)amino)methyl)piperidin-1-yl)pyrimidin-4-yl)methylene)thiazolidine-2,4-dione | $C_{25}H_{26}N_6O_2S$ | 474.578 | A17 | B18 |
| 442 | (Z)-5-((2-(4-(((2-(isoquinolin-4-yl)benzyl)amino)methyl)piperidin-1-yl)pyrimidin-4-yl)methylene)thiazolidine-2,4-dione | $C_{30}H_{28}N_6O_2S$ | 536.647 | A16 | B19 |
| 443 | (Z)-5-((2-(4-(((3-(isoquinolin-4-yl)benzyl)amino)methyl)piperidin-1-yl)pyrimidin-4-yl)methylene)thiazolidine-2,4-dione | $C_{30}H_{28}N_6O_2S$ | 536.647 | A17 | B19 |
| 444 | (Z)-5-((2-(4-(((2-(quinolin-4-yl)benzyl)amino)methyl)piperidin-1-yl)pyrimidin-4-yl)methylene)thiazolidine-2,4-dione | $C_{30}H_{28}N_6O_2S$ | 536.647 | A16 | B20 |
| 445 | (Z)-5-((2-(4-(((3-(quinolin-4-yl)benzyl)amino)methyl)piperidin-1-yl)pyrimidin-4-yl)methylene)thiazolidine-2,4-dione | $C_{30}H_{28}N_6O_2S$ | 536.647 | A17 | B20 |
| 446 | (Z)-5-((2-(4-(((2-(3-fluoropyridin-4-yl)benzyl)amino)methyl)piperidin-1-yl)pyrimidin-4-yl)methylene)thiazolidine-2,4-dione | $C_{26}H_{25}FN_6O_2S$ | 504.579 | A16 | B21 |
| 447 | (Z)-5-((2-(4-(((3-(3-fluoropyridin-4-yl)benzyl)amino)methyl)piperidin-1-yl)pyrimidin-4-yl)methylene)thiazolidine-2,4-dione | $C_{26}H_{25}FN_6O_2S$ | 504.579 | A17 | B21 |
| 448 | (Z)-5-((2-(4-(((2-(2,6-difluoropyridin-4-yl)benzyl)amino)methyl)piperidin-1-yl)pyrimidin-4-yl)methylene)thiazolidine-2,4-dione | $C_{26}H_{24}F_2N_6O_2S$ | 522.57 | A16 | B22 |
| 449 | (Z)-5-((2-(4-(((3-(2,6-difluoropyridin-4-yl)benzyl)amino)methyl)piperidin-1-yl)pyrimidin-4-yl)methylene)thiazolidine-2,4-dione | $C_{26}H_{24}F_2N_6O_2S$ | 522.57 | A17 | B22 |
| 450 | (Z)-5-((2-(4-(((2-(6-(dimethylamino)pyridin-3-yl)benzyl)amino)methyl)piperidin-1-yl)pyrimidin-4-yl)methylene)thiazolidine-2,4-dione | $C_{28}H_{31}N_7O_2S$ | 529.656 | A16 | B23 |
| 451 | (Z)-5-((2-(4-(((3-(6-(dimethylamino)pyridin-3-yl)benzyl)amino)methyl)piperidin-1-yl)pyrimidin-4-yl)methylene)thiazolidine-2,4-dione | $C_{28}H_{31}N_7O_2S$ | 529.656 | A17 | B23 |
| 452 | (Z)-5-((2-(4-(((2-(2-(dimethylamino)pyrimidin-5-yl)benzyl)amino)methyl)piperidin-1-yl)pyrimidin-4-yl)methylene)thiazolidine-2,4-dione | $C_{27}H_{30}N_8O_2S$ | 530.645 | A16 | B24 |
| 453 | (Z)-5-((2-(4-(((3-(2-(dimethylamino)pyrimidin-5-yl)benzyl)amino)methyl)piperidin-1-yl)pyrimidin-4-yl)methylene)thiazolidine-2,4-dione | $C_{27}H_{30}N_8O_2S$ | 530.645 | A17 | B24 |
| 454 | (Z)-5-((2-(4-(((2-(3,5-dimethylisoxazol-4-yl)benzyl)amino)methyl)piperidin-1-yl)pyrimidin-4-yl)methylene)thiazolidine-2,4-dione | $C_{26}H_{28}N_6O_3S$ | 504.604 | A16 | B25 |
| 455 | (Z)-5-((2-(4-(((3-(3,5-dimethylisoxazol-4-yl)benzyl)amino)methyl)piperidin-1-yl)pyrimidin-4-yl)methylene)thiazolidine-2,4-dione | $C_{26}H_{28}N_6O_3S$ | 504.604 | A17 | B25 |
| 456 | (Z)-5-((2-(4-(((2-(1H-pyrazol-4-yl)benzyl)amino)methyl)piperidin-1-yl)pyrimidin-4-yl)methylene)thiazolidine-2,4-dione | $C_{24}H_{25}N_7O_2S$ | 475.566 | A16 | B26 |
| 457 | (Z)-5-((2-(4-(((3-(1H-pyrazol-4-yl)benzyl)amino)methyl)piperidin-1-yl)pyrimidin-4-yl)methylene)thiazolidine-2,4-dione | $C_{24}H_{25}N_7O_2S$ | 475.566 | A17 | B26 |
| 458 | (Z)-5-((2-(4-(((2-(1H-pyrazol-5-yl)benzyl)amino)methyl)piperidin-1-yl)pyrimidin-4-yl)methylene)thiazolidine-2,4-dione | $C_{24}H_{25}N_7O_2S$ | 475.566 | A16 | B27 |
| 459 | (Z)-5-((2-(4-(((3-(1H-pyrazol-5-yl)benzyl)amino)methyl)piperidin-1-yl)pyrimidin-4-yl)methylene)thiazolidine-2,4-dione | $C_{24}H_{25}N_7O_2S$ | 475.566 | A17 | B27 |

In addition, it may be convenient or desirable to prepare, purify, and/or handle the active compound in a chemically protected form. The term "chemically protected form," as used herein, pertains to a compound in which one or more reactive functional groups are protected from undesirable chemical reactions (i.e., they have been modified with a protecting group).

By protecting a reactive functional group, reactions involving other unprotected reactive functional groups can be performed without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl(diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Pharmaceutical Compositions

One or more compounds of this invention can be administered to a mammal by themselves or in pharmaceutical compositions where they are mixed with suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a compound of formula I, or a pharmaceutically acceptable salt, solvate, enantiomer or stereoisomer thereof; and a pharmaceutically acceptable diluent or carrier.

Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer a compound in a local rather than a systemic manner, for example, via injection of the compound directly into an edematous site, often in a depot or sustained release formulation.

Furthermore, one may administer a compound in a targeted drug delivery system, for example, in a liposome coated with endothelial-cell-specific antibody.

The pharmaceutical compositions of the present invention may be manufactured, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for reconstitution before use with a suitable vehicle, e.g., sterile pyrogen-free water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical compounds may be employed. Liposomes and emulsions are examples of delivery vehicles or carriers for hydrophobic drugs. Certain organic solvents such as dimethysulfoxide also may be employed. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols or cyclodextrins.

Methods of Treatment

Provided herein are methods of modulating the activity of CK1 and subtypes thereof, CK2, the Wnt pathway, and/or the TGFβ pathway. Also provided herein are methods of treating or preventing conditions and diseases the course of which can be influenced by modulating the activity of CK1 (e.g., CK1γ), CK2, the Wnt pathway, and/or the TGFβ pathway. Such methods typically comprise administering to a subject in need thereof a therapeutically effective amount of a compound or composition of the invention.

Also provided herein are methods of modulating the activity of PIM, such as PIM 1, PIM 2 or PIM 3, the JAK/STAT pathway, and/or the mTOR pathway, and/or Pgp. Also provided herein are methods of treating or preventing conditions and diseases, the course of which can be influenced by modulating the activity of the PIMs, the JAK/STAT pathway, and/or the mTOR pathway, and/or Pgp. Such methods typically comprise administering to a subject in need thereof a therapeutically effective amount of a compound or composition of the invention.

Various diseases, such as cancers, inflammation, and inflammatory diseases (e.g., osteoarthritis and rheumatoid arthritis), and neurological conditions (e.g., Alzheimer's disease) and neurodegeneration can be treated by administration of modulators of CK1 (e.g., CK1γ), CK2, the Wnt pathway and/or the TGFβ pathway. Bone-related diseases and conditions, including osteoporosis and bone formation, also can be treated by administration of modulators of CK1 (e.g., CK1γ), CK2, the Wnt pathway and/or the TGFβ pathway. Bone restoration can be facilitated by administration of modulators of CK1 (e.g., CK1γ), CK2, the Wnt pathway and/or the TGFβ pathway. Additional conditions that can be treated by administration of modulators of CK1 (e.g., CK1γ), CK2, the Wnt pathway and/or the TGFβ pathway include hypoglycemia, metabolic syndrome and diabetes. Modulators of CK1 (e.g., CK1γ), CK2, the Wnt pathway and/or the TGFβ pathway are also useful for influencing apoptosis (e.g., increasing the rate of apoptosis in cancerous cells). Modulators of CK1 (e.g., CK1γ), CK2, the Wnt pathway and/or the TGFβ pathway are also useful in treatment or prevention of aberrant embryonic development.

Based at least on the fact that increased CK1γ has been found to be associated with certain cancers, a method for treating cancer in a subject comprises administering to the subject in need thereof a therapeutically effective amount of a compound that inhibits CK1γ. Pim-1, Pim-2, Pim-3, the JAK/STAT pathway, and/or the mTOR pathway have also been found to be associated with certain cancers. Therefore, provided herein is a method for treating cancer comprising administering to a subject in need thereof a therapeutically effective amount of a compound that inhibits Pim-1 and/or Pim-2 and/or Pim-3.

Pim-1, Pim-2, and Pim-3 have also been associated with protecting Pgp from degradation, which can regulate drug efflux and drug resistance. Therefore, provided herein is a method for treating malignancies comprising administering to a subject in need thereof a therapeutically effective amount of a compound that inhibits Pim-1 and/or Pim-2 and/or Pim-3 in conjunction with another drug, compound or material to abrogate resistance to the drug, compound or material.

The compounds described herein can be used for modulating cell proliferation, generally. Accordingly, diseases that may be treated include hyperproliferative diseases, such as benign cell growth and malignant cell growth.

Exemplary cancers that may be treated include leukemias, e.g., acute lymphoid leukemia and myeloid leukemia, and carcinomas, such as colorectal carcinoma and hepatocarcinoma. Other cancers include Acute Lymphoblastic Leukemia; Acute Lymphoblastic Leukemia; Acute Myeloid Leukemia; Acute Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Brain Tumor; Breast Cancer; Breast Cancer and Pregnancy; Breast Cancer; Breast Cancer, Male; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cerebral Astrocytoma/Malignant Glioma; Cervical Cancer; Childhood Cancers; Chronic Lymphocytic Leukemia; Chronic Myelogenous Leukemia; Chronic Myeloproliferative Disorders; Colon Cancer; Colorectal Cancer; Cutaneous T-Cell Lymphoma, see Mycosis Fungoides and Sezary Syndrome; Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hematologic (Blood) Cancer, Hepatocellular (Liver) Cancer, Adult (Primary); Hepatocellular (Liver) Cancer, Childhood (Primary); Hodgkin's Lymphoma; Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's; Lymphoma, Hodgkin's During Pregnancy; Lymphoma, Non-Hodgkin's; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma; Non-Hodgkin's Lymphoma; Non-Hodgkin's Lymphoma During Pregnancy; Non-Small Cell Lung Cancer; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Unknown Primary Site, Carcinoma of; Unknown Primary Site, Cancer of; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include. Alzheimer's disease, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease), Dentatorubropallidoluysian Atrophy (DRPLA), Spinocerebellar Ataxia 1 (SCAT), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which the Wnt pathway, TGFβ pathway, JAK/STAT pathway, the mTOR pathway, Pgp modulation, CK1, CK1γ, CK2, or PIMs plays a role may be treatable or preventable using compounds and methods described herein.

Dosage

As used herein, a "therapeutically effective amount" or "therapeutically effective dose" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount may be determined by methods known to those of skill in the art.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the CK1, CK1γ, CK2, Pim1-3, Wnt pathway, TGFβ pathway, JAK/STAT pathway, mTOR pathway, or Pgp modulating effects, or minimal effective concentration (MEC). The MEC will vary for each compound but can be estimated from in vitro data. Dosages necessary to achieve the MEC will depend on individual characteristics and route of administration. HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Kits

The compounds and compositions of the invention (e.g., compounds and compositions of formula I and formula II) may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Instructions for use may also be provided.

EXEMPLIFICATION

The invention now being generally described, it will be more readily understood by reference to the following examples, which are included merely for purposes of illustration of certain aspects and embodiments of the present invention, and are not intended to limit the invention. The geometric isomers depicted below are believed to be correct, but final structural assignment will be made via 2-D NMR experiments. Although the exemplary compounds described below are believed to be the Z-geometric isomers, the E-geometric isomers and mixtures of the E- and Z-isomers are also contemplated by the present disclosure.

Example 1

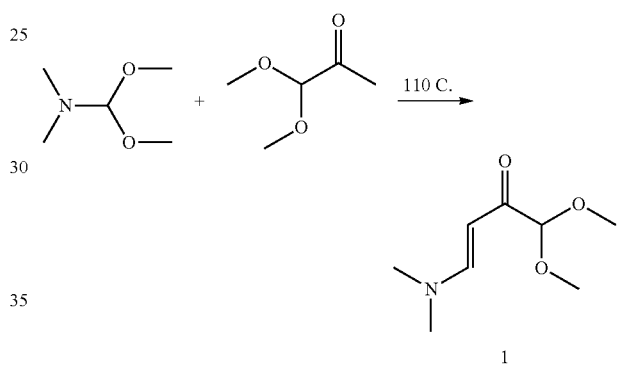

(E)-4-(dimethylamino)-1,1-dimethoxybut-3-en-2-one
(1)

1,1-dimethoxy-N,N-dimethylmethanamine (100 g, 839 mmol, 1.02 equiv.) and 1,1-dimethoxypropan-2-one (97 g, 821 mmol) were added and stirred at 110° C. for 3 hours. The produced methanol was removed by a Dean-Stark apparatus. After the solution was cooled to room temperature, the remaining volatile materials were removed in vacuo to provide 130 g of the crude product, (E)-4-(dimethylamino)-1,1-dimethoxybut-3-en-2-one (1) (130 g, 143 g theoretical, 91%). LC-MS m/z 283 (M+1). Reference: WO 2006/0097341A1 (incorporated by reference), pg 67.

Example 2

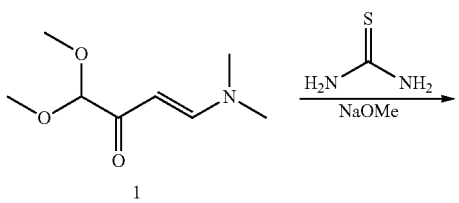

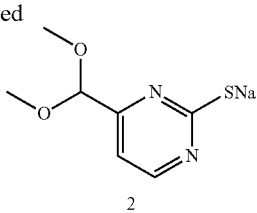

Sodium 4-(dimethoxymethyl)pyrimidine-2-thiolate (2)

A solution of thiourea (64.7 g, 850 mmol, 1.13 equiv.), sodium methanolate (95%, 40.5 g, 751 mmol, 1.0 equiv.) in methanol (500 mL, 1.5 M) was stirred at room temperature for 30 minutes. A solution of (E)-4-(dimethylamino)-1,1-dimethoxybut-3-en-2-one (1) (130 g, 751 mmol) in methanol (200 mL) was added and the reaction stirred at room temperature for 2 h. The crude sodium 4-(dimethoxymethyl)pyrimidine-2-thiolate (2) was used directly in the next step without further purification. LC-MS m/z 209 (M+1). Reference: WO 2006/0097341A1 (incorporated by reference), pg 67.

Example 3

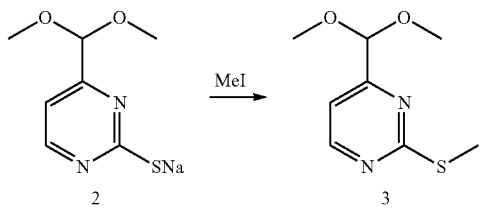

4-(dimethoxymethyl)-2-(methylthio)pyrimidine (3)

Iodomethane (128 g, 902 mmol, 1.20 equiv.) was added carefully to the crude solution of sodium 4-(dimethoxymethyl)pyrimidine-2-thiolate (2) (156 g, 751 mmol) in methanol (700 mL, 1.1 M) while maintaining the reaction temperature below 28° C. using an ice-water bath for cooling. The resulting mixture was stirred at room temperature for 16 h. After removal of the solvent under reduced pressure, the residue was diluted with water (300 mL) and extracted with ethyl acetate (2×150 mL). The combined organic layer was concentrated under reduced pressure and the crude residue purified by passing through a short silica gel pad and washing with diethyl ether (200 mL) to afford 4-(dimethoxymethyl)-2-(methylthio)pyrimidine (3) as a brown oil (53.7 g, 150 g theoretical, 35.7%). LC-MS m/z 201 (M+1). Reference: WO 2006/0097341A1 (incorporated by reference), pg 67.

Example 4

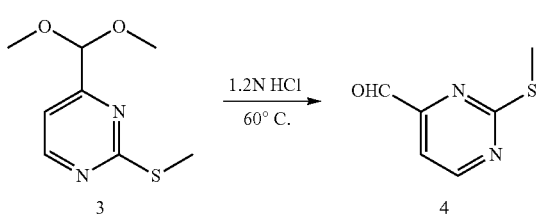

2-(methylthio)pyrimidine-4-carbaldehyde (4)

4-(dimethoxymethyl)-2-(methylthio)pyrimidine (3) (53.7 g, 268 mmol) was added carefully to 1.2 N aqueous HCl (300 mL, 268 mmol, 1.0 equiv.) and stirred at 60° C. for 3 hours. The reaction mixture was then cooled to room temperature and neutralized by the slow addition of solid sodium bicarbonate. The crude mixture was extracted with diethyl ether (3×150 mL) and the combined organic layer was concentrated under reduced pressure to afford 2-(methylthio)pyrimidine-4-carbaldehyde (4) as a yellow solid (14.2 g, 41.5 g theoretical, 34%). LC-MS m/z 155 (M+1). Reference: WO 2006/009734 A1 (incorporated by reference), pg 67.

Example 5

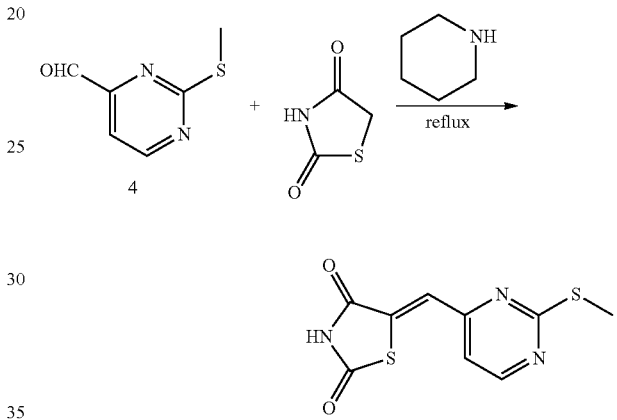

(Z)-5-((2-(methylthio)pyrimidin-4-yl)methylene)thiazolidine-2,4-dione (5)

A 40 mL round-bottomed vial was charged with 2-(methylthio)pyrimidine-4-carbaldehyde (4) (771 mg, 5 mmol), thiazolidine-2,4-dione (586 mg, 5 mmol, 1.0 equiv.), and piperidine (400 µL, 4 mmol, 0.8 equiv.) in ethanol (20 mL, 0.25 M). The reaction mixture was heated to 80° C. and shaken for 20 h. The resulting yellow precipitate was isolated by filtration and washed with ethanol (1×20 mL) and dried in vacuo to afford (Z)-5-((2-(methylthio)pyrimidin-4-yl)methylene)thiazolidine-2,4-dione (5) as a yellow solid (550 mg, 898 mg theoretical, 61%). LC-MS m/z 254 (M+1).

Example 6

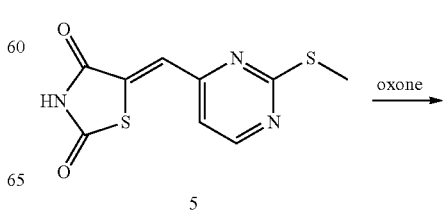

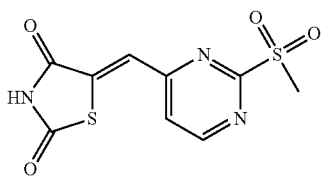

(Z)-5-((2-(methylsulfonyl)pyrimidin-4-yl)methyl-ene)thiazolidine-2,4-dione (6)

A mixture of (Z)-5-((2-(methylthio)pyrimidin-4-yl)methyl-ene)thiazolidine-2,4-dione (5) (3.5 g, 13.82 mmol) in THF (100 mL, 0.13 M) was treated with a solution of oxone (25.8 g, 41.5 mmol, 3.0 equiv.) in water (175 mL). The resulting mixture was stirred at room temperature for 48 h. The resulting precipitate was filtered and washed with water (20 mL) and diethyl ether (20 mL) to afford (Z)-5-((2-(methylsulfonyl)pyrimidin-4-yl)methylene)thiazolidine-2,4-dione (6) as a solid (2.48 g, 3.94 g theoretical, 63%). LC-MS m/z 286 (M+1).

Example 7

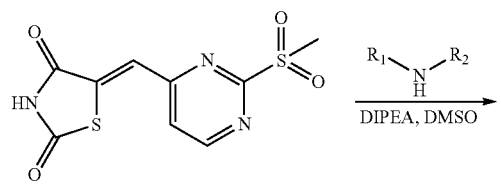

General Displacement Procedure 2-dram round-bottomed vials were charged with (Z)-5-((2-(methylsulfonyl)pyrimidin-4-yl)methylene)thiazolidine-2,4-dione (25 mg, 0.0877 mmol) prepared according to the general procedure, DMSO (1 mL, 0.08 M), diisopropylethylamine (50 µL, 0.288 mmol, 3.2 equiv.), and the appropriate amine (0.0877 mmol, 1.0 equiv.). The reaction mixture was heated to 110° C. and shaken for 24 h. The solvent was removed under reduced pressure (Genvac HT-4) and the crude residues were purified using reverse phase HPLC (MS-triggered fraction collection) with an acetonitrile/water gradient and trifluoroacetic acid as a modifier. The pure fractions were then concentrated under reduced pressure (Genevac HT-4).

Example 8

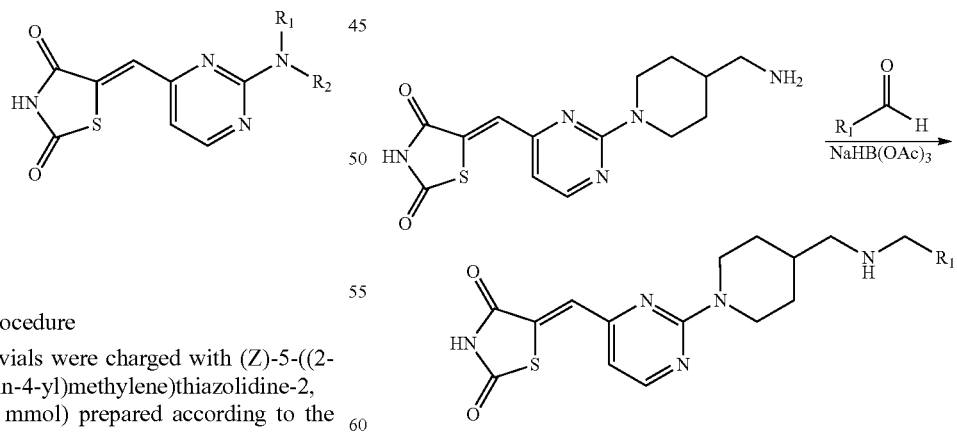

Displacement/De-Protection of Mono-Boc Diamines
General De-Protection Procedure

The crude protected amine was prepared using the General Displacement Procedure and was then treated with 2 mL DCE and 500 µL of TFA and shaken for 24 h. The solvent was removed under reduced pressure (Genevac HT-4) and the crude residues were purified using reverse phase HPLC (MS-triggered fraction collection) with an acetonitrile/water or methanol/water gradient and trifluoroacetic acid as a modifier. The pure fractions were then concentrated under reduced pressure (Genevac HT-4).

Example 9

Reductive Amination Analogs
General Reductive Amination Procedure

A 2-dram round-bottomed vial was charged with the crude amine/TFA salt prepared using the general displacement procedure followed by the general TFA de-protection procedure (0.115 mmol), DCE (2 mL), DIPEA (6 eq. 0.690 mmol), DMF (1 mL), the aldehyde or ketone (1 equiv., 0.115 mmol), and the reaction mixture was shaken for 1 h at RT. The reaction mixture was then treated with NaBH(OAc)₃ (2.5 equiv., 0.230 mmol) and the reaction was shaken 16 h at RT. The reaction mixture was then diluted with DCE (2 mL) and NaHCO₃ (2 mL). The aqueous layer was back extracted with DCE (2×2 mL) and the combined organic layer was concentrated under reduced pressure (Genevac HT-4) and the crude residue was purified using reverse phase HPLC (MS-triggered fraction collection) with an acetonitrile/water or methanol/water gradient and trifluoroacetic acid as the modifier. The pure fractions were then concentrated under reduced pressure (Genevac HT-4) to afford the pure products as the TFA salt.

Example 10

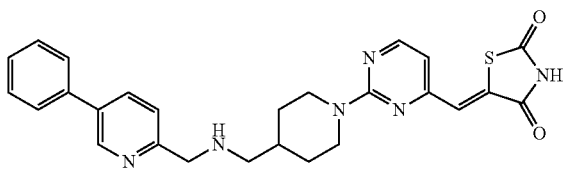 [SMILES: O=C1NC(=O)/C(=C/c2ccnc(N3CCC(CNCc4ccc(-c5ccccc5)cn4)CC3)n2)S1]

(Z)-5-((2-(4-((((5-phenylpyridin-2-yl)methyl)amino)methyl)piperidin-1-yl)pyrimidin-4-yl)methylene)thiazolidine-2,4-dione was prepared using the general reductive amination procedure and 5-phenylpicolinaldehyde (33.7 mg, 40.4 mg theoretical, 83%). LC-MS m/z 487.6 (M+1).

Example 11

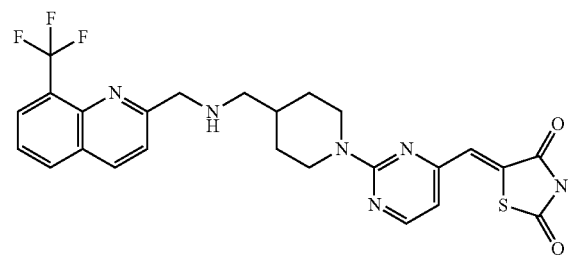

(Z)-5-((2-(4-((((8-(trifluoromethyl)quinolin-2-yl)methyl)amino)methyl)piperidin-1-yl)pyrimidin-4-yl)methylene)thiazolidine-2,4-dione was prepared using the general reductive amination procedure and 8-(trifluoromethyl)-2-naphthaldehyde (8.5 mg, 43.9 mg theoretical, 19.3%). LC-MS m/z 529.5 (M+1).

Example 12

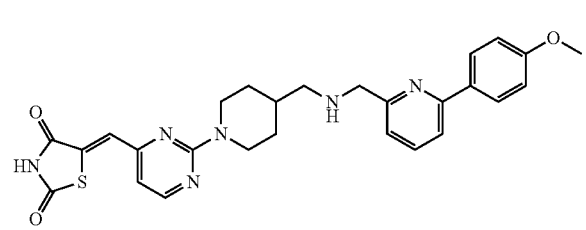 [SMILES: COc1ccc(-c2cccc(CNCC3CCN(c4nccc(/C=C5\SC(=O)NC5=O)n4)CC3)n2)cc1]

(Z)-5-((2-(4-((((6-(4-methoxyphenyl)pyridin-2-yl)methyl)amino)methyl)piperidin-1-yl)pyrimidin-4-yl)methylene)thiazolidine-2,4-dione was prepared using the general reductive amination procedure and 5-phenylpicolinaldehyde (32 mg, 42.9 mg theoretical, 74.6%). LC-MS m/z 517.6 (M+1).

Example 13

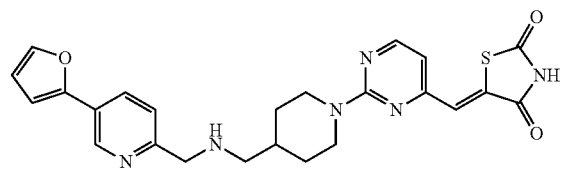 [SMILES: O=C1NC(=O)/C(=C/c2ccnc(N3CCC(CNCc4ccc(-c5ccco5)cn4)CC3)n2)S1]

(Z)-5-((2-(4-((((5-(furan-2-yl)pyridin-2-yl)methyl)amino)methyl)piperidin-1-yl)pyrimidin-4-yl)methylene)thiazolidine-2,4-dione was prepared using the general reductive amination procedure and 5-(furan-2-yl)picolinaldehyde (24 mg, 39.6 mg theoretical, 60.7%). LC-MS m/z 477.6 (M+1).

Example 14

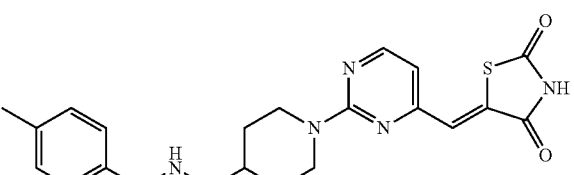

(Z)-5-((2-(4-((((5-methylpyridin-2-yl)methyl)amino)methyl)piperidin-1-yl)pyrimidin-4-yl)methylene)thiazolidine-2,4-dione was prepared using the general reductive amination procedure and 5-methylpicolinaldehyde (25.3 mg, 35.2 mg theoretical, 71.8%). LC-MS m/z 425.5 (M+1).

Example 15

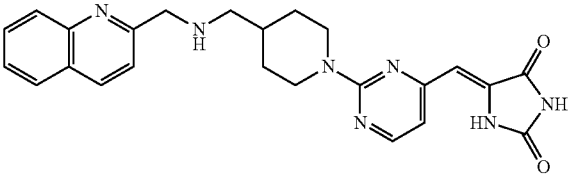 [SMILES: O=C1NC(=O)/C(=C/c2ccnc(N3CCC(CNCc4ccc5ccccc5n4)CC3)n2)N1]

(Z)-5-((2-(4-(((quinolin-2-ylmethyl)amino)methyl)piperidin-1-yl)pyrimidin-4-yl)methylene)imidazolidine-2,4-dione was prepared using the general reductive amination procedure and quinoline-2-carbaldehyde (3.2 mg, 24.9 mg theoretical, 12.8%). LC-MS m/z 444.5 (M+1).

Example 16

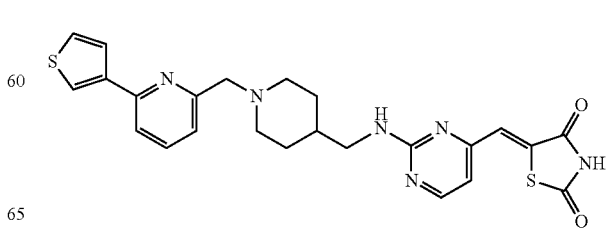

(Z)-5-((2-(((1-((6-(thiophen-3-yl)pyridin-2-yl)methyl)piperidin-4-yl)methyl)amino)pyrimidin-4-yl)methylene)thiazolidine-2,4-dione was prepared using the general reductive amination procedure and 6-(thiophen-3-yl)picolinaldehyde (38.8 mg, 46.8 mg theoretical, 83%). LC-MS m/z 493.6 (M+1).

Example 17

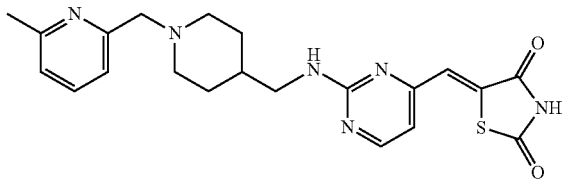 [SMILES: Cc1cccc(CN2CCC(CNc3nccc(/C=C4\SC(=O)NC4=O)n3)CC2)n1]

(Z)-5-((2-(((1-((6-methylpyridin-2-yl)methyl)piperidin-4-yl)methyl)amino)pyrimidin-4-yl)methylene)thiazolidine-2,4-dione was prepared using the general reductive amination procedure and 6-methylpicolinaldehyde (40.3 mg, 40.3 mg theoretical, 100%). LC-MS m/z 425.5 (M+1).

Example 18

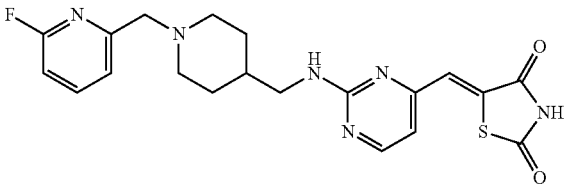 [SMILES: O=C1NC(=O)/C(=C/c2ccnc(NCC3CCN(Cc4cccc(F)n4)CC3)n2)S1]

(Z)-5-((2-(((1-((6-fluoropyridin-2-yl)methyl)piperidin-4-yl)methyl)amino)pyrimidin-4-yl)methylene)thiazolidine-2,4-dione was prepared using the general reductive amination procedure and 6-fluoropicolinaldehyde (16.2 mg, 40.7 mg theoretical, 39.8%). LC-MS m/z 429.5 (M+1).

Example 19

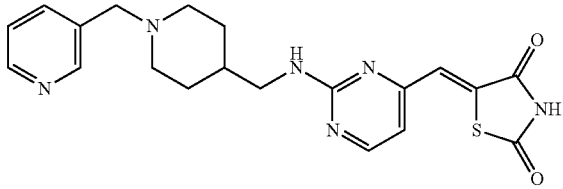 [SMILES: O=C1NC(=O)/C(=C/c2ccnc(NCC3CCN(Cc4cccnc4)CC3)n2)S1]

(Z)-5-((2-(((1-(pyridin-3-ylmethyl)piperidin-4-yl)methyl)amino)pyrimidin-4-yl)methylene)thiazolidine-2,4-dione was prepared using the general reductive amination procedure and nicotinaldehyde (38.6 mg, 39.0 mg theoretical, 99%). LC-MS m/z 411.5 (M+1).

Example 20

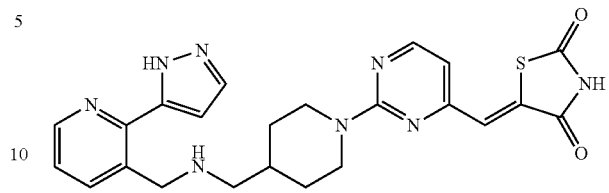

(Z)-5-((2-(4-((((2-(1H-pyrazol-5-yl)pyridin-3-yl)methyl)amino)methyl)piperidin-1-yl)pyrimidin-4-yl)methylene)thiazolidine-2,4-dione was prepared using the general reductive amination procedure and tert-butyl 5-(3-formylpyridin-2-yl)-1H-pyrazole-1-carboxylate followed by the general de-protection procedure (6.8 mg, 34.3 mg theoretical, 19.8%). LC-MS m/z 477.6 (M+1).

Example 21

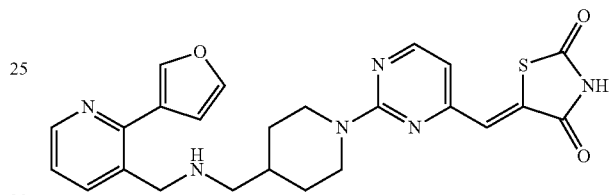

(Z)-5-((2-(4-((((2-(furan-3-yl)pyridin-3-yl)methyl)amino)methyl)piperidin-1-yl)pyrimidin-4-yl)methylene)thiazolidine-2,4-dione was prepared using the general reductive amination procedure and 2-(furan-3-yl)nicotinaldehyde (40.5 mg, 42.5 mg theoretical, 95%). LC-MS m/z 477.6 (M+1).

Example 22

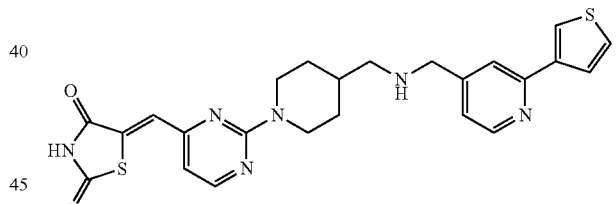

(Z)-5-((2-(4-((((2-(thiophen-3-yl)pyridin-4-yl)methyl)amino)methyl)piperidin-1-yl)pyrimidin-4-yl)methylene)thiazolidine-2,4-dione was prepared using the general reductive amination procedure and 2-(thiophen-3-yl)isonicotinaldehyde (20.8 mg, 35.5 mg theoretical, 58.6%). LC-MS m/z 493.6 (M+1).

Example 23

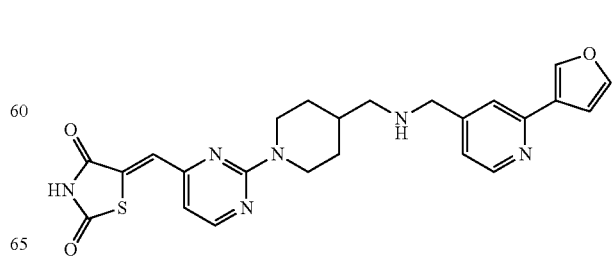

(Z)-5-((2-(4-((((2-(furan-3-yl)pyridin-4-yl)methyl)amino)methyl)piperidin-1-yl)pyrimidin-4-yl)methylene)thiazolidine-2,4-dione was prepared using the general reductive amination procedure and 2-(furan-3-yl)isonicotinaldehyde (22.2 mg, 34.3 mg theoretical, 64.7%). LC-MS m/z 477.6 (M+1).

Example 24

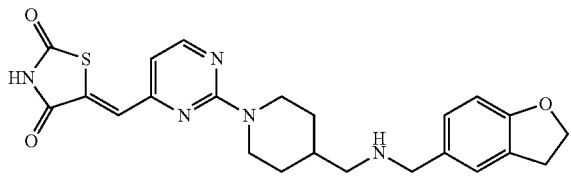 [SMILES: O=C1NC(=O)/C(=C/c2ccnc(N3CCC(CNCc4ccc5c(c4)CCO5)CC3)n2)S1]

(Z)-5-((2-(4-((((2,3-dihydrobenzofuran-5-yl)methyl)amino)methyl)piperidin-1-yl)pyrimidin-4-yl)methylene)thiazolidine-2,4-dione was prepared using the general reductive amination procedure and 2,3-dihydrobenzofuran-5-carbaldehyde (2.0 mg, 32.5 mg theoretical, 6.1%). LC-MS m/z 452.5 (M+1).

Example 25

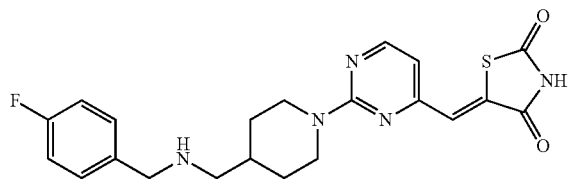 [SMILES: O=C1NC(=O)/C(=C/c2ccnc(N3CCC(CNCc4ccc(F)cc4)CC3)n2)S1]

(Z)-5-((2-(4-(((4-fluorobenzyl)amino)methyl)piperidin-1-yl)pyrimidin-4-yl)methylene)thiazolidine-2,4-dione was prepared using the general reductive amination procedure and 4-fluorobenzaldehyde (8.7 mg, 30.8 mg theoretical, 28.3%). LC-MS m/z 428.5 (M+1).

Example 26

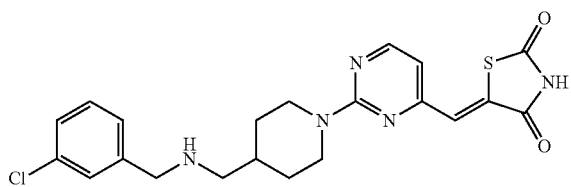 [SMILES: O=C1NC(=O)/C(=C/c2ccnc(N3CCC(CNCc4cccc(Cl)c4)CC3)n2)S1]

(Z)-5-((2-(4-(((3-chlorobenzyl)amino)methyl)piperidin-1-yl)pyrimidin-4-yl)methylene)thiazolidine-2,4-dione was prepared using the general reductive amination procedure and 3-chlorobenzaldehyde (13.8 mg, 32.0 mg theoretical, 43.2%). LC-MS m/z 444.9 (M+1).

Example 27

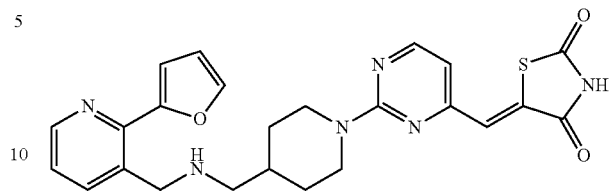

(Z)-5-((2-(4-((((2-(furan-2-yl)pyridin-3-yl)methyl)amino)methyl)piperidin-1-yl)pyrimidin-4-yl)methylene)thiazolidine-2,4-dione was prepared using the general reductive amination procedure and 2-(furan-2-yl)nicotinaldehyde (14.0 mg, 34.3 mg theoretical, 40.8%). LC-MS m/z 477.6 (M+1).

Example 28

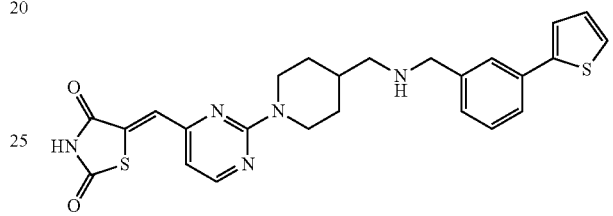

(Z)-5-((2-(4-(((3-(thiophen-2-yl)benzyl)amino)methyl)piperidin-1-yl)pyrimidin-4-yl)methylene)thiazolidine-2,4-dione was prepared using the general reductive amination procedure and 3-(thiophen-2-yl)benzaldehyde (34.0 mg, 46.2 mg theoretical, 73.6%). LC-MS m/z 492.6 (M+1).

Example 29

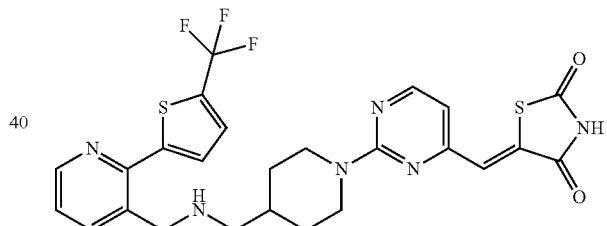

(Z)-5-((2-(4-((((2-(5-(trifluoromethyl)thiophen-2-yl)pyridin-3-yl)methyl)amino)methyl)piperidin-1-yl)pyrimidin-4-yl)methylene)thiazolidine-2,4-dione was prepared using the general reductive amination procedure and 2-(5-(trifluoromethyl)thiophen-2-yl)nicotinaldehyde (19.9 mg, 26.9 mg theoretical, 74%). LC-MS m/z 561.6 (M+1).

Example 30

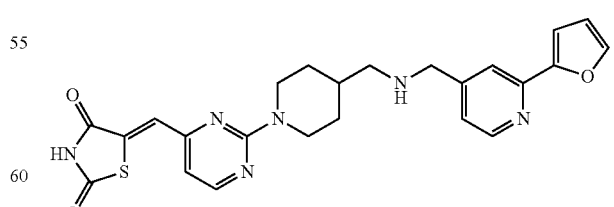

(Z)-5-((2-(4-((((2-(furan-2-yl)pyridin-4-yl)methyl)amino)methyl)piperidin-1-yl)pyrimidin-4-yl)methylene)thiazolidine-2,4-dione was prepared using the general reductive amination procedure and 2-(furan-2-yl)isonicotinaldehyde (16.0 mg, 34.3 mg theoretical, 46.6%). LC-MS m/z 477.6 (M+1).

Example 31

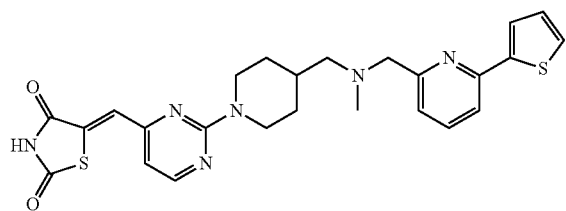 [SMILES: CN(Cc1cccc(-c2cccs2)n1)CC1CCN(c2nccc(/C=C3\SC(=O)NC3=O)n2)CC1]

(Z)-5-((2-(4-((methyl((6-(thiophen-2-yl)pyridin-2-yl)methyl)amino)methyl)piperidin-1-yl)pyrimidin-4-yl)methylene)thiazolidine-2,4-dione was prepared using the general reductive amination procedure and 6-(thiophen-2-yl)picolinaldehyde (14.0 mg, 34.4 mg theoretical, 46.1%). LC-MS m/z 507.6 (M+1).

Example 32

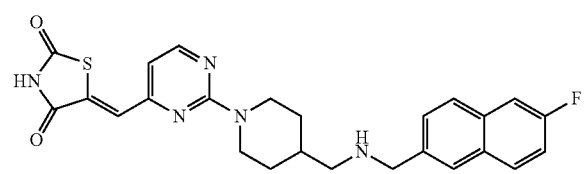 [SMILES: O=C1NC(=O)/C(=C/c2ccnc(N3CCC(CNCc4ccc5cc(F)ccc5c4)CC3)n2)S1]

(Z)-5-((2-(4-((((6-fluoronaphthalen-2-yl)methyl)amino)methyl)piperidin-1-yl)pyrimidin-4-yl)methylene)thiazolidine-2,4-dione was prepared using the general reductive amination procedure and 6-fluoro-2-naphthaldehyde (18.7 mg, 22.9 mg theoretical, 82%). LC-MS m/z 478.6 (M+1).

Example 33

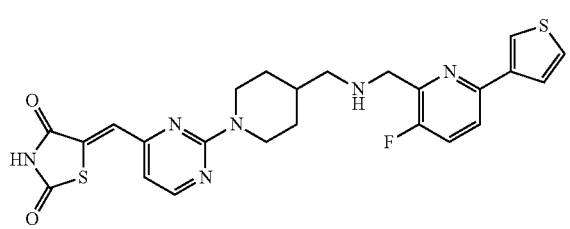 [SMILES: O=C1NC(=O)/C(=C/c2ccnc(N3CCC(CNCc4nc(-c5ccsc5)ccc4F)CC3)n2)S1]

(Z)-5-((2-(4-((((3-fluoro-6-(thiophen-3-yl)pyridin-2-yl)methyl)amino)methyl)piperidin-1-yl)pyrimidin-4-yl)methylene)thiazolidine-2,4-dione was prepared using the general reductive amination procedure and 3-fluoro-6-(thiophen-3-yl)picolinaldehyde (13.3 mg, 24.5 mg theoretical, 54.3%). LC-MS m/z 511.6 (M+1).

Example 34

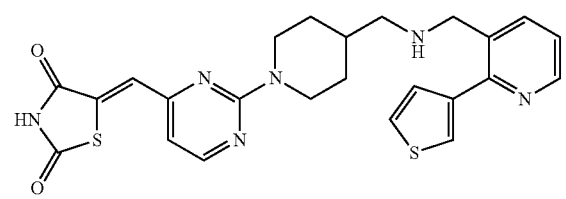 [SMILES: O=C1NC(=O)/C(=C/c2ccnc(N3CCC(CNCc4cccnc4-c4ccsc4)CC3)n2)S1]

(Z)-5-((2-(4-((((2-(thiophen-3-yl)pyridin-3-yl)methyl)amino)methyl)piperidin-1-yl)pyrimidin-4-yl)methylene)thiazolidine-2,4-dione was prepared using the general reductive amination procedure and 2-(thiophen-3-yl)nicotinaldehyde (21.0 mg, 26.6 mg theoretical, 79%). LC-MS m/z 555.5 (M+1).

Example 35

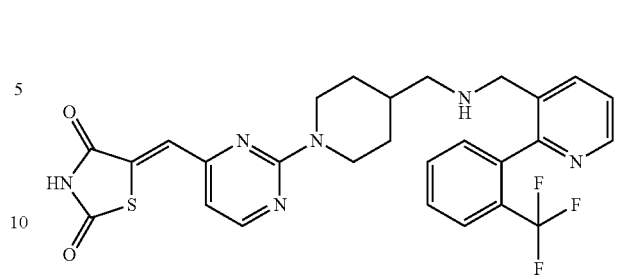

(Z)-5-((2-(4-((((2-(2-(trifluoromethyl)phenyl)pyridin-3-yl)methyl)amino)methyl)piperidin-1-yl)pyrimidin-4-yl)methylene)thiazolidine-2,4-dione was prepared using the general reductive amination procedure and 2-(2-(trifluoromethyl)phenyl)nicotinaldehyde (24.5 mg, 26.6 mg theoretical, 92%). LC-MS m/z 555.5 (M+1).

Example 36

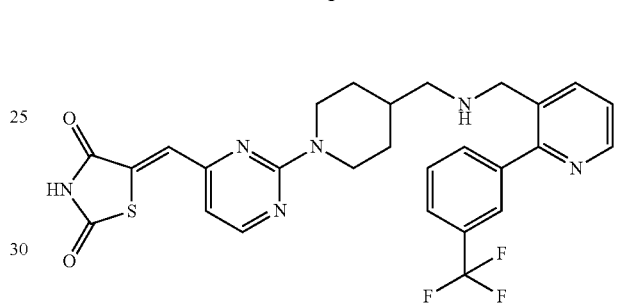

(Z)-5-((2-(4-((((2-(3-(trifluoromethyl)phenyl)pyridin-3-yl)methyl)amino)methyl)piperidin-1-yl)pyrimidin-4-yl)methylene)thiazolidine-2,4-dione was prepared using the general reductive amination procedure and 2-(3-(trifluoromethyl)phenyl)nicotinaldehyde (25.1 mg, 26.6 mg theoretical, 94%). LC-MS m/z 555.5 (M+1).

Example 37

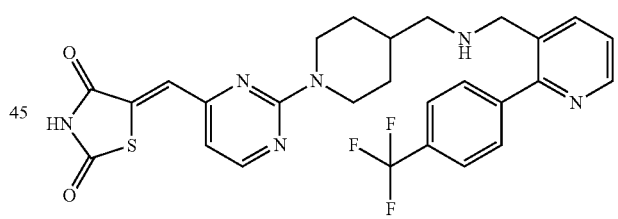

(Z)-5-((2-(4-((((2-(4-(trifluoromethyl)phenyl)pyridin-3-yl)methyl)amino)methyl)piperidin-1-yl)pyrimidin-4-yl)methylene)thiazolidine-2,4-dione was prepared using the general reductive amination procedure and 2-(4-(trifluoromethyl)phenyl)nicotinaldehyde (9.1 mg, 26.6 mg theoretical, 34.2%). LC-MS m/z 555.5 (M+1).

Example 38

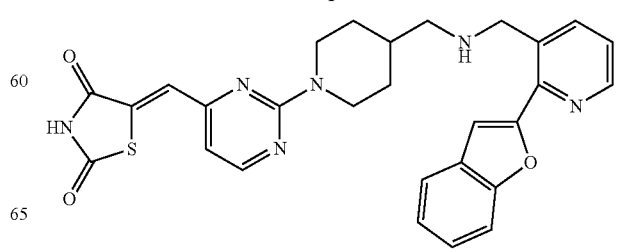

(Z)-5-((2-(4-((((2-(benzofuran-2-yl)pyridin-3-yl)methyl)amino)methyl)piperidin-1-yl)pyrimidin-4-yl)methylene)thiazolidine-2,4-dione was prepared using the general reductive amination procedure and 2-(benzofuran-2-yl)nicotinaldehyde (8.9 mg, 25.3 mg theoretical, 35.2%). LC-MS m/z 527.6 (M+1).

Example 39

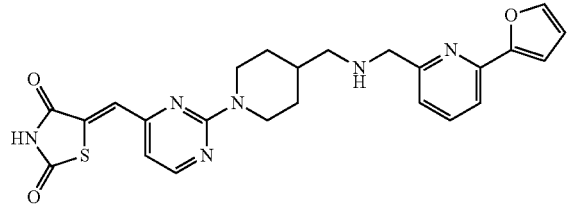 [SMILES: O=C1NC(=O)/C(=C/c2ccnc(N3CCC(CNCc4cccc(-c5ccco5)n4)CC3)n2)S1]

(Z)-5-((2-(4-((((6-(furan-2-yl)pyridin-2-yl)methyl)amino)methyl)piperidin-1-yl)pyrimidin-4-yl)methylene)thiazolidine-2,4-dione was prepared using the general reductive amination procedure and 6-(furan-2-yl)picolinaldehyde (13.9 mg, 22.8 mg theoretical, 60.8%). LC-MS m/z 477.5 (M+1).

Example 40

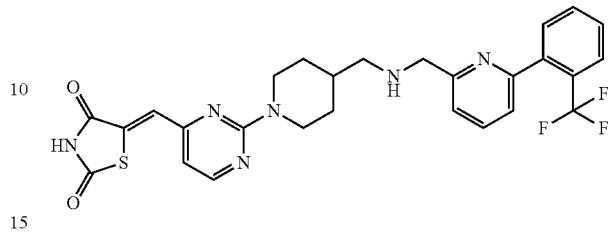

(Z)-5-((2-(4-((((6-(2-(trifluoromethyl)phenyl)pyridin-2-yl)methyl)amino)methyl)piperidin-1-yl)pyrimidin-4-yl)methylene)thiazolidine-2,4-dione was prepared using the general reductive amination procedure and 6-(2-(trifluoromethyl)phenyl)picolinaldehyde (14 mg, 26.6 mg theoretical, 52.6%). LC-MS m/z 555.5 (M+1).

Example 41

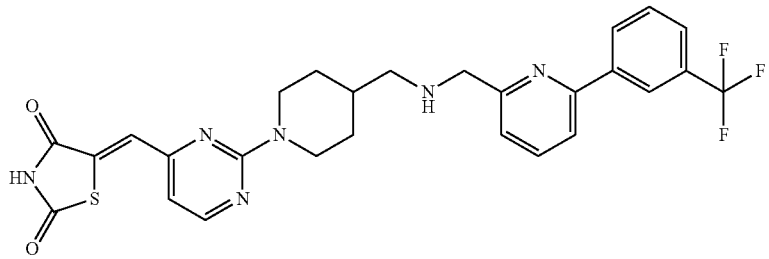 [SMILES: O=C1NC(=O)/C(=C/c2ccnc(N3CCC(CNCc4cccc(-c5cccc(C(F)(F)F)c5)n4)CC3)n2)S1]

(Z)-5-((2-(4-((((6-(3-(trifluoromethyl)phenyl)pyridin-2-yl)methyl)amino)methyl)piperidin-1-yl)pyrimidin-4-yl)methylene)thiazolidine-2,4-dione was prepared using the general reductive amination procedure and 6-(3-(trifluoromethyl)phenyl)picolinaldehyde (21.0 mg, 26.6 mg theoretical, 79%). LC-MS m/z 555.5 (M+1).

Example 42

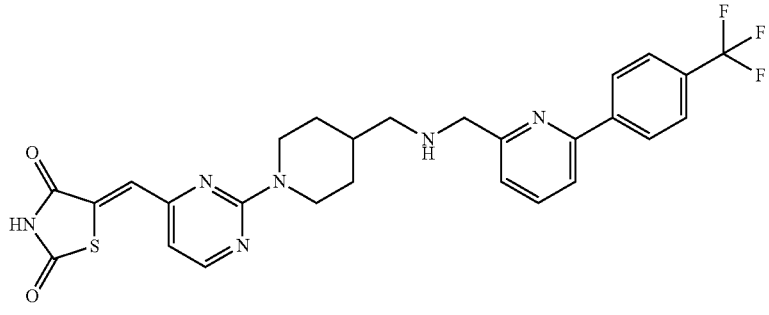 [SMILES: O=C1NC(=O)/C(=C/c2ccnc(N3CCC(CNCc4cccc(-c5ccc(C(F)(F)F)cc5)n4)CC3)n2)S1]

(Z)-5-((2-(4-((((6-(4-(trifluoromethyl)phenyl)pyridin-2-yl)methyl)amino)methyl)piperidin-1-yl)pyrimidin-4-yl)methylene)thiazolidine-2,4-dione was prepared using the general reductive amination procedure and 6-(4-(trifluoromethyl)phenyl)picolinaldehyde (13.8 mg, 26.6 mg theoretical, 51.8%). LC-MS m/z 555.5 (M+1).

Example 43

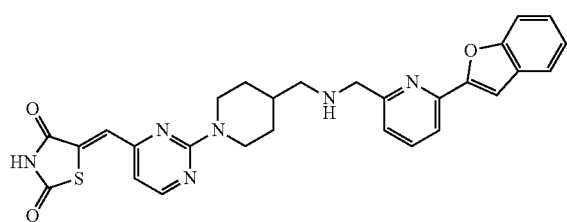 [SMILES: O=C1NC(=O)/C(=C/c2ccnc(N3CCC(CNCc4cccc(-c5cc6ccccc6o5)n4)CC3)n2)S1]

(Z)-5-((2-(4-((((6-(benzofuran-2-yl)pyridin-2-yl)methyl) amino)methyl)piperidin-1-yl)pyrimidin-4-yl)methylene) thiazolidine-2,4-dione was prepared using the general reductive amination procedure and 6-(benzofuran-2-yl) picolinaldehyde (13.3 mg, 25.3 mg theoretical, 52.6%). LC-MS m/z 527.6 (M+1).

Example 44

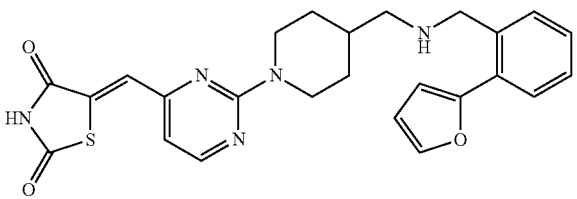 [SMILES: O=C1NC(=O)/C(=C/c2ccnc(N3CCC(CNCc4ccccc4-c4ccco4)CC3)n2)S1]

(Z)-5-((2-(4-(((2-(furan-2-yl)benzyl)amino)methyl)piperidin-1-yl)pyrimidin-4-yl)methylene)thiazolidine-2,4-dione was prepared using the general reductive amination procedure and 2-(furan-2-yl)benzaldehyde (10.2 mg, 22.8 mg theoretical, 44.7%). LC-MS m/z 476.5 (M+1).

Example 45

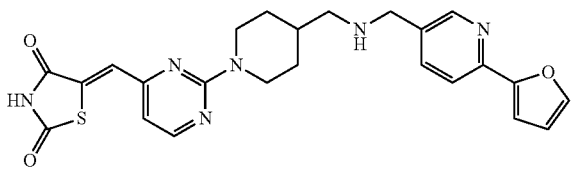 [SMILES: O=C1NC(=O)/C(=C/c2ccnc(N3CCC(CNCc4ccc(-c5ccco5)nc4)CC3)n2)S1]

(Z)-5-((2-(4-((((6-(furan-2-yl)pyridin-3-yl)methyl)amino) methyl)piperidin-1-yl)pyrimidin-4-yl)methylene)thiazolidine-2,4-dione was prepared using the general reductive amination procedure and 6-(furan-2-yl)nicotinaldehyde (18.0 mg, 22.8 mg theoretical, 79%). LC-MS m/z 477.5 (M+1).

Example 46

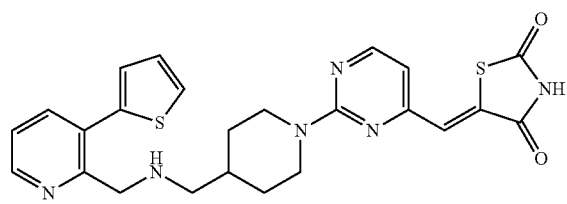 [SMILES: O=C1NC(=O)/C(=C/c2ccnc(N3CCC(CNCc4ncccc4-c4cccs4)CC3)n2)S1]

(Z)-5-((2-(4-((((3-(thiophen-2-yl)pyridin-2-yl)methyl) amino)methyl)piperidin-1-yl)pyrimidin-4-yl)methylene) thiazolidine-2,4-dione was prepared using the general reductive amination procedure and 3-(thiophen-2-yl) picolinaldehyde (10.9 mg, 23.6 mg theoretical, 46%). LC-MS m/z 493 (M+1).

Example 47

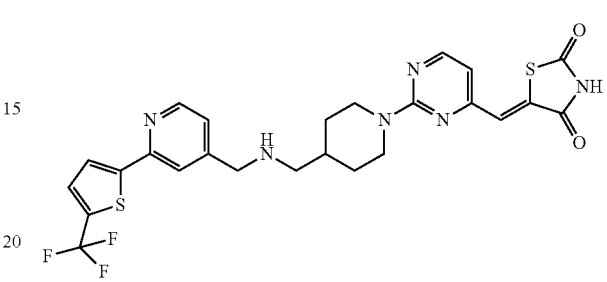

(Z)-5-((2-(4-((((2-(5-(trifluoromethyl)thiophen-2-yl)pyridin-4-yl)methyl)amino)methyl)piperidin-1-yl)pyrimidin-4-yl)methylene)thiazolidine-2,4-dione was prepared using the general reductive amination procedure and 2-(5-(trifluoromethyl)thiophen-2-yl)isonicotinaldehyde (3.0 mg, 26.9 mg theoretical, 11%). LC-MS m/z 561 (M+1).

Example 48

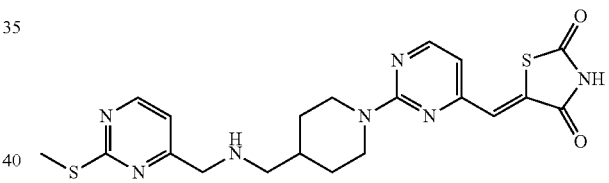

(Z)-5-((2-(4-((((2-(methylthio)pyrimidin-4-yl)methyl) amino)methyl)piperidin-1-yl)pyrimidin-4-yl)methylene) thiazolidine-2,4-dione was prepared using the general reductive amination procedure and 2-(methylthio)pyrimidine-4-carbaldehyde (12.6 mg, 62.6 mg theoretical, 20.1%). LC-MS m/z 458 (M+1).

Example 49

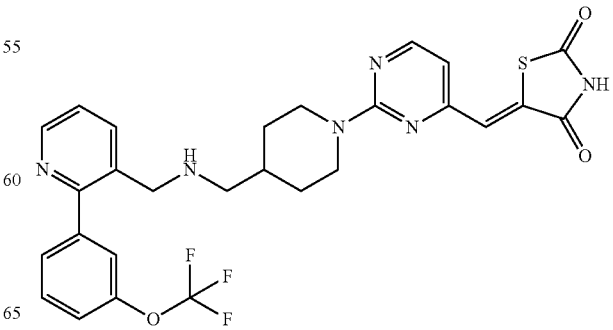

(Z)-5-((2-(4-((((2-(3-(trifluoromethoxy)phenyl)pyridin-3-yl)methyl)amino)methyl)piperidin-1-yl)pyrimidin-4-yl)methylene)thiazolidine-2,4-dione was prepared using the general reductive amination procedure and 2-(3-(trifluoromethoxy)phenyl)nicotinaldehyde (11.6 mg, 27.4 mg theoretical, 42%). LC-MS m/z 571 (M+1).

Example 50

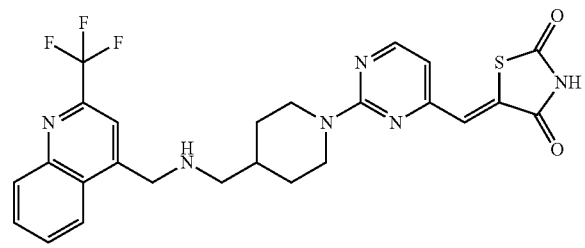 [SMILES: O=C1NC(=O)/C(=C/c2ccnc(N3CCC(CNCc4cc(C(F)(F)F)nc5ccccc45)CC3)n2)S1]

(Z)-5-((2-(4-((((2-(trifluoromethyl)quinolin-4-yl)methyl)amino)methyl)piperidin-1-yl)pyrimidin-4-yl)methylene)thiazolidine-2,4-dione was prepared using the general reductive amination procedure and 2-(trifluoromethyl)quinoline-4-carbaldehyde (5.3 mg, 25.4 mg theoretical, 21%). LC-MS m/z 529 (M+1).

Example 51

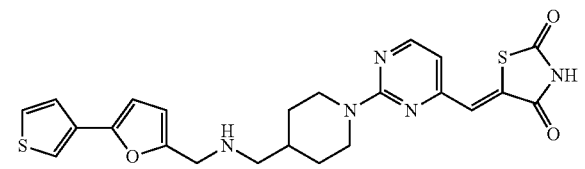 [SMILES: O=C1NC(=O)/C(=C/c2ccnc(N3CCC(CNCc4ccc(-c5ccsc5)o4)CC3)n2)S1]

(Z)-5-((2-(4-((((5-(thiophen-3-yl)furan-2-yl)methyl)amino)methyl)piperidin-1-yl)pyrimidin-4-yl)methylene)thiazolidine-2,4-dione was prepared using the general reductive amination procedure and 5-(thiophen-3-yl)furan-2-carbaldehyde (12.0 mg, 23.1 mg theoretical, 52%). LC-MS m/z 482 (M+1).

Example 52

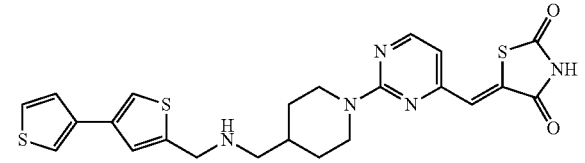 [SMILES: O=C1NC(=O)/C(=C/c2ccnc(N3CCC(CNCc4cc(-c5ccsc5)cs4)CC3)n2)S1]

(Z)-5-((2-(4-((((([3,3'-bithiophen]-5-ylmethyl)amino)methyl)piperidin-1-yl)pyrimidin-4-yl)methylene)thiazolidine-2,4-dione was prepared using the general reductive amination procedure and 3,3'-bithiophene]-5-carbaldehyde (3.5 mg, 23.8 mg theoretical, 14%). LC-MS m/z 498 (M+1).

Example 53

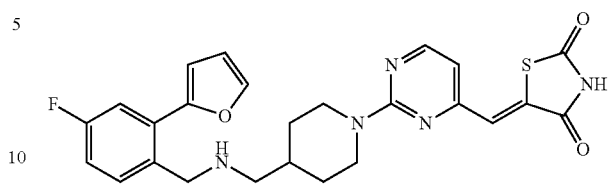

(Z)-5-((2-(4-(((4-fluoro-2-(furan-2-yl)benzyl)amino)methyl)piperidin-1-yl)pyrimidin-4-yl)methylene)thiazolidine-2,4-dione was prepared using the general reductive amination procedure and 4-fluoro-2-(furan-2-yl)benzaldehyde (9.6 mg, 23.6 mg theoretical, 40%). LC-MS m/z 494 (M+1).

Example 54

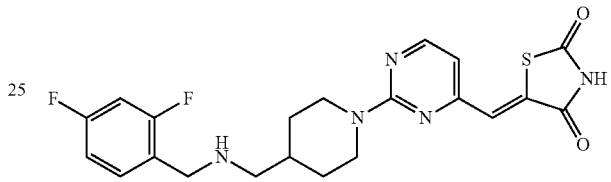

(Z)-5-((2-(4-(((2,4-difluorobenzyl)amino)methyl)piperidin-1-yl)pyrimidin-4-yl)methylene)thiazolidine-2,4-dione was prepared using the general reductive amination procedure and 2,4-difluorobenzaldehyde (4.2 mg, 21.3 mg theoretical, 20%). LC-MS m/z 446 (M+1).

Example 55

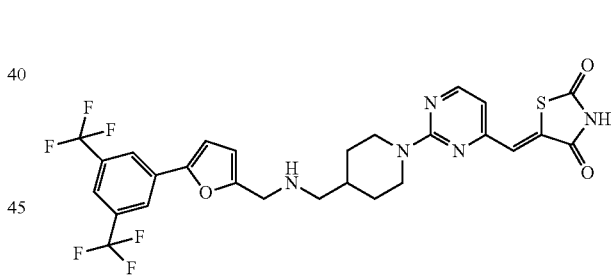

(Z)-5-((2-(4-((((5-(3,5-bis(trifluoromethyl)phenyl)furan-2-yl)methyl)amino)methyl)piperidin-1-yl)pyrimidin-4-yl)methylene)thiazolidine-2,4-dione was prepared using the general reductive amination procedure and 5-(3,5-bis(trifluoromethyl)phenyl)furan-2-carbaldehyde (10.9 mg, 29.4 mg theoretical, 37%). LC-MS m/z 612 (M+1).

Example 56

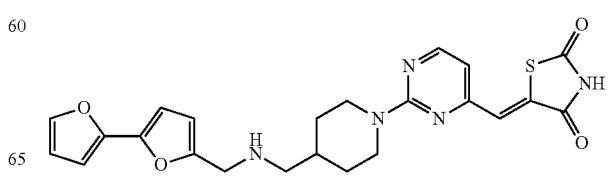

(Z)-5-((2-(4-((([2,2'-bifuran]-5-ylmethyl)amino)methyl) piperidin-1-yl)pyrimidin-4-yl)methylene)thiazolidine-2,4-dione was prepared using the general reductive amination procedure and 2,2'-bifuran-5-carbaldehyde (6.0 mg, 22.3 mg theoretical, 27%). LC-MS m/z 466 (M+1).

Example 57

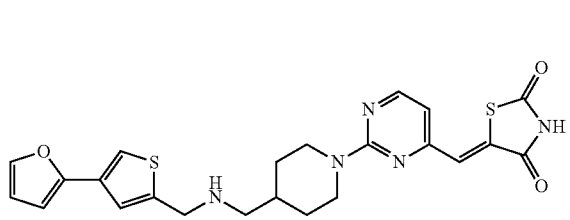 [SMILES: O=C1NC(=O)/C(=C/c2ccnc(N3CCC(CNCc4cc(-c5ccco5)cs4)CC3)n2)S1]

(Z)-5-((2-(4-((((4-(furan-2-yl)thiophen-2-yl)methyl)amino) methyl)piperidin-1-yl)pyrimidin-4-yl)methylene)thiazolidine-2,4-dione was prepared using the general reductive amination procedure and 4-(furan-2-yl)thiophene-2-carbaldehyde (3.0 mg, 23.1 mg theoretical, 13%). LC-MS m/z 482 (M+1).

Example 58

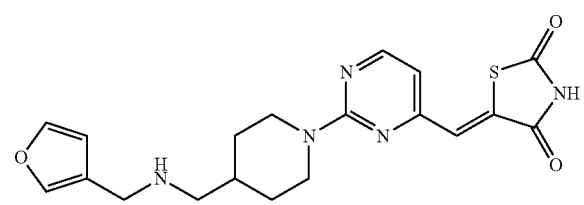 [SMILES: O=C1NC(=O)/C(=C/c2ccnc(N3CCC(CNCc4ccoc4)CC3)n2)S1]

(Z)-5-((2-(4-(((furan-3-ylmethyl)amino)methyl)piperidin-1-yl)pyrimidin-4-yl)methylene)thiazolidine-2,4-dione was prepared using the general reductive amination procedure and furan-3-carbaldehyde (2.0 mg, 19.1 mg theoretical, 10%). LC-MS m/z 400 (M+1).

Example 59

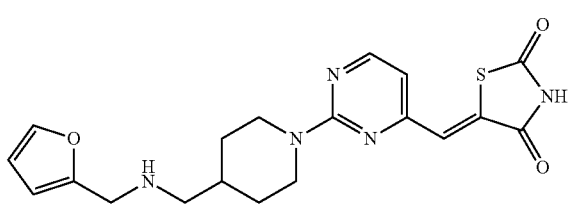 [SMILES: O=C1NC(=O)/C(=C/c2ccnc(N3CCC(CNCc4ccco4)CC3)n2)S1]

(Z)-5-((2-(4-(((furan-2-ylmethyl)amino)methyl)piperidin-1-yl)pyrimidin-4-yl)methylene)thiazolidine-2,4-dione was prepared using the general reductive amination procedure and furan-2-carbaldehyde (7.4 mg, 19.1 mg theoretical, 38%). LC-MS m/z 400 (M+1).

Example 60

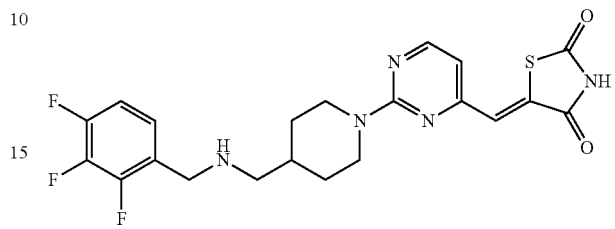

(Z)-5-((2-(4-(((2,3,4-trifluorobenzyl)amino)methyl)piperidin-1-yl)pyrimidin-4-yl)methylene)thiazolidine-2,4-dione was prepared using the general reductive amination procedure and 2,3,4-trifluorobenzaldehyde (6.6 mg, 22.2 mg theoretical, 30%). LC-MS m/z 464 (M+1).

Example 61

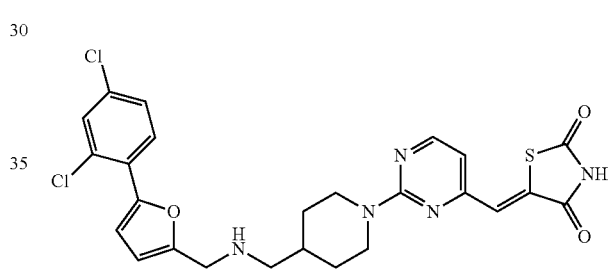

(Z)-5-((2-(4-((((5-(2,4-dichlorophenyl)furan-2-yl)methyl) amino)methyl)piperidin-1-yl)pyrimidin-4-yl)methylene) thiazolidine-2,4-dione was prepared using the general displacement procedure and 5-(2,4-dichlorophenyl)furan-2-carbaldehyde (19 mg, 39 mg theoretical, 48%). LC-MS m/z 545.5 (M+1).

Example 62

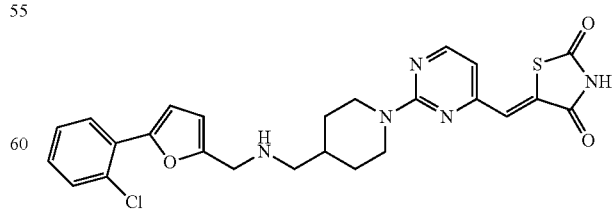

(Z)-5-((2-(4-((((5-(2-chlorophenyl)furan-2-yl)methyl) amino)methyl)piperidin-1-yl)pyrimidin-4-yl)methylene) thiazolidine-2,4-dione was prepared using the general reductive amination procedure and 5-(2-chlorophenyl)furan-2-carbaldehyde (17.2 mg, 36.7 mg theoretical, 46.8%). LC-MS m/z 511.5 (M+1).

Example 63

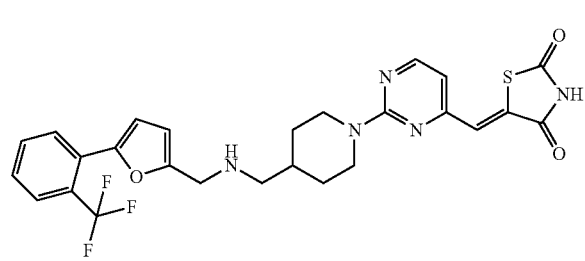 [SMILES: O=C1NC(=O)/C(=C/c2ccnc(N3CCC(CNCc4ccc(-c5ccccc5C(F)(F)F)o4)CC3)n2)S1]

(Z)-5-((2-(4-((((5-(2-(trifluoromethyl)phenyl)furan-2-yl)methyl)amino)methyl)piperidin-1-yl)pyrimidin-4-yl)methylene)thiazolidine-2,4-dione was prepared using the general reductive amination procedure and 5-(2-(trifluoromethyl)phenyl)furan-2-carbaldehyde (23.9 mg, 39.1 mg theoretical, 66%). LC-MS m/z 544.5 (M+1).

Example 64

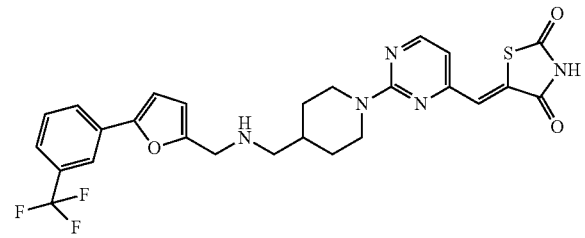 [SMILES: O=C1NC(=O)/C(=C/c2ccnc(N3CCC(CNCc4ccc(-c5cccc(C(F)(F)F)c5)o4)CC3)n2)S1]

(Z)-5-((2-(4-((((5-(3-(trifluoromethyl)phenyl)furan-2-yl)methyl)amino)methyl)piperidin-1-yl)pyrimidin-4-yl)methylene)thiazolidine-2,4-dione was prepared using the general reductive amination procedure and 5-(3-(trifluoromethyl)phenyl)furan-2-carbaldehyde (20.5 mg, 39.1 mg theoretical, 52.4%). LC-MS m/z 544 (M+1).

Example 65

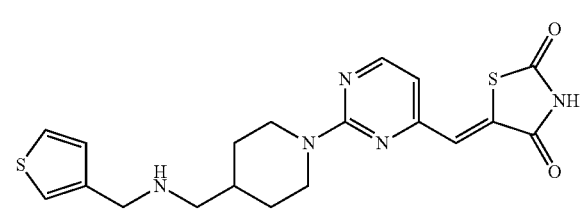 [SMILES: O=C1NC(=O)/C(=C/c2ccnc(N3CCC(CNCc4ccsc4)CC3)n2)S1]

(Z)-5-((2-(4-(((thiophen-3-ylmethyl)amino)methyl)piperidin-1-yl)pyrimidin-4-yl)methylene)thiazolidine-2,4-dione was prepared using the general reductive amination procedure and thiophene-3-carbaldehyde (9.7 mg, 19.5 mg theoretical, 47%). LC-MS m/z 416 (M+1).

Example 66

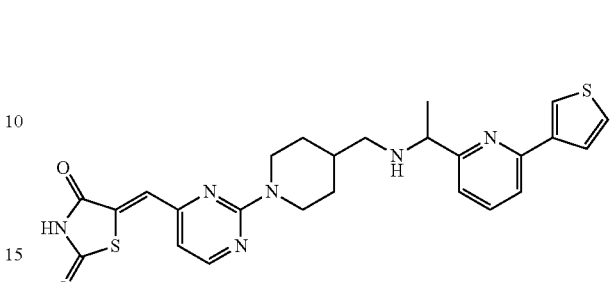

(Z)-5-((2-(4-(((1-(6-(thiophen-3-yl)pyridin-2-yl)ethyl)amino)methyl)piperidin-1-yl)pyrimidin-4-yl)methylene)thiazolidine-2,4-dione was prepared using the general reductive amination procedure and 1-(6-(thiophen-3-yl)pyridin-2-yl)ethanone (3 mg, 37.4 mg theoretical, 8.6%). LC-MS m/z 507 (M+1).

Example 67

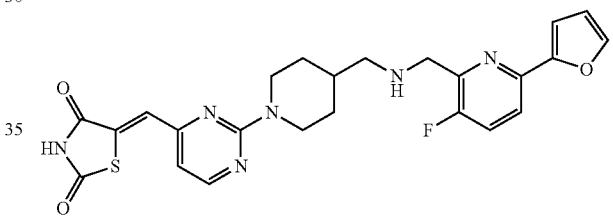

(Z)-5-((2-(4-((((3-fluoro-6-(furan-2-yl)pyridin-2-yl)methyl)amino)methyl)piperidin-1-yl)pyrimidin-4-yl)methylene)thiazolidine-2,4-dione was prepared using the general reductive amination procedure and 3-fluoro-6-(furan-2-yl)picolinaldehyde (13.6 mg, 23.7 mg theoretical, 57%). LC-MS m/z 495 (M+1).

Example 68

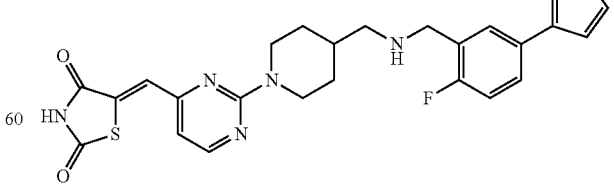

(Z)-5-((2-(4-(((2-fluoro-5-(thiophen-3-yl)benzyl)amino)methyl)piperidin-1-yl)pyrimidin-4-yl)methylene)thiazolidine-2,4-dione was prepared using the general reductive amination procedure and 2-fluoro-5-(thiophen-3-yl) benzaldehyde (7.6 mg, 24.4 mg theoretical, 31%). LC-MS m/z 510 (M+1).

Example 69

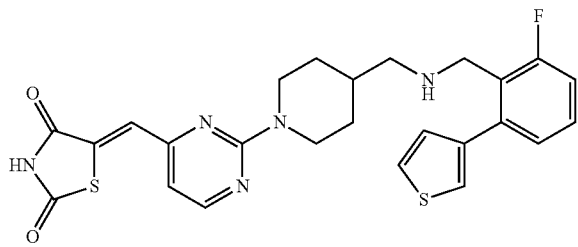 [SMILES: O=C1NC(=O)/C(=C/c2ccnc(N3CCC(CNCc4c(F)cccc4-c4ccsc4)CC3)n2)S1]

(Z)-5-((2-(4-(((2-fluoro-6-(thiophen-3-yl)benzyl)amino) methyl)piperidin-1-yl)pyrimidin-4-yl)methylene)thiazolidine-2,4-dione was prepared using the general reductive amination procedure and 2-fluoro-6-(thiophen-3-yl) benzaldehyde (8.9 mg, 24.4 mg theoretical, 36%). LC-MS m/z 510 (M+1).

Example 70

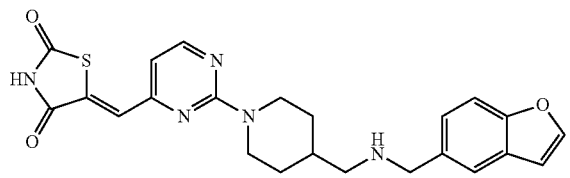 [SMILES: O=C1NC(=O)/C(=C/c2ccnc(N3CCC(CNCc4ccc5occc5c4)CC3)n2)S1]

(Z)-5-((2-(4-(((benzofuran-5-ylmethyl)amino)methyl)piperidin-1-yl)pyrimidin-4-yl)methylene)thiazolidine-2,4-dione was prepared using the general reductive amination procedure and benzofuran-5-carbaldehyde (5.5 mg, 21.5 mg theoretical, 26%). LC-MS m/z 450 (M+1).

Example 71

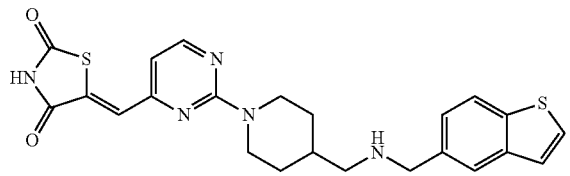

(Z)-5-((2-(4-(((benzo[b]thiophen-5-ylmethyl)amino)methyl)piperidin-1-yl)pyrimidin-4-yl)methylene)thiazolidine-2,4-dione was prepared using the general reductive amination procedure and benzo[b]thiophene-5-carbaldehyde (14.3 g, 22.3 mg theoretical, 64%). LC-MS m/z 466 (M+1).

Example 72

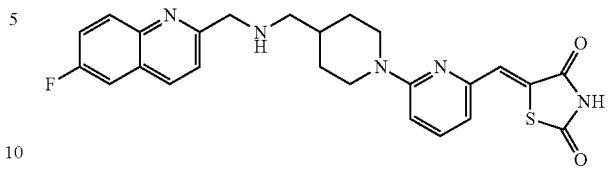

(Z)-5-β6-(4-(((((6-fluoroquinolin-2-yl)methyl)amino)methyl)piperidin-1-yl)pyridin-2-yl)methylene)thiazolidine-2,4-dione was prepared using the general reductive amination procedure and 6-fluoroquinoline-2-carbaldehyde (6 mg, 18.9 mg theoretical, 31.7%). LC-MS m/z 478 (M+1).

Example 73

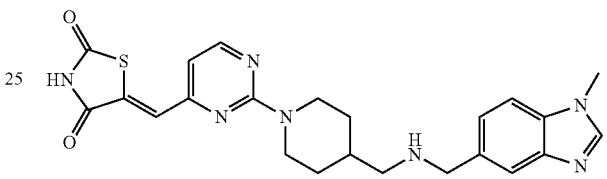

(Z)-5-((2-(4-(((((1-methyl-1H-benzo[d]imidazol-5-yl)methyl)amino)methyl)piperidin-1-yl)pyrimidin-4-yl)methylene)thiazolidine-2,4-dione was prepared using the general reductive amination procedure and 1-methyl-1H-benzo[d]imidazole-5-carbaldehyde (5.6 mg, 22.5 mg theoretical, 25%). LC-MS m/z 464 (M+1).

Example 74

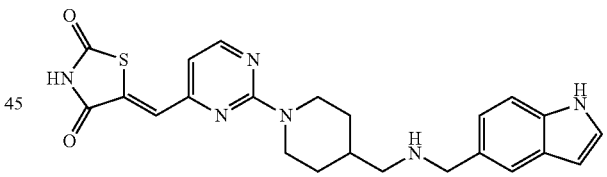

(Z)-5-((2-(4-(((((1H-indol-5-yl)methyl)amino)methyl)piperidin-1-yl)pyrimidin-4-yl)methylene)thiazolidine-2,4-dione was prepared using the general reductive amination procedure and 1H-indole-5-carbaldehyde (5.2 mg, 24.5 mg theoretical, 24%). LC-MS m/z 449 (M+1).

Example 75

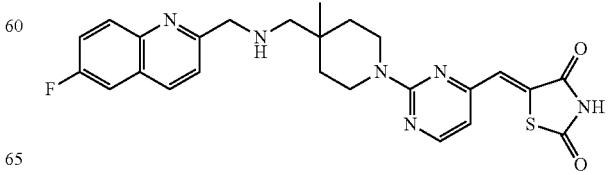

(Z)-5-((2-(4-((((6-fluoroquinolin-2-yl)methyl)amino) methyl)-4-methylpiperidin-1-yl)pyrimidin-4-yl)methylene) thiazolidine-2,4-dione was prepared using the general reductive amination procedure and 6-fluoroquinoline-2-carbaldehyde (25.3 mg, 64.2 mg theoretical, 18%). LC-MS m/z 334 (M+1).

Example 76

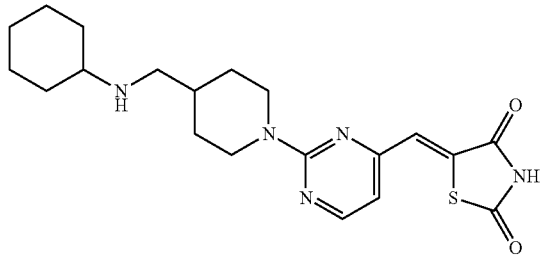 [SMILES: O=C1NC(=O)/C(=C/c2ccnc(N3CCC(CNC4CCCCC4)CC3)n2)S1]

(Z)-5-((2-(4-((((2-(2-(trifluoromethyl)phenyl)pyridin-3-yl) methyl)amino)methyl)piperidin-1-yl)pyrimidin-4-yl)methylene)thiazolidine-2,4-dione was prepared using the general reductive amination procedure and cyclohexanone (18 mg, 28.9 mg theoretical, 63%). LC-MS m/z 402.5 (M+1).

Example 77

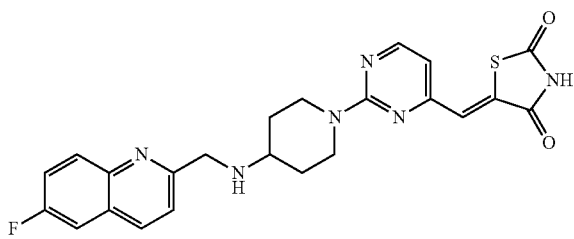 [SMILES: O=C1NC(=O)/C(=C/c2ccnc(N3CCC(NCc4ccc5cc(F)ccc5n4)CC3)n2)S1]

(Z)-5-((2-(4-((((6-fluoroquinolin-2-yl)methyl)amino)piperidin-1-yl)pyrimidin-4-yl)methylene)thiazolidine-2,4-dione was prepared using the general reductive amination procedure 6-fluoroquinoline-2-carbaldehyde (5.7 mg, 34.4 mg theoretical, 16.5%). LC-MS m/z 465.5 (M+1).

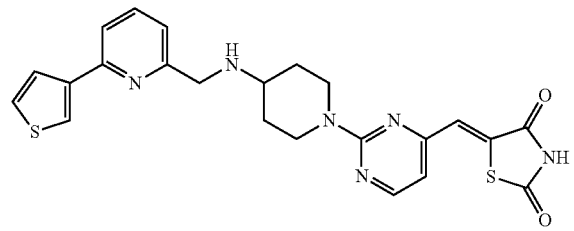 [SMILES: O=C1NC(=O)/C(=C/c2ccnc(N3CCC(NCc4cccc(-c5ccsc5)n4)CC3)n2)S1]

Example 78

(Z)-5-((2-(4-(((6-(thiophen-3-yl)pyridin-2-yl)methyl) amino)piperidin-1-yl)pyrimidin-4-yl)methylene)thiazolidine-2,4-dione was prepared using the general reductive amination procedure and 6-(thiophen-3-yl)picolinaldehyde (13.6 mg, 35.4 mg theoretical, 38.4%). LC-MS m/z 479.5 (M+1).

Example 79

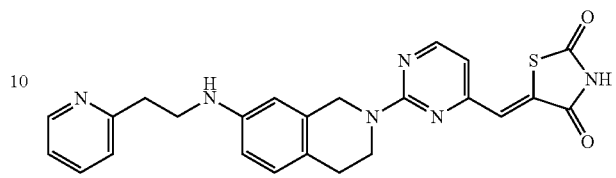

(Z)-5-((2-(7-((2-(pyridin-2-yl)ethyl)amino)-3,4-dihydroisoquinolin-2(1H)-yl)pyrimidin-4-yl)methylene)thiazolidine-2,4-dione was prepared using the general reductive amination procedure and 2-(pyridin-2-yl)acetaldehyde (18.6 mg, 32.4 mg theoretical, 57.3%). LC-MS m/z 459.5 (M+1).

Example 80

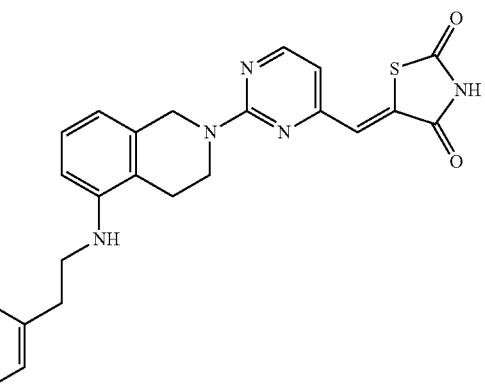

(Z)-5-((2-(5-((2-(pyridin-2-yl)ethyl)amino)-3,4-dihydroisoquinolin-2(1H)-yl)pyrimidin-4-yl)methylene)thiazolidine-2,4-dione was prepared using the general reductive amination procedure and 2-(pyridin-2-yl)acetaldehyde (9.3 mg, 32.4 mg theoretical, 28.7%). LC-MS m/z 459.5 (M+1).

Example 81

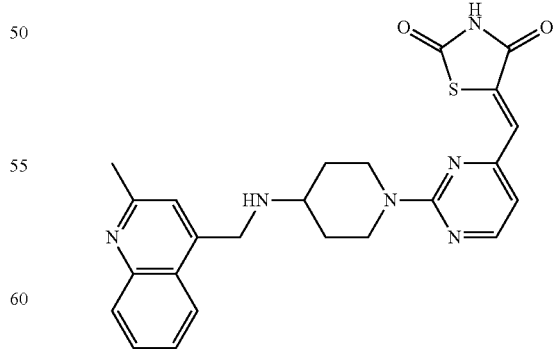

(Z)-5-((2-(4-(((2-methylquinolin-4-yl)methyl)amino)piperidin-1-yl)pyrimidin-4-yl)methylene)thiazolidine-2,4-dione was prepared using the general reductive amination procedure and 2-methylquinoline-4-carbaldehyde (5.1 mg, 34.1 mg theoretical, 15%). LC-MS m/z 461.5 (M+1).

Example 82

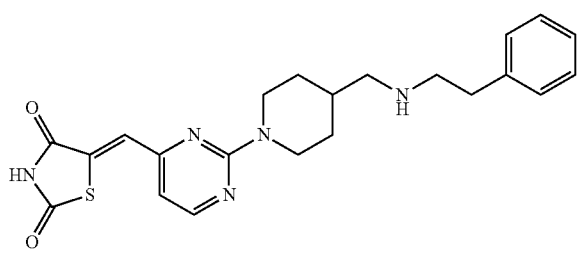 [SMILES: O=C1NC(=O)/C(=C/c2ccnc(N3CCC(CNCCc4ccccc4)CC3)n2)S1]

(Z)-5-((2-(4-((phenethylamino)methyl)piperidin-1-yl)pyrimidin-4-yl)methylene)thiazolidine-2,4-dione was prepared using the general reductive amination procedure and 2-phenylacetaldehyde (9.6 mg, 30.5 mg theoretical, 31.5%). LC-MS m/z 424.5 (M+1).

Example 83

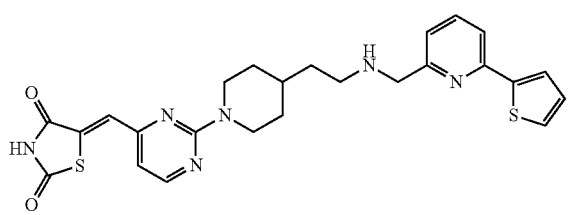 [SMILES: O=C1NC(=O)/C(=C/c2ccnc(N3CCC(CCNCc4cccc(-c5cccs5)n4)CC3)n2)S1]

(Z)-5-((2-(4-(2-(((6-(thiophen-2-yl)pyridin-2-yl)methyl)amino)ethyl)piperidin-1-yl)pyrimidin-4-yl)methylene)thiazolidine-2,4-dione was prepared using the general reductive amination procedure and 6-(thiophen-2-yl)picolinaldehyde (2.6 mg, 35 mg theoretical, 7.4%). LC-MS m/z 507 (M+1).

Example 84

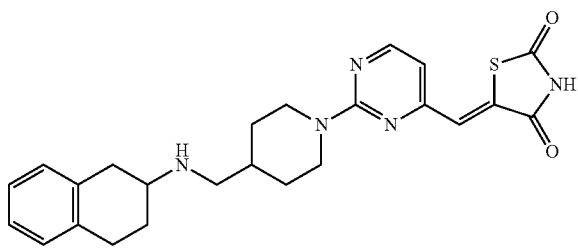 [SMILES: O=C1NC(=O)/C(=C/c2ccnc(N3CCC(CNC4CCc5ccccc5C4)CC3)n2)S1]

(Z)-5-((2-(4-(((1,2,3,4-tetrahydronaphthalen-2-yl)amino)methyl)piperidin-1-yl)pyrimidin-4-yl)methylene)thiazolidine-2,4-dione was prepared using the general reductive amination procedure and 3,4-dihydronaphthalen-2(1H)-one (2.0 mg, 32.4 mg theoretical, 6%). LC-MS m/z 450 (M+1).

Example 85

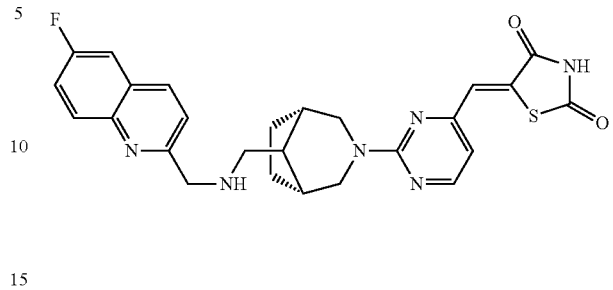

(Z)-5-((2-((1R,5S)-8-((((6-fluoroquinolin-2-yl)methyl)amino)methyl)-3-azabicyclo[3.2.1]octan-3-yl)pyrimidin-4-yl)methylene)thiazolidine-2,4-dione was prepared using the general reductive amination procedure and 6-fluoroquinoline-2-carbaldehyde (4.7 mg, 33.8 mg theoretical, 13.9%). LC-MS m/z 505.5 (M+1).

Example 86

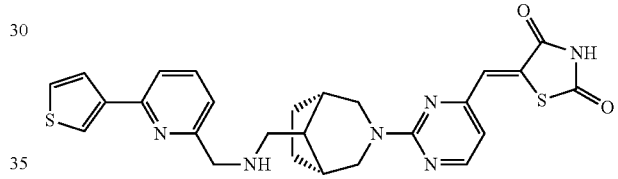

(Z)-5-((2-((1R,5S)-8-((((6-(thiophen-3-yl)pyridin-2-yl)methyl)amino)methyl)-3-azabicyclo[3.2.1]octan-3-yl)pyrimidin-4-yl)methylene)thiazolidine-2,4-dione was prepared using the general reductive amination procedure and 6-(thiophen-2-yl)picolinaldehyde (2.3 mg, 34.7 mg theoretical, 6.6%). LC-MS m/z 519.5 (M+1).

Example 87

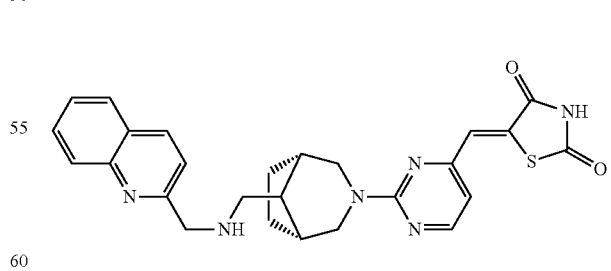

(Z)-5-((2-((1R,5S)-8-(((quinolin-2-ylmethyl)amino)methyl)-3-azabicyclo[3.2.1]octan-3-yl)pyrimidin-4-yl)methylene)thiazolidine-2,4-dione was prepared using the general reductive amination procedure and quinoline-2-carbaldehyde (1.4 mg, 32.6 mg theoretical, 4.3%). LC-MS m/z 487.5 (M+1).

Example 88

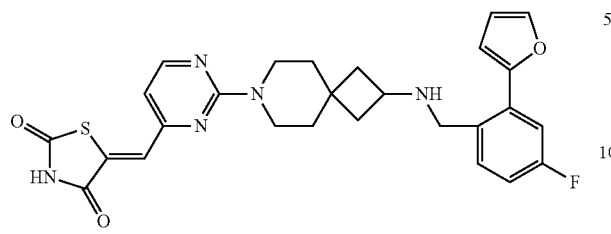

(Z)-5-((2-(2-((4-fluoro-2-(furan-2-yl)benzyl)amino)-7-azaspiro[3.5]nonan-7-yl)pyrimidin-4-yl)methylene)thiazolidine-2,4-dione was prepared using the general reductive amination procedure and 4-fluoro-2-(furan-2-yl)benzaldehyde (9.1 mg, 34.8 mg theoretical, 26.1%). LC-MS m/z 520.5 (M+1).

Example 89

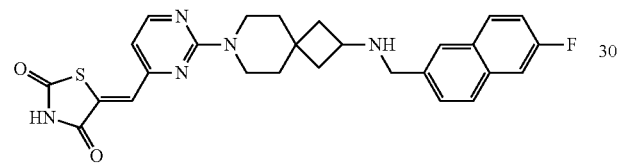

(Z)-5-((2-(2-(((6-fluoronaphthalen-2-yl)methyl)amino)-7-azaspiro[3.5]nonan-7-yl)pyrimidin-4-yl)methylene)thiazolidine-2,4-dione was prepared using the general reductive amination procedure and 6-fluoro-2-naphthaldehyde (16.9 mg, 33.7 mg theoretical, 50.1%). LC-MS m/z 504.5 (M+1).

Example 90

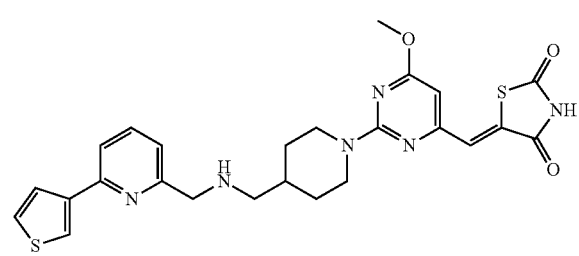 [SMILES: COc1cc(/C=C2\SC(=O)NC2=O)nc(N2CCC(CNCc3cccc(-c4ccsc4)n3)CC2)n1]

(Z)-5-((6-methoxy-2-(4-((((6-(thiophen-3-yl)pyridin-2-yl)methyl)amino)methyl)piperidin-1-yl)pyrimidin-4-yl)methylene)thiazolidine-2,4-dione was prepared using (Z)-5-((2-(4-(aminomethyl)piperidin-1-yl)-6-methoxypyrimidin-4-yl)methylene)thiazolidine-2,4-dione (Example 153), the general reductive amination procedure and 6-(thiophen-3-yl)picolinaldehyde (34.3 mg, 65 mg theoretical, 52.8%). LC-MS m/z 523 (M+1).

Example 91

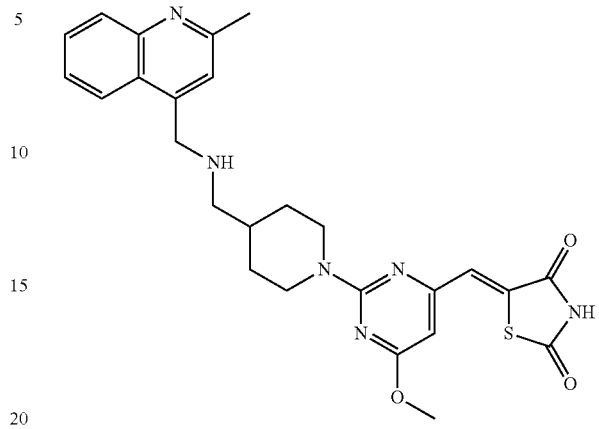

(Z)-5-((6-methoxy-2-(4-((((2-methylquinolin-4-yl)methyl)amino)methyl)piperidin-1-yl)pyrimidin-4-yl)methylene)thiazolidine-2,4-dione was prepared using (Z)-5-((2-(4-(aminomethyl)piperidin-1-yl)-6-methoxypyrimidin-4-yl)methylene)thiazolidine-2,4-dione (Example 153), the general reductive amination procedure and 2-methylquinoline-4-carbaldehyde (45.8 mg, 63 mg theoretical, 72.2%). LC-MS m/z 505 (M+1).

Example 92

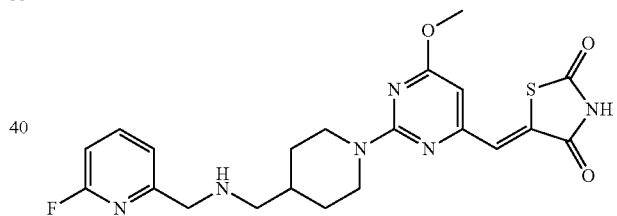

(Z)-5-((2-(4-((((6-fluoropyridin-2-yl)methyl)amino)methyl)piperidin-1-yl)-6-methoxypyrimidin-4-yl)methylene)thiazolidine-2,4-dione was prepared using (Z)-5-((2-(4-(aminomethyl)piperidin-1-yl)-6-methoxypyrimidin-4-yl)methylene)thiazolidine-2,4-dione (Example 153), the general reductive amination procedure and 6-fluoropicolinaldehyde (26.1 mg, 59 mg theoretical, 43.9%). LC-MS m/z 459 (M+1).

Example 93

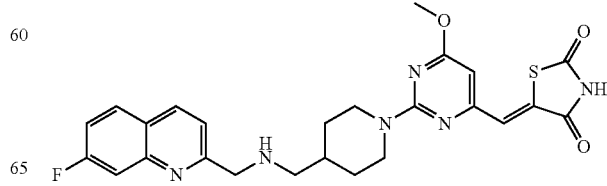

(Z)-5-((6-methoxy-2-(4-((((6-(thiophen-3-yl)pyridin-2-yl)methyl)amino)methyl)piperidin-1-yl)pyrimidin-4-yl)methylene)thiazolidine-2,4-dione was prepared using (Z)-5-((2-(4-(aminomethyl)piperidin-1-yl)-6-methoxypyrimidin-4-yl)methylene)thiazolidine-2,4-dione (Example 153), the general reductive amination procedure and 7-fluoroquinoline-2-carbaldehyde (15.1 mg, 64 mg theoretical, 23.7%). LC-MS m/z 509 (M+1).

Example 94

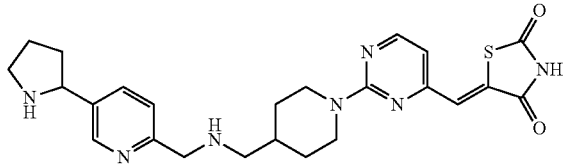 [SMILES: O=C1NC(=O)/C(=C/c2ccnc(N3CCC(CNCc4ccc(C5CCCN5)cn4)CC3)n2)S1]

(Z)-5-((2-(4-((((5-(pyrrolidin-2-yl)pyridin-2-yl)methyl)amino)methyl)piperidin-1-yl)pyrimidin-4-yl)methylene)thiazolidine-2,4-dione was prepared using the general reductive amination procedure and tert-butyl 2-(6-formylpyridin-3-yl)pyrrolidine-1-carboxylate followed by the general de-protection procedure (29.3 mg, 39.8 mg theoretical, 73.6%). LC-MS m/z 480.6 (M+1).

Example 95

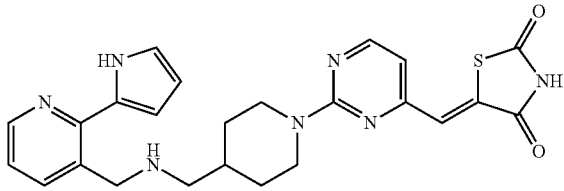

(Z)-5-((2-(4-((((2-(1H-pyrrol-2-yl)pyridin-3-yl)methyl)amino)methyl)piperidin-1-yl)pyrimidin-4-yl)methylene)thiazolidine-2,4-dione was prepared using the general reductive amination procedure and tert-butyl 2-(3-formylpyridin-2-yl)-1H-pyrrole-1-carboxylate followed by the general de-protection procedure (16.5 mg, 17.1 mg theoretical, 96%). LC-MS m/z 476.6 (M+1).

Example 96

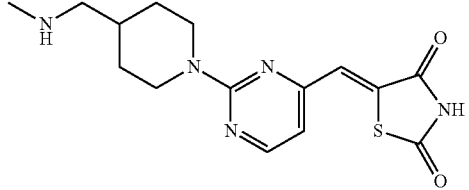 [SMILES: CNCC1CCN(c2nccc(/C=C3\SC(=O)NC3=O)n2)CC1]

(Z)-5-((2-(4-((methylamino)methyl)piperidin-1-yl)pyrimidin-4-yl)methylene)thiazolidine-2,4-dione was prepared using the general displacement procedure and tert-butyl methyl(piperidin-4-ylmethyl)carbamate followed by the general de-protection procedure (28.3 mg, 28.5 mg theoretical, 99%). LC-MS m/z 334.4 (M+1).

Example 97

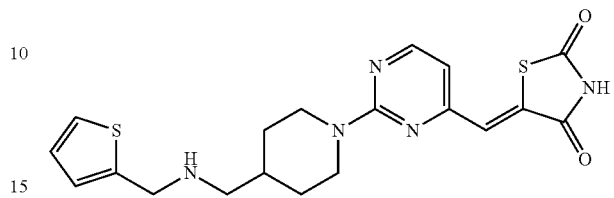

(Z)-5-((2-(4-(((thiophen-2-ylmethyl)amino)methyl)piperidin-1-yl)pyrimidin-4-yl)methylene)thiazolidine-2,4-dione was prepared using the general reductive amination procedure and thiophene-2-carbaldehyde followed by the general de-protection procedure (7.6 mg, 19.9 mg theoretical, 38%). LC-MS m/z 416 (M+1).

Example 98

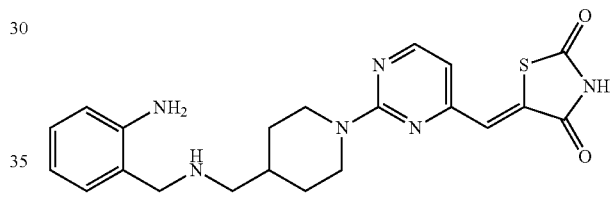

(Z)-5-((2-(4-(((2-aminobenzyl)amino)methyl)piperidin-1-yl)pyrimidin-4-yl)methylene)thiazolidine-2,4-dione was prepared using the general reductive amination procedure and tert-butyl(2-formylphenyl)carbamate followed by the general de-protection procedure (17.4 mg, 18.7 mg theoretical, 93%). LC-MS m/z 425.5 (M+1).

Example 99

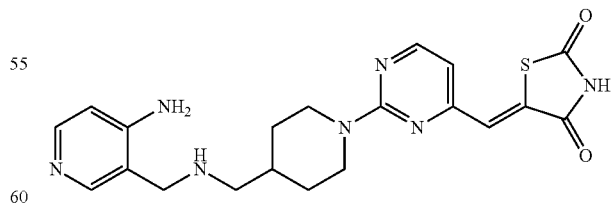

(Z)-5-((2-(4-((((4-aminopyridin-3-yl)methyl)amino)methyl)piperidin-1-yl)pyrimidin-4-yl)methylene)thiazolidine-2,4-dione was prepared using the general reductive amination procedure and tert-butyl(3-formylpyridin-4-yl)carbamate followed by the general de-protection procedure (4.3 mg, 7.3 mg theoretical, 59%). LC-MS m/z 426.5 (M+1).

Example 100

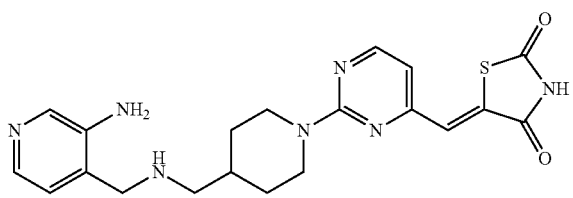 [SMILES: Nc1cnccc1CNCC1CCN(c2nccc(/C=C3\SC(=O)NC3=O)n2)CC1]

(Z)-5-((2-(4-((((3-aminopyridin-4-yl)methyl)amino)methyl)piperidin-1-yl)pyrimidin-4-yl)methylene)thiazolidine-2,4-dione was prepared using the general reductive amination procedure and tert-butyl(4-formylpyridin-3-yl)carbamate followed by the general de-protection procedure (11.5 mg, 15.3 mg theoretical, 75%). LC-MS m/z 426.5 (M+1).

Example 101

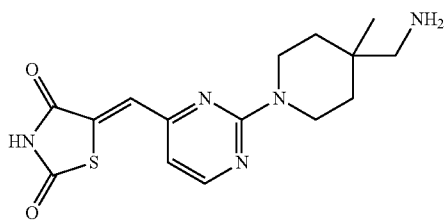 [SMILES: CC1(CN)CCN(c2nccc(/C=C3\SC(=O)NC3=O)n2)CC1]

(Z)-5-((2-(4-(aminomethyl)-4-methylpiperidin-1-yl)pyrimidin-4-yl)methylene)thiazolidine-2,4-dione was prepared using the general reductive amination procedure and tert-butyl((4-methylpiperidin-4-yl)methyl)carbamate followed by the general de-protection procedure (29.9 mg, 168 mg theoretical, 17.8%). LC-MS m/z 334 (M+1).

Example 102

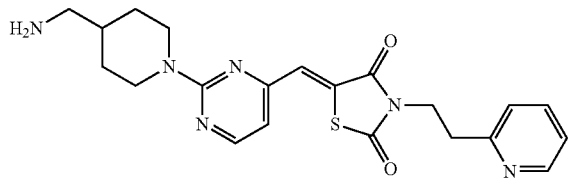 [SMILES: NCC1CCN(c2nccc(/C=C3\SC(=O)N(CCc4ccccn4)C3=O)n2)CC1]

(Z)-5-((6-(4-(aminomethyl)piperidin-1-yl)pyrimidin-4-yl)methylene)thiazolidine-2,4-dione was prepared using the general reductive amination procedure, (Z)-5-((2-(methylsulfonyl)pyrimidin-4-yl)methylene)-3-(2-(pyridin-2-yl)ethyl)thiazolidine-2,4-dione, and tert-butyl(piperidin-4-ylmethyl)carbamate followed by the general de-protection procedure (16 mg, 30.6 mg theoretical, 52.3%). LC-MS m/z 425.5 (M+1).

Example 103

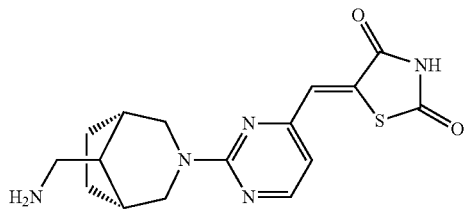 [SMILES: NCC1[C@@H]2CC[C@H]1CN(c1nccc(/C=C3\SC(=O)NC3=O)n1)C2]

(Z)-5-((2-((1R,5S)-8-(aminomethyl)-3-azabicyclo[3.2.1]octan-3-yl)pyrimidin-4-yl)methylene)thiazolidine-2,4-dione was prepared using the general reductive amination procedure and tert-butyl((1R,5S)-3-azabicyclo[3.2.1]octan-8-ylmethyl)carbamate followed by the general de-protection procedure (15.1 mg, 17.1 mg theoretical, 89%). LC-MS m/z 346 (M+1).

Example 104

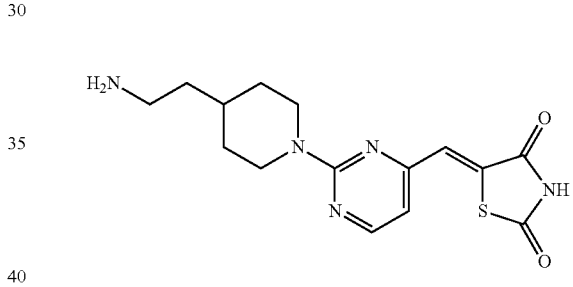

(Z)-5-((2-(4-(2-aminoethyl)piperidin-1-yl)pyrimidin-4-yl)methylene)thiazolidine-2,4-dione, was prepared using the general reductive amination procedure and tert-butyl(2-(piperidin-4-yl)ethyl)carbamate followed by the general de-protection procedure (6.8 mg, 23.1 mg theoretical, 29.5%). LC-MS m/z 334 (M+1).

Example 105

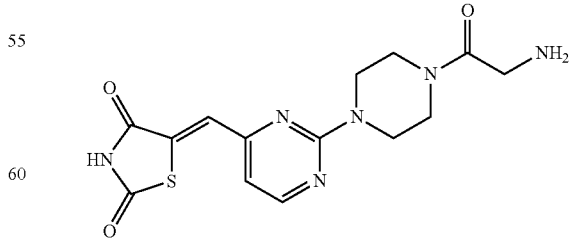

(Z)-5-((2-(4-(2-aminoacetyl)piperazin-1-yl)pyrimidin-4-yl)methylene)thiazolidine-2,4-dione was prepared using the general reductive amination procedure and tert-butyl(2-oxo- 2-(piperazin-1-yl)ethyl)carbamate followed by the general de-protection procedure (3.9 mg, 26.5 mg theoretical, 15%). LC-MS m/z 348 (M+1).

Example 106

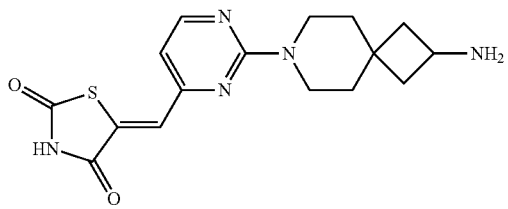 [SMILES: NC1CC2(CCN(c3nccc(/C=C4\SC(=O)NC4=O)n3)CC2)C1]

(Z)-5-((2-(2-amino-7-azaspiro[3.5]nonan-7-yl)pyrimidin-4-yl)methylene)thiazolidine-2,4-dione was prepared using the general reductive amination procedure and tert-butyl 7-azaspiro[3.5]nonan-2-ylcarbamate followed by the general de-protection procedure (17.2 mg, 11.6 mg theoretical, 148%). LC-MS m/z 346 (M+1).

Example 107

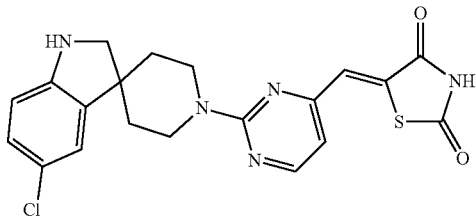 [SMILES: O=C1NC(=O)/C(=C/c2ccnc(N3CCC4(CC3)CNc3ccc(Cl)cc34)n2)S1]

(Z)-5-((2-(5-chlorospiro[indoline-3,4'-piperidin]-1'-yl)pyrimidin-4-yl)methylene)thiazolidine-2,4-dione was prepared using the general displacement procedure and 5-chlorospiro[indoline-3,4'-piperidine] (9.1 mg, 27.1 mg theoretical, 33.6%). LC-MS m/z 428 (M+1).

Example 108

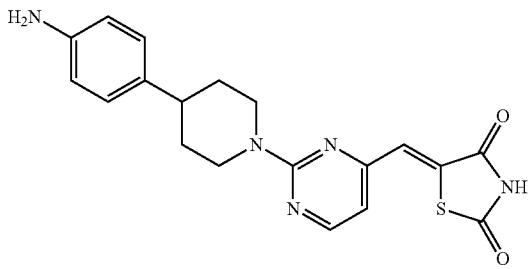 [SMILES: Nc1ccc(C2CCN(c3nccc(/C=C4\SC(=O)NC4=O)n3)CC2)cc1]

(Z)-5-((2-(4-(4-aminophenyl)piperidin-1-yl)pyrimidin-4-yl)methylene)thiazolidine-2,4-dione was prepared using the general displacement procedure and 4-(piperidin-4-yl)aniline (10.2 mg, 40.1 mg theoretical, 25.4%). LC-MS m/z 382 (M+1).

Example 109

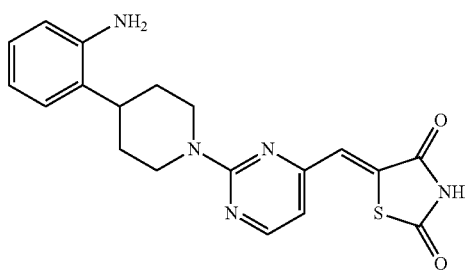 [SMILES: Nc1ccccc1C1CCN(c2nccc(/C=C3\SC(=O)NC3=O)n2)CC1]

(Z)-5-((2-(4-(2-aminophenyl)piperidin-1-yl)pyrimidin-4-yl)methylene)thiazolidine-2,4-dione was prepared using the general displacement procedure and 2-(piperidin-4-yl)aniline (24 mg, 40.1 mg theoretical, 59.8%). LC-MS m/z 382 (M+1).

Example 110

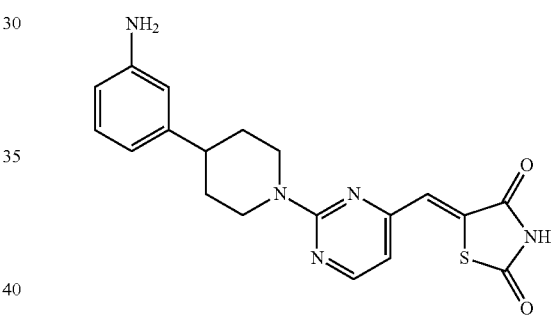

(Z)-5-((2-(4-(2-aminophenyl)piperidin-1-yl)pyrimidin-4-yl)methylene)thiazolidine-2,4-dione was prepared using the general displacement procedure and 3-(piperidin-4-yl)aniline (19.7 mg, 40.1 mg theoretical, 49.1%). LC-MS m/z 382 (M+1).

Example 111

Synthesized Sulfonamide Analogs

General Procedure for the Preparation of Sulfonamides/Amides

A 2-dram round-bottomed vial was charged with the appropriate sulfonyl chloride (0.072 mmol, 1 equiv.) in 0.5 mL of DMF, and then treated carefully with a solution of (Z)-5-((2-(4-(aminomethyl)piperidin-1-yl)pyrimidin-4-yl)methylene)thiazolidine-2,4-dione, prepared using the general displacement procedure followed by the general de-protection procedure, (0.072 mmol, 1 equiv.), DIPEA (0.288 mmol, 4 equiv.), and 1 mL of DMF. The reaction mixture was then shaken at room temperature overnight. The reaction mixture was partitioned between 2 mL DCE and 1 mL sat. NaHCO$_3$ and the aqueous layer was extracted with DCE (2×2 mL). The combined organic layer was the concentrated under reduced pressure (Genevac HT-4) and the crude residue was purified using reverse phase HPLC (MS-triggered fraction collection) with an acetonitrile/water or methanol/water gradient and trifluoroacetic acid as the modifier. The pure fractions were then concentrated under reduced pressure (Genevac HT-4) to afford the sulfonamide analogs.

Example 112

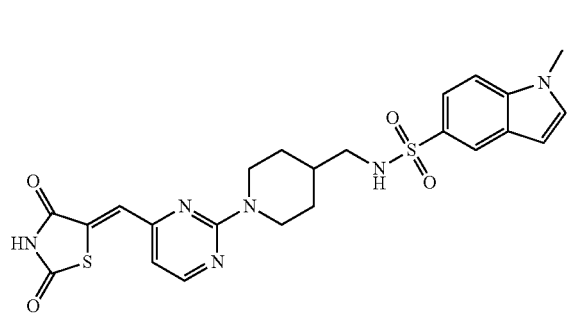 [SMILES: Cn1ccc2cc(S(=O)(=O)NCC3CCN(c4nccc(/C=C5\SC(=O)NC5=O)n4)CC3)ccc21]

(Z)—N-((1-(4-((2,4-dioxothiazolidin-5-ylidene)methyl)pyrimidin-2-yl)piperidin-4-yl)methyl)-1-methyl-1H-indole-5-sulfonamide was prepared using General Procedure for the Preparation of Sulfonamides and 1-methyl-1H-indole-5-sulfonyl chloride (13.2 mg, 36.9 mg theoretical, 35.8%). LC-MS m/z 513.6 (M+1).

Example 113

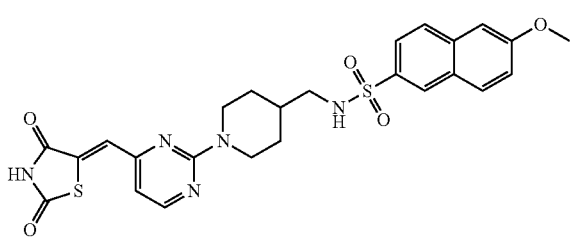 [SMILES: COc1ccc2cc(S(=O)(=O)NCC3CCN(c4nccc(/C=C5\SC(=O)NC5=O)n4)CC3)ccc2c1]

(Z)—N-((1-(4-((2,4-dioxothiazolidin-5-ylidene)methyl)pyrimidin-2-yl)piperidin-4-yl)methyl)-6-methoxynaphthalene-2-sulfonamide was prepared using General Procedure for the Preparation of Sulfonamides and 6-methoxynaphthalene-2-sulfonyl chloride (15.2 mg, 38.9 mg theoretical, 39.1%). LC-MS m/z 540.6 (M+1).

Example 114

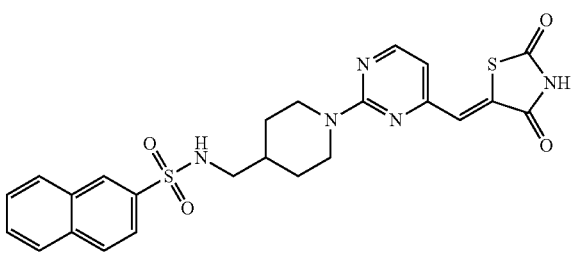 [SMILES: O=C1NC(=O)/C(=C/c2ccnc(N3CCC(CNS(=O)(=O)c4ccc5ccccc5c4)CC3)n2)S1]

(Z)—N-((1-(4-((2,4-dioxothiazolidin-5-ylidene)methyl)pyrimidin-2-yl)piperidin-4-yl)methyl)naphthalene-2-sulfonamide was prepared using General Procedure for the Preparation of Sulfonamides naphthalene-2-sulfonyl chloride (7.7 mg, 36.7 mg theoretical, 20.9%). LC-MS m/z 510.6 (M+1).

Example 115

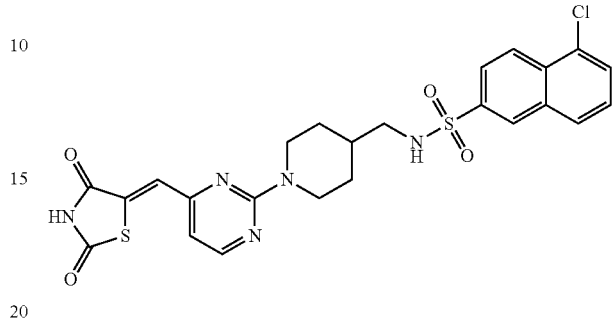

(Z)-5-chloro-N-((1-(4-((2,4-dioxothiazolidin-5-ylidene)methyl)pyrimidin-2-yl)piperidin-4-yl)methyl)naphthalene-2-sulfonamide was prepared using General Procedure for the Preparation of Sulfonamides and 5-chloronaphthalene-2-sulfonyl chloride (9.2 mg, 39.2 mg theoretical, 23.4%). LC-MS m/z 545.0 (M+1).

Example 116

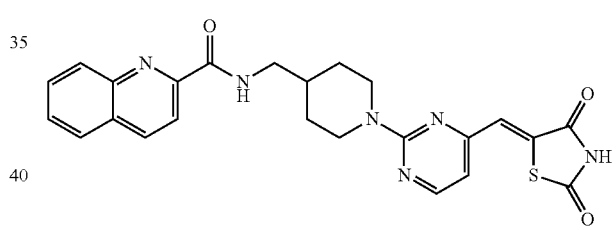

(Z)—N-((1-(4-((2,4-dioxothiazolidin-5-ylidene)methyl)pyrimidin-2-yl)piperidin-4-yl)methyl)quinoline-2-carboxamide was prepared using General Procedure for the Preparation of Sulfonamides/Amides and quinoline-2-carbonyl chloride (8.9 mg, 34.2 mg theoretical, 26%). LC-MS m/z 475 (M+1).

Example 117

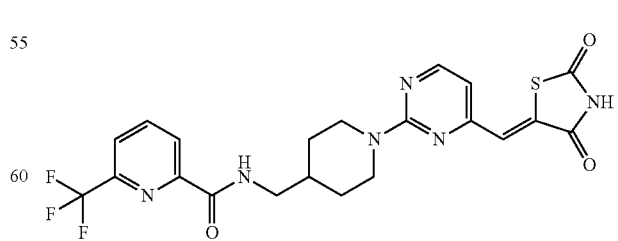

(Z)—N-((1-(4-((2,4-dioxothiazolidin-5-ylidene)methyl)pyrimidin-2-yl)piperidin-4-yl)methyl)-6-(trifluoromethyl)picolinamide was prepared using General Procedure for the Preparation of Sulfonamides/Amides and 6-(trifluoromethyl) picolinoyl chloride (15.7 mg, 35.5 mg theoretical, 44.3%). LC-MS m/z 493 (M+1).

Example 118

General Boronic Acid Coupling Procedures

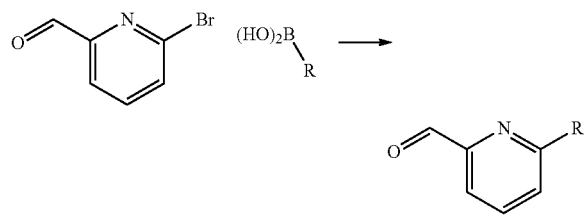

A 2-dram round-bottomed vial was charged with 6-bromopicolinaldehyde (100 mg, 0.538 mmol) and the boronic acid (0.538 mmol, 1 equiv.) were added in THF (2 mL). Then 2 M $Na_2CO_3$ (0.403 mL, 0.806 mmol, 1.5 equiv.) and $Pd(Ph_3P)_4$ (31.0 mg, 0.027 mmol, 0.05 equiv.) were added and shaken at 85° C. overnight. The solvent was removed in the Genevac and the residue was washed with saturated $NaHCO_3$ (1 mL). The aqueous layer was extracted with EtOAc (3×1 mL). The combined organic layers were dried on the Genevac and the crude was purified using flash purification with a gradient of 5-40% EtOAc in hexane.

Example 119

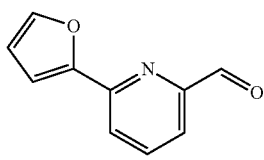 [SMILES: O=Cc1cccc(-c2ccco2)n1]

6-(furan-2-yl)picolinaldehyde was prepared using the general boronic acid coupling procedure for 6-bromopicolinaldehyde and furan-2-ylboronic acid (60 mg, 93.2 mg theoretical, 64.4%). LC-MS m/z 174.2 (M+1).

Example 120

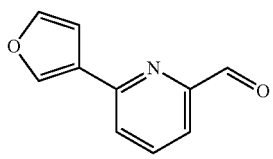 [SMILES: O=Cc1cccc(-c2ccoc2)n1]

6-(furan-3-yl)picolinaldehyde was prepared using the general boronic acid coupling procedure for 6-bromopicolinaldehyde and furan-3-ylboronic acid (65 mg, 93.2 mg theoretical, 69.8%). LC-MS m/z 174.2 (M+1).

Example 121

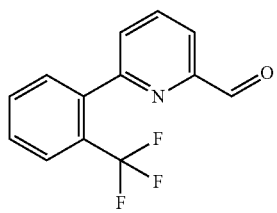 [SMILES: O=Cc1cccc(-c2ccccc2C(F)(F)F)n1]

6-(2-(trifluoromethyl)phenyl)picolinaldehyde was prepared using the general boronic acid coupling procedure for 6-bromopicolinaldehyde and (2-(trifluoromethyl)phenyl)boronic acid (43.5 mg, 135.1 mg theoretical, 32.2%). LC-MS m/z 252.2 (M+1).

Example 122

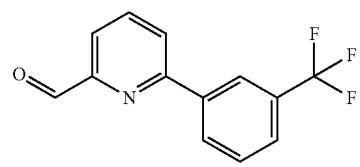 [SMILES: O=Cc1cccc(-c2cccc(C(F)(F)F)c2)n1]

6-(3-(trifluoromethyl)phenyl)picolinaldehyde was prepared using the general boronic acid coupling procedure for 6-bromopicolinaldehyde and (3-(trifluoromethyl)phenyl)boronic acid (115 mg, 135.1 mg theoretical, 85.1%). LC-MS m/z 252.2 (M+1).

Example 123

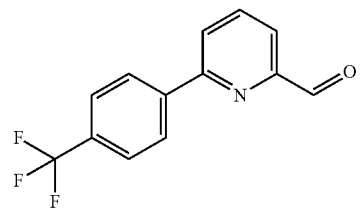 [SMILES: O=Cc1cccc(-c2ccc(C(F)(F)F)cc2)n1]

6-(4-(trifluoromethyl)phenyl)picolinaldehyde was prepared using the general boronic acid coupling procedure for 6-bromopicolinaldehyde and (4-(trifluoromethyl)phenyl)boronic acid (79 mg, 135.1 mg theoretical, 58.5%). LC-MS m/z 252.2 (M+1).

Example 124

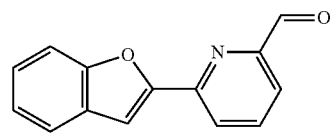 [SMILES: O=Cc1cccc(-c2cc3ccccc3o2)n1]

6-(benzofuran-2-yl)picolinaldehyde was prepared using the general boronic acid coupling procedure for 6-bromopicolinaldehyde and benzofuran-2-ylboronic acid (41 mg, 120.1 mg theoretical, 34.1%). LC-MS m/z 224.2 (M+1).

Example 125

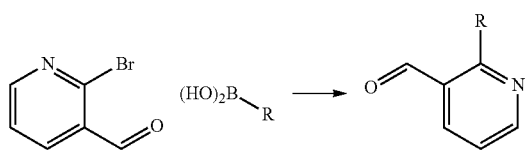

A 2-dram round-bottomed vial was charged with 2-bromonicotinaldehyde (100 mg, 0.538 mmol) and the boronic acid (0.538 mmol, 1 equiv.) were added in THF (2 mL). Then 2M $Na_2CO_3$ (0.403 mL, 0.806 mmol, 1.5 equiv.) and $Pd(Ph_3P)_4$ (31.0 mg, 0.027 mmol, 0.05 equiv.) were added and shaken at 85° C. overnight. The solvent was removed in the Genevac and the residue was washed with saturated $NaHCO_3$ (1 mL). The aqueous layer was extracted with EtOAc (3×1 mL). The combined organic layers were dried on the Genevac and the crude was purified using flash purification with a gradient of 5-40% EtOAc in hexane.

Example 126

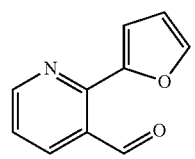

2-(furan-3-yl)nicotinaldehyde was prepared using the general boronic acid coupling procedure for 2-bromonicotinaldehyde and furan-3-ylboronic acid (40 mg, 93.2 mg theoretical, 42.9%). LC-MS m/z 174.2 (M+1).

Example 127

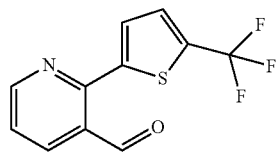 [SMILES: O=Cc1cccnc1-c1ccc(C(F)(F)F)s1]

2-(furan-2-yl)nicotinaldehyde was prepared using the general boronic acid coupling procedure for 2-bromonicotinaldehyde and furan-2-ylboronic acid (38 mg, 93.2 mg theoretical, 40.8%). LC-MS m/z 174.2 (M+1).

Example 128

2-(5-(trifluoromethyl)thiophen-2-yl)nicotinaldehyde was prepared using the general boronic acid coupling procedure for 2-bromonicotinaldehyde and (5-(trifluoromethyl)thiophen-2-yl)boronic acid (47.7 mg, 62.3 mg theoretical, 76.6%). LC-MS m/z 258.2 (M+1).

Example 129

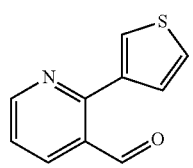 [SMILES: O=Cc1cccnc1-c1ccsc1]

2-(thiophen-3-yl)nicotinaldehyde was prepared using the general boronic acid coupling procedure for 2-bromonicotinaldehyde and thiophen-3-ylboronic acid (60 mg, 101.8 mg theoretical, 58.9%). LC-MS m/z 190.2 (M+1).

Example 130

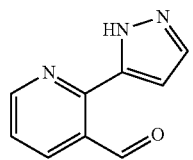 [SMILES: O=Cc1cccnc1-c1ccn[nH]1]

2-(1H-pyrazol-5-yl)nicotinaldehyde was prepared using the general boronic acid coupling procedure for 2-bromonicotinaldehyde and (1H-pyrazol-5-yl)boronic acid (60 mg, 93.2 mg theoretical, 64.4%). LC-MS m/z 174.2 (M+1).

Example 131

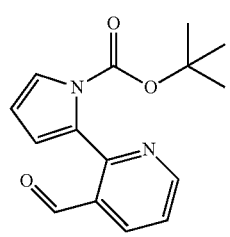 [SMILES: CC(C)(C)OC(=O)n1cccc1-c1ncccc1C=O]

tert-butyl 2-(3-formylpyridin-2-yl)-1H-pyrrole-1-carboxylate was prepared using the general boronic acid coupling procedure for 2-bromonicotinaldehyde and (1-(tert-butoxycarbonyl)-1H-pyrrol-2-yl)boronic acid (66 mg, 146.5 mg theoretical, 45.1%). LC-MS m/z 273.3 (M+1).

Example 132

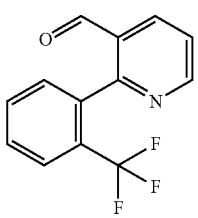 [SMILES: O=Cc1cccnc1-c1ccccc1C(F)(F)F]

2-(2-(trifluoromethyl)phenyl)nicotinaldehyde was prepared using the general boronic acid coupling procedure for 2-bromonicotinaldehyde and (2-(trifluoromethyl)phenyl)boronic acid (40 mg, 93.2 mg theoretical, 42.9%). LC-MS m/z 252.2 (M+1).

Example 133

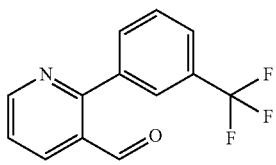 [SMILES: O=Cc1cccnc1-c1cccc(C(F)(F)F)c1]

2-(3-(trifluoromethyl)phenyl)nicotinaldehyde was prepared using the general boronic acid coupling procedure for 2-bromonicotinaldehyde and (3-(trifluoromethyl)phenyl)boronic acid (100 mg, 135.1 mg theoretical, 74%). LC-MS m/z 252.2 (M+1).

Example 134

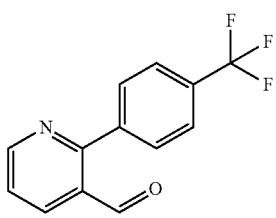 [SMILES: O=Cc1cccnc1-c1ccc(C(F)(F)F)cc1]

2-(4-(trifluoromethyl)phenyl)nicotinaldehyde was prepared using the general boronic acid coupling procedure for 2-bromonicotinaldehyde and (4-(trifluoromethyl)phenyl)boronic acid (93.8 mg, 135.1 mg theoretical, 69.4%). LC-MS m/z 252.2 (M+1).

Example 135

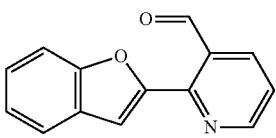

2-(benzofuran-2-yl)nicotinaldehyde was prepared using the general boronic acid coupling procedure for 2-bromonicotinaldehyde and benzofuran-2-ylboronic acid (72 mg, 120.1 mg theoretical, 60%). LC-MS m/z 224.2 (M+1).

Example 136

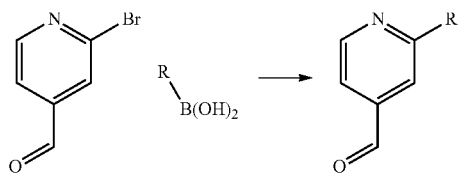

A 2-dram round-bottomed vial was charged with 2-bromoisonicotinaldehyde (100 mg, 0.538 mmol) and the boronic acid (0.538 mmol, 1 equiv.) were added in THF (2 mL). Then 2M $Na_2CO_3$ (0.403 mL, 0.806 mmol, 1.5 equiv.) and $Pd(Ph_3P)_4$ (31.0 mg, 0.027 mmol, 0.05 equiv.) were added and shaken at 85° C. overnight. The solvent was removed in the Genevac and the residue was washed with saturated $NaHCO_3$ (1 mL). The aqueous layer was extracted with EtOAc (3×1 mL). The combined organic layers were dried on the Genevac and the crude was purified using flash purification with a gradient of 5-40% EtOAc in hexane.

Example 137

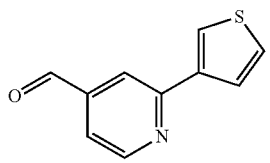 [SMILES: O=Cc1ccnc(-c2ccsc2)c1]

2-(thiophen-3-yl)isonicotinaldehyde was prepared using the general boronic acid coupling procedure for 2-bromoisonicotinaldehyde and thiophen-3-ylboronic acid (89 mg, 101.8 mg theoretical, 87.4%). LC-MS m/z 190.2 (M+1).

Example 138

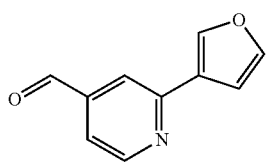 [SMILES: O=Cc1ccnc(-c2ccoc2)c1]

2-(furan-3-yl)isonicotinaldehyde was prepared using the general boronic acid coupling procedure for 2-bromoisonicotinaldehyde and furan-3-ylboronic acid (67 mg, 93.2 mg theoretical, 61.2%). LC-MS m/z 174.2 (M+1).

Example 139

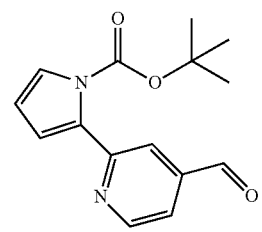 [SMILES: CC(C)(C)OC(=O)n1cccc1-c1cc(C=O)ccn1]

tert-butyl 2-(4-formylpyridin-2-yl)-1H-pyrrole-1-carboxylate was prepared using the general boronic acid coupling procedure for 2-bromoisonicotinaldehyde and (1-(tert-butoxycarbonyl)-1H-pyrrol-2-yl)boronic acid (56 mg, 146.5 mg theoretical, 38.2%). LC-MS m/z 273.3 (M+1).

Example 140

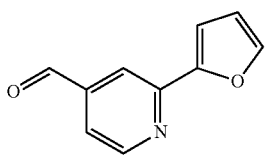 [SMILES: O=Cc1ccnc(-c2ccco2)c1]

2-(furan-2-yl)isonicotinaldehyde was prepared using the general boronic acid coupling procedure for 2-bromoisonicotinaldehyde and furan-2-ylboronic acid (39.6 mg, 93.2 mg theoretical, 42.5%). LC-MS m/z 174.2 (M+1).

Example 141

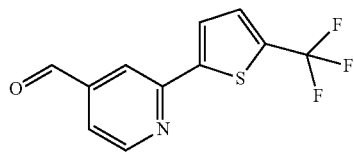 [SMILES: O=Cc1ccnc(-c2ccc(C(F)(F)F)s2)c1]

2-(5-(trifluoromethyl)thiophen-2-yl)isonicotinaldehyde was prepared using the general boronic acid coupling procedure for 2-bromoisonicotinaldehyde and (5-(trifluoromethyl)thiophen-2-yl)boronic acid (29.4 mg, 62.3 mg theoretical, 47.2%). LC-MS m/z 258.2 (M+1).

Example 142

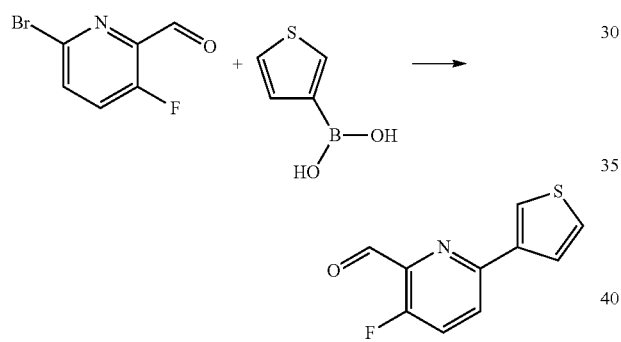

A 2-dram round-bottomed vial was charged with 6-bromo-3-fluoropicolinaldehyde (100 mg, 0.490 mmol) and thiophen-3-ylboronic acid (62.7 mg, 0.490 mmol, 1 equiv.) were added in THF (2 mL). Then 2 M $Na_2CO_3$ (0.368 mL, 0.735 mmol, 1.5 equiv.) and $Pd(Ph_3P)_4$ (28.3 mg, 0.025 mmol, 0.05 equiv.) were added and shaken at 85° C. overnight. The solvent was removed in the Genevac and the residue was washed with saturated $NaHCO_3$ (1 mL). The aqueous layer was extracted with EtOAc (3×1 mL). The combined organic layers were dried on the Genevac and the crude was purified using flash purification with a gradient of 5-40% EtOAc in hexane.

Example 143

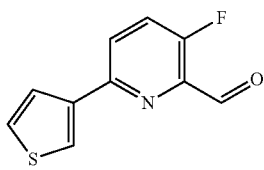 [SMILES: O=Cc1nc(-c2ccsc2)ccc1F]

3-fluoro-6-(thiophen-3-yl)picolinaldehyde was prepared using the general boronic acid coupling procedure for 6-bromo-3-fluoropicolinaldehyde and thiophen-3-ylboronic acid (80.5 mg, 101.5 mg theoretical, 79.3%). LC-MS m/z 208.2 (M+1).

Example 144

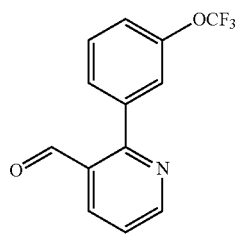 [SMILES: O=Cc1cccnc1-c1cccc(OC(F)(F)F)c1]

2-(3-(trifluoromethoxy)phenyl)nicotinaldehyde was prepared using the general boronic acid coupling procedure with 2-bromonicotinaldehyde and (3-(trifluoromethoxy)phenyl)boronic acid (101 mg, 144 mg theoretical, 70.1%). LC-MS m/z 268 (M+1).

Example 145

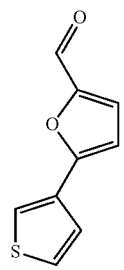 [SMILES: O=Cc1ccc(-c2ccsc2)o1]

2-(3-(trifluoromethoxy)phenyl)nicotinaldehyde was prepared using the general boronic acid coupling procedure with 5-bromofuran-2-carbaldehyde and thiophen-3-ylboronic acid (68 mg, 102 mg theoretical, 66.7%). LC-MS m/z 179 (M+1).

Example 146

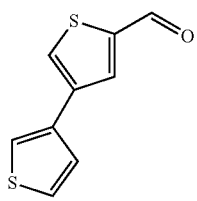 [SMILES: O=Cc1cc(-c2ccsc2)cs1]

[3,3'-bithiophene]-5-carbaldehyde was prepared using the general boronic acid coupling procedure with 4-bromothiophene-2-carbaldehyde and thiophen-3-ylboronic acid (56 mg, 102 mg theoretical, 54.9%). LC-MS m/z 195 (M+1).

Example 147

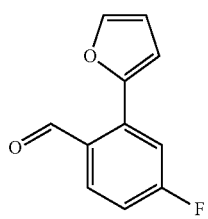 [SMILES: O=Cc1ccc(F)cc1-c1ccco1]

4-fluoro-2-(furan-2-yl)benzaldehyde was prepared using the general boronic acid coupling procedure with 2-bromo-4-fluorobenzaldehyde and furan-2-ylboronic acid (20 mg, 94 mg theoretical, 21.3%). LC-MS m/z 191 (M+1).

Example 148

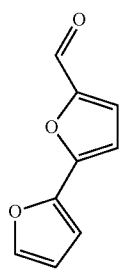 [SMILES: O=Cc1ccc(-c2ccco2)o1]

[2,2'-bifuran]-5-carbaldehyde was prepared using the general boronic acid coupling procedure with 5-bromofuran-2-carbaldehyde and furan-2-ylboronic acid (24 mg, 93 mg theoretical, 25.8%). LC-MS m/z 163 (M+1).

Example 149

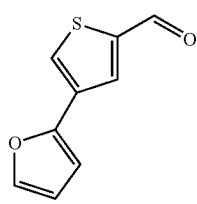 [SMILES: O=Cc1cc(-c2ccco2)cs1]

4-(furan-2-yl)thiophene-2-carbaldehyde was prepared using the general boronic acid coupling procedure with 4-bromothiophene-2-carbaldehyde and furan-2-ylboronic acid (26 mg, 93 mg theoretical, 28.0%). LC-MS m/z 179 (M+1).

Example 150

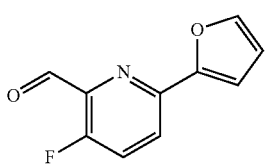 [SMILES: O=Cc1nc(-c2ccco2)ccc1F]

3-fluoro-6-(furan-2-yl)picolinaldehyde was prepared using the general boronic acid coupling procedure with 6-bromo-3-fluoropicolinaldehyde and furan-2-ylboronic acid (41 mg, 94 mg theoretical, 43.6%). LC-MS m/z 192 (M+1).

Example 151

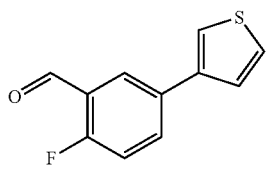 [SMILES: O=Cc1cc(-c2ccsc2)ccc1F]

2-fluoro-5-(thiophen-3-yl)benzaldehyde was prepared using the general boronic acid coupling procedure with 5-bromo-2-fluorobenzaldehyde and thiophen-3-ylboronic acid (27 mg, 102 mg theoretical, 26.5%). LC-MS m/z 207 (M+1).

Example 152

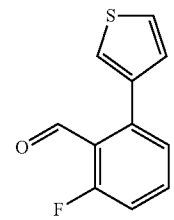 [SMILES: O=Cc1c(F)cccc1-c1ccsc1]

2-fluoro-6-(thiophen-3-yl)benzaldehyde was prepared using the boronic acid coupling procedure with 2-bromo-6-fluorobenzaldehyde and thiophen-3-ylboronic acid (66 mg, 102 mg theoretical, 64.7%). LC-MS m/z 207 (M+1).

Example 153

Preparation of Methoxyaminopyrimidine Intermediate (Z)-5-((2-(4-(aminomethyl)piperidin-1-yl)-6-methoxypyrimidin-4-yl)methylene)thiazolidine-2,4-dione was prepared as follows.

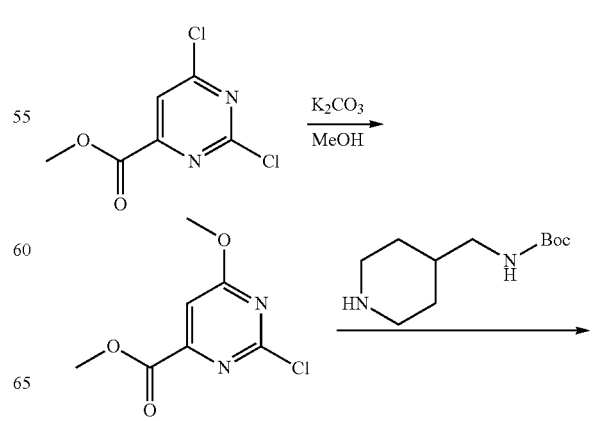

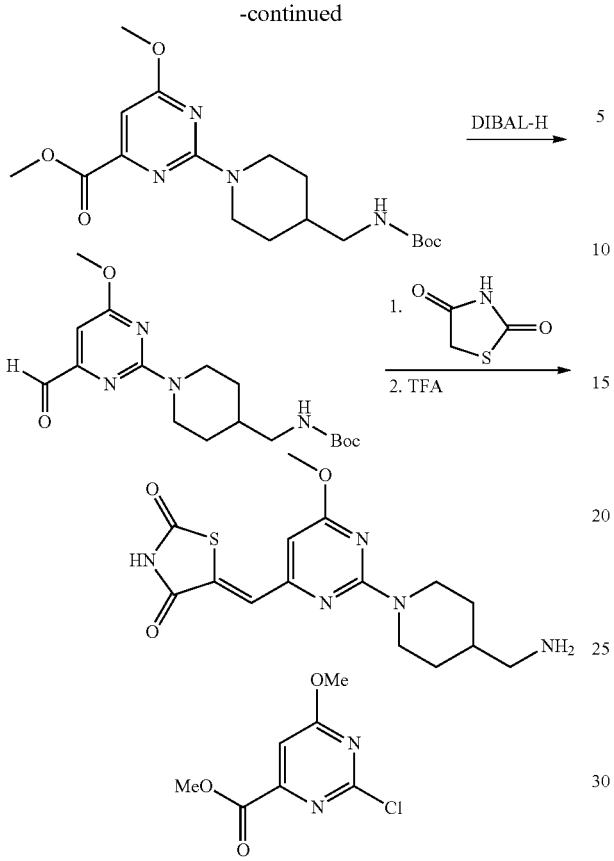

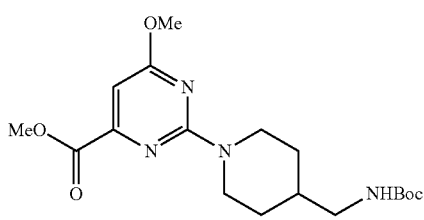 [SMILES: COC(=O)c1cc(OC)nc(N2CCC(CNC(=O)OC(C)(C)C)CC2)n1]

Methyl
2-chloro-6-methoxypyrimidine-4-carboxylate

A 30 mL round-bottomed vial was charged with methyl 2,6-dichloropyrimidine-4-carboxylate (0.6 g, 2.9 mmol, 1 equiv.), methanol (6 mL, 0.97 M), $K_2CO_3$ (0.401 g, 2.9 mmol, 1 equiv.), and the reaction mixture was shaken at 65° C. for 1.5 h. The solvent was concentrated under reduced pressure and the residue was partitioned between EtOAc (25 mL) and $H_2O$ (25 mL) and the water layer was extracted with EtOAc (2×20 mL). The combined organic layer was dried over $Na_2SO_4$ and concentrated under reduced pressure to provide the crude chloropyrimidine (441 mg, 588 mg theoretical, 75%), which was used in the next step without further purification.

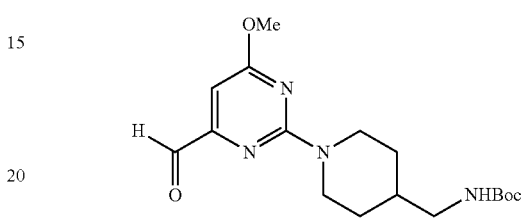

Methyl 2-(4-(((tert-butoxycarbonyl)amino)methyl) piperidin-1-yl)-6-methoxypyrimidine-4-carboxylate An 8 mL round-bottomed vial was charged with the 2-chloropyrimidine (150 mg, 0.74 mmol, 1.5 equiv.), methanol (1.5 mL, 0.49 M), tert-Butyl(piperidin-4-ylmethyl)carbamate (159 mg, 0.49 mmol, 1 equiv.), DIPEA (258 µL, 0.99 mmol, 2 equiv.), and the reaction mixture was shaken at 65° C. for 3 h. The solvent was concentrated under reduced pressure and the residue was partitioned between EtOAc (25 mL) and saturated $NaHCO_3$ (10 mL). The organic layer was dried over $Na_2SO_4$ and dried under reduced pressure to provide the crude product. Purification using the Biotage ($SiO_2$, 10 g cartridge, Hexanes/EtOAc 95:5 to 40:60) afforded the desired pyrimidine intermediate as a white solid (219 mg, 281 mg theoretical, 78%).

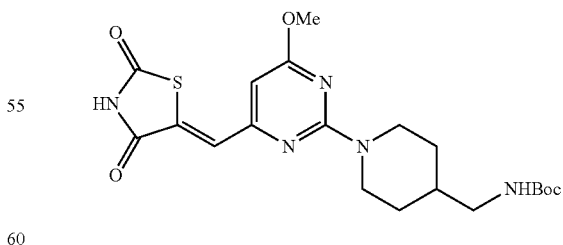

tert-Butyl((1-(4-formyl-6-methoxypyrimidin-2-yl) piperidin-4-yl)methyl)carbamate A 50 mL 2-neck round-bottomed flask was charged with the methyl ester intermediate (150 mg, 0.39 mmol, 1 equiv.), $CH_2Cl_2$ (2 mL, 0.195 M), and then DIBAL-H 1 M in $CH_2Cl_2$ (0.59 mL, 0.59 mmol, 1.5 equiv.) was added over a 4 minute period at −78° C. The reaction was then stirred for 1.5 h at −78° C. and for 1.5 h between −78° C. and RT. LC-MS showed mostly starting material so the reaction mixture was re-cooled to −78° C. and DIBAL-H (0.8 mL, 0.8 mmol, 2 equiv.) was added. LC-MS showed mostly starting material. The reaction mixture was stored at −20° C. for 3 d. The reaction mixture was cooled to −78° C. and treated with 1 M DIBAL-H in hexanes (0.59 mL, 0.59 mmol, 1 equiv.) over a 5 min. period, which produced a white precipitate. After 2.5 h, another equivalent of DiBAL-H (1 M in Hexanes, 0.59 mL) was added over a 15 min. period at −78° C. The reaction was quenched at −78° C. after 35 min. with methanol (1 mL). The solvent were concentrated under reduced pressure and the residue was partitioned between $CH_2Cl_2$ (20 mL) and saturated $NaHCO_3$ (20 mL). The organic layer was dried over $Na_2SO_4$ and the solvent was concentrated under reduced pressure to provide the crude product, which was used in the next step without further purification.

(Z)-tert-Butyl((1-(4-((2,4-dioxothiazolidin-5-ylidene)methyl)-6-methoxypyrimidin-2-yl)piperidin-4-yl)methyl)carbamate An 8 mL round-bottomed vial was charged with the crude aldehyde (0.2 mmol, estimated), ethanol (2 mL), thiazolidine-2,4-dione (23 mg, 0.2 mmol, 1 equiv.), triethylamine (56 µL, 0.4 mmol, 2 equiv.), purged with Ar, and the reaction mixture was shaken at 80° C. for 24 h. The crude mixture was purified using the Biotage (SiO$_2$, 10 g cartridge, CH$_2$Cl$_2$/MeOH 99:1 to 94:6) afforded 113 mg of the partially purified product. The sample was re-purified using reverse phase HPLC (methanol/water 10-90%, 0.4% TFA, 3 equal injections) provided the pure product as a TFA salt (47.3 mg, 225 mg theoretical, 21%). LC-MS m/z 450 (M+1).

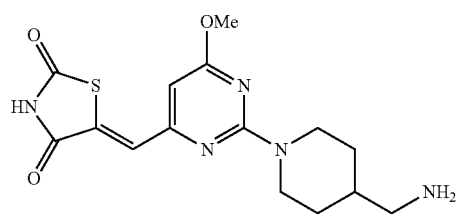 [SMILES: COc1cc(/C=C2\SC(=O)NC2=O)nc(N2CCC(CN)CC2)n1]

(Z)-5-((2-(4-(aminomethyl)piperidin-1-yl)-6-methoxypyrimidin-4-yl)methylene)thiazolidine-2,4-dione An 8 mL round-bottomed vial was charged with the MeO-pyrimidine boc protected amine (47.3 mg, 105 µmol, 1 equiv.), CH$_2$Cl$_2$ (1.3 mL, 0.08 M), TFA (0.5 mL, 6.5 mmol, 62 equiv.), and the reaction mixture was stirred for 1 h at RT. The solvents were concentrated under reduced pressure and the residue was re-dissolved in DMSO (0.9 mL) and purified by reverse phase HPLC (methanol/water with 0.4% TFA, 10-90% method, 2 injections of 500 µL) to provide (Z)-5-((2-(4-(aminomethyl)piperidin-1-yl)-6-methoxypyrimidin-4-yl)methylene)thiazolidine-2,4-dione as the TFA salt (43.9 mg, 48.8 mg theoretical, 90%). LC-MS m/z 350.1 (M+1).

Example 154

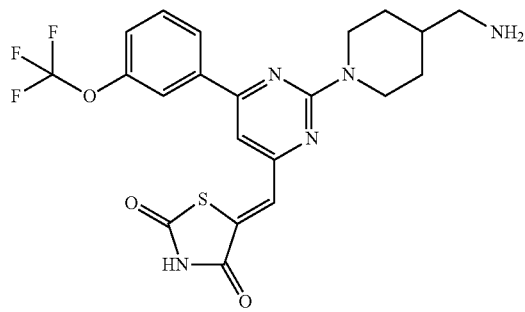 [SMILES: NCC1CCN(c2nc(/C=C3\SC(=O)NC3=O)cc(-c3cccc(OC(F)(F)F)c3)n2)CC1]

(Z)-5-((6-methoxy-2-(4-((((6-(thiophen-3-yl)pyridin-2-yl)methyl)amino)methyl)piperidin-1-yl)pyrimidin-4-yl)methylene)thiazolidine-2,4-dione (4.1 mg, 5.9 mg theoretical, 69%) LC-MS m/z 480 (M+1), was prepared according to the following synthetic scheme using the general boronic acid coupling conditions and other methods similar to those used in the preparation of (Z)-5-((2-(4-aminomethyl)piperidin-1-yl)-6-methoxypyrimidin-4-yl)methylene)thiazolidine-2,4-dione.

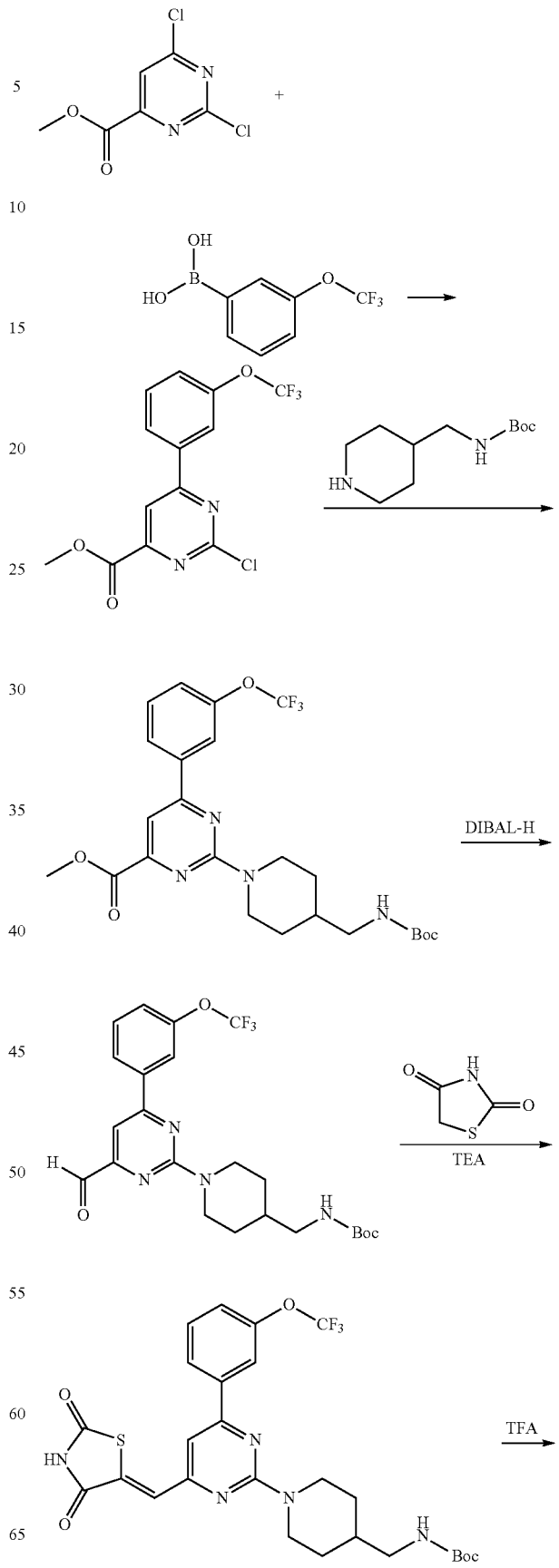

-continued

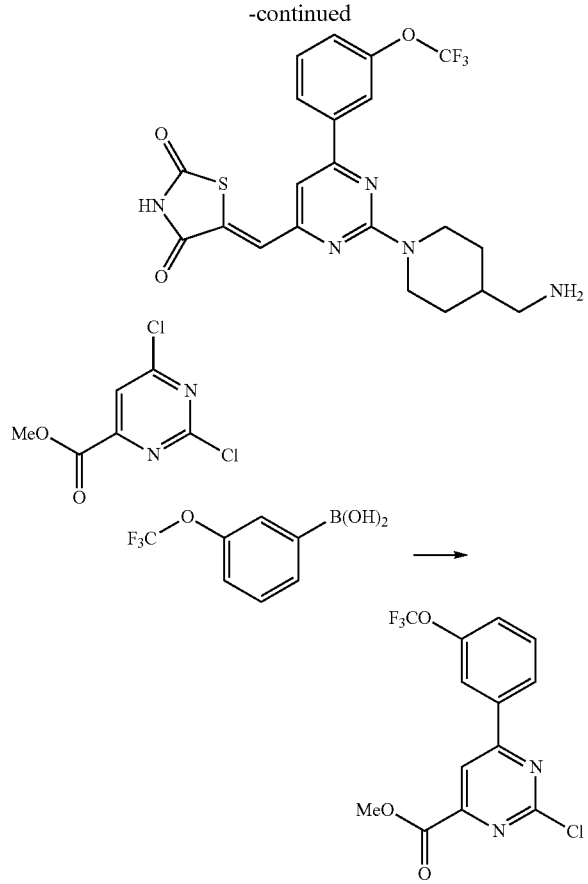

General Boronic Acid Coupling Conditions for the First Step

A 2-dram round-bottom vial was charged with methyl 2,6-dichloropyrimidine-4-carboxylate (100 mg, 0.483 mmol) and (3-(trifluoromethoxy)phenyl)boronic acid (80 mg, 0.386 mmol, 0.8 equiv) were added in THF (2 mL). Then 2M Na₂CO₃ (0.362 mL, 0.725 mmol, 1.5 equiv) and Pd(tetrakis)Ph₃P (27.9 mg, 0.024 mmol, 0.05 equiv) were added and shaken at 85° C. overnight. The solvent was removed in the Genevac and the residue was washed with saturated NaHCO₃ (1 mL). The aqueous layer was extracted with EtOAc (3×1 mL). The combined organic layers were dried on the Genevac and the crude was purified using flash purification with a gradient of 5-40% EtOAc in hexane to provide methyl 2-chloro-6-(3-(trifluoromethoxy)phenyl)pyrimidine-4-carboxylate.

Example 155

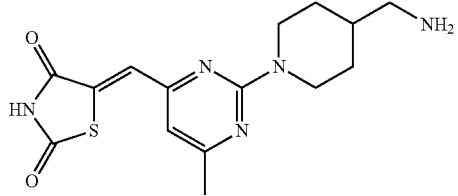 [SMILES: Cc1cc(/C=C2\SC(=O)NC2=O)nc(N2CCC(CN)CC2)n1]

(Z)-5-((6-methoxy-2-(4-((((6-(thiophen-3-yl)pyridin-2-yl)methyl)amino)methyl)piperidin-1-yl)pyrimidin-4-yl)methylene)thiazolidine-2,4-dione (292 mg, 360 mg theoretical, 81%) LC-MS m/z 334 (M+1), was prepared according to the following synthetic scheme using methods similar to those used in the preparation of (Z)-5-((2-(4-(aminomethyl)piperidin-1-yl)-6-methoxypyrimidin-4-yl)methylene)thiazolidine-2,4-dione (Example 153):

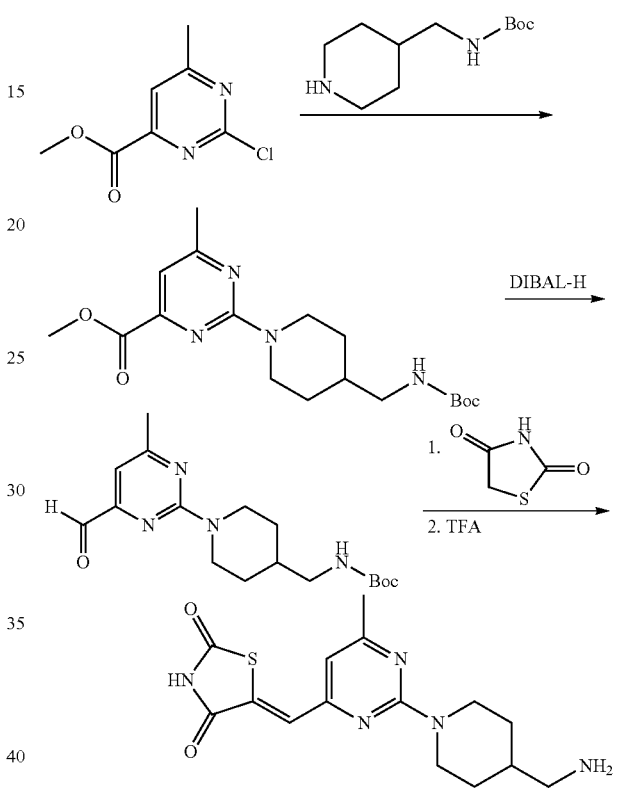

Example 156

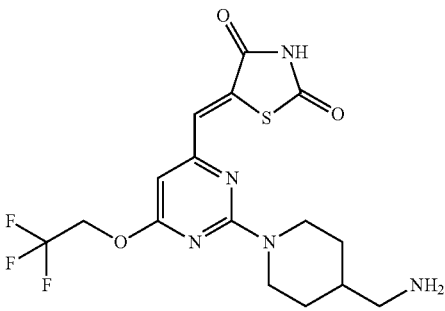 [SMILES: NCC1CCN(c2nc(/C=C3\SC(=O)NC3=O)cc(OCC(F)(F)F)n2)CC1]

(Z)-5-((2-(4-(aminomethyl)piperidin-1-yl)-6-(2,2,2-trifluoroethoxy)pyrimidin-4-yl)methylene)thiazolidine-2,4-dione (203 mg, 236 mg theoretical, 86%) LC-MS m/z 418 (M+1), was prepared according to the following synthetic scheme using methods similar to those used in the preparation of (Z)-5-((2-(4-(aminomethyl)piperidin-1-yl)-6-methoxypyrimidin-4-yl)methylene)thiazolidine-2,4-dione (Example 153).

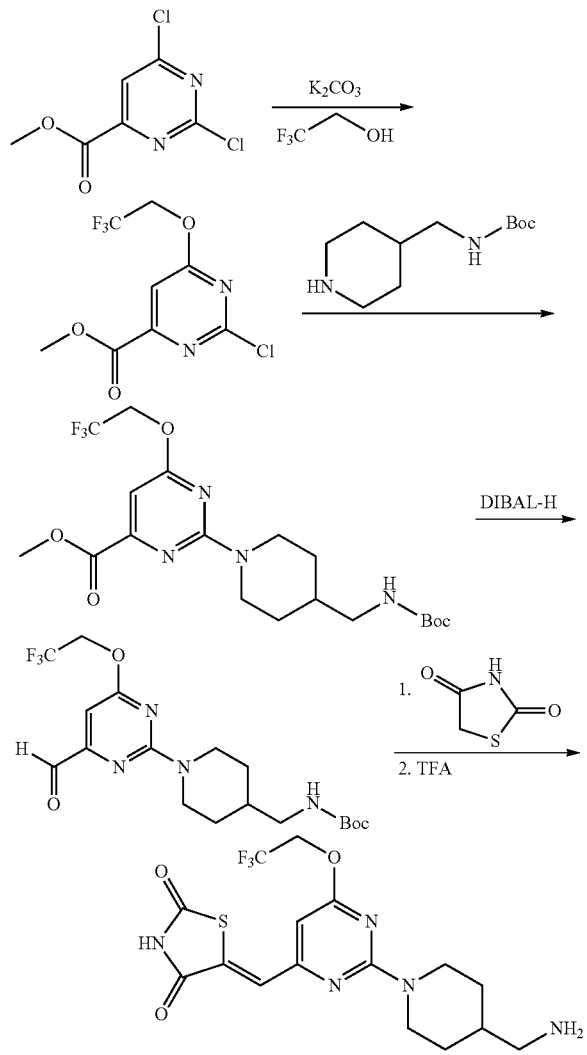

Example 157

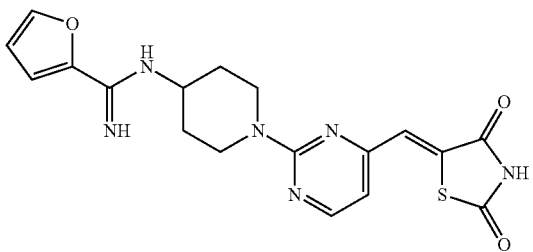 [SMILES: N=C(NC1CCN(c2nccc(/C=C3\SC(=O)NC3=O)n2)CC1)c1ccco1]

(Z)—N-(1-(4-((2,4-dioxothiazolidin-5-ylidene)methyl)pyrimidin-2-yl)piperidin-4-yl)furan-2-carboximidamide was prepared using the following procedure (16.6 mg, 29.5 mg theoretical, 56.3%). LC-MS m/z 399.1 (M+1).

Step 1.

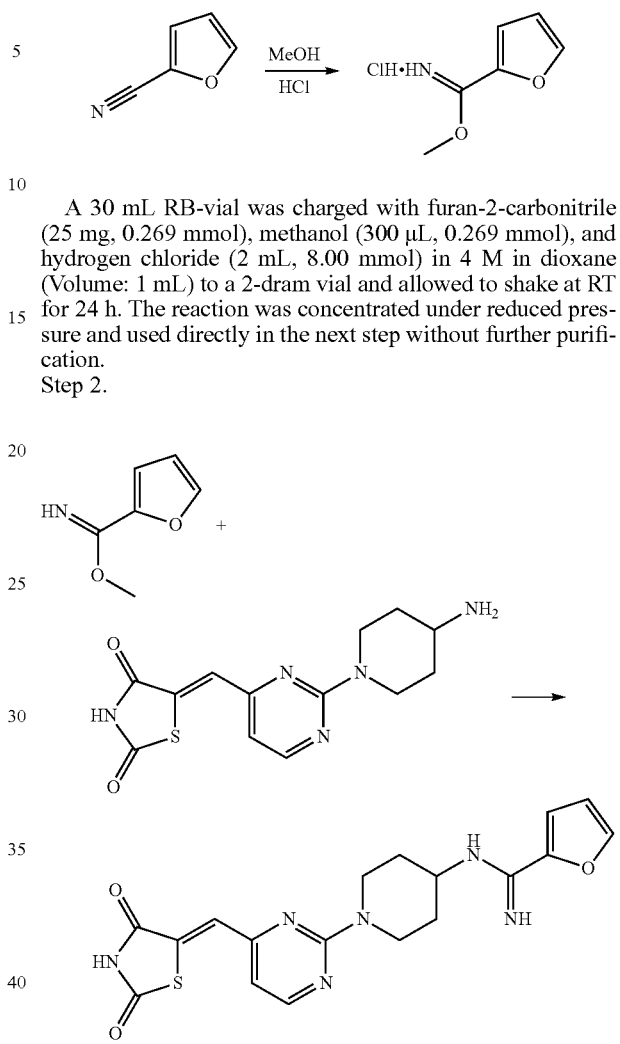

A 30 mL RB-vial was charged with furan-2-carbonitrile (25 mg, 0.269 mmol), methanol (300 µL, 0.269 mmol), and hydrogen chloride (2 mL, 8.00 mmol) in 4 M in dioxane (Volume: 1 mL) to a 2-dram vial and allowed to shake at RT for 24 h. The reaction was concentrated under reduced pressure and used directly in the next step without further purification.

Step 2.

A 2-dram RB-vial was charged with the crude material from step 1, methyl furan-2-carbimidate (37 mg, 296 µmol) and then treated with MeOH (Volume: 1.5 mL), (Z)-5-((2-(4-aminopiperidin-1-yl)pyrimidin-4-yl)methylene)thiazolidine-2,4-dione (22.6 mg, 74 µmol), and 2 mL of DMSO was added providing a homogeneous solution. After 2 h at RT, DIPEA was added (250 µl). After 24 h at RT, the reaction was purified using RP-HPLC with TFA as the modifier to provide (Z)—N-(1-(4-((2,4-dioxothiazolidin-5-ylidene)methyl)pyrimidin-2-yl)piperidin-4-yl)furan-2-carboximidamide.

Example 158

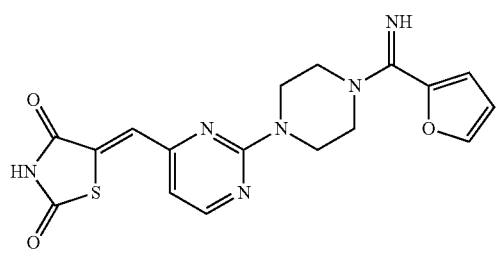

(Z)-5-((2-(4-(furan-2-yl(imino)methyl)piperazin-1-yl)pyrimidin-4-yl)methylene)thiazolidine-2,4-dione was prepared using the following procedure (1.8 mg, 29.1 mg theoretical, 6.2%). LC-MS m/z 385.1 (M+1).

Step 1.

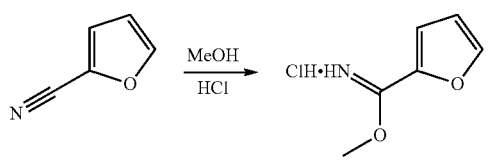

A 30 mL RB-vial was charged with furan-2-carbonitrile (25 mg, 0.269 mmol), methanol (300 µL, 0.269 mmol), and hydrogen chloride (2 mL, 8.00 mmol) in 4 M in dioxane (Volume: 1 mL) to a 2-dram vial and allowed to shake at RT for 24 h. The reaction was concentrated under reduced pressure and used directly in the next step without further purification.

Step 2.

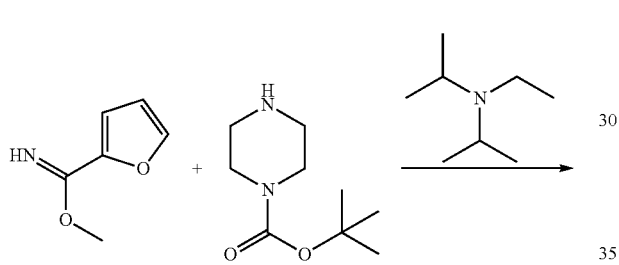

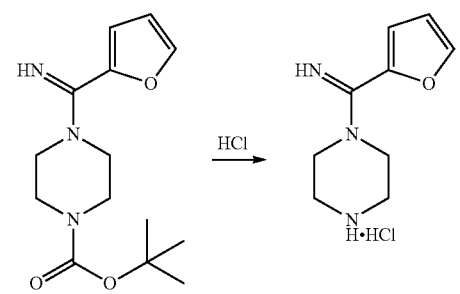

Crude reaction from Step 1, methyl furan-2-carbimidate (26 mg, 0.208 mmol) was dried down and then diluted in MeOH (Volume: 1 mL) and treated with tert-butyl piperazine-1-carboxylate (122 mg, 0.655 mmol) was added to the solution. N-ethyl-N-isopropylpropan-2-amine (50 mg, 0.387 mmol) was added and the solution shaken at RT for 24 h. The sample was purified by RP-HPLC with TFA as the modifier to provide the Boc-piperazine intermediate. The dry material was then treated with 1 mL MeOH and 1 mL 4.0 M HCl in dioxane. After 30 minutes the final product (M+1=180) was the only peak in the chromatogram. The reaction was concentrated under reduced pressure and used directly in the next step without further purification.

Step 3.

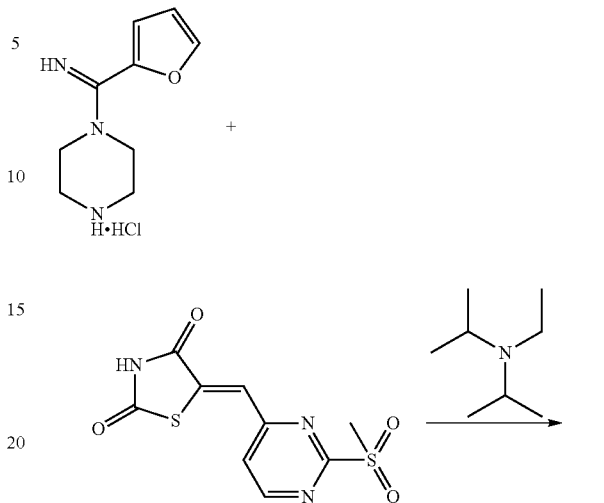

The crude material from Step 2, furan-2-yl(piperazin-1-yl)methanimine hydrochloride (16.3 mg, 0.076 mmol) was diluted in DMSO (Volume: 0.75 mL) and added to (Z)-5-((2-(methylsulfonyl)pyrimidin-4-yl)methylene)thiazolidine-2,4-dione (19.4 mg, 0.068 mmol) in a 2-dram vial. The reaction solution was then treated with N-ethyl-N-isopropylpropan-2-amine (50 mg, 0.387 mmol) and then shaken at 100° C. for 16 h. The reaction was then purified by RP-HPLC using TFA as the modifier to provide (Z)-5-((2-(4-(furan-2-yl(imino)methyl)piperazin-1-yl)pyrimidin-4-yl)methylene)thiazolidine-2,4-dione.

Example 159

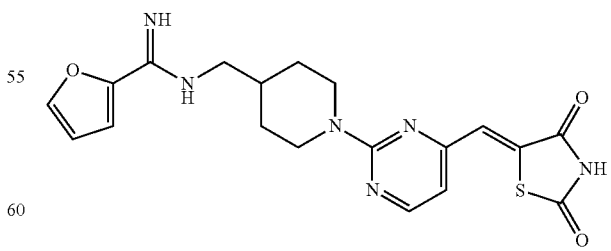

(Z)—N-((1-(4-((2,4-dioxothiazolidin-5-ylidene)methyl)pyrimidin-2-yl)piperidin-4-yl)methyl)furan-2-carboximidamide was prepared using the following procedure (4.7 mg, 31.4 mg theoretical, 15%). LC-MS m/z 413.1 (M+1).

Step 1.

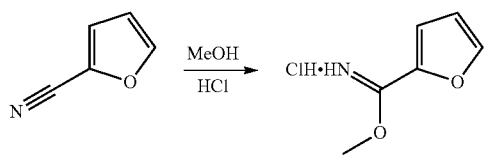

A 30 mL RB-vial was charged with furan-2-carbonitrile (25 mg, 0.269 mmol), methanol (300 μL, 0.269 mmol), and hydrogen chloride (2 mL, 8.00 mmol) in 4 M in dioxane (Volume: 1 mL) to a 2-dram vial and allowed to shake at RT for 24 h. The reaction was concentrated under reduced pressure and used directly in the next step without further purification.

Step 2.

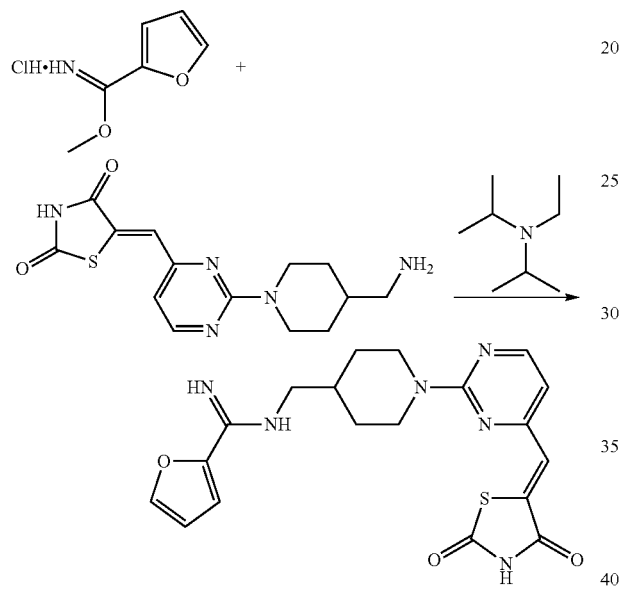

The crude material from Step 1, methyl furan-2-carbimidate hydrochloride (12.3 mg, 0.076 mmol) was diluted in DMSO (Volume: 0.5 mL) and added to (Z)-5-(2-(4-(aminomethyl)piperidin-1-yl)pyrimidin-4-yl)methylene)thiazolidine-2,4-dione (23 mg, 0.072 mmol) in a 2-dram vial. The reaction solution was then treated with N-ethyl-N-isopropylpropan-2-amine (50 mg, 0.387 mmol) and the reaction was shaken at RT for 16 h. The reaction was then purified by RP-HPLC using TFA as the modifier to provide (Z)—N-((1-(4-((2,4-dioxothiazolidin-5-ylidene)methyl)pyrimidin-2-yl)piperidin-4-yl)methyl)furan-2-carboximidamide.

Example 160

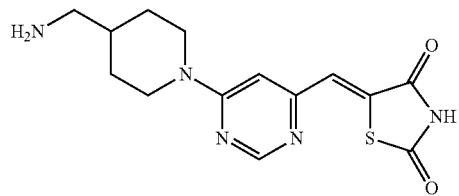 [SMILES: NCC1CCN(c2cc(/C=C3\SC(=O)NC3=O)ncn2)CC1]

(Z)-5-((6-(4-(aminomethyl)piperidin-1-yl)pyrimidin-4-yl)methylene)thiazolidine-2,4-dione was prepared as follows (36.0 mg, 104 mg theoretical, 34.6%). LC-MS m/z 320 (M+1).

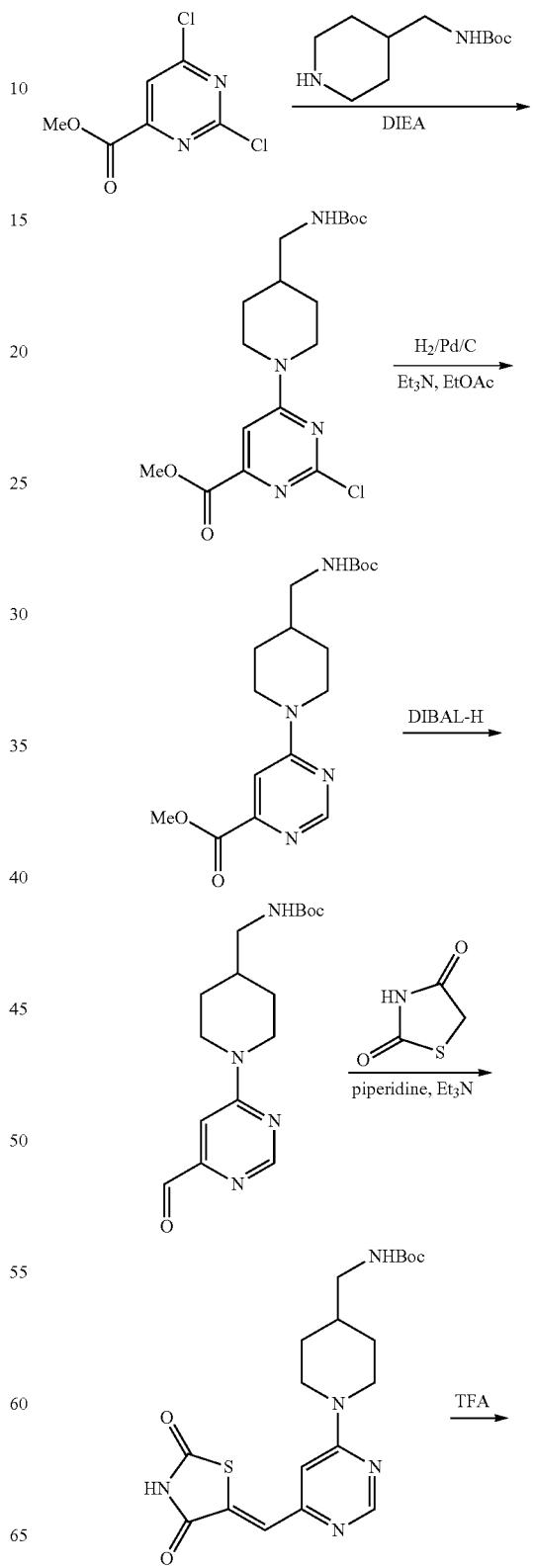

167

-continued

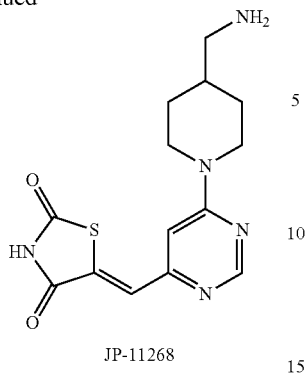

JP-11268

Step 1: Synthesis of methyl 6-(4-(((tert-butoxycarbonyl)amino)methyl)piperidin-1-yl)-2-chloropyrimidine-4-carboxylate

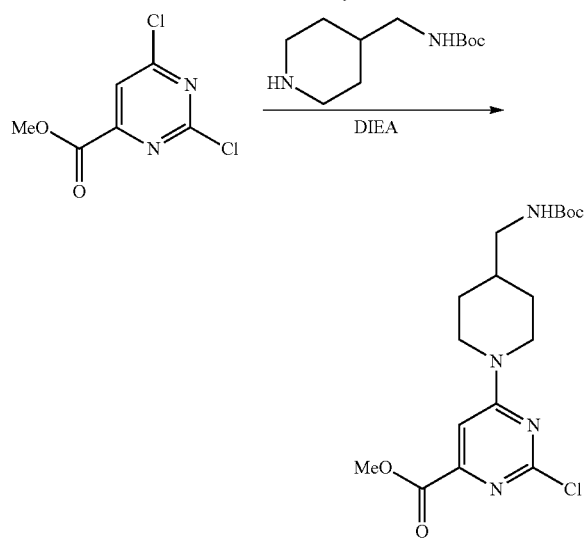

A 30 mL round-bottomed vial methyl 2,6-dichloropyrimidine-4-carboxylate (300 mg, 1 equiv.) was partially dissolved in anhydrous THF (5 mL). DIEA (278 µL, 1.1 equiv.) was added at once at 0° C. tert-Butyl(piperidin-4-ylmethyl)carbamate (311 mg, 1 equiv.) dissolved in THF (5 mL) was added at 0° C. in 5 min. The reaction mixture was warmed to RT in 3 h15. LC-MS showed mostly the desired product (2.77 min, M+1=385) and a small amount of the other regioisomer (3.28 min, M+1-isobutene=329). The solvent was evaporated and the residue was purified by biotage (SiO$_2$, 10 g, Hex/EtOAc 9:1 to 1:1) to give the desired isomer (386.8 mg, 69.4%) as a white solid. LC-MS m/z 385 (M+1).

Step 2: Synthesis of methyl 6-(4-(((tert-butoxycarbonyl)amino)methyl)piperidin-1-yl)pyrimidine-4-carboxylate

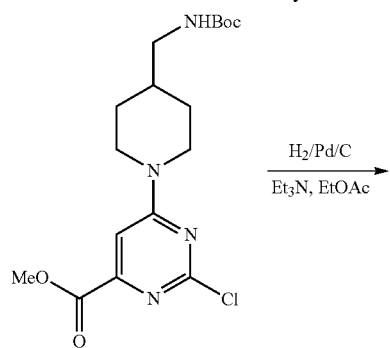

168

-continued

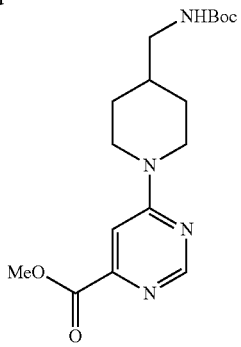

A 50 mL round-bottomed flask was charged with methyl 6-(4-(((tert-butoxycarbonyl)amino)methyl)piperidin-1-yl)-2-chloropyrimidine-4-carboxylate and MeOH (4 mL) and Et$_3$N (0.4 mL). 10% Pd/C (104 mg, 0.25 equiv.) was added under argon. The reaction mixture was stirred for 6 h under 1 atm H$_2$. The catalyst was filtered and the solvent was evaporated to give the crude desired product (150 mg, 110% crude yield) which was used directly in the next step. LC-MS m/z 351 (M+1).

Step 3: Synthesis of tert-butyl((1-(6-formylpyrimidin-4-yl)piperidin-4-yl)methyl)carbamate

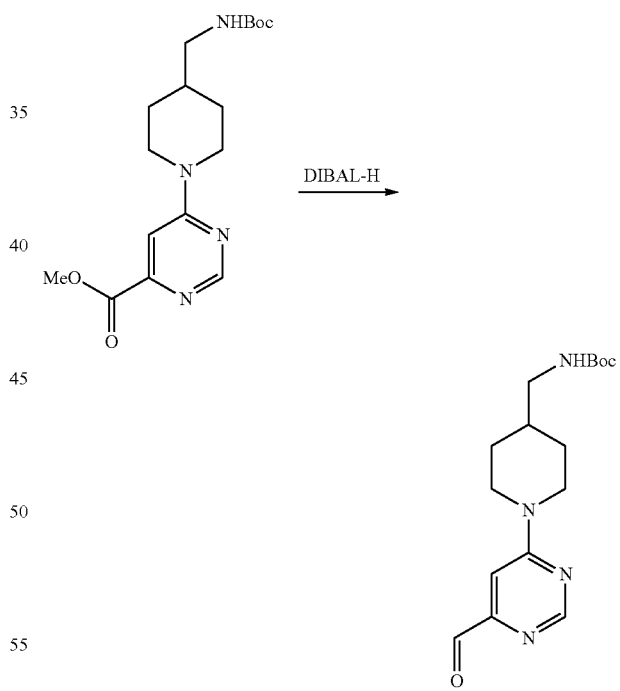

A 25 mL round-bottomed flask was charged with methyl 6-(4-(((tert-butoxycarbonyl)amino)methyl)piperidin-1-yl)pyrimidine-4-carboxylate (150 mg, 0.43 mmol, 1 equiv.) and CH$_2$Cl$_2$ (2 mL). The reaction mixture was cooled to −78° C. DIBAL-H 1 M in CH$_2$Cl$_2$ (0.64 mL, 0.64 mmol, 1.5 equiv.) was added in 3 minutes at −78° C. The reaction was stirred for 4 h at −78° C. LC-MS showed some starting material. Another portion of DIBAL-H 1 M in CH$_2$Cl$_2$ (0.5 mL, 0.5 mmol, 1.2 equiv.) was added in 1 min at −78° C. LC-MS after 30 min showed the reaction was complete. The reaction was quenched at −78° C. after 40 min with methanol (1 mL). The solvents were concentrated in vacuo. The residue was partitioned between CH$_2$Cl$_2$ (10 mL) and 1 N NaOH (6 mL). The aqueous layer was extracted with CH$_2$Cl$_2$ (2×10 mL). The organic layer was dried over Na$_2$SO$_4$. The solvent was evaporated to give the crude desired aldehyde (77.9 mg, 56.8% crude yield) as an yellowish oil. The crude reaction aldehyde was carried on the next step without any further purification. LC-MS m/z 339 (M+1+H$_2$O) and 351 (M+1+MeOH).

Step 4: (Z)-tert-butyl((1-(6-((2,4-dioxothiazolidin-5-ylidene)methyl)pyrimidin-4-yl)piperidin-4-yl)methyl)carbamate

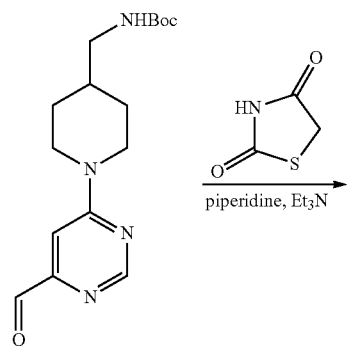

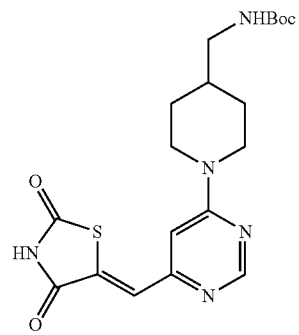

An 8 mL round-bottomed vial was charged with tert-butyl ((1-(6-formylpyrimidin-4-yl)piperidin-4-yl)methyl)carbamate (77.9 mg, 0.24 mmol, 1 equiv.), ethanol (1 mL), thiazolidine-2,4-dione (28.5 mg, 0.24 mmol, 1 equiv.) and triethylamine (68 µL, 0.48 mmol, 2 equiv.). Piperidine (1.04 mg, 23 µL of a solution of 52 µL in 0.95 mL ethanol, 0.012 mmol, 5% eq.) was added and Argon was bubbled through the solution. The reaction mixture was shaken at 85° C. for 18 h. LC-MS of the crude reaction mixture showed mostly the desired product. The solvent was evaporated. The residue was partitioned between EtOAc (10 mL) and 10% NH$_4$Cl (5 mL). The organic layer was dried over Na$_2$SO$_4$. Evaporation of solvent gave the crude (Z)-tert-butyl((1-(6-((2,4-dioxothiazolidin-5-ylidene)methyl)pyrimidin-4-yl)piperidin-4-yl)methyl)carbamate (79.8 mg, 78%). LC-MS: M+1=420.

Example 161

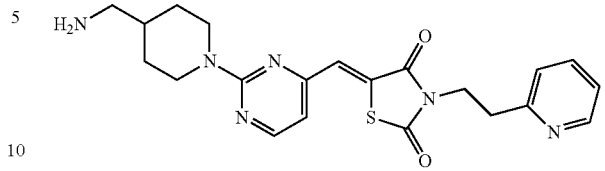

(Z)-5-((2-(4-(aminomethyl)piperidin-1-yl)pyrimidin-4-yl)methylene)-3-(2-(pyridin-2-yl)ethyl)thiazolidine-2,4-dione (Example 102) was also prepared using the general displacement procedure with tert-butyl(piperidin-4-ylmethyl)carbamate, alkylation with 2-(2-bromoethyl)pyridine, followed by the general de-protection procedure (16 mg, 30.6 mg theoretical, 52.3%). LC-MS m/z 525.5 (M+1).

Example 162

Cell Proliferation Inhibition

TABLE 4

| Human cancer | Cell line | Medium | Positive drug | Incubation time |
| --- | --- | --- | --- | --- |
| Prostate cancer | LNCaP | RPMI 1640 | Cisplatin | 72 h |
| Leukemia | KU812 | RPMI 1640 | | |
| Pancreas cancer | Panc-1 | DMEM | | |

All cells were cultured in the media supplemented with 10% FBS in the temperature of 37° C., 5% CO$_2$ and 95% humidity. All culture media were purchased from GIBCO.

Reagents:

CellTiter 96® Aqueous MTS Reagent Powder (Cat. No.: G1112, Promega. Store MTS Reagent Powder desiccated at 4° C. protected from light.)

Phenazine Methosulfate (PMS)

(Product No.: P9625, SIGMA. Store PMS Powder desiccated at 4° C. protected from light.)

Equipment:

Synergy2, Gene Company Limited; CO$_2$ Water Jacketed Incubator, Thermo (USA). Reverse microscope, Chongguang XDS-1B, Chongqing Guangdian Corp. (Chongqing, P.R.China).

Cytotoxicity and IC$_{50}$ Determination:

1. Cells were harvested respectively during the logarithmic growth period and counted with hemocytometer. Cell viability was over 98% by trypan blue exclusion.
2. Dilute cells with respective medium to achieve 1.11×10$^5$ cells/mL for LNCaP cells, 2.22×10$^5$ cells/mL for KU812 cells, 5.56×10$^4$ cells/mL for Panc-1 cells.
3. Add 90 µL cell suspensions to 96-well plate, the final cell densities are 1×10$^4$ cells/well for LNCaP cells, 2×10$^4$ cells/well for KU812 cells, and 4×10$^3$ cells/well for Panc-1 cells, respectively.
4. The next day, dilute the test article or positive drugs with DMSO or PBS.
5. Dispense 10 µL drug solution in each well (triplicate for each drug concentration).

6. The plates were cultured for another 72 hours, then measured using MTS assay.
7. Prepare MTS/PMS solution immediately prior to use, pipet 20 μL of the mixture into each well of the 96 well assay plate containing 100 μL culture medium. (The final reaction volume is 120 μL).
8. Incubate the plate for 1-4 hours at 37° C. in a humidified, 5% $CO_2$ atmosphere.
9. Record the absorbance at 490 nm using Synergy2 Microplate Reader.

Data Analysis:

The software of GraphPad Prism version 5 was used to calculate $IC_{50}$. The graphical curve was fitted using a nonlinear regression model with a sigmoidal dose response.

Results:

Results are shown in Table 5.

TABLE 5

| Compound | $IC_{50}$ values (μM) | | |
|---|---|---|---|
| | LNCaP | KU812 | Panc-1 |
| 10903 | 4.050 | NA | 21.20 |
| 10904 | 24.20 | NA | 9.943e+007 |
| 10905 | 10.76 | NA | 68.46 |
| 10906 | 6.416 | NA | 27.57 |
| 10907 | 6.523 | NA | 8.164 |
| 10909 | 10.70 | NA | 13.64 |
| 10910 | 6.222 | NA | 7.441 |
| 10913 | 6.710 | NA | 10.88 |
| 10914 | 6.574 | NA | 7.498 |
| 10915 | 10.37 | NA | 8.998 |
| 11086 | NA | 259.8 | 153.9 |
| 11087 | NA | 1.776 | 11.05 |
| 11088 | NA | 2.225 | 12.16 |
| 11089 | NA | 11.86 | 8.908 |
| 11090 | NA | 15.26 | 18.92 |
| 11091 | NA | 6.622 | 16.80 |
| 11092 | NA | 7.284 | 56.35 |
| 11093 | NA | 4.041 | 13.76 |
| 11094 | NA | 41.30 | NA |
| 11100 | NA | 4.300e+007 | 12.96 |
| 11101 | NA | 13.97 | 9.555 |
| 11102 | NA | 10.59 | 162.9 |
| 11103 | NA | 6.538 | 11.35 |
| 11104 | NA | 22.48 | 151.24 |
| 11105 | NA | 3.462 | 7.333 |
| 11106 | NA | 3.383e+012 | 29.56 |
| 11193 | NA | >30 | 11.9 |
| 11196 | NA | 16.2 | >30 |
| 11198 | NA | 12 | 22.2 |
| 11204 | NA | 3.4 | >30 |
| 11205 | NA | 14.2 | 6 |
| 11206 | NA | 15 | >30 |
| 11207 | NA | 12.9 | >30 |
| 11209 | NA | 15.5 | >30 |
| 11210 | NA | 10.1 | 25.1 |
| 11211 | NA | 6.2 | >30 |
| 11212 | NA | 20 | >30 |
| 11213 | NA | >30 | >30 |
| 11214 | NA | 6.6 | >30 |
| 11215 | NA | 7.7 | >30 |
| 11216 | NA | 5.3 | >30 |
| 11217 | NA | >30 | >30 |
| 11220 | NA | >30 | >30 |
| 11221 | NA | 12 | >30 |
| 11222 | NA | 22.8 | >30 |
| 11223 | NA | 18.2 | >30 |
| 11224 | NA | >30 | >30 |
| 11225 | NA | >30 | >30 |
| 11226 | NA | >30 | >30 |
| 11227 | NA | 28.1 | >30 |
| 11232 | NA | >30 | >30 |
| 11234 | NA | 11.5 | >30 |
| 11235 | NA | 13.5 | >30 |
| 11236 | NA | 18.8 | >30 |
| 11237 | NA | 10.8 | >30 |
| 11240 | NA | >30 | >30 |
| 11241 | NA | 13.3 | >30 |
| 11242 | NA | >30 | >30 |
| 11243 | NA | 10.4 | >30 |
| 11244 | NA | 15.4 | >30 |
| 11246 | NA | 22.3 | >30 |
| 11247 | NA | 11.9 | >30 |
| 11248 | NA | 14.7 | >30 |
| 11249 | NA | 9.7 | >30 |
| 11250 | NA | 9.6 | >30 |
| 11251 | NA | 20.7 | >30 |
| 11263 | NA | 7.1 | >30 |
| 11264 | NA | 26.1 | >30 |
| 11266 | NA | >30 | >30 |
| 11267 | NA | >30 | >30 |
| 11268 | NA | >30 | >30 |
| 11269 | NA | 13.2 | 21.5 |
| 11271 | NA | NA | NA |
| 11272 | NA | NA | NA |
| 11273 | NA | NA | NA |
| 11274 | NA | NA | NA |
| 11275 | NA | NA | NA |
| 11276 | NA | NA | NA |
| 11279 | NA | NA | NA |
| 11280 | NA | NA | NA |
| 11288 | NA | NA | NA |
| 11289 | NA | NA | NA |
| 11290 | NA | NA | NA |
| 11291 | NA | NA | NA |
| 11293 | NA | NA | NA |
| 11299 | NA | NA | NA |
| 11300 | NA | NA | NA |
| 11301 | NA | NA | NA |
| 11303 | NA | NA | NA |
| 11304 | NA | NA | NA |
| 11306 | NA | NA | NA |
| 11307 | NA | NA | NA |
| 11308 | NA | NA | NA |
| 11352 | NA | NA | NA |
| 11355 | NA | NA | NA |
| 11666 | NA | NA | NA |
| 11667 | NA | NA | NA |

NA = not available

Example 163

Cell Proliferation Inhibition

TABLE 6

| Human cancer | Cell line | Medium | Positive drug | Incubation time |
|---|---|---|---|---|
| Multiple Myeloma | MV4-11 RPMI-8226 NCI-H929 | IMDM RPMI-1640 RPMI-1640 + 0.05 mM 2-mercaptoethanol | Cisplatin | 72 hours |

All cells were cultured in media supplemented with 10% FBS except for which are marked specially, in the temperature of 37° C., 5% $CO_2$ and 95% humidity. All culture media were purchased from GIBCO (USA, IMDM Cat. 12200-036; RPMI Medium 1640 Cat. 31800-022; 2-mercaptoethanol Cat. 21985-023).

Reagents:
CellTiter 96® Aqueous MTS Reagent Powder
(Cat. No.: G11 12, Promega. Store MTS Reagent Powder desiccated at 4° C. protected from light.)
Phenazine Methosulfate (PMS)
(Product No.: P9625, SIGMA. Store PMS Powder desiccated at 4° C. protected from light.)
Preparation of PMS Solution:
  0.92 mg/mL PMS in DPBS Filter-sterilize through a 0.2 m filter into a sterile, light-protected container. Store at −20° C.
Preparation of MTS Solution:
The following protocol is recommended for the preparation of 21 mL of MTS solution (sufficient for ten 96-well plates).
a. Select a light-protected container or wrap a container with foil.
b. Add 21 mL of DPBS to the container.
c. Weigh out 42 mg of MTS Reagent Powder and add to DPBS.
d. Mix at moderate speed on a magnetic stir plate for 15 minutes or until the MTS is completely dissolved.
e. Measure the pH of the MTS solution. The optimum pH is between pH 6.0 to 6.5. If the solution is above pH 6.5, adjust to pH 6.5 with 1 N HCl.
f. Filter-sterilize the MTS solution through a 0.2 µm filter into a sterile, light protected container.
g. Store the MTS solution at −20° C., protected from light.
Preparation of the Mixture of MTS/PMS:
a. In order to prepare reagents sufficient for one 96-well plate containing cells cultured in a 100 µL volume, thaw the MTS solution and the PMS solution. It should take approximately 90 minutes at room temperature or 10 minutes in a 37° C. water bath to completely thaw the 20 mL size of MTS solution. (Note: For convenience, the first time the product is thawed, the entire contents of the 1 mL tube of PMS solution can be transferred to the 20 mL bottle of MTS solution. This mixture should be stored at −20° C. between uses. If storing PMS and MTS solutions at 4° C., do not combine these solutions until immediately before addition to the assay plate.)
b. Remove 2.0 mL of MTS solution from the amber reagent bottle using aseptic technique and transfer to a test tube.
c. Add 100 µL of PMS solution to the 2.0 mL of MTS solution immediately before addition to the culture plate containing cells.
d. Gently swirl the tube to ensure complete mixing of the combined MTS/PMS solution.
Equipment:
  SpectraMAX plus microplate spectrophotometer Model 3011, Molecular Devices Corp. (California, USA); $CO_2$ water jacketed incubator, Therma (USA). Reverse microscope, Chongguang XDS-1B, Chongqing Guangdian Corp. (Chongqing, P.R.China).
Cytotoxicity and $IC_{50}$ Determination:
1. The cells were harvested respectively during the logarithmic growth period and counted with hemocytometer. The cell viability was over 98% by trypan blue exclusion.
2. Cell concentrations were adjusted to $2.22 \times 10^5$ or $1.11 \times 10^5$ or $5.56 \times 10^4$ cells/mL with respective medium.
3. 90 µL cell suspensions were added to 96-well plates (triplicates for each cell concentration), the final cell densities were $2 \times 10^4$ or $1 \times 10^4$ or $5 \times 10^3$ cells/well. The density of $5 \times 10^3$ cells/well was used for the first test. The appropriate cell density was determined and adjusted according to the results of the first test.
4. The next day, test article or positive drugs were dissolved with DMSO as stock solution at the concentration of 20 mM.
5. 10 µL drug solution was dispensed in each well (triplicate for each drug concentration).
6. Plates were cultured for another 72 hours, then measured by means of MTS assay.
7. MTS/PMS solution was prepared immediately prior to use. 20 µL of the mixture was introduced into each well of the 96-well assay plate containing 100 µL culture medium. (The final reaction volume was 120 µL).
8. Plate was incubated for 1-4 hours at 37° C. in a humidified 5% $CO_2$ atmosphere.
9. Absorbance at 490 nm was recorded using SpectraMAX Plus microplate spectrophotometer.
Data Analysis:
  The software of GraphPad Prism version 5 was used to calculate $IC_{50}$. The graphical curves were fitted using a non-linear regression model with a sigmoidal dose.
Results
  Results are shown in Table 7.

TABLE 7

| | $IC_{50}$ values (µM) | | |
| --- | --- | --- | --- |
| Compound | MV4-11 | RPMI 8226 | NCI-H929 |
| 10903 | 4.990 | NA | 12.09 |
| 10904 | 7.176 | NA | 3.871 |
| 10905 | 4.478 | NA | 6.975 |
| 10906 | 4.036 | NA | 14.94 |
| 10907 | 7.452 | NA | 13.09 |
| 10909 | 8.415 | NA | 11.83 |
| 10910 | 11.37 | NA | 9.746 |
| 10913 | 9.954 | NA | NA |
| 10914 | 11.75 | NA | 41.02 |
| 10915 | 7.072 | NA | 28.94 |
| 11086 | NA | 1.31e+006 | 7.131 |
| 11087 | NA | 17.78 | 2.748 |
| 11088 | NA | 11.70 | 9.976 |
| 11089 | NA | 9.030 | 12.67 |
| 11090 | NA | 6.033e+007 | 12.44 |
| 11091 | NA | 10.46 | 18.69 |
| 11092 | NA | 16.16 | 11.75 |
| 11093 | NA | 78.70 | 5.537 |
| 11094 | NA | 3.229 | 29.77 |
| 11100 | NA | 58.46 | 3.508e+010 |
| 11101 | NA | 12.78 | 15.67 |
| 11102 | NA | 20.23 | 14.63 |
| 11103 | NA | 28.83 | 12.84 |
| 11104 | NA | 21.90 | 21.58 |
| 11105 | NA | 11.71 | 10.62 |
| 11106 | NA | 18.59 | 6.319 |
| 11193 | NA | >30 | 28.1 |
| 11196 | NA | 19.4 | 254. |
| 11198 | NA | 8.2 | 3.5 |
| 11204 | NA | 7.4 | 10.1 |
| 11205 | NA | 3.4 | 3 |
| 11206 | NA | >30 | 29 |
| 11207 | NA | 11.8 | 11.5 |
| 11209 | NA | 23.2 | 16.9 |
| 11210 | NA | 11.3 | 11.5 |
| 11211 | NA | 23.3 | 27.7 |
| 11212 | NA | 7.7 | >30 |
| 11213 | NA | >30 | >30 |
| 11214 | NA | 11.1 | 7.8 |
| 11215 | NA | 12.7 | 12.7 |
| 11216 | NA | 11.2 | 8.1 |
| 11217 | NA | >30 | >30 |
| 11220 | NA | >30 | >30 |
| 11221 | NA | 14 | 17.5 |
| 11222 | NA | 20.3 | 11.7 |
| 11223 | NA | 25.3 | 28.7 |
| 11224 | NA | >30 | 14.3 |
| 11225 | NA | >30 | 16.1 |
| 11226 | NA | >30 | >30 |
| 11227 | NA | 24.8 | 12.4 |
| 11232 | NA | >30 | >30 |
| 11234 | NA | 7.9 | 22.3 |

TABLE 7-continued

IC$_{50}$ values (μM)

| Compound | MV4-11 | RPMI 8226 | NCI-H929 |
|---|---|---|---|
| 11235 | NA | 11.5 | 18.6 |
| 11236 | NA | 12.2 | >30 |
| 11237 | NA | 8.9 | >30 |
| 11240 | NA | >30 | 19 |
| 11241 | NA | 5.7 | 8.7 |
| 11242 | NA | 16 | 9.1 |
| 11243 | NA | 12.4 | 6.2 |
| 11244 | NA | 11.4 | 8.6 |
| 11246 | NA | 21.8 | 7 |
| 11247 | NA | 11.5 | 12.3 |
| 11248 | NA | 14.7 | 9.6 |
| 11249 | NA | 11.1 | 6 |
| 11250 | NA | 9.9 | 7.1 |
| 11251 | NA | 15.8 | 14.9 |
| 11263 | NA | 12.3 | 4 |
| 11264 | NA | >30 | 11.3 |
| 11266 | NA | >30 | 17 |
| 11267 | NA | >30 | >30 |
| 11268 | NA | >30 | >30 |
| 11269 | NA | 12.7 | >30 |
| 11271 | 7.2 | NA | 7.5 |
| 11272 | 8.3 | NA | 9 |
| 11273 | 4.7 | NA | 7.8 |
| 11274 | >30 | NA | >30 |
| 11275 | 7.5 | NA | >30 |
| 11276 | >30 | NA | >30 |
| 11279 | 1.4 | NA | 10.7 |
| 11280 | >30 | NA | >30 |
| 11288 | 11.7 | NA | >30 |
| 11289 | 0.63 | NA | 2.4 |
| 11290 | >30 | NA | >30 |
| 11291 | >30 | NA | >30 |
| 11293 | 26.7 | NA | 8.4 |
| 11299 | 5.4 | NA | 11.1 |
| 11300 | 1.8 | NA | 12.1 |
| 11301 | 24.5 | NA | >30 |
| 11303 | >30 | NA | >30 |
| 11304 | >30 | NA | >30 |
| 11306 | 13.5 | NA | >30 |
| 11307 | 0.43 | NA | 3.1 |
| 11308 | 6.8 | NA | >30 |
| 11352 | >30 | NA | >30 |
| 11355 | 4.7 | NA | 14.7 |
| 11666 | NA | NA | NA |
| 11667 | NA | NA | NA |

NA = not available

Example 164

TABLE 8

Percent Activity of Enzyme When Treated with 100 nM of Compound (ATP Concentration = Km of Enzyme)

| Compound | CK1γ2(h) | CK1(y) | CK2(h) | Pim-1(h) | Pim-2(h) | Pim-3(h) |
|---|---|---|---|---|---|---|
| 11193 | 85 | 91 | 92 | 33 | 31 | 30 |
| 11196 | 94 | 108 | 101 | 71 | 72 | 93 |
| 11198 | 85 | 45 | 76 | 8 | 13 | 6 |
| 11204 | 106 | 97 | 102 | 26 | 73 | 61 |
| 11205 | 95 | 107 | 108 | 56 | 55 | 38 |
| 11206 | 100 | 102 | 101 | 65 | 104 | 43 |
| 11207 | 88 | 105 | 106 | 53 | 66 | 54 |
| 11209 | 70 | 98 | 95 | 70 | 73 | 48 |
| 11210 | 89 | 109 | 100 | 108 | 106 | 102 |
| 11211 | 68 | 72 | 93 | 16 | 56 | 42 |
| 11212 | 76 | 89 | 94 | 17 | 35 | 24 |

IC$_{50}$ (nM) for compound 11198 (with ATP concentration = Km of enzyme): Pim-1(h), 25; Pim-2(h), 15; Pim-3(h), 6.

Example 165

TABLE 9

Percent Activity of Enzyme When Treated with 300 nM of Compound (ATP Concentration = Km of Enzyme)

| Compound | CK1γ2(h) | CK1(y) | CK2(h) | Pim-1(h) | Pim-2(h) | Pim-3(h) |
|---|---|---|---|---|---|---|
| 10903 | 69 | 76 | 79 | 18 | 14 | 17 |
| 10904 | 63 | 31 | 92 | 2 | 4 | 3 |
| 10905 | 77 | 61 | 55 | 18 | 21 | 10 |
| 10906 | 47 | 56 | 73 | 7 | 11 | 12 |
| 10907 | 10 | 78 | 63 | 53 | 44 | 100 |
| 10909 | 45 | 70 | 50 | 10 | 12 | 5 |
| 10910 | 96 | 81 | 54 | 18 | 21 | 5 |
| 10913 | 23 | 80 | 81 | 75 | 63 | 96 |
| 10914 | 23 | 76 | 76 | 66 | 57 | 91 |
| 10915 | 28 | 82 | 78 | 74 | 72 | 96 |
| 10917 | 84 | 97 | 109 | 75 | 69 | 63 |
| 11019 | 73 | 86 | 14 | 39 | 10 | 10 |
| 11020 | 96 | 98 | 12 | 48 | 20 | 11 |
| 11021 | 102 | 96 | 11 | 42 | 25 | 11 |
| 11022 | 94 | 103 | 8 | 34 | 21 | 9 |
| 11086 | 81 | 41 | 62 | 8 | 10 | 4 |
| 11087 | 35 | −3 | 41 | 7 | −1 | 0 |
| 11088 | 39 | 39 | 79 | 8 | 10 | 10 |
| 11089 | 55 | 61 | 68 | 9 | 11 | 9 |
| 11090 | 80 | 81 | 78 | 17 | 24 | 9 |
| 11091 | 78 | 88 | 75 | 32 | 21 | 11 |
| 11092 | 52 | 58 | 73 | 12 | 12 | 7 |
| 11093 | 32 | 12 | 83 | 14 | 44 | 11 |
| 11094 | 95 | 95 | 79 | 30 | 29 | 12 |
| 11213 | 103 | 112 | 79 | 60 | 66 | 43 |
| 11214 | 23 | 34 | 70 | 3 | 16 | 10 |
| 11215 | 17 | 46 | 88 | 18 | 16 | 38 |
| 11216 | 58 | 18 | 52 | 3 | 1 | 3 |
| 11217 | 94 | 100 | 75 | 46 | 35 | 19 |
| 11220 | 82 | 111 | 62 | 59 | 58 | 39 |
| 11221 | 83 | 113 | 91 | 91 | 75 | 78 |
| 11222 | 52 | 62 | 74 | 5 | 19 | 12 |
| 11223 | 34 | 69 | 90 | 22 | 30 | 43 |
| 11224 | 102 | 89 | 81 | 44 | 51 | 27 |
| 11225 | 112 | 88 | 84 | 37 | 47 | 25 |
| 11226 | 83 | 82 | 85 | 22 | 31 | 22 |
| 11227 | 80 | 84 | 71 | 31 | 38 | 22 |
| 11232 | 128 | 102 | 107 | 90 | 109 | 76 |
| 11234 | 47 | 67 | 91 | 22 | 32 | 47 |
| 11235 | 39 | 57 | 86 | 9 | 17 | 28 |
| 11236 | 43 | 70 | 86 | 16 | 25 | 38 |
| 11237 | 39 | 66 | 94 | 24 | 41 | 52 |
| 11240 | 26 | 98 | 77 | 57 | 49 | 40 |
| 11241 | 55 | 85 | 88 | 53 | 27 | 86 |
| 11242 | 83 | 79 | 64 | 25 | 24 | 7 |
| 11243 | 63 | 79 | 80 | 5 | 21 | 10 |
| 11244 | 68 | 98 | 80 | 66 | 35 | 69 |
| 11246 | 56 | 44 | 67 | 3 | 4 | 4 |
| 11247 | 31 | 45 | 83 | 13 | 12 | 37 |
| 11248 | 34 | −3 | 68 | 3 | 7 | 5 |
| 11249 | 72 | 71 | 64 | 17 | 18 | 10 |
| 11250 | 32 | 65 | 81 | 11 | 12 | 11 |
| 11251 | 92 | 97 | 87 | 4 | 18 | 7 |
| 11263 | 75 | 72 | 72 | 30 | 22 | 9 |
| 11264 | 33 | 71 | 74 | 24 | 20 | 14 |
| 11266 | 75 | 62 | 87 | 21 | 20 | 11 |
| 11267 | 58 | 92 | 91 | 8 | 23 | 9 |
| 11268 | 95 | 114 | 85 | 115 | 108 | 80 |
| 11269 | 105 | 90 | 90 | 105 | 120 | 97 |
| 11271 | 102 | 96 | 71 | 51 | 69 | 32 |
| 11272 | 67 | 96 | 89 | 83 | 76 | 66 |
| 11273 | 60 | 83 | 71 | 52 | 66 | 49 |
| 11274 | 108 | 100 | 80 | 95 | 99 | 99 |
| 11275 | 106 | 107 | 97 | 116 | 112 | 106 |
| 11276 | 90 | 94 | 84 | 98 | 101 | 85 |
| 11279 | 73 | 82 | 73 | 94 | 89 | 87 |
| 11280 | 107 | 92 | 84 | 87 | 99 | 80 |
| 11288 | 94 | 97 | 84 | 39 | 7 | 11 |
| 11289 | 85 | 58 | 63 | 6 | 2 | 1 |
| 11290 | −7 | 99 | 92 | 86 | 90 | 103 |

TABLE 9-continued

Percent Activity of Enzyme When Treated with 300 nM of Compound (ATP Concentration = Km of Enzyme)

| Compound | CK1γ2(h) | CK1(y) | CK2(h) | Pim-1(h) | Pim-2(h) | Pim-3(h) |
|---|---|---|---|---|---|---|
| 11291 | 89 | 86 | 42 | 26 | 15 | 10 |
| 11293 | 71 | 92 | 70 | 13 | 17 | 10 |
| 11299 | 82 | 67 | 71 | 6 | 27 | 31 |
| 11300 | 93 | 93 | 63 | 32 | 20 | 21 |
| 11301 | 34 | 106 | 76 | 84 | 89 | 104 |
| 11303 | 0 | 89 | 75 | 93 | 91 | 95 |
| 11304 | 21 | 104 | 82 | 89 | 71 | 97 |
| 11306 | 93 | 94 | 82 | 59 | 30 | 85 |
| 11307 | 39 | 73 | 78 | 4 | 3 | 12 |
| 11308 | 82 | 105 | 84 | 35 | 14 | 53 |
| 11352 | 76 | 77 | 70 | 45 | 48 | 38 |
| 11355 | 47 | 67 | 52 | 6 | 5 | 6 |
| 11666 | 24 | 42 | 84 | 11 | 4 | 8 |
| 11667 | −1 | 22 | 73 | 17 | 8 | 10 |

Example 166

TABLE 10

IC$_{50}$ (nM) of Compound When ATP Concentration = Km of Enzyme

| Compound | CK1γ2(h) | CK1(y) | CK2(h) | Pim-1(h) | Pim-2(h) | Pim-3(h) |
|---|---|---|---|---|---|---|
| 11214 | | | | 16 | 38 | 27 |
| 11216 | | | | 17 | 5 | 4 |
| 11243 | | | | 8 | 57 | 36 |
| 11248 | | | | 4 | 2 | 3 |
| 11249 | | | | 89 | 27 | 16 |
| 11250 | | | | 35 | 18 | 80 |
| 11251 | | | | 5 | 33 | 6 |
| 11267 | | | | 7 | 27 | 48 |
| 11289 | | | | 0.7 | 0.9 | 1 |
| 11290 | 1 | | | | | |
| 11293 | | | | 83 | 60 | 62 |

INCORPORATION BY REFERENCE

All of the U.S. patents and U.S. published patent applications cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound, or a pharmaceutically acceptable salt thereof, selected from the group consisting of:

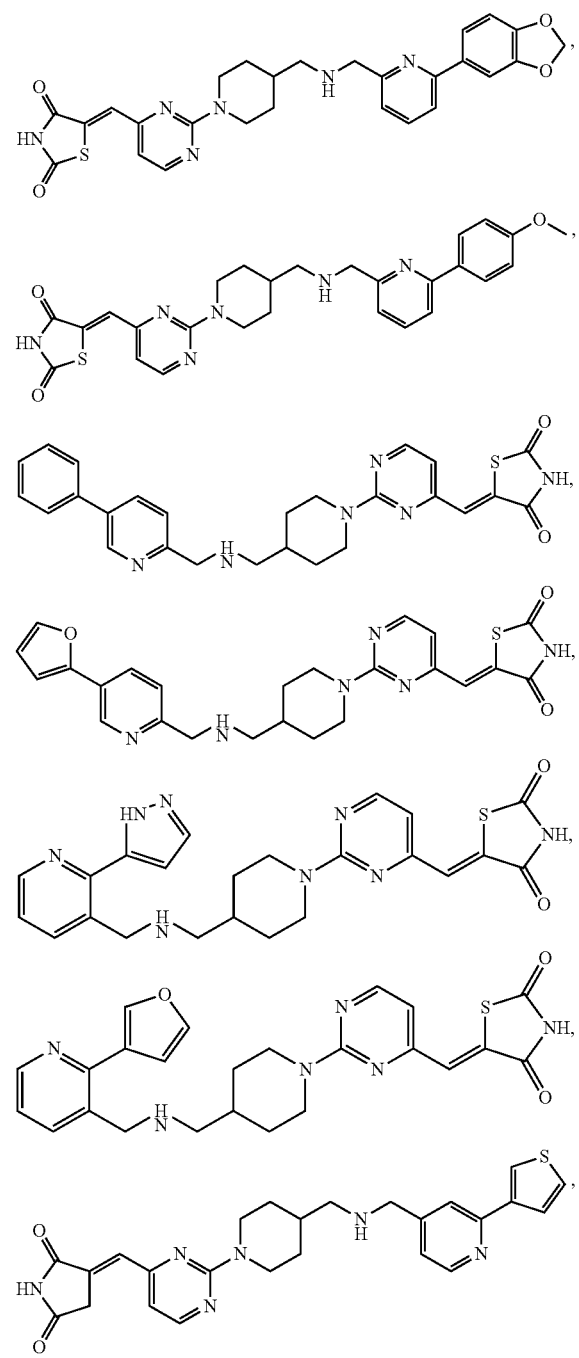

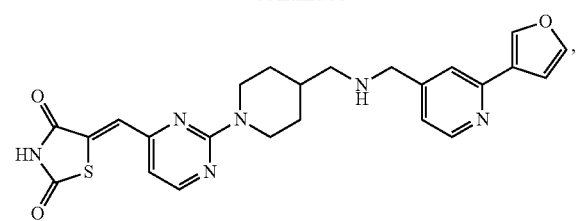
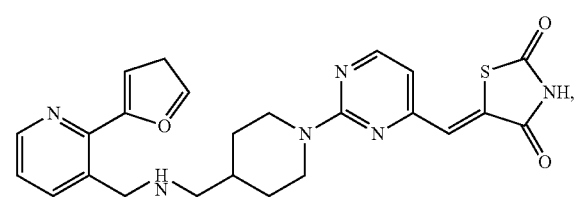
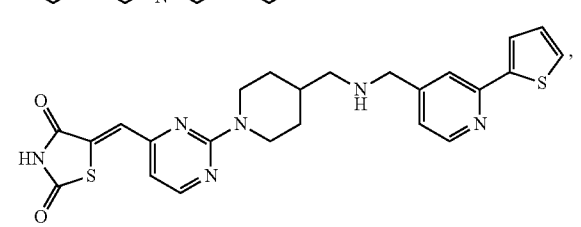
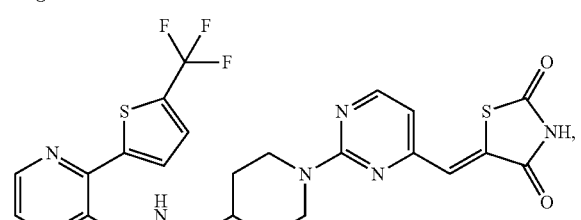
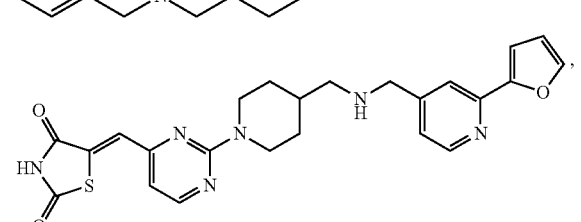
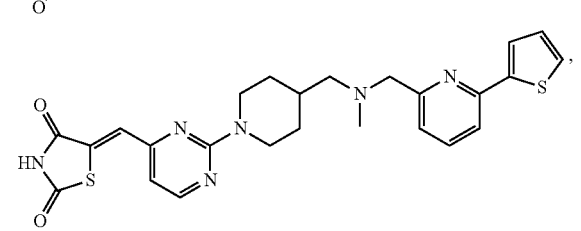
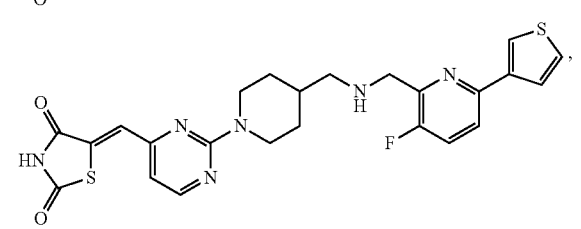
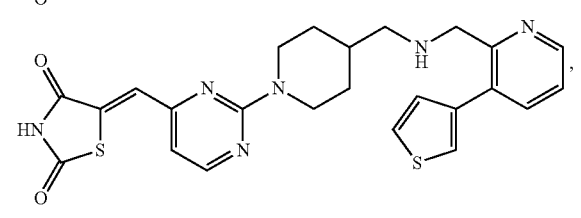
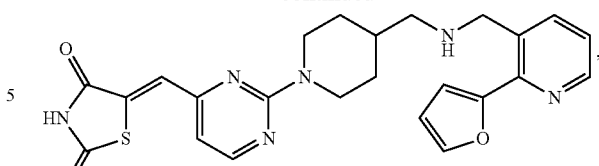
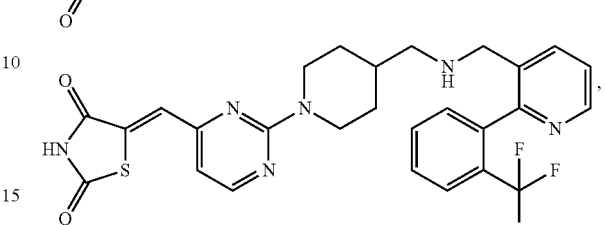
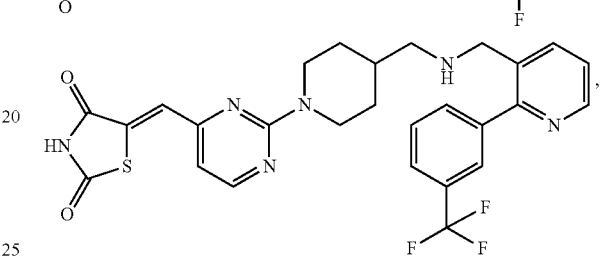
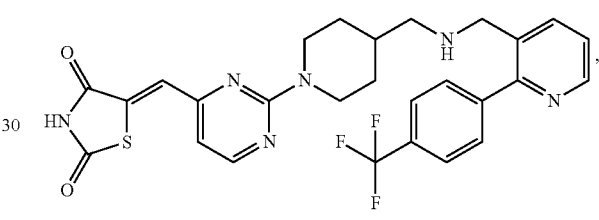
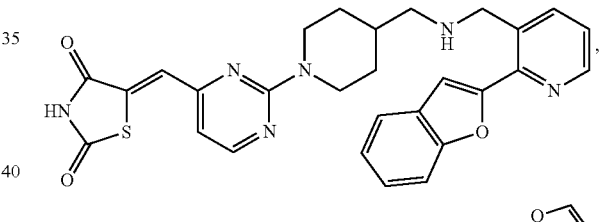
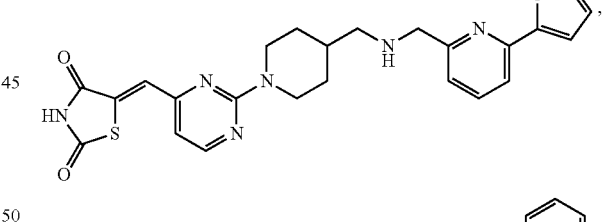
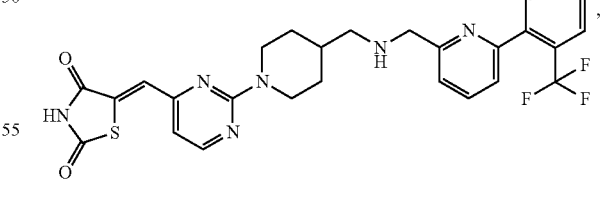
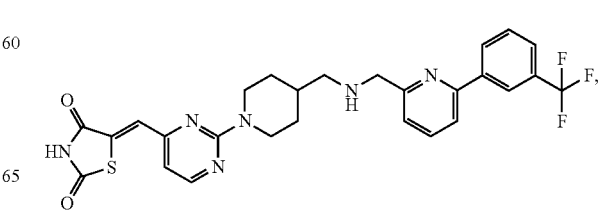

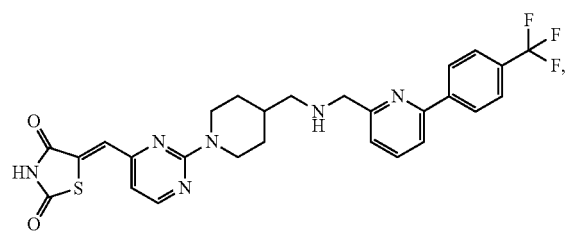
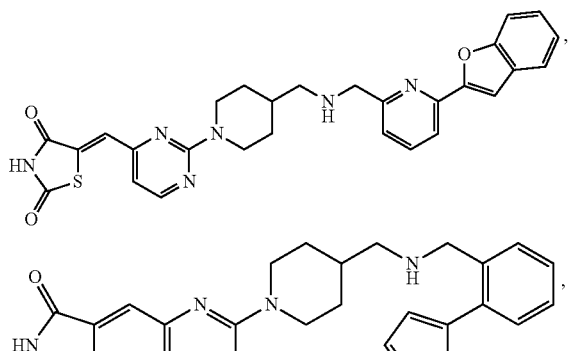
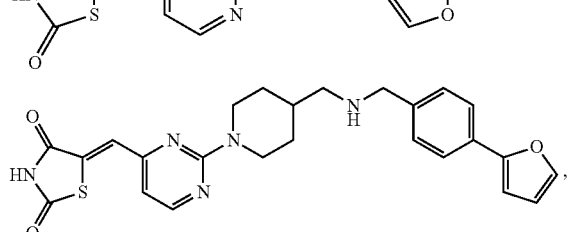
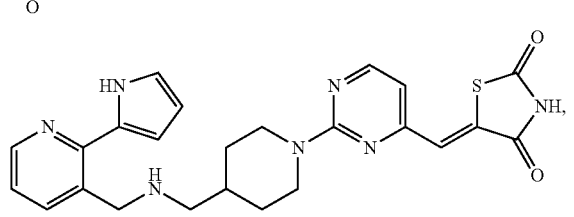
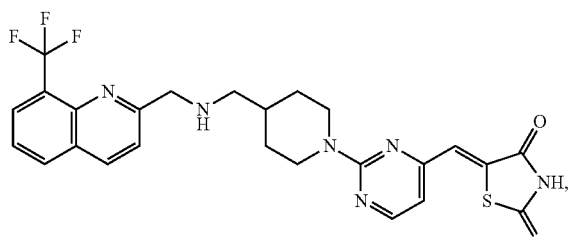
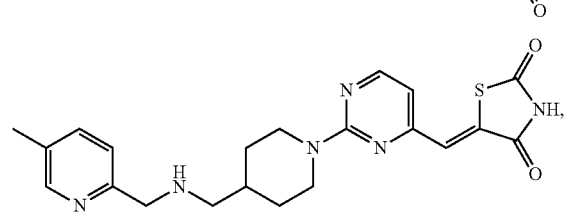
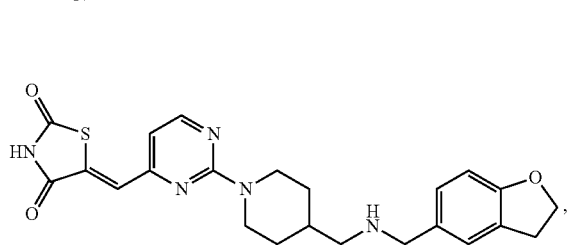
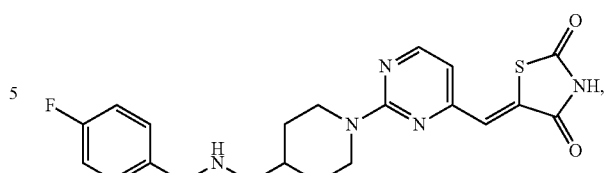
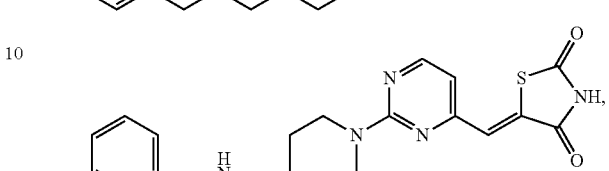
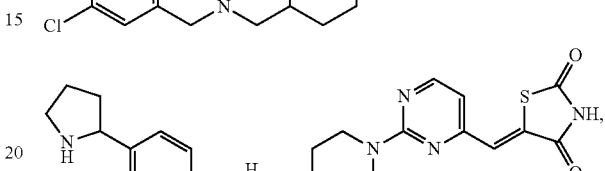
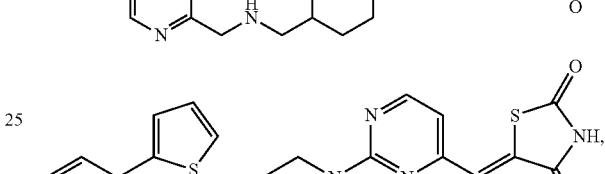
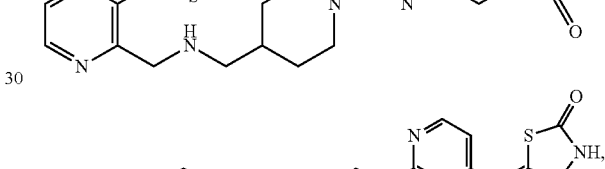
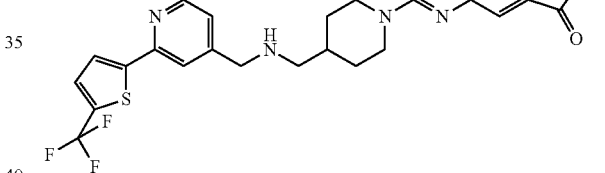
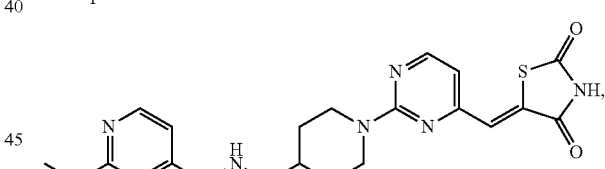
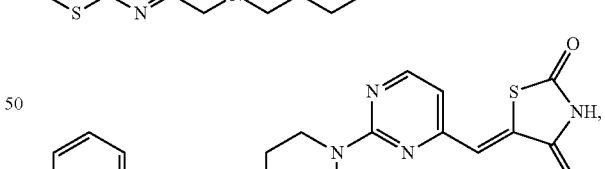
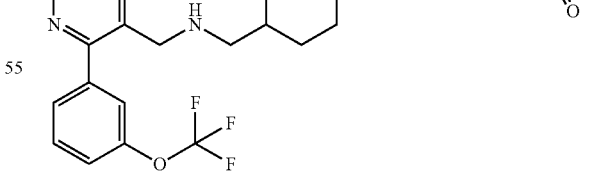
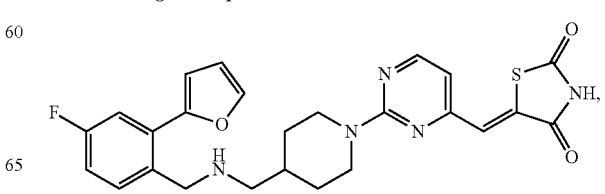

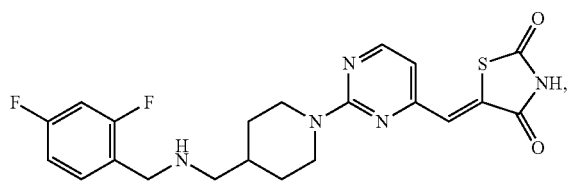
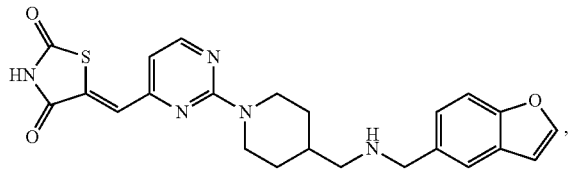
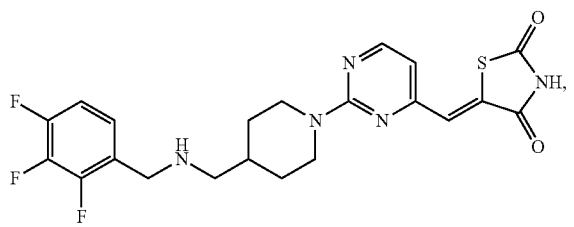
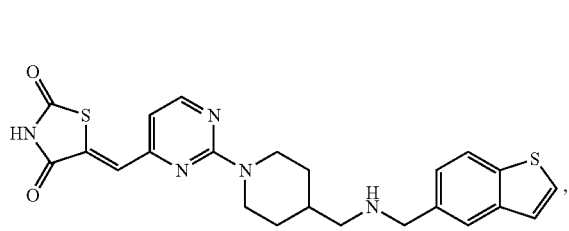
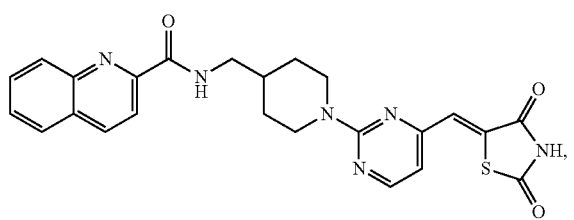
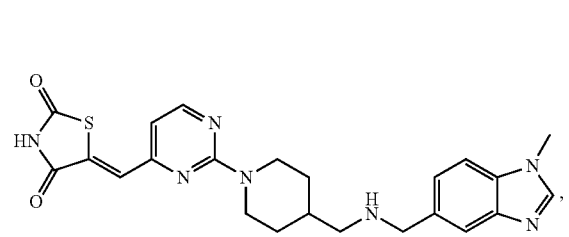
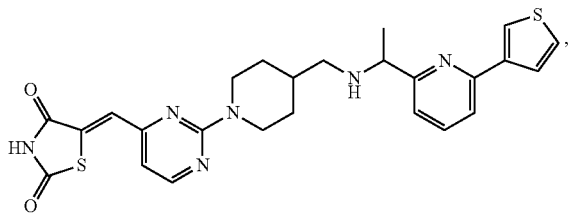
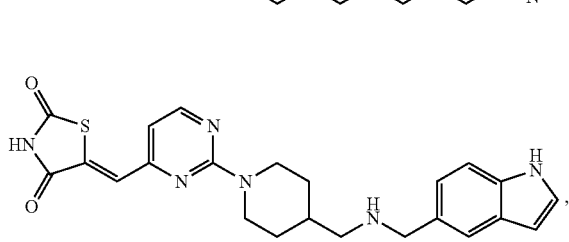
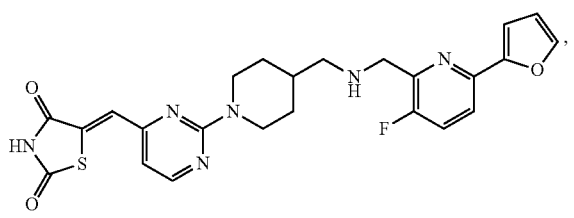
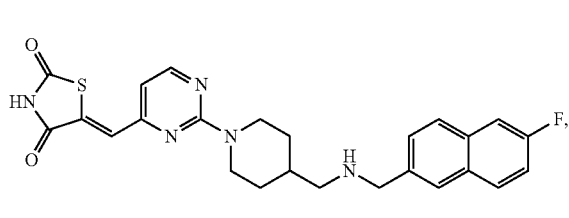
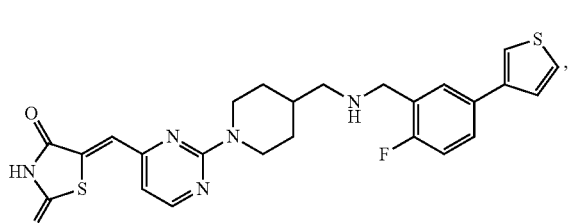
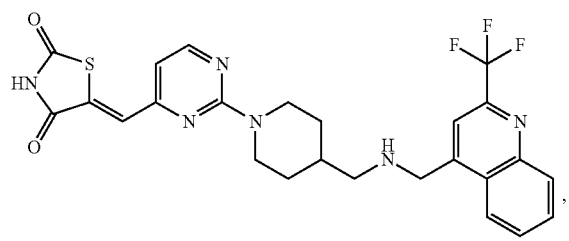
and
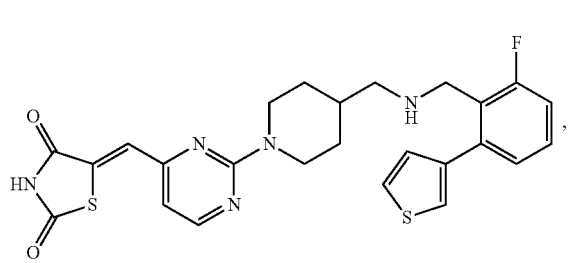
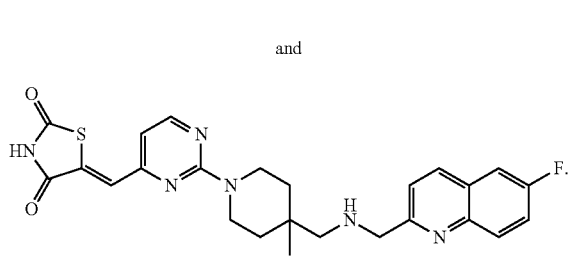

2. The compound of claim 1, or a pharmaceutically acceptable salt thereof, selected from the group consisting of:
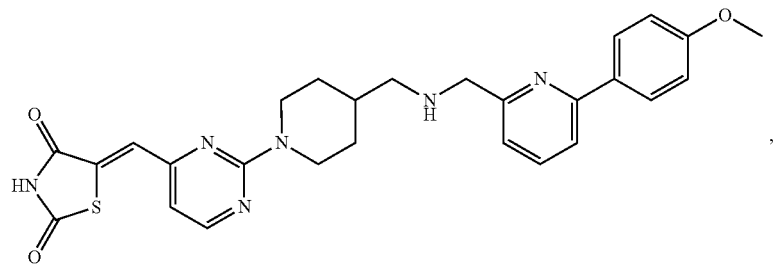
,
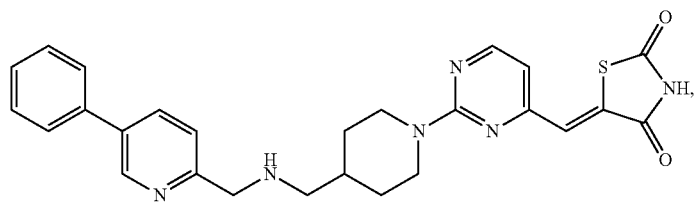
,
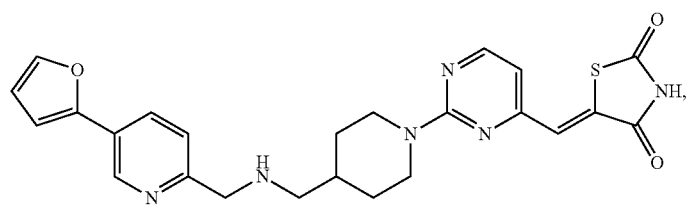
,
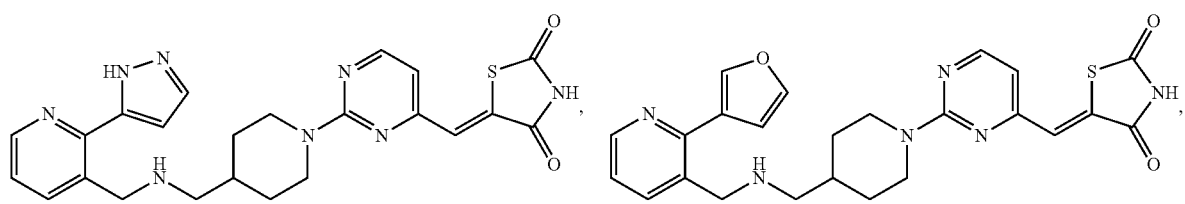
,
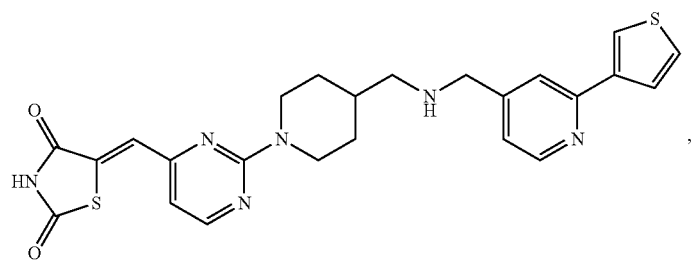
,
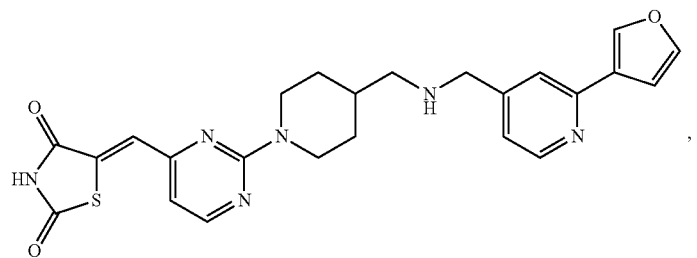
,
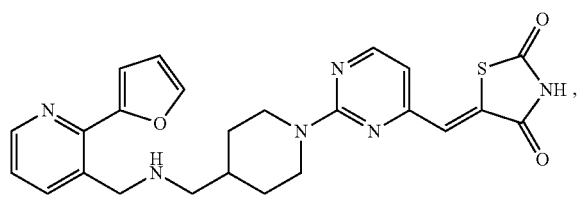
,

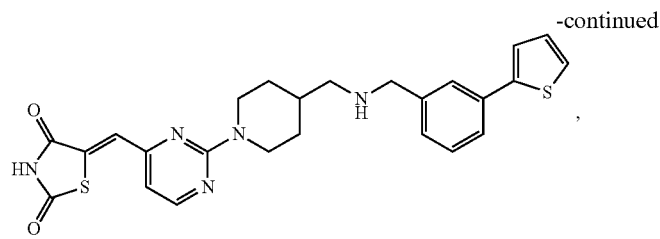
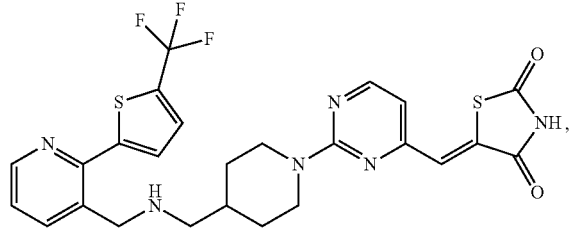
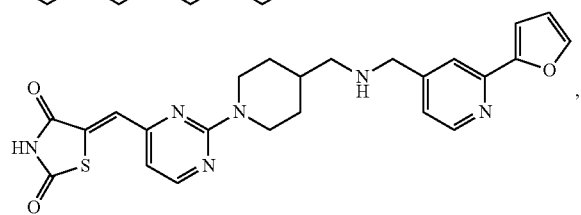
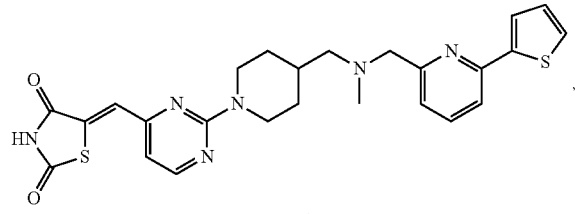 [SMILES: O=C1NC(=O)/C(=C/c2ccnc(N3CCC(CNCc4ccnc(-c5cccs5)c4)CC3)n2)S1]
and
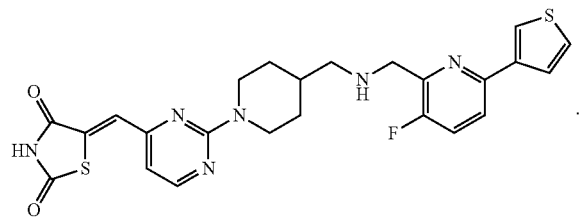
3. The compound of claim 1, or a pharmaceutically acceptable salt thereof, selected from the group consisting of:
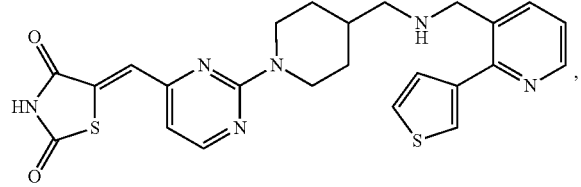
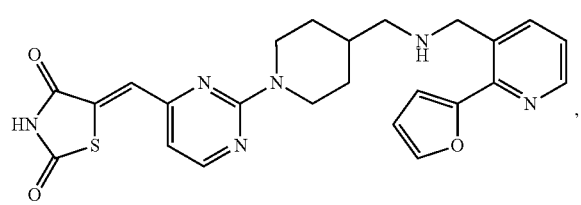
-continued
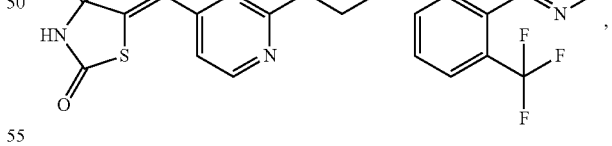
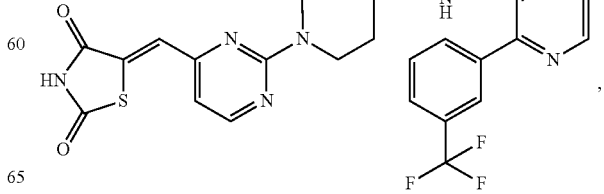

189
-continued
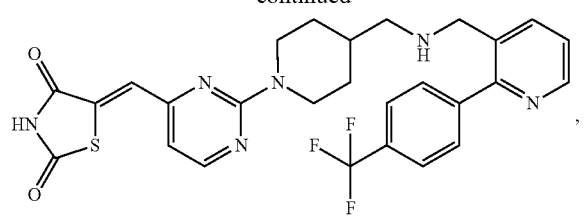
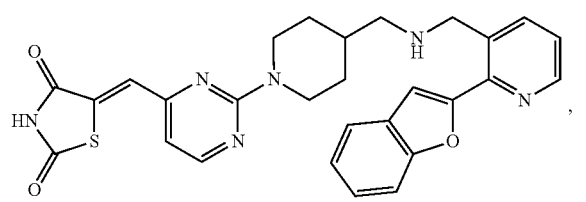
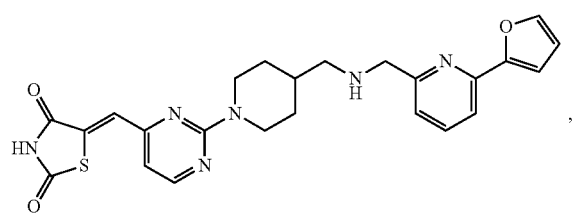
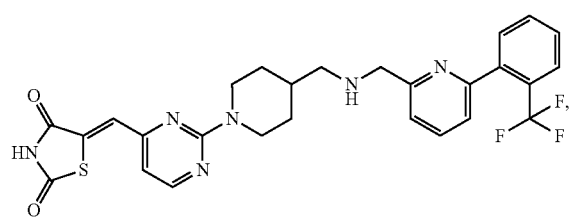
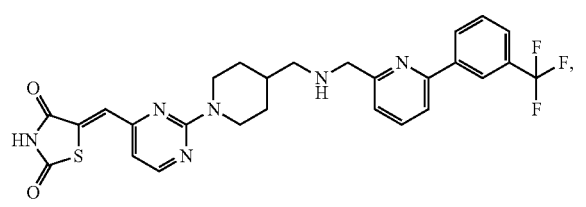
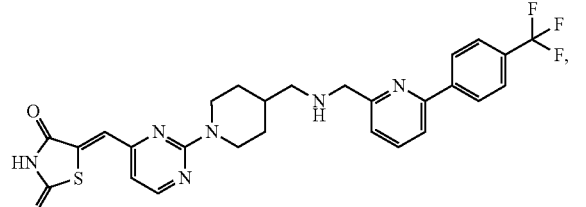
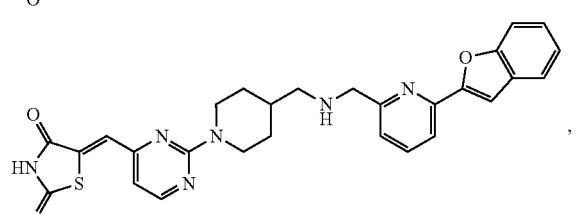
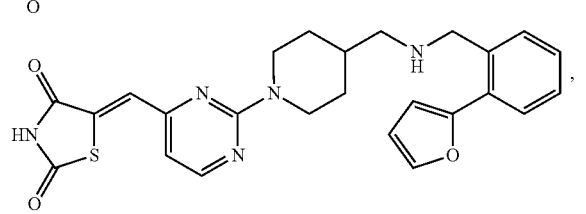
190
-continued
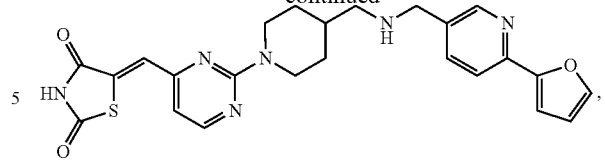
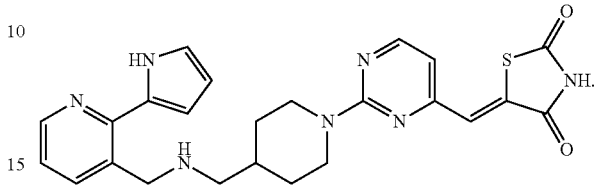
4. The compound of claim 1, or a pharmaceutically acceptable salt thereof, selected from the group consisting of:
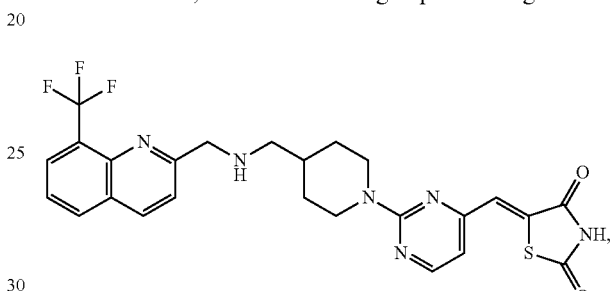
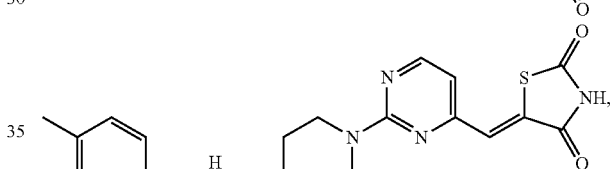
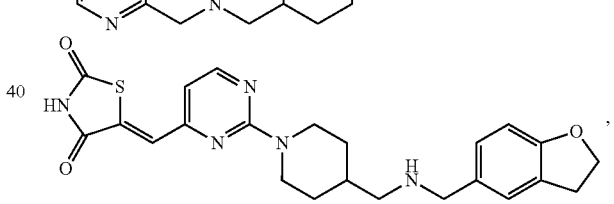
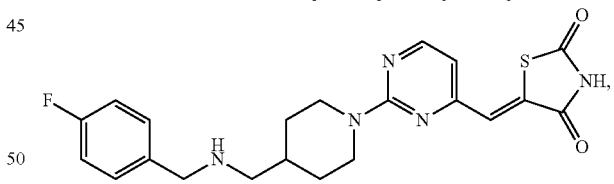
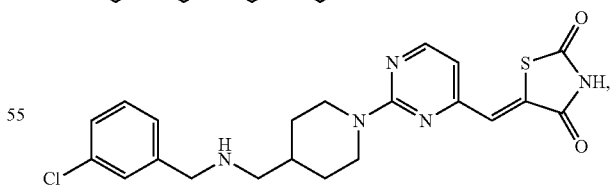
and
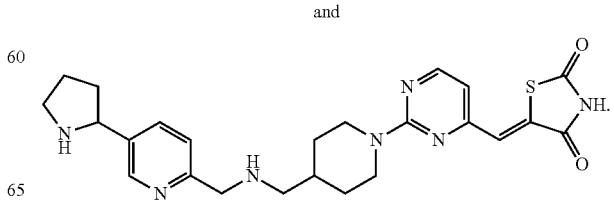

5. The compound of claim 1, or a pharmaceutically acceptable salt thereof, selected from the group consisting of:
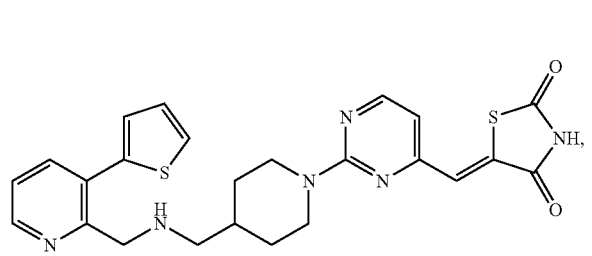
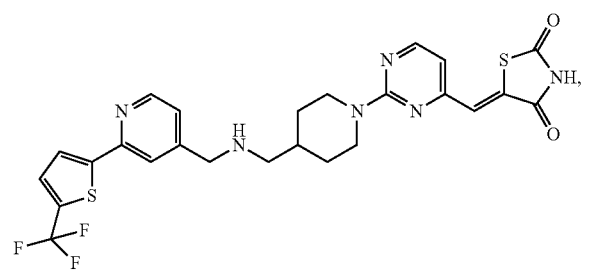
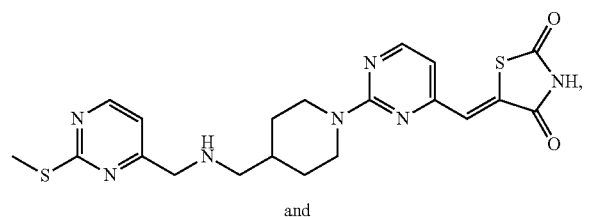
and
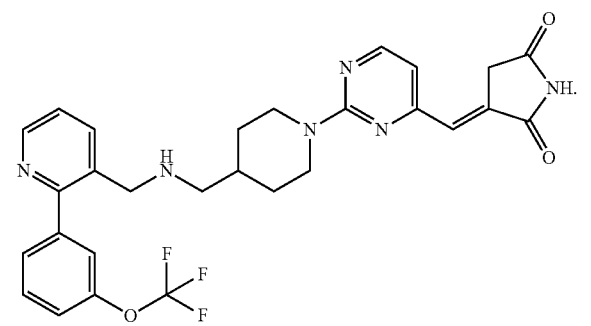
6. The compound of claim 1, or a pharmaceutically acceptable salt thereof, selected from the group consisting of:
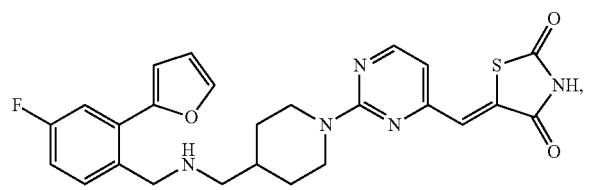 [SMILES: O=C1NC(=O)/C(=C/c2ccnc(N3CCC(CNCc4ccc(F)cc4-c4ccco4)CC3)n2)S1]
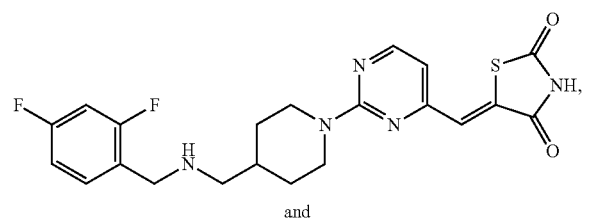
and
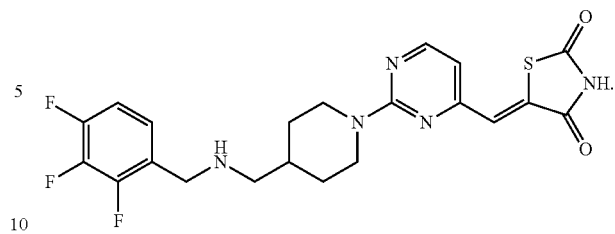
7. The compound of claim 1, or a pharmaceutically acceptable salt thereof, selected from the group consisting of:
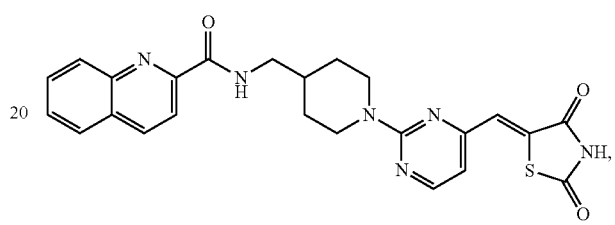
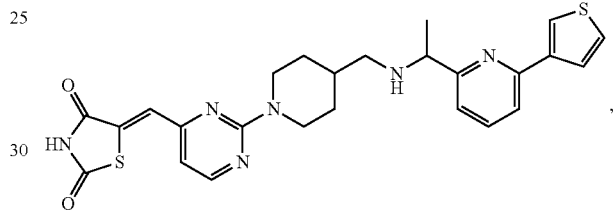
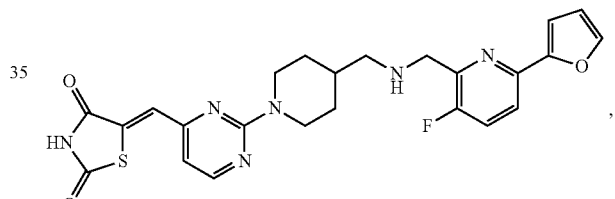
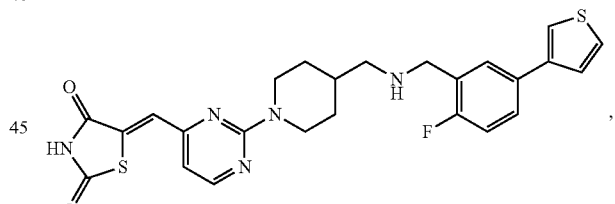
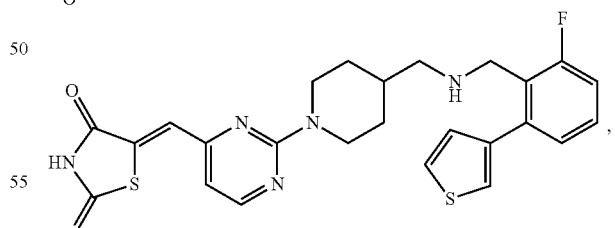
and
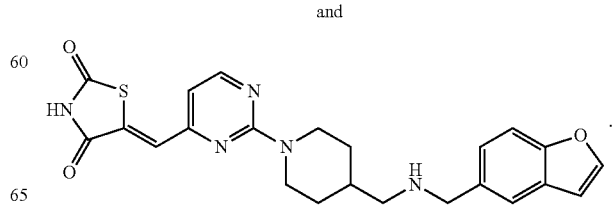

8. The compound of claim 1, or a pharmaceutically acceptable salt thereof, selected from the group consisting of:

[chemical structure]

[chemical structure] and

[chemical structure].

9. A pharmaceutical composition, comprising a compound of claim 1, or a pharmaceutically acceptable salt thereof, and a pharmaceutically acceptable excipient.

10. The compound of claim 1, represented by the following structure:

[chemical structure]

or a pharmaceutically acceptable salt thereof.

11. A compound, or a pharmaceutically acceptable salt thereof, selected from the group consisting of:

(Z)-5-((2-(4-((((6-(2,4-bis(trifluoromethyl)phenyl)-4-fluoropyridin-2-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)pyridin-2-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)-4-methylpyridin-2-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)-3-methoxypyridin-2-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(2,4-bis(trifluoromethyl)phenyl)isoquinolin-1-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)pyridin-3-yl)methyl)amino)methyl)piperidin-1-yl)pyrimidin-4-yl)methylene)thiazolidine-2,4-dione;

(Z)-5-((2-(4-((((2-(2,4-bis(trifluoromethyl)phenyl)quinolin-3-yl)methyl)amino)methyl)piperidin-1-yl)pyrimidin-4-yl)methylene)thiazolidine-2,4-dione;

(Z)-5-((2-(4-((((6-(2,4-bis(trifluoromethyl)phenyl)pyridin-3-yl)methyl)amino)methyl)piperidin-1-yl)pyrimidin-4-yl)methylene)thiazolidine-2,4-dione;

(Z)-5-((2-(4-((((2-(2,4-bis(trifluoromethyl)phenyl)pyridin-4-yl)methyl)amino)methyl)piperidin-1-yl)pyrimidin-4-yl)methylene)thiazolidine-2,4-dione;

(Z)-5-((2-(4-((((2-(2,4-bis(trifluoromethyl)phenyl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(2,4-bis(trifluoromethyl)phenyl)-5-fluoropyridin-4-yl)methyl)amino)methyl)piperidin-1-yl)pyrimidin-4-yl)methylene)thiazolidine-2,4-dione;

(Z)-5-((2-(4-((((6-amino-2-(2,4-bis(trifluoromethyl)phenyl)pyridin-3-yl)methyl)amino)methyl)piperidin-1-yl)pyrimidin-4-yl)methylene)thiazolidine-2,4-dione;

(Z)-5-((2-(4-((((6-(2,4-dimethoxyphenyl)-4-fluoropyridin-2-yl)methyl)amino)methyl)piperidin-1-yl)pyrimidin-4-yl)methylene)thiazolidine-2,4-dione;

(Z)-5-((2-(4-((((6-(2,4-dimethoxyphenyl)pyridin-2-yl)methyl)amino)methyl)piperidin-1-yl)pyrimidin-4-yl)methylene)thiazolidine-2,4-dione;

(Z)-5-((2-(4-((((6-(2,4-dimethoxyphenyl)-4-methylpyridin-2-yl)methyl)amino)methyl)piperidin-1-yl)pyrimidin-4-yl)methylene)thiazolidine-2,4-dione;

(Z)-5-((2-(4-((((6-(2,4-dimethoxyphenyl)-3-methoxypyridin-2-yl)methyl)amino)methyl)piperidin-1-yl)pyrimidin-4-yl)methylene)thiazolidine-2,4-dione;

(Z)-5-((2-(4-((((6-(2,4-dimethoxyphenyl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(2,4-dimethoxyphenyl)isoquinolin-1-yl)methyl)amino)methyl)piperidin-1-yl)pyrimidin-4-yl)methylene)thiazolidine-2,4-dione;

(Z)-5-((2-(4-((((2-(2,4-dimethoxyphenyl)pyridin-3-yl)methyl)amino)methyl)piperidin-1-yl)pyrimidin-4-yl)methylene)thiazolidine-2,4-dione;

(Z)-5-((2-(4-((((2-(2,4-dimethoxyphenyl)quinolin-3-yl)methyl)amino)methyl)piperidin-1-yl)pyrimidin-4-yl)methylene)thiazolidine-2,4-dione;

(Z)-5-((2-(4-((((6-(2,4-dimethoxyphenyl)pyridin-3-yl)methyl)amino)methyl)piperidin-1-yl)pyrimidin-4-yl)methylene)thiazolidine-2,4-dione;

(Z)-5-((2-(4-((((2-(2,4-dimethoxyphenyl)pyridin-4-yl)methyl)amino)methyl)piperidin-1-yl)pyrimidin-4-yl)methylene)thiazolidine-2,4-dione;

(Z)-5-((2-(4-((((2-(2,4-dimethoxyphenyl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(2,4-dimethoxyphenyl)-5-fluoropyridin-4-yl)methyl)amino)methyl)piperidin-1-yl)pyrimidin-4-yl)methylene)thiazolidine-2,4-dione;

(Z)-5-((2-(4-((((6-amino-2-(2,4-dimethoxyphenyl)pyridin-3-yl)methyl)amino)methyl)piperidin-1-yl)pyrimidin-4-yl)methylene)thiazolidine-2,4-dione;

(Z)-5-((2-(4-((((4-fluoro-6-(2-(trifluoromethoxy)phenyl)pyridin-2-yl)methyl)amino)methyl)piperidin-1-yl)pyrimidin-4-yl)methylene)thiazolidine-2,4-dione;

(Z)-5-((2-(4-((((6-(2-(trifluoromethoxy)phenyl)pyridin-2-yl)methyl)amino)methyl)piperidin-1-yl)pyrimidin-4-yl)methylene)thiazolidine-2,4-dione;

(Z)-5-((2-(4-((((4-methyl-6-(2-(trifluoromethoxy)phenyl)pyridin-2-yl)methyl)amino)methyl)piperidin-1-yl)pyrimidin-4-yl)methylene)thiazolidine-2,4-dione;

(Z)-5-((2-(4-((((3-methoxy-6-(2-(trifluoromethoxy)phenyl)pyridin-2-yl)methyl)amino)methyl)piperidin-1-yl)pyrimidin-4-yl)methylene)thiazolidine-2,4-dione;

(Z)-5-((2-(4-((((6-(2-(trifluoromethoxy)phenyl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(2-(trifluoromethoxy)phenyl)isoquinolin-1-yl)methyl)amino)methyl)piperidin-1-yl)pyrimidin-4-yl)methylene)thiazolidine-2,4-dione;

(Z)-5-((2-(4-((((2-(2-(trifluoromethoxy)phenyl)pyridin-3-yl)methyl)amino)methyl)piperidin-1-yl)pyrimidin-4-yl)methylene)thiazolidine-2,4-dione;

(Z)-5-((2-(4-((((2-(2-(trifluoromethoxy)phenyl)quinolin-3-yl)methyl)amino)methyl)piperidin-1-yl)pyrimidin-4-yl)methylene)thiazolidine-2,4-dione;

(Z)-5-((2-(4-((((6-(2-(trifluoromethoxy)phenyl)pyridin-3-yl)methyl)amino)methyl)piperidin-1-yl)pyrimidin-4-yl)methylene)thiazolidine-2,4-dione;

(Z)-5-((2-(4-((((2-(2-(trifluoromethoxy)phenyl)pyridin-4-yl)methyl)amino)methyl)piperidin-1-yl)pyrimidin-4-yl)methylene)thiazolidine-2,4-dione;

(Z)-5-((2-(4-((((2-(2-(trifluoromethoxy)phenyl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(2-(trifluoromethoxy)phenyl)pyridin-4-yl)methyl)amino)methyl)piperidin-1-yl)pyrimidin-4-yl)methylene)thiazolidine-2,4-dione;

(Z)-5-((2-(4-((((6-amino-2-(2-(trifluoromethoxy)phenyl)pyridin-3-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)-4-fluoropyridin-2-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)pyridin-2-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)-4-methylpyridin-2-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(benzo[d][1,3]dioxol-5-yl)isoquinolin-1-yl)methyl)amino)methyl)piperidin-1-yl)pyrimidin-4-yl)methylene)thiazolidine-2,4-dione;

(Z)-5-((2-(4-((((2-(benzo[d][1,3]dioxol-5-yl)pyridin-3-yl)methyl)amino)methyl)piperidin-1-yl)pyrimidin-4-yl)methylene)thiazolidine-2,4-dione;

(Z)-5-((2-(4-((((2-(benzo[d][1,3]dioxol-5-yl)quinolin-3-yl)methyl)amino)methyl)piperidin-1-yl)pyrimidin-4-yl)methylene)thiazolidine-2,4-dione;

(Z)-5-((2-(4-((((6-(benzo[d][1,3]dioxol-5-yl)pyridin-3-yl)methyl)amino)methyl)piperidin-1-yl)pyrimidin-4-yl)methylene)thiazolidine-2,4-dione;

(Z)-5-((2-(4-((((2-(benzo[d][1,3]dioxol-5-yl)pyridin-4-yl)methyl)amino)methyl)piperidin-1-yl)pyrimidin-4-yl)methylene)thiazolidine-2,4-dione;

(Z)-5-((2-(4-((((2-(benzo[d][1,3]dioxol-5-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(benzo[d][1,3]dioxol-5-yl)-5-fluoropyridin-4-yl)methyl)amino)methyl)piperidin-1-yl)pyrimidin-4-yl)methylene)thiazolidine-2,4-dione;

(Z)-5-((2-(4-((((6-amino-2-(benzo[d][1,3]dioxol-5-yl)pyridin-3-yl)methyl)amino)methyl)piperidin-1-yl)pyrimidin-4-yl)methylene)thiazolidine-2,4-dione;

(Z)-5-((2-(4-((((6-(3-(dimethylamino)phenyl)-4-fluoropyridin-2-yl)methyl)amino)methyl)piperidin-1-yl)pyrimidin-4-yl)methylene)thiazolidine-2,4-dione;

(Z)-5-((2-(4-((((6-(3-(dimethylamino)phenyl)pyridin-2-yl)methyl)amino)methyl)piperidin-1-yl)pyrimidin-4-yl)methylene)thiazolidine-2,4-dione;

(Z)-5-((2-(4-((((6-(3-(dimethylamino)phenyl)-4-methylpyridin-2-yl)methyl)amino)methyl)piperidin-1-yl)pyrimidin-4-yl)methylene)thiazolidine-2,4-dione;

(Z)-5-((2-(4-((((6-(3-(dimethylamino)phenyl)-3-methoxypyridin-2-yl)methyl)amino)methyl)piperidin-1-yl)pyrimidin-4-yl)methylene)thiazolidine-2,4-dione;

(Z)-5-((2-(4-((((6-(3-(dimethylamino)phenyl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(3-(dimethylamino)phenyl)isoquinolin-1-yl)methyl)amino)methyl)piperidin-1-yl)pyrimidin-4-yl)methylene)thiazolidine-2,4-dione;

(Z)-5-((2-(4-((((2-(3-(dimethylamino)phenyl)pyridin-3-yl)methyl)amino)methyl)piperidin-1-yl)pyrimidin-4-yl)methylene)thiazolidine-2,4-dione;

(Z)-5-((2-(4-((((2-(3-(dimethylamino)phenyl)quinolin-3-yl)methyl)amino)methyl)piperidin-1-yl)pyrimidin-4-yl)methylene)thiazolidine-2,4-dione;

(Z)-5-((2-(4-((((6-(3-(dimethylamino)phenyl)pyridin-3-yl)methyl)amino)methyl)piperidin-1-yl)pyrimidin-4-yl)methylene)thiazolidine-2,4-dione;

(Z)-5-((2-(4-((((2-(3-(dimethylamino)phenyl)pyridin-4-yl)methyl)amino)methyl)piperidin-1-yl)pyrimidin-4-yl)methylene)thiazolidine-2,4-dione;

(Z)-5-((2-(4-((((2-(3-(dimethylamino)phenyl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(3-(dimethylamino)phenyl)-5-fluoropyridin-4-yl)methyl)amino)methyl)piperidin-1-yl)pyrimidin-4-yl)methylene)thiazolidine-2,4-dione;

(Z)-5-((2-(4-((((6-amino-2-(3-(dimethylamino)phenyl)pyridin-3-yl)methyl)amino)methyl)piperidin-1-yl)pyrimidin-4-yl)methylene)thiazolidine-2,4-dione;

(Z)-5-((2-(4-((((4-fluoro-6-(4-phenoxyphenyl)pyridin-2-yl)methyl)amino)methyl)piperidin-1-yl)pyrimidin-4-yl)methylene)thiazolidine-2,4-dione;

(Z)-5-((2-(4-((((6-(4-phenoxyphenyl)pyridin-2-yl)methyl)amino)methyl)piperidin-1-yl)pyrimidin-4-yl)methylene)thiazolidine-2,4-dione;

(Z)-5-((2-(4-((((4-methyl-6-(4-phenoxyphenyl)pyridin-2-yl)methyl)amino)methyl)piperidin-1-yl)pyrimidin-4-yl)methylene)thiazolidine-2,4-dione;

(Z)-5-((2-(4-((((3-methoxy-6-(4-phenoxyphenyl)pyridin-2-yl)methyl)amino)methyl)piperidin-1-yl)pyrimidin-4-yl)methylene)thiazolidine-2,4-dione;

(Z)-5-((2-(4-((((6-(4-phenoxyphenyl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(4-phenoxyphenyl)isoquinolin-1-yl)methyl)amino)methyl)piperidin-1-yl)pyrimidin-4-yl)methylene)thiazolidine-2,4-dione;

(Z)-5-((2-(4-((((2-(4-phenoxyphenyl)pyridin-3-yl)methyl)amino)methyl)piperidin-1-yl)pyrimidin-4-yl)methylene)thiazolidine-2,4-dione;

(Z)-5-((2-(4-((((2-(4-phenoxyphenyl)quinolin-3-yl)methyl)amino)methyl)piperidin-1-yl)pyrimidin-4-yl)methylene)thiazolidine-2,4-dione;

(Z)-5-((2-(4-((((6-(4-phenoxyphenyl)pyridin-3-yl)methyl)amino)methyl)piperidin-1-yl)pyrimidin-4-yl)methylene)thiazolidine-2,4-dione;

(Z)-5-((2-(4-((((2-(4-phenoxyphenyl)pyridin-4-yl)methyl)amino)methyl)piperidin-1-yl)pyrimidin-4-yl)methylene)thiazolidine-2,4-dione;

(Z)-5-((2-(4-((((2-(4-phenoxyphenyl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(4-phenoxyphenyl)pyridin-4-yl)methyl)amino)methyl)piperidin-1-yl)pyrimidin-4-yl)methylene)thiazolidine-2,4-dione;

(Z)-5-((2-(4-((((6-amino-2-(4-phenoxyphenyl)pyridin-3-yl)methyl)amino)methyl)piperidin-1-yl)pyrimidin-4-yl)methylene)thiazolidine-2,4-dione;

(Z)-5-((2-(4-((((4-fluoro-6-(1H-indol-5-yl)pyridin-2-yl)methyl)amino)methyl)piperidin-1-yl)pyrimidin-4-yl)methylene)thiazolidine-2,4-dione;

(Z)-5-((2-(4-((((6-(1H-indol-5-yl)pyridin-2-yl)methyl)amino)methyl)piperidin-1-yl)pyrimidin-4-yl)methylene)thiazolidine-2,4-dione;

(Z)-5-((2-(4-((((6-(1H-indol-5-yl)-4-methylpyridin-2-yl)methyl)amino)methyl)piperidin-1-yl)pyrimidin-4-yl)methylene)thiazolidine-2,4-dione;

(Z)-5-((2-(4-((((6-(1H-indol-5-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(1H-indol-5-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(1H-indol-5-yl)isoquinolin-1-yl)methyl)amino)methyl)piperidin-1-yl)pyrimidin-4-yl)methylene)thiazolidine-2,4-dione;

(Z)-5-((2-(4-((((2-(1H-indol-5-yl)pyridin-3-yl)methyl)amino)methyl)piperidin-1-yl)pyrimidin-4-yl)methylene)thiazolidine-2,4-dione;

(Z)-5-((2-(4-((((2-(1H-indol-5-yl)quinolin-3-yl)methyl)amino)methyl)piperidin-1-yl)pyrimidin-4-yl)methylene)thiazolidine-2,4-dione;

(Z)-5-((2-(4-((((6-(1H-indol-5-yl)pyridin-3-yl)methyl)amino)methyl)piperidin-1-yl)pyrimidin-4-yl)methylene)thiazolidine-2,4-dione;

(Z)-5-((2-(4-((((2-(1H-indol-5-yl)pyridin-4-yl)methyl)amino)methyl)piperidin-1-yl)pyrimidin-4-yl)methylene)thiazolidine-2,4-dione;

(Z)-5-((2-(4-((((2-(1H-indol-5-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(1H-indol-5-yl)pyridin-4-yl)methyl)amino)methyl)piperidin-1-yl)pyrimidin-4-yl)methylene)thiazolidine-2,4-dione;

(Z)-5-((2-(4-((((6-amino-2-(1H-indol-5-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(isoquinolin-5-yl)pyridin-2-yl)methyl)amino)methyl)piperidin-1-yl)pyrimidin-4-yl)methylene)thiazolidine-2,4-dione;

(Z)-5-((2-(4-((((6-(isoquinolin-5-yl)pyridin-2-yl)methyl)amino)methyl)piperidin-1-yl)pyrimidin-4-yl)methylene)thiazolidine-2,4-dione;

(Z)-5-((2-(4-((((6-(isoquinolin-5-yl)-4-methylpyridin-2-yl)methyl)amino)methyl)piperidin-1-yl)pyrimidin-4-yl)methylene)thiazolidine-2,4-dione;

(Z)-5-((2-(4-((((6-(isoquinolin-5-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(isoquinolin-5-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((([3,5'-biisoquinolin]-1-ylmethyl)amino)methyl)piperidin-1-yl)pyrimidin-4-yl)methylene)thiazolidine-2,4-dione;

(Z)-5-((2-(4-((((2-(isoquinolin-5-yl)pyridin-3-yl)methyl)amino)methyl)piperidin-1-yl)pyrimidin-4-yl)methylene)thiazolidine-2,4-dione;

(Z)-5-((2-(4-((((2-(isoquinolin-5-yl)quinolin-3-yl)methyl)amino)methyl)piperidin-1-yl)pyrimidin-4-yl)methylene)thiazolidine-2,4-dione;

(Z)-5-((2-(4-((((6-(isoquinolin-5-yl)pyridin-3-yl)methyl)amino)methyl)piperidin-1-yl)pyrimidin-4-yl)methylene)thiazolidine-2,4-dione;

(Z)-5-((2-(4-((((2-(isoquinolin-5-yl)pyridin-4-yl)methyl)amino)methyl)piperidin-1-yl)pyrimidin-4-yl)methylene)thiazolidine-2,4-dione;

(Z)-5-((2-(4-((((2-(isoquinolin-5-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(isoquinolin-5-yl)pyridin-4-yl)methyl)amino)methyl)piperidin-1-yl)pyrimidin-4-yl)methylene)thiazolidine-2,4-dione;

(Z)-5-((2-(4-((((6-amino-2-(isoquinolin-5-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(thiophen-3-yl)pyridin-2-yl)methyl)amino)methyl)piperidin-1-yl)pyrimidin-4-yl)methylene)thiazolidine-2,4-dione;

(Z)-5-((2-(4-((((6-(thiophen-3-yl)pyridin-2-yl)methyl)amino)methyl)piperidin-1-yl)pyrimidin-4-yl)methylene)thiazolidine-2,4-dione;

(Z)-5-((2-(4-((((4-methyl-6-(thiophen-3-yl)pyridin-2-yl)methyl)amino)methyl)piperidin-1-yl)pyrimidin-4-yl)methylene)thiazolidine-2,4-dione;

(Z)-5-((2-(4-((((3-methoxy-6-(thiophen-3-yl)pyridin-2-yl)methyl)amino)methyl)piperidin-1-yl)pyrimidin-4-yl)methylene)thiazolidine-2,4-dione;

(Z)-5-((2-(4-((((6-(thiophen-3-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(thiophen-3-yl)isoquinolin-1-yl)methyl)amino)methyl)piperidin-1-yl)pyrimidin-4-yl)methylene)thiazolidine-2,4-dione;

(Z)-5-((2-(4-((((2-(thiophen-3-yl)pyridin-3-yl)methyl)amino)methyl)piperidin-1-yl)pyrimidin-4-yl)methylene)thiazolidine-2,4-dione;

(Z)-5-((2-(4-((((2-(thiophen-3-yl)quinolin-3-yl)methyl)amino)methyl)piperidin-1-yl)pyrimidin-4-yl)methylene)thiazolidine-2,4-dione;

(Z)-5-((2-(4-((((6-(thiophen-3-yl)pyridin-3-yl)methyl)amino)methyl)piperidin-1-yl)pyrimidin-4-yl)methylene)thiazolidine-2,4-dione;

(Z)-5-((2-(4-((((2-(thiophen-3-yl)pyridin-4-yl)methyl)amino)methyl)piperidin-1-yl)pyrimidin-4-yl)methylene)thiazolidine-2,4-dione;

(Z)-5-((2-(4-((((2-(thiophen-3-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-(((((5-fluoro-2-(thiophen-3-yl)pyridin-4-yl)
methyl)amino)methyl)piperidin-1-yl)pyrimidin-4-yl)
methylene)thiazolidine-2,4-dione;
(Z)-5-((2-(4-(((((6-amino-2-(thiophen-3-yl)pyridin-3-yl)
methyl)amino)methyl)piperidin-1-yl)pyrimidin-4-yl)
methylene)thiazolidine-2,4-dione;
(Z)-5-((2-(4-((((6-(benzo[b]thiophen-3-yl)-4-fluoropyridin-2-yl)methyl)amino)methyl)piperidin-1-yl)pyrimidin-4-yl)methylene)thiazolidine-2,4-dione;
(Z)-5-((2-(4-((((6-(benzo[b]thiophen-3-yl)pyridin-2-yl)
methyl)amino)methyl)piperidin-1-yl)pyrimidin-4-yl)
methylene)thiazolidine-2,4-dione;
(Z)-5-((2-(4-((((6-(benzo[b]thiophen-3-yl)-4-methylpyridin-2-yl)methyl)amino)methyl)piperidin-1-yl)pyrimidin-4-yl)methylene)thiazolidine-2,4-dione;
(Z)-5-((2-(4-((((6-(benzo[b]thiophen-3-yl)-3-methoxypyridin-2-yl)methyl)amino)methyl)piperidin-1-yl)pyrimidin-4-yl)methylene)thiazolidine-2,4-dione;
(Z)-5-((2-(4-((((6-(benzo[b]thiophen-3-yl)-4-(trifluoromethyl)pyridin-2-yl)methyl)amino)methyl)piperidin-1-yl)pyrimidin-4-yl)methylene)thiazolidine-2,4-dione;
(Z)-5-((2-(4-((((3-(benzo[b]thiophen-3-yl)isoquinolin-1-yl)methyl)amino)methyl)piperidin-1-yl)pyrimidin-4-yl)methylene)thiazolidine-2,4-dione;
(Z)-5-((2-(4-((((2-(benzo[b]thiophen-3-yl)pyridin-3-yl)
methyl)amino)methyl)piperidin-1-yl)pyrimidin-4-yl)
methylene)thiazolidine-2,4-dione;
(Z)-5-((2-(4-((((2-(benzo[b]thiophen-3-yl)quinolin-3-yl)
methyl)amino)methyl)piperidin-1-yl)pyrimidin-4-yl)
methylene)thiazolidine-2,4-dione;
(Z)-5-((2-(4-((((6-(benzo[b]thiophen-3-yl)pyridin-3-yl)
methyl)amino)methyl)piperidin-1-yl)pyrimidin-4-yl)
methylene)thiazolidine-2,4-dione;
(Z)-5-((2-(4-((((2-(benzo[b]thiophen-3-yl)pyridin-4-yl)
methyl)amino)methyl)piperidin-1-yl)pyrimidin-4-yl)
methylene)thiazolidine-2,4-dione;
(Z)-5-((2-(4-((((2-(benzo[b]thiophen-3-yl)-6-(trifluoromethyl)pyridin-4-yl)methyl)amino)methyl)piperidin-1-yl)pyrimidin-4-yl)methylene)thiazolidine-2,4-dione;
(Z)-5-((2-(4-((((2-(benzo[b]thiophen-3-yl)-5-fluoropyridin-4-yl)methyl)amino)methyl)piperidin-1-yl)pyrimidin-4-yl)methylene)thiazolidine-2,4-dione;
(Z)-5-((2-(4-((((6-amino-2-(benzo[b]thiophen-3-yl)pyridin-3-yl)methyl)amino)methyl)piperidin-1-yl)pyrimidin-4-yl)methylene)thiazolidine-2,4-dione;
(Z)-5-((2-(4-(((((6-(5-acetylthiophen-2-yl)-4-fluoropyridin-2-yl)methyl)amino)methyl)piperidin-1-yl)pyrimidin-4-yl)methylene)thiazolidine-2,4-dione;
(Z)-5-((2-(4-(((((6-(5-acetylthiophen-2-yl)pyridin-2-yl)
methyl)amino)methyl)piperidin-1-yl)pyrimidin-4-yl)
methylene)thiazolidine-2,4-dione;
(Z)-5-((2-(4-(((((6-(5-acetylthiophen-2-yl)-4-methylpyridin-2-yl)methyl)amino)methyl)piperidin-1-yl)pyrimidin-4-yl)methylene)thiazolidine-2,4-dione;
(Z)-5-((2-(4-(((((6-(5-acetylthiophen-2-yl)-3-methoxypyridin-2-yl)methyl)amino)methyl)piperidin-1-yl)pyrimidin-4-yl)methylene)thiazolidine-2,4-dione;
(Z)-5-((2-(4-(((((6-(5-acetylthiophen-2-yl)-4-(trifluoromethyl)pyridin-2-yl)methyl)amino)methyl)piperidin-1-yl)pyrimidin-4-yl)methylene)thiazolidine-2,4-dione;
(Z)-5-((2-(4-((((3-(5-acetylthiophen-2-yl)isoquinolin-1-yl)methyl)amino)methyl)piperidin-1-yl)pyrimidin-4-yl)methylene)thiazolidine-2,4-dione;
(Z)-5-((2-(4-(((((2-(5-acetylthiophen-2-yl)pyridin-3-yl)
methyl)amino)methyl)piperidin-1-yl)pyrimidin-4-yl)
methylene)thiazolidine-2,4-dione;
(Z)-5-((2-(4-(((((2-(5-acetylthiophen-2-yl)quinolin-3-yl)
methyl)amino)methyl)piperidin-1-yl)pyrimidin-4-yl)
methylene)thiazolidine-2,4-dione;
(Z)-5-((2-(4-(((((6-(5-acetylthiophen-2-yl)pyridin-3-yl)
methyl)amino)methyl)piperidin-1-yl)pyrimidin-4-yl)
methylene)thiazolidine-2,4-dione;
(Z)-5-((2-(4-(((((2-(5-acetylthiophen-2-yl)pyridin-4-yl)
methyl)amino)methyl)piperidin-1-yl)pyrimidin-4-yl)
methylene)thiazolidine-2,4-dione;
(Z)-5-((2-(4-(((((2-(5-acetylthiophen-2-yl)-6-(trifluoromethyl)pyridin-4-yl)methyl)amino)methyl)piperidin-1-yl)pyrimidin-4-yl)methylene)thiazolidine-2,4-dione;
(Z)-5-((2-(4-(((((2-(5-acetylthiophen-2-yl)-5-fluoropyridin-4-yl)methyl)amino)methyl)piperidin-1-yl)pyrimidin-4-yl)methylene)thiazolidine-2,4-dione;
(Z)-5-((2-(4-(((((2-(5-acetylthiophen-2-yl)-6-aminopyridin-3-yl)methyl)amino)methyl)piperidin-1-yl)pyrimidin-4-yl)methylene)thiazolidine-2,4-dione;
(Z)-5-((2-(4-((((4-fluoro-6-(furan-2-yl)pyridin-2-yl)methyl)amino)methyl)piperidin-1-yl)pyrimidin-4-yl)methylene)thiazolidine-2,4-dione;
(Z)-5-((2-(4-((((6-(furan-2-yl)pyridin-2-yl)methyl)
amino)methyl)piperidin-1-yl)pyrimidin-4-yl)methylene)thiazolidine-2,4-dione;
(Z)-5-((2-(4-((((6-(furan-2-yl)-4-methylpyridin-2-yl)methyl)amino)methyl)piperidin-1-yl)pyrimidin-4-yl)methylene)thiazolidine-2,4-dione;
(Z)-5-((2-(4-((((6-(furan-2-yl)-3-methoxypyridin-2-yl)
methyl)amino)methyl)piperidin-1-yl)pyrimidin-4-yl)
methylene)thiazolidine-2,4-dione;
(Z)-5-((2-(4-((((6-(furan-2-yl)-4-(trifluoromethyl)pyridin-2-yl)methyl)amino)methyl)piperidin-1-yl)pyrimidin-4-yl)methylene)thiazolidine-2,4-dione;
(Z)-5-((2-(4-((((3-(furan-2-yl)isoquinolin-1-yl)methyl)
amino)methyl)piperidin-1-yl)pyrimidin-4-yl)methylene)thiazolidine-2,4-dione;
(Z)-5-((2-(4-((((2-(furan-2-yl)pyridin-3-yl)methyl)
amino)methyl)piperidin-1-yl)pyrimidin-4-yl)methylene)thiazolidine-2,4-dione;
(Z)-5-((2-(4-((((2-(furan-2-yl)quinolin-3-yl)methyl)
amino)methyl)piperidin-1-yl)pyrimidin-4-yl)methylene)thiazolidine-2,4-dione;
(Z)-5-((2-(4-((((6-(furan-2-yl)pyridin-3-yl)methyl)
amino)methyl)piperidin-1-yl)pyrimidin-4-yl)methylene)thiazolidine-2,4-dione;
(Z)-5-((2-(4-((((2-(furan-2-yl)pyridin-4-yl)methyl)
amino)methyl)piperidin-1-yl)pyrimidin-4-yl)methylene)thiazolidine-2,4-dione;
(Z)-5-((2-(4-((((2-(furan-2-yl)-6-(trifluoromethyl)pyridin-4-yl)methyl)amino)methyl)piperidin-1-yl)pyrimidin-4-yl)methylene)thiazolidine-2,4-dione;
(Z)-5-((2-(4-((((5-fluoro-2-(furan-2-yl)pyridin-4-yl)methyl)amino)methyl)piperidin-1-yl)pyrimidin-4-yl)methylene)thiazolidine-2,4-dione;
(Z)-5-((2-(4-((((6-amino-2-(furan-2-yl)pyridin-3-yl)methyl)amino)methyl)piperidin-1-yl)pyrimidin-4-yl)methylene)thiazolidine-2,4-dione;
(Z)-5-((2-(4-((((6-(benzofuran-2-yl)-4-fluoropyridin-2-yl)methyl)amino)methyl)piperidin-1-yl)pyrimidin-4-yl)methylene)thiazolidine-2,4-dione;
(Z)-5-((2-(4-((((6-(benzofuran-2-yl)pyridin-2-yl)methyl)
amino)methyl)piperidin-1-yl)pyrimidin-4-yl)methylene)thiazolidine-2,4-dione;
(Z)-5-((2-(4-((((6-(benzofuran-2-yl)-4-methylpyridin-2-yl)methyl)amino)methyl)piperidin-1-yl)pyrimidin-4-yl)methylene)thiazolidine-2,4-dione;

(Z)-5-((2-(4-((((6-(benzofuran-2-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(benzofuran-2-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(benzofuran-2-yl)isoquinolin-1-yl)methyl)amino)methyl)piperidin-1-yl)pyrimidin-4-yl)methylene)thiazolidine-2,4-dione;

(Z)-5-((2-(4-((((2-(benzofuran-2-yl)pyridin-3-yl)methyl)amino)methyl)piperidin-1-yl)pyrimidin-4-yl)methylene)thiazolidine-2,4-dione;

(Z)-5-((2-(4-((((2-(benzofuran-2-yl)quinolin-3-yl)methyl)amino)methyl)piperidin-1-yl)pyrimidin-4-yl)methylene)thiazolidine-2,4-dione;

(Z)-5-((2-(4-((((6-(benzofuran-2-yl)pyridin-3-yl)methyl)amino)methyl)piperidin-1-yl)pyrimidin-4-yl)methylene)thiazolidine-2,4-dione;

(Z)-5-((2-(4-((((2-(benzofuran-2-yl)pyridin-4-yl)methyl)amino)methyl)piperidin-1-yl)pyrimidin-4-yl)methylene)thiazolidine-2,4-dione;

(Z)-5-((2-(4-((((2-(benzofuran-2-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(benzofuran-2-yl)-5-fluoropyridin-4-yl)methyl)amino)methyl)piperidin-1-yl)pyrimidin-4-yl)methylene)thiazolidine-2,4-dione;

(Z)-5-((2-(4-((((6-amino-2-(benzofuran-2-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(furan-3-yl)pyridin-2-yl)methyl)amino)methyl)piperidin-1-yl)pyrimidin-4-yl)methylene)thiazolidine-2,4-dione;

(Z)-5-((2-(4-((((6-(furan-3-yl)pyridin-2-yl)methyl)amino)methyl)piperidin-1-yl)pyrimidin-4-yl)methylene)thiazolidine-2,4-dione;

(Z)-5-((2-(4-((((6-(furan-3-yl)-4-methylpyridin-2-yl)methyl)amino)methyl)piperidin-1-yl)pyrimidin-4-yl)methylene)thiazolidine-2,4-dione;

(Z)-5-((2-(4-((((6-(furan-3-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(furan-3-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(furan-3-yl)isoquinolin-1-yl)methyl)amino)methyl)piperidin-1-yl)pyrimidin-4-yl)methylene)thiazolidine-2,4-dione;

(Z)-5-((2-(4-((((2-(furan-3-yl)pyridin-3-yl)methyl)amino)methyl)piperidin-1-yl)pyrimidin-4-yl)methylene)thiazolidine-2,4-dione;

(Z)-5-((2-(4-((((2-(furan-3-yl)quinolin-3-yl)methyl)amino)methyl)piperidin-1-yl)pyrimidin-4-yl)methylene)thiazolidine-2,4-dione;

(Z)-5-((2-(4-((((6-(furan-3-yl)pyridin-3-yl)methyl)amino)methyl)piperidin-1-yl)pyrimidin-4-yl)methylene)thiazolidine-2,4-dione;

(Z)-5-((2-(4-((((2-(furan-3-yl)pyridin-4-yl)methyl)amino)methyl)piperidin-1-yl)pyrimidin-4-yl)methylene)thiazolidine-2,4-dione;

(Z)-5-((2-(4-((((2-(furan-3-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(furan-3-yl)pyridin-4-yl)methyl)amino)methyl)piperidin-1-yl)pyrimidin-4-yl)methylene)thiazolidine-2,4-dione;

(Z)-5-((2-(4-((((6-amino-2-(furan-3-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(1H-pyrrol-2-yl)pyridin-2-yl)methyl)amino)methyl)piperidin-1-yl)pyrimidin-4-yl)methylene)thiazolidine-2,4-dione;

(Z)-5-((2-(4-((((6-(1H-pyrrol-2-yl)pyridin-2-yl)methyl)amino)methyl)piperidin-1-yl)pyrimidin-4-yl)methylene)thiazolidine-2,4-dione;

(Z)-5-((2-(4-((((4-methyl-6-(1H-pyrrol-2-yl)pyridin-2-yl)methyl)amino)methyl)piperidin-1-yl)pyrimidin-4-yl)methylene)thiazolidine-2,4-dione;

(Z)-5-((2-(4-((((3-methoxy-6-(1H-pyrrol-2-yl)pyridin-2-yl)methyl)amino)methyl)piperidin-1-yl)pyrimidin-4-yl)methylene)thiazolidine-2,4-dione;

(Z)-5-((2-(4-((((6-(1H-pyrrol-2-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(1H-pyrrol-2-yl)isoquinolin-1-yl)methyl)amino)methyl)piperidin-1-yl)pyrimidin-4-yl)methylene)thiazolidine-2,4-dione;

(Z)-5-((2-(4-((((2-(1H-pyrrol-2-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrrol-2-yl)quinolin-3-yl)methyl)amino)methyl)piperidin-1-yl)pyrimidin-4-yl)methylene)thiazolidine-2,4-dione;

(Z)-5-((2-(4-((((6-(1H-pyrrol-2-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrrol-2-yl)pyridin-4-yl)methyl)amino)methyl)piperidin-1-yl)pyrimidin-4-yl)methylene)thiazolidine-2,4-dione;

(Z)-5-((2-(4-((((2-(1H-pyrrol-2-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(1H-pyrrol-2-yl)pyridin-4-yl)methyl)amino)methyl)piperidin-1-yl)pyrimidin-4-yl)methylene)thiazolidine-2,4-dione;

(Z)-5-((2-(4-((((6-amino-2-(1H-pyrrol-2-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(isoquinolin-4-yl)pyridin-2-yl)methyl)amino)methyl)piperidin-1-yl)pyrimidin-4-yl)methylene)thiazolidine-2,4-dione;

(Z)-5-((2-(4-((((6-(isoquinolin-4-yl)pyridin-2-yl)methyl)amino)methyl)piperidin-1-yl)pyrimidin-4-yl)methylene)thiazolidine-2,4-dione;

(Z)-5-((2-(4-((((6-(isoquinolin-4-yl)-4-methylpyridin-2-yl)methyl)amino)methyl)piperidin-1-yl)pyrimidin-4-yl)methylene)thiazolidine-2,4-dione;

(Z)-5-((2-(4-((((6-(isoquinolin-4-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(isoquinolin-4-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((([3,4'-biisoquinolin]-1-ylmethyl)amino)methyl)piperidin-1-yl)pyrimidin-4-yl)methylene)thiazolidine-2,4-dione;

(Z)-5-((2-(4-((((2-(isoquinolin-4-yl)pyridin-3-yl)methyl)amino)methyl)piperidin-1-yl)pyrimidin-4-yl)methylene)thiazolidine-2,4-dione;

(Z)-5-((2-(4-((((2-(isoquinolin-4-yl)quinolin-3-yl)methyl)amino)methyl)piperidin-1-yl)pyrimidin-4-yl)methylene)thiazolidine-2,4-dione;

(Z)-5-((2-(4-(((((6-(isoquinolin-4-yl)pyridin-3-yl)methyl)amino)methyl)piperidin-1-yl)pyrimidin-4-yl)methylene)thiazolidine-2,4-dione;

(Z)-5-((2-(4-((((2-(isoquinolin-4-yl)pyridin-4-yl)methyl)amino)methyl)piperidin-1-yl)pyrimidin-4-yl)methylene)thiazolidine-2,4-dione;

(Z)-5-((2-(4-((((2-(isoquinolin-4-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(isoquinolin-4-yl)pyridin-4-yl)methyl)amino)methyl)piperidin-1-yl)pyrimidin-4-yl)methylene)thiazolidine-2,4-dione;

(Z)-5-((2-(4-((((6-amino-2-(isoquinolin-4-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(quinolin-4-yl)pyridin-2-yl)methyl)amino)methyl)piperidin-1-yl)pyrimidin-4-yl)methylene)thiazolidine-2,4-dione;

(Z)-5-((2-(4-((((6-(quinolin-4-yl)pyridin-2-yl)methyl)amino)methyl)piperidin-1-yl)pyrimidin-4-yl)methylene)thiazolidine-2,4-dione;

(Z)-5-((2-(4-((((4-methyl-6-(quinolin-4-yl)pyridin-2-yl)methyl)amino)methyl)piperidin-1-yl)pyrimidin-4-yl)methylene)thiazolidine-2,4-dione;

(Z)-5-((2-(4-((((3-methoxy-6-(quinolin-4-yl)pyridin-2-yl)methyl)amino)methyl)piperidin-1-yl)pyrimidin-4-yl)methylene)thiazolidine-2,4-dione;

(Z)-5-((2-(4-((((6-(quinolin-4-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(quinolin-4-yl)isoquinolin-1-yl)methyl)amino)methyl)piperidin-1-yl)pyrimidin-4-yl)methylene)thiazolidine-2,4-dione;

(Z)-5-((2-(4-((((2-(quinolin-4-yl)pyridin-3-yl)methyl)amino)methyl)piperidin-1-yl)pyrimidin-4-yl)methylene)thiazolidine-2,4-dione;

(Z)-5-((2-(4-((([2,4'-biquinolin]-3-ylmethyl)amino)methyl)piperidin-1-yl)pyrimidin-4-yl)methylene)thiazolidine-2,4-dione;

(Z)-5-((2-(4-((((6-(quinolin-4-yl)pyridin-3-yl)methyl)amino)methyl)piperidin-1-yl)pyrimidin-4-yl)methylene)thiazolidine-2,4-dione;

(Z)-5-((2-(4-((((2-(quinolin-4-yl)pyridin-4-yl)methyl)amino)methyl)piperidin-1-yl)pyrimidin-4-yl)methylene)thiazolidine-2,4-dione;

(Z)-5-((2-(4-((((2-(quinolin-4-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(quinolin-4-yl)pyridin-4-yl)methyl)amino)methyl)piperidin-1-yl)pyrimidin-4-yl)methylene)thiazolidine-2,4-dione;

(Z)-5-((2-(4-((((6-amino-2-(quinolin-4-yl)pyridin-3-yl)methyl)amino)methyl)piperidin-1-yl)pyrimidin-4-yl)methylene)thiazolidine-2,4-dione;

(Z)-5-((2-(4-((((3',4-difluoro-[2,4'-bipyridin]-6-yl)methyl)amino)methyl)piperidin-1-yl)pyrimidin-4-yl)methylene)thiazolidine-2,4-dione;

(Z)-5-((2-(4-((((3'-fluoro-[2,4'-bipyridin]-6-yl)methyl)amino)methyl)piperidin-1-yl)pyrimidin-4-yl)methylene)thiazolidine-2,4-dione;

(Z)-5-((2-(4-((((3'-fluoro-4-methyl-[2,4'-bipyridin]-6-yl)methyl)amino)methyl)piperidin-1-yl)pyrimidin-4-yl)methylene)thiazolidine-2,4-dione;

(Z)-5-((2-(4-((((3'-fluoro-5-methoxy-[2,4'-bipyridin]-6-yl)methyl)amino)methyl)piperidin-1-yl)pyrimidin-4-yl)methylene)thiazolidine-2,4-dione;

(Z)-5-((2-(4-((((3'-fluoro-4-(trifluoromethyl)-[2,4'-bipyridin]-6-yl)methyl)amino)methyl)piperidin-1-yl)pyrimidin-4-yl)methylene)thiazolidine-2,4-dione;

(Z)-5-((2-(4-((((3-(3-fluoropyridin-4-yl)isoquinolin-1-yl)methyl)amino)methyl)piperidin-1-yl)pyrimidin-4-yl)methylene)thiazolidine-2,4-dione;

(Z)-5-((2-(4-((((3'-fluoro-[2,4'-bipyridin]-3-yl)methyl)amino)methyl)piperidin-1-yl)pyrimidin-4-yl)methylene)thiazolidine-2,4-dione;

(Z)-5-((2-(4-((((2-(3-fluoropyridin-4-yl)quinolin-3-yl)methyl)amino)methyl)piperidin-1-yl)pyrimidin-4-yl)methylene)thiazolidine-2,4-dione;

(Z)-5-((2-(4-((((3'-fluoro-[2,4'-bipyridin]-5-yl)methyl)amino)methyl)piperidin-1-yl)pyrimidin-4-yl)methylene)thiazolidine-2,4-dione;

(Z)-5-((2-(4-((((3'-fluoro-[2,4'-bipyridin]-4-yl)methyl)amino)methyl)piperidin-1-yl)pyrimidin-4-yl)methylene)thiazolidine-2,4-dione;

(Z)-5-((2-(4-((((3'-fluoro-6-(trifluoromethyl)-[2,4'-bipyridin]-4-yl)methyl)amino)methyl)piperidin-1-yl)pyrimidin-4-yl)methylene)thiazolidine-2,4-dione;

(Z)-5-((2-(4-((((3',5-difluoro-[2,4'-bipyridin]-4-yl)methyl)amino)methyl)piperidin-1-yl)pyrimidin-4-yl)methylene)thiazolidine-2,4-dione;

(Z)-5-((2-(4-((((6-amino-3'-fluoro-[2,4'-bipyridin]-3-yl)methyl)amino)methyl)piperidin-1-yl)pyrimidin-4-yl)methylene)thiazolidine-2,4-dione;

(Z)-5-((2-(4-((((2',4,6-trifluoro-[2,4'-bipyridin]-6-yl)methyl)amino)methyl)piperidin-1-yl)pyrimidin-4-yl)methylene)thiazolidine-2,4-dione;

(Z)-5-((2-(4-((((2',6'-difluoro-[2,4'-bipyridin]-6-yl)methyl)amino)methyl)piperidin-1-yl)pyrimidin-4-yl)methylene)thiazolidine-2,4-dione;

(Z)-5-((2-(4-((((2',6'-difluoro-4-methyl-[2,4'-bipyridin]-6-yl)methyl)amino)methyl)piperidin-1-yl)pyrimidin-4-yl)methylene)thiazolidine-2,4-dione;

(Z)-5-((2-(4-((((2',6'-difluoro-5-methoxy-[2,4'-bipyridin]-6-yl)methyl)amino)methyl)piperidin-1-yl)pyrimidin-4-yl)methylene)thiazolidine-2,4-dione;

(Z)-5-((2-(4-((((2',6'-difluoro-4-(trifluoromethyl)-[2,4'-bipyridin]-6-yl)methyl)amino)methyl)piperidin-1-yl)pyrimidin-4-yl)methylene)thiazolidine-2,4-dione;

(Z)-5-((2-(4-((((3-(2,6-difluoropyridin-4-yl)isoquinolin-1-yl)methyl)amino)methyl)piperidin-1-yl)pyrimidin-4-yl)methylene)thiazolidine-2,4-dione;

(Z)-5-((2-(4-((((2',6'-difluoro-[2,4'-bipyridin]-3-yl)methyl)amino)methyl)piperidin-1-yl)pyrimidin-4-yl)methylene)thiazolidine-2,4-dione;

(Z)-5-((2-(4-((((2-(2,6-difluoropyridin-4-yl)quinolin-3-yl)methyl)amino)methyl)piperidin-1-yl)pyrimidin-4-yl)methylene)thiazolidine-2,4-dione;

(Z)-5-((2-(4-((((2',6'-difluoro-[2,4'-bipyridin]-5-yl)methyl)amino)methyl)piperidin-1-yl)pyrimidin-4-yl)methylene)thiazolidine-2,4-dione;

(Z)-5-((2-(4-((((2',6'-difluoro-[2,4'-bipyridin]-4-yl)methyl)amino)methyl)piperidin-1-yl)pyrimidin-4-yl)methylene)thiazolidine-2,4-dione;

(Z)-5-((2-(4-((((2',6'-difluoro-6-(trifluoromethyl)-[2,4'-bipyridin]-4-yl)methyl)amino)methyl)piperidin-1-yl)pyrimidin-4-yl)methylene)thiazolidine-2,4-dione;

(Z)-5-((2-(4-((((2',5,6'-trifluoro-[2,4'-bipyridin]-4-yl)methyl)amino)methyl)piperidin-1-yl)pyrimidin-4-yl)methylene)thiazolidine-2,4-dione;

(Z)-5-((2-(4-((((6-amino-2',6'-difluoro-[2,4'-bipyridin]-3-yl)methyl)amino)methyl)piperidin-1-yl)pyrimidin-4-yl)methylene)thiazolidine-2,4-dione;

(Z)-5-((2-(4-(((((6'-(dimethylamino)-4-fluoro-[2,3'-bipyridin]-6-yl)methyl)amino)methyl)piperidin-1-yl)pyrimidin-4-yl)methylene)thiazolidine-2,4-dione;

(Z)-5-((2-(4-(((((6'-(dimethylamino)-[2,3'-bipyridin]-6-yl)methyl)amino)methyl)piperidin-1-yl)pyrimidin-4-yl)methylene)thiazolidine-2,4-dione;

(Z)-5-((2-(4-(((((6'-(dimethylamino)-4-methyl-[2,3'-bipyridin]-6-yl)methyl)amino)methyl)piperidin-1-yl)pyrimidin-4-yl)methylene)thiazolidine-2,4-dione;

(Z)-5-((2-(4-(((((6'-(dimethylamino)-5-methoxy-[2,3'-bipyridin]-6-yl)methyl)amino)methyl)piperidin-1-yl)pyrimidin-4-yl)methylene)thiazolidine-2,4-dione;

(Z)-5-((2-(4-(((((6'-(dimethylamino)-4-(trifluoromethyl)-[2,3'-bipyridin]-6-yl)methyl)amino)methyl)piperidin-1-yl)pyrimidin-4-yl)methylene)thiazolidine-2,4-dione;

(Z)-5-((2-(4-((((3-(6-(dimethylamino)pyridin-3-yl)isoquinolin-1-yl)methyl)amino)methyl)piperidin-1-yl)pyrimidin-4-yl)methylene)thiazolidine-2,4-dione;

(Z)-5-((2-(4-(((((6'-(dimethylamino)-[2,3'-bipyridin]-3-yl)methyl)amino)methyl)piperidin-1-yl)pyrimidin-4-yl)methylene)thiazolidine-2,4-dione;

(Z)-5-((2-(4-((((2-(6-(dimethylamino)pyridin-3-yl)quinolin-3-yl)methyl)amino)methyl)piperidin-1-yl)pyrimidin-4-yl)methylene)thiazolidine-2,4-dione;

(Z)-5-((2-(4-(((((6-(dimethylamino)-[2,3'-bipyridin]-5-yl)methyl)amino)methyl)piperidin-1-yl)pyrimidin-4-yl)methylene)thiazolidine-2,4-dione;

(Z)-5-((2-(4-(((((6-(dimethylamino)-[2,3'-bipyridin]-4-yl)methyl)amino)methyl)piperidin-1-yl)pyrimidin-4-yl)methylene)thiazolidine-2,4-dione;

(Z)-5-((2-(4-(((((6-(dimethylamino)-6-(trifluoromethyl)-[2,3'-bipyridin]-4-yl)methyl)amino)methyl)piperidin-1-yl)pyrimidin-4-yl)methylene)thiazolidine-2,4-dione;

(Z)-5-((2-(4-(((((6-(dimethylamino)-5-fluoro-[2,3'-bipyridin]-4-yl)methyl)amino)methyl)piperidin-1-yl)pyrimidin-4-yl)methylene)thiazolidine-2,4-dione;

(Z)-5-((2-(4-(((((6-amino-6'-(dimethylamino)-[2,3'-bipyridin]-3-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)-4-fluoropyridin-2-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)pyridin-2-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)-4-methylpyridin-2-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)-3-methoxypyridin-2-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(2-(dimethylamino)pyrimidin-5-yl)isoquinolin-1-yl)methyl)amino)methyl)piperidin-1-yl)pyrimidin-4-yl)methylene)thiazolidine-2,4-dione;

(Z)-5-((2-(4-((((2-(2-(dimethylamino)pyrimidin-5-yl)pyridin-3-yl)methyl)amino)methyl)piperidin-1-yl)pyrimidin-4-yl)methylene)thiazolidine-2,4-dione;

(Z)-5-((2-(4-((((2-(2-(dimethylamino)pyrimidin-5-yl)quinolin-3-yl)methyl)amino)methyl)piperidin-1-yl)pyrimidin-4-yl)methylene)thiazolidine-2,4-dione;

(Z)-5-((2-(4-((((6-(2-(dimethylamino)pyrimidin-5-yl)pyridin-3-yl)methyl)amino)methyl)piperidin-1-yl)pyrimidin-4-yl)methylene)thiazolidine-2,4-dione;

(Z)-5-((2-(4-((((2-(2-(dimethylamino)pyrimidin-5-yl)pyridin-4-yl)methyl)amino)methyl)piperidin-1-yl)pyrimidin-4-yl)methylene)thiazolidine-2,4-dione;

(Z)-5-((2-(4-((((2-(2-(dimethylamino)pyrimidin-5-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(2-(dimethylamino)pyrimidin-5-yl)-5-fluoropyridin-4-yl)methyl)amino)methyl)piperidin-1-yl)pyrimidin-4-yl)methylene)thiazolidine-2,4-dione;

(Z)-5-((2-(4-(((((6-amino-2-(2-(dimethylamino)pyrimidin-5-yl)pyridin-3-yl)methyl)amino)methyl)piperidin-1-yl)pyrimidin-4-yl)methylene)thiazolidine-2,4-dione;

(Z)-5-((2-(4-(((((6-(3,5-dimethylisoxazol-4-yl)-4-fluoropyridin-2-yl)methyl)amino)methyl)piperidin-1-yl)pyrimidin-4-yl)methylene)thiazolidine-2,4-dione;

(Z)-5-((2-(4-(((((6-(3,5-dimethylisoxazol-4-yl)pyridin-2-yl)methyl)amino)methyl)piperidin-1-yl)pyrimidin-4-yl)methylene)thiazolidine-2,4-dione;

(Z)-5-((2-(4-(((((6-(3,5-dimethylisoxazol-4-yl)-4-methylpyridin-2-yl)methyl)amino)methyl)piperidin-1-yl)pyrimidin-4-yl)methylene)thiazolidine-2,4-dione;

(Z)-5-((2-(4-(((((6-(3,5-dimethylisoxazol-4-yl)-3-methoxypyridin-2-yl)methyl)amino)methyl)piperidin-1-yl)pyrimidin-4-yl)methylene)thiazolidine-2,4-dione;

(Z)-5-((2-(4-(((((6-(3,5-dimethylisoxazol-4-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(3,5-dimethylisoxazol-4-yl)isoquinolin-1-yl)methyl)amino)methyl)piperidin-1-yl)pyrimidin-4-yl)methylene)thiazolidine-2,4-dione;

(Z)-5-((2-(4-((((2-(3,5-dimethylisoxazol-4-yl)pyridin-3-yl)methyl)amino)methyl)piperidin-1-yl)pyrimidin-4-yl)methylene)thiazolidine-2,4-dione;

(Z)-5-((2-(4-((((2-(3,5-dimethylisoxazol-4-yl)quinolin-3-yl)methyl)amino)methyl)piperidin-1-yl)pyrimidin-4-yl)methylene)thiazolidine-2,4-dione;

(Z)-5-((2-(4-((((6-(3,5-dimethylisoxazol-4-yl)pyridin-3-yl)methyl)amino)methyl)piperidin-1-yl)pyrimidin-4-yl)methylene)thiazolidine-2,4-dione;

(Z)-5-((2-(4-((((2-(3,5-dimethylisoxazol-4-yl)pyridin-4-yl)methyl)amino)methyl)piperidin-1-yl)pyrimidin-4-yl)methylene)thiazolidine-2,4-dione;

(Z)-5-((2-(4-((((2-(3,5-dimethylisoxazol-4-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((2-(3,5-dimethylisoxazol-4-yl)-5-fluoropyridin-4-yl)methyl)amino)methyl)piperidin-1-yl)pyrimidin-4-yl)methylene)thiazolidine-2,4-dione;

(Z)-5-((2-(4-(((((6-amino-2-(3,5-dimethylisoxazol-4-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(1H-pyrazol-4-yl)pyridin-2-yl)methyl)amino)methyl)piperidin-1-yl)pyrimidin-4-yl)methylene)thiazolidine-2,4-dione;

(Z)-5-((2-(4-((((6-(1H-pyrazol-4-yl)pyridin-2-yl)methyl)amino)methyl)piperidin-1-yl)pyrimidin-4-yl)methylene)thiazolidine-2,4-dione;

(Z)-5-((2-(4-((((4-methyl-6-(1H-pyrazol-4-yl)pyridin-2-yl)methyl)amino)methyl)piperidin-1-yl)pyrimidin-4-yl)methylene)thiazolidine-2,4-dione;

(Z)-5-((2-(4-((((3-methoxy-6-(1H-pyrazol-4-yl)pyridin-2-yl)methyl)amino)methyl)piperidin-1-yl)pyrimidin-4-yl)methylene)thiazolidine-2,4-dione;

(Z)-5-((2-(4-(((((6-(1H-pyrazol-4-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(1H-pyrazol-4-yl)isoquinolin-1-yl)methyl)amino)methyl)piperidin-1-yl)pyrimidin-4-yl)methylene)thiazolidine-2,4-dione;

(Z)-5-((2-(4-((((2-(1H-pyrazol-4-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrazol-4-yl)quinolin-3-yl)methyl)amino)methyl)piperidin-1-yl)pyrimidin-4-yl)methylene)thiazolidine-2,4-dione;

(Z)-5-((2-(4-((((6-(1H-pyrazol-4-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrazol-4-yl)pyridin-4-yl)methyl)amino)methyl)piperidin-1-yl)pyrimidin-4-yl)methylene)thiazolidine-2,4-dione;

(Z)-5-((2-(4-((((2-(1H-pyrazol-4-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-((((5-fluoro-2-(1H-pyrazol-4-yl)pyridin-4-yl)methyl)amino)methyl)piperidin-1-yl)pyrimidin-4-yl)methylene)thiazolidine-2,4-dione;

(Z)-5-((2-(4-(((((6-amino-2-(1H-pyrazol-4-yl)pyridin-3-yl)methyl)amino)methyl)piperidin-1-yl)pyrimidin-4-yl)methylene)thiazolidine-2,4-dione;

(Z)-5-((2-(4-((((4-fluoro-6-(1H-pyrazol-5-yl)pyridin-2-yl)methyl)amino)methyl)piperidin-1-yl)pyrimidin-4-yl)methylene)thiazolidine-2,4-dione;

(Z)-5-((2-(4-((((6-(1H-pyrazol-5-yl)pyridin-2-yl)methyl)amino)methyl)piperidin-1-yl)pyrimidin-4-yl)methylene)thiazolidine-2,4-dione;

(Z)-5-((2-(4-((((4-methyl-6-(1H-pyrazol-5-yl)pyridin-2-yl)methyl)amino)methyl)piperidin-1-yl)pyrimidin-4-yl)methylene)thiazolidine-2,4-dione;

(Z)-5-((2-(4-((((3-methoxy-6-(1H-pyrazol-5-yl)pyridin-2-yl)methyl)amino)methyl)piperidin-1-yl)pyrimidin-4-yl)methylene)thiazolidine-2,4-dione;

(Z)-5-((2-(4-(((((6-(1H-pyrazol-5-yl)-4-(trifluoromethyl)pyridin-2-yl)methyl)amino)methyl)piperidin-1-yl)pyrimidin-4-yl)methylene)thiazolidine-2,4-dione;

(Z)-5-((2-(4-((((3-(1H-pyrazol-5-yl)isoquinolin-1-yl)methyl)amino)methyl)piperidin-1-yl)pyrimidin-4-yl)methylene)thiazolidine-2,4-dione;

(Z)-5-((2-(4-((((2-(1H-pyrazol-5-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrazol-5-yl)quinolin-3-yl)methyl)amino)methyl)piperidin-1-yl)pyrimidin-4-yl)methylene)thiazolidine-2,4-dione;

(Z)-5-((2-(4-((((6-(1H-pyrazol-5-yl)pyridin-3-yl)methyl)amino)methyl)piperidin-1-yl)pyrimidin-4-yl)methylene)thiazolidine-2,4-dione;

(Z)-5-((2-(4-((((2-(1H-pyrazol-5-yl)pyridin-4-yl)methyl)amino)methyl)piperidin-1-yl)pyrimidin-4-yl)methylene)thiazolidine-2,4-dione;

(Z)-5-((2-(4-((((2-(1H-pyrazol-5-yl)-6-(trifluoromethyl)pyridin-4-yl)methyl)amino)methyl)piperidin-1-yl)pyrimidin-4-yl)methylene)thiazolidine-2,4-dione;

(Z)-5-((2-(4-(((((5-fluoro-2-(1H-pyrazol-5-yl)pyridin-4-yl)methyl)amino)methyl)piperidin-1-yl)pyrimidin-4-yl)methylene)thiazolidine-2,4-dione;

(Z)-5-((2-(4-(((((6-amino-2-(1H-pyrazol-5-yl)pyridin-3-yl)methyl)amino)methyl)piperidin-1-yl)pyrimidin-4-yl)methylene)thiazolidine-2,4-dione;

(Z)-5-((2-(4-((((2',4'-bis(trifluoromethyl)-[1,1'-biphenyl]-2-yl)methyl)amino)methyl)piperidin-1-yl)pyrimidin-4-yl)methylene)thiazolidine-2,4-dione;

(Z)-5-((2-(4-((((2',4'-bis(trifluoromethyl)-[1,1'-biphenyl]-3-yl)methyl)amino)methyl)piperidin-1-yl)pyrimidin-4-yl)methylene)thiazolidine-2,4-dione;

(Z)-5-((2-(4-((((2',4'-dimethoxy-[1,1'-biphenyl]-2-yl)methyl)amino)methyl)piperidin-1-yl)pyrimidin-4-yl)methylene)thiazolidine-2,4-dione;

(Z)-5-((2-(4-((((2',4'-dimethoxy-[1,1'-biphenyl]-3-yl)methyl)amino)methyl)piperidin-1-yl)pyrimidin-4-yl)methylene)thiazolidine-2,4-dione;

(Z)-5-((2-(4-((((2'-(trifluoromethoxy)-[1,1'-biphenyl]-2-yl)methyl)amino)methyl)piperidin-1-yl)pyrimidin-4-yl)methylene)thiazolidine-2,4-dione;

(Z)-5-((2-(4-((((2'-(trifluoromethoxy)-[1,1'-biphenyl]-3-yl)methyl)amino)methyl)piperidin-1-yl)pyrimidin-4-yl)methylene)thiazolidine-2,4-dione;

(Z)-5-((2-(4-(((2-(benzo[d][1,3]dioxol-5-yl)benzyl)amino)methyl)piperidin-1-yl)pyrimidin-4-yl)methylene)thiazolidine-2,4-dione;

(Z)-5-((2-(4-(((3-(benzo[d][1,3]dioxol-5-yl)benzyl)amino)methyl)piperidin-1-yl)pyrimidin-4-yl)methylene)thiazolidine-2,4-dione;

(Z)-5-((2-(4-((((3'-(dimethylamino)-[1,1'-biphenyl]-2-yl)methyl)amino)methyl)piperidin-1-yl)pyrimidin-4-yl)methylene)thiazolidine-2,4-dione;

(Z)-5-((2-(4-((((3'-(dimethylamino)-[1,1'-biphenyl]-3-yl)methyl)amino)methyl)piperidin-1-yl)pyrimidin-4-yl)methylene)thiazolidine-2,4-dione;

(Z)-5-((2-(4-((((4'-phenoxy-[1,1'-biphenyl]-2-yl)methyl)amino)methyl)piperidin-1-yl)pyrimidin-4-yl)methylene)thiazolidine-2,4-dione;

(Z)-5-((2-(4-((((4'-phenoxy-[1,1'-biphenyl]-3-yl)methyl)amino)methyl)piperidin-1-yl)pyrimidin-4-yl)methylene)thiazolidine-2,4-dione;

(Z)-5-((2-(4-(((2-(1H-indol-5-yl)benzyl)amino)methyl)piperidin-1-yl)pyrimidin-4-yl)methylene)thiazolidine-2,4-dione;

(Z)-5-((2-(4-(((3-(1H-indol-5-yl)benzyl)amino)methyl)piperidin-1-yl)pyrimidin-4-yl)methylene)thiazolidine-2,4-dione;

(Z)-5-((2-(4-(((2-(isoquinolin-5-yl)benzyl)amino)methyl)piperidin-1-yl)pyrimidin-4-yl)methylene)thiazolidine-2,4-dione;

(Z)-5-((2-(4-(((3-(isoquinolin-5-yl)benzyl)amino)methyl)piperidin-1-yl)pyrimidin-4-yl)methylene)thiazolidine-2,4-dione;

(Z)-5-((2-(4-(((2-(thiophen-3-yl)benzyl)amino)methyl)piperidin-1-yl)pyrimidin-4-yl)methylene)thiazolidine-2,4-dione;

(Z)-5-((2-(4-(((3-(thiophen-3-yl)benzyl)amino)methyl)piperidin-1-yl)pyrimidin-4-yl)methylene)thiazolidine-2,4-dione;

(Z)-5-((2-(4-(((2-(benzo[b]thiophen-3-yl)benzyl)amino)methyl)piperidin-1-yl)pyrimidin-4-yl)methylene)thiazolidine-2,4-dione;

(Z)-5-((2-(4-(((3-(benzo[b]thiophen-3-yl)benzyl)amino)methyl)piperidin-1-yl)pyrimidin-4-yl)methylene)thiazolidine-2,4-dione;

(Z)-5-((2-(4-(((2-(5-acetylthiophen-2-yl)benzyl)amino)methyl)piperidin-1-yl)pyrimidin-4-yl)methylene)thiazolidine-2,4-dione;

(Z)-5-((2-(4-(((3-(5-acetylthiophen-2-yl)benzyl)amino)methyl)piperidin-1-yl)pyrimidin-4-yl)methylene)thiazolidine-2,4-dione;

(Z)-5-((2-(4-(((2-(furan-2-yl)benzyl)amino)methyl)piperidin-1-yl)pyrimidin-4-yl)methylene)thiazolidine-2,4-dione;

(Z)-5-((2-(4-(((3-(furan-2-yl)benzyl)amino)methyl)piperidin-1-yl)pyrimidin-4-yl)methylene)thiazolidine-2,4-dione;

(Z)-5-((2-(4-(((2-(benzofuran-2-yl)benzyl)amino)methyl)piperidin-1-yl)pyrimidin-4-yl)methylene)thiazolidine-2,4-dione;

(Z)-5-((2-(4-(((3-(benzofuran-2-yl)benzyl)amino)methyl)piperidin-1-yl)pyrimidin-4-yl)methylene)thiazolidine-2,4-dione;

(Z)-5-((2-(4-(((2-(furan-3-yl)benzyl)amino)methyl)piperidin-1-yl)pyrimidin-4-yl)methylene)thiazolidine-2,4-dione;

(Z)-5-((2-(4-(((3-(furan-3-yl)benzyl)amino)methyl)piperidin-1-yl)pyrimidin-4-yl)methylene)thiazolidine-2,4-dione;

(Z)-5-((2-(4-(((2-(1H-pyrrol-2-yl)benzyl)amino)methyl)piperidin-1-yl)pyrimidin-4-yl)methylene)thiazolidine-2,4-dione;

(Z)-5-((2-(4-(((3-(1H-pyrrol-2-yl)benzyl)amino)methyl)piperidin-1-yl)pyrimidin-4-yl)methylene)thiazolidine-2,4-dione;

(Z)-5-((2-(4-(((2-(isoquinolin-4-yl)benzyl)amino)methyl)piperidin-1-yl)pyrimidin-4-yl)methylene)thiazolidine-2,4-dione;

(Z)-5-((2-(4-(((3-(isoquinolin-4-yl)benzyl)amino)methyl)piperidin-1-yl)pyrimidin-4-yl)methylene)thiazolidine-2,4-dione;

(Z)-5-((2-(4-(((2-(quinolin-4-yl)benzyl)amino)methyl)piperidin-1-yl)pyrimidin-4-yl)methylene)thiazolidine-2,4-dione;

(Z)-5-((2-(4-(((3-(quinolin-4-yl)benzyl)amino)methyl)piperidin-1-yl)pyrimidin-4-yl)methylene)thiazolidine-2,4-dione;

(Z)-5-((2-(4-(((2-(3-fluoropyridin-4-yl)benzyl)amino)methyl)piperidin-1-yl)pyrimidin-4-yl)methylene)thiazolidine-2,4-dione;

(Z)-5-((2-(4-(((3-(3-fluoropyridin-4-yl)benzyl)amino)methyl)piperidin-1-yl)pyrimidin-4-yl)methylene)thiazolidine-2,4-dione;

(Z)-5-((2-(4-(((2-(2,6-difluoropyridin-4-yl)benzyl)amino)methyl)piperidin-1-yl)pyrimidin-4-yl)methylene)thiazolidine-2,4-dione;

(Z)-5-((2-(4-(((3-(2,6-difluoropyridin-4-yl)benzyl)amino)methyl)piperidin-1-yl)pyrimidin-4-yl)methylene)thiazolidine-2,4-dione;

(Z)-5-((2-(4-(((2-(6-(dimethylamino)pyridin-3-yl)benzyl)amino)methyl)piperidin-1-yl)pyrimidin-4-yl)methylene)thiazolidine-2,4-dione;

(Z)-5-((2-(4-(((3-(6-(dimethylamino)pyridin-3-yl)benzyl)amino)methyl)piperidin-1-yl)pyrimidin-4-yl)methylene)thiazolidine-2,4-dione;

(Z)-5-((2-(4-(((2-(2-(dimethylamino)pyrimidin-5-yl)benzyl)amino)methyl)piperidin-1-yl)pyrimidin-4-yl)methylene)thiazolidine-2,4-dione;

(Z)-5-((2-(4-(((3-(2-(dimethylamino)pyrimidin-5-yl)benzyl)amino)methyl)piperidin-1-yl)pyrimidin-4-yl)methylene)thiazolidine-2,4-dione;

(Z)-5-((2-(4-(((2-(3,5-dimethylisoxazol-4-yl)benzyl)amino)methyl)piperidin-1-yl)pyrimidin-4-yl)methylene)thiazolidine-2,4-dione;

(Z)-5-((2-(4-(((3-(3,5-dimethylisoxazol-4-yl)benzyl)amino)methyl)piperidin-1-yl)pyrimidin-4-yl)methylene)thiazolidine-2,4-dione;

(Z)-5-((2-(4-(((2-(1H-pyrazol-4-yl)benzyl)amino)methyl)piperidin-1-yl)pyrimidin-4-yl)methylene)thiazolidine-2,4-dione;

(Z)-5-((2-(4-(((3-(1H-pyrazol-4-yl)benzyl)amino)methyl)piperidin-1-yl)pyrimidin-4-yl)methylene)thiazolidine-2,4-dione;

(Z)-5-((2-(4-(((2-(1H-pyrazol-5-yl)benzyl)amino)methyl)piperidin-1-yl)pyrimidin-4-yl)methylene)thiazolidine-2,4-dione; and (Z)-5-((2-(4-(((3-(1H-pyrazol-5-yl)benzyl)amino)methyl)piperidin-1-yl)pyrimidin-4-yl)methylene)thiazolidine-2,4-dione.

\* \* \* \* \*